US012799533B2

(12) United States Patent
Shoemaker et al.

(10) Patent No.: US 12,799,533 B2
(45) **Date of Patent: *Nov. 17, 2026**

(54) RARE CELL ANALYSIS USING SAMPLE SPLITTING AND DNA TAGS

(71) Applicants: The General Hospital Corporation, Boston, MA (US); GPB Scientific, LLC, Richmond, VA (US); Verinata Health, Inc., Redwood City, CA (US)

(72) Inventors: Daniel Shoemaker, San Diego, CA (US); Mehmet Toner, Charlestown, MA (US); Ravi Kapur, Sharon, MA (US); Roland B. Stoughton, The Sea Ranch, CA (US); Ronald W. Davis, Palo Alto, CA (US)

(73) Assignees: The General Hospital Corporation, Boston, MA (US); GPB Scientific, LLC, Richmond, VA (US); Verinata Health, Inc., Redwood City, CA (US)

(*) Notice: Subject to any disclaimer, the term of this patent is extended or adjusted under 35 U.S.C. 154(b) by 572 days.

This patent is subject to a terminal disclaimer.

(21) Appl. No.: 18/463,607

(22) Filed: Sep. 8, 2023

(65) Prior Publication Data

US 2024/0279738 A1 Aug. 22, 2024

Related U.S. Application Data

(63) Continuation of application No. 16/193,916, filed on Nov. 16, 2018, now Pat. No. 11,781,187, which is a (Continued)

(51) Int. Cl.
*C12Q 1/6809* (2018.01)
*C12Q 1/6869* (2018.01)
(Continued)

(52) U.S. Cl.
CPC ......... *C12Q 1/6883* (2013.01); *C12Q 1/6809* (2013.01); *C12Q 1/6869* (2013.01);
(Continued)

(58) Field of Classification Search
None
See application file for complete search history.

(56) References Cited

U.S. PATENT DOCUMENTS 3,560,754 A 2/1971 Kamentsky
4,508,625 A 4/1985 Graham
(Continued)

FOREIGN PATENT DOCUMENTS

CN 1308726 A 8/2001
CN 1539992 A 10/2004
(Continued)

OTHER PUBLICATIONS

Yamanishi et al., "Enrichment of rare fetal cells from maternal peripheral blood," Expert Review of Molecular Diagnostics, Jul. 2002, 2(4):303-11.

(Continued)

*Primary Examiner* — Samuel C Woolwine
(74) *Attorney, Agent, or Firm* — Fish & Richardson P.C.

(57) ABSTRACT

The present invention provides systems, apparatuses, and methods to detect the presence of fetal cells when mixed with a population of maternal cells in a sample and to test fetal abnormalities, e.g. aneuploidy. The present invention involves labeling regions of genomic DNA in each cell in said mixed sample with different labels wherein each label is specific to each cell and quantifying the labeled regions of genomic DNA from each cell in the mixed sample. More particularly the invention involves quantifying labeled DNA polymorphisms from each cell in the mixed sample.

18 Claims, 46 Drawing Sheets

Specification includes a Sequence Listing.

Related U.S. Application Data continuation of application No. 14/697,372, filed on Apr. 27, 2015, now Pat. No. 10,155,984, which is a continuation of application No. 13/835,926, filed on Mar. 15, 2013, now Pat. No. 9,017,942, which is a continuation of application No. 13/306,640, filed on Nov. 29, 2011, now abandoned, which is a continuation of application No. 12/230,628, filed on Sep. 2, 2008, now Pat. No. 8,168,389, which is a continuation of application No. 11/763,421, filed on Jun. 14, 2007, now Pat. No. 8,372,584.

(60) Provisional application No. 60/820,778, filed on Jul. 28, 2006, provisional application No. 60/804,819, filed on Jun. 14, 2006.

(51) Int. Cl.

*C12Q 1/6881* (2018.01)
*C12Q 1/6883* (2018.01)
*B01L 3/00* (2006.01)
*G01N 15/10* (2024.01)

(52) U.S. Cl.

CPC ...... *C12Q 1/6881* (2013.01); *B01L 3/502761* (2013.01); *C12Q 2600/156* (2013.01); *C12Q 2600/158* (2013.01); *C12Q 2600/16* (2013.01); *G01N 2015/1006* (2013.01); *G01N 2015/1029* (2024.01); *Y10T 436/143333* (2015.01)

(56) References Cited

U.S. PATENT DOCUMENTS 4,675,286 A 6/1987 Calenoff
4,683,202 A 7/1987 Mullis
4,789,628 A 12/1988 Nayak
4,800,159 A 1/1989 Mullis et al.
4,886,761 A 12/1989 Gustafson et al.
4,936,465 A 6/1990 Zoeld
4,971,904 A 11/1990 Luddy
4,977,078 A 12/1990 Niimura et al.
5,153,117 A 10/1992 Simons
5,215,926 A 6/1993 Etchells, III et al.
5,296,375 A 3/1994 Kricka et al.
5,300,779 A 4/1994 Hillman et al.
5,302,509 A 4/1994 Cheeseman
5,304,487 A 4/1994 Wilding et al.
5,310,674 A 5/1994 Weinreb et al.
5,427,663 A 6/1995 Austin et al.
5,427,946 A 6/1995 Kricka et al.
5,432,054 A 7/1995 Saunders et al.
5,447,842 A 9/1995 Simons
5,486,335 A 1/1996 Wilding et al.
5,489,506 A 2/1996 Crane
5,498,392 A 3/1996 Wilding et al.
5,506,141 A 4/1996 Weinreb
5,508,169 A 4/1996 Deugau et al.
5,529,903 A 6/1996 Kübler et al.
5,541,072 A 7/1996 Wang et al.
5,556,773 A 9/1996 Youmo
5,587,070 A 12/1996 Pall et al.
5,622,831 A 4/1997 Liberti et al.
5,629,147 A 5/1997 Asgari et al.
5,635,358 A 6/1997 Wilding et al.
5,637,469 A 6/1997 Wilding et al.
5,639,669 A 6/1997 Ledley
5,641,628 A 6/1997 Bianchi
5,646,001 A 7/1997 Terstappen et al.
5,670,325 A 9/1997 Lapidus et al.
5,676,849 A 10/1997 Sammons et al.
5,695,934 A 12/1997 Brenner
5,707,799 A 1/1998 Hansmann et al.
5,709,943 A 1/1998 Coleman et al.
5,715,946 A 2/1998 Reichenbach
5,726,026 A 3/1998 Wilding et al.
5,750,339 A 5/1998 Smith
5,766,843 A 6/1998 Asgari et al.
5,770,029 A 6/1998 Nelson et al.
5,795,716 A 8/1998 Chee
5,798,042 A 8/1998 Chu et al.
5,837,115 A 11/1998 Austin et al.
5,840,502 A 11/1998 Van Vlasselaer
5,842,787 A 12/1998 Koph-Sill et al.
5,843,767 A 12/1998 Beattie
5,846,708 A 12/1998 Hollis et al.
5,858,649 A 1/1999 Asgari et al.
5,861,253 A 1/1999 Asgari et al.
5,863,502 A 1/1999 Southgate et al.
5,866,345 A 2/1999 Wilding et al.
5,879,624 A 3/1999 Boehringer et al.
5,879,883 A 3/1999 Benson et al.
5,891,651 A 4/1999 Roche et al.
5,906,724 A 5/1999 Sammons et al.
5,928,880 A 7/1999 Wilding et al.
5,944,971 A 8/1999 Foote
5,952,173 A 9/1999 Hansmann et al.
5,962,234 A 10/1999 Golbus
5,962,237 A 10/1999 Ts'o et al.
5,962,332 A 10/1999 Singer et al.
5,972,721 A 10/1999 Bruno et al.
5,993,665 A 11/1999 Terstappen et al.
5,994,057 A 11/1999 Mansfield
5,994,517 A 11/1999 Ts'o et al.
6,007,690 A 12/1999 Nelson et al.
6,008,007 A 12/1999 Fruehauf et al.
6,008,010 A 12/1999 Greenberger et al.
6,013,188 A 1/2000 Terstappen et al.
6,030,581 A 2/2000 Virtanen
6,036,857 A 3/2000 Chen et al.
6,066,449 A 5/2000 Ditkoff et al.
6,071,394 A 6/2000 Cheng et al.
6,074,827 A 6/2000 Nelson et al.
6,100,029 A 8/2000 Lapidus et al.
6,124,120 A 9/2000 Lizardi
6,129,848 A 10/2000 Chen et al.
6,132,607 A 10/2000 Chen et al.
6,143,496 A 11/2000 Brown et al.
6,143,576 A 11/2000 Buechler
6,150,119 A 11/2000 Kopf-sill et al.
6,154,707 A 11/2000 Livak et al.
6,156,270 A 12/2000 Buechler
6,159,685 A 12/2000 Pinkel et al.
6,176,962 B1 1/2001 Soane et al.
6,184,029 B1 2/2001 Wilding et al.
6,184,043 B1 2/2001 Fodstad et al.
6,186,660 B1 2/2001 Koph-Sill et al.
6,190,870 B1 2/2001 Schmitz et al.
6,197,523 B1 3/2001 Rimm et al.
6,200,765 B1 3/2001 Murphy et al.
6,210,574 B1 4/2001 Sammons et al.
6,210,891 B1 4/2001 Nyren et al.
6,210,910 B1 4/2001 Walt et al.
6,214,558 B1 4/2001 Shuber et al.
6,235,474 B1 5/2001 Feinberg
6,242,209 B1 6/2001 Ransom et al.
6,258,540 B1 7/2001 Lo et al.
6,265,229 B1 7/2001 Fodstad et al.
6,274,337 B1 8/2001 Parce et al.
6,277,489 B1 8/2001 Abbott et al.
6,280,967 B1 8/2001 Ransom et al.
6,300,077 B1 10/2001 Shuber et al.
6,344,326 B1 2/2002 Nelson et al.
6,361,958 B1 3/2002 Shieh et al.
6,365,362 B1 4/2002 Terstappen et al.
6,368,871 B1 4/2002 Christel et al.
6,372,432 B1 4/2002 Tocque et al.
6,376,181 B2 4/2002 Ramsey et al.
6,377,721 B1 4/2002 Walt et al.
6,383,759 B1 5/2002 Murphy et al.
6,387,707 B1 5/2002 Seul et al.
6,391,559 B1 5/2002 Brown et al.
6,394,942 B2 5/2002 Moon et al.
6,399,364 B1 6/2002 Reeve et al.

(56) References Cited

U.S. PATENT DOCUMENTS

| | | | |
|---|---|---|---|
| 6,432,630 | B1 | 8/2002 | Blankenstein |
| 6,440,706 | B1 | 8/2002 | Vogelstein et al. |
| 6,444,461 | B1 | 9/2002 | Knapp et al. |
| 6,454,938 | B2 | 9/2002 | Moon et al. |
| 6,479,299 | B1 | 11/2002 | Parce et al. |
| 6,488,895 | B1 | 12/2002 | Kennedy |
| 6,511,967 | B1 | 1/2003 | Weissleder et al. |
| 6,517,234 | B1 | 2/2003 | Koph-Sill et al. |
| 6,540,895 | B1 | 4/2003 | Spence et al. |
| 6,551,841 | B1 | 4/2003 | Wilding et al. |
| 6,566,101 | B1 | 5/2003 | Shuber et al. |
| 6,573,082 | B1 | 6/2003 | Choi et al. |
| 6,576,478 | B1 | 6/2003 | Wagner et al. |
| 6,582,904 | B2 | 6/2003 | Dahm |
| 6,582,969 | B1 | 6/2003 | Wagner et al. |
| 6,596,144 | B1 | 7/2003 | Regnier et al. |
| 6,596,545 | B1 | 7/2003 | Wagner et al. |
| 6,605,454 | B2 | 8/2003 | Barenburg et al. |
| 6,613,525 | B2 | 9/2003 | Nelson et al. |
| 6,618,679 | B2 | 9/2003 | Loehrlein et al. |
| 6,632,619 | B1 | 10/2003 | Harrison et al. |
| 6,632,652 | B1 | 10/2003 | Austin et al. |
| 6,632,655 | B1 | 10/2003 | Mehta et al. |
| 6,637,463 | B1 | 10/2003 | Lei et al. |
| 6,641,997 | B1 | 11/2003 | Mackinnon |
| 6,645,731 | B2 | 11/2003 | Terstappen et al. |
| 6,664,056 | B2 | 12/2003 | Lo et al. |
| 6,664,104 | B2 | 12/2003 | Pourahmadi et al. |
| 6,673,541 | B1 | 1/2004 | Klein et al. |
| 6,674,525 | B2 | 1/2004 | Bardell et al. |
| 6,685,841 | B2 | 2/2004 | Lopez et al. |
| 6,689,615 | B1 | 2/2004 | Murto et al. |
| 6,746,503 | B1 | 6/2004 | Benett et al. |
| 6,753,147 | B2 | 6/2004 | Vogelstein et al. |
| 6,783,647 | B2 | 8/2004 | Culbertson et al. |
| 6,783,928 | B2 | 8/2004 | Hvichia et al. |
| 6,815,664 | B2 | 11/2004 | Wang et al. |
| 6,818,184 | B2 | 11/2004 | Fulwyler et al. |
| 6,830,936 | B2 | 12/2004 | Anderson et al. |
| 6,858,439 | B1 | 2/2005 | Xu et al. |
| 6,875,619 | B2 | 4/2005 | Blackburn |
| 6,893,881 | B1 | 5/2005 | Fodstad et al. |
| 6,906,182 | B2 | 6/2005 | Ts'o et al. |
| 6,911,345 | B2 | 6/2005 | Quake et al. |
| 6,913,697 | B2 | 7/2005 | Lopez et al. |
| 6,927,028 | B2 | 8/2005 | Lo et al. |
| 6,947,583 | B2 | 9/2005 | Ellis et al. |
| 6,953,668 | B1 | 10/2005 | Israeli et al. |
| 6,958,245 | B2 | 10/2005 | Seul et al. |
| 6,960,449 | B2 | 11/2005 | Wang et al. |
| 7,115,709 | B1 | 10/2006 | Gray et al. |
| 7,150,812 | B2 | 12/2006 | Huang et al. |
| 7,171,975 | B2 | 2/2007 | Moon et al. |
| 7,190,818 | B2 | 3/2007 | Ellis et al. |
| 7,192,698 | B1 | 3/2007 | Kinch et al. |
| 7,198,787 | B2 | 4/2007 | Fodstad et al. |
| 7,208,275 | B2 | 4/2007 | Gocke et al. |
| 7,208,295 | B2 | 4/2007 | Faham et al. |
| 7,212,660 | B2 | 5/2007 | Wetzel et al. |
| 7,220,594 | B2 | 5/2007 | Foster et al. |
| 7,224,839 | B2 | 5/2007 | Zeineh |
| 7,227,002 | B1 | 6/2007 | Kufer et al. |
| 7,229,838 | B2 | 6/2007 | Foster et al. |
| 7,250,256 | B2 | 7/2007 | Reinhard et al. |
| 7,252,976 | B2 | 8/2007 | Lin et al. |
| 7,258,987 | B2 | 8/2007 | Lamorte et al. |
| 7,262,177 | B2 | 8/2007 | Ts'o et al. |
| 7,262,269 | B2 | 8/2007 | Lam et al. |
| 7,264,972 | B2 | 9/2007 | Foster |
| 7,272,252 | B2 | 9/2007 | De La Torre-Bueno et al. |
| 7,276,170 | B2 | 10/2007 | Oakey et al. |
| 7,332,277 | B2 | 2/2008 | Dhallan |
| 7,407,757 | B2 | 8/2008 | Brenner |
| 7,428,325 | B2 | 9/2008 | Douglass et al. |
| 7,442,506 | B2 | 10/2008 | Dhallan |
| 7,476,363 | B2 | 1/2009 | Unger et al. |
| 7,645,576 | B2 | 1/2010 | Lo et al. |
| 7,655,399 | B2 | 2/2010 | Cantor et al. |
| 7,709,194 | B2 | 5/2010 | Lo et al. |
| 7,718,367 | B2 | 5/2010 | Lo et al. |
| 7,727,720 | B2 | 6/2010 | Dhallan et al. |
| 7,754,428 | B2 | 7/2010 | Lo et al. |
| 7,783,098 | B2 | 8/2010 | Douglass et al. |
| 7,838,647 | B2 | 11/2010 | Hahn et al. |
| 7,888,017 | B2 | 2/2011 | Quake et al. |
| RE42,315 | E | 5/2011 | Lopez et al. |
| 8,008,018 | B2 | 8/2011 | Quake et al. |
| 8,024,128 | B2 | 9/2011 | Rabinowitz et al. |
| 8,137,912 | B2 | 3/2012 | Kapur et al. |
| 8,195,415 | B2 | 6/2012 | Fan et al. |
| 8,515,679 | B2 | 8/2013 | Rabinowitz et al. |
| 8,532,930 | B2 | 9/2013 | Rabinowitz et al. |
| 8,682,592 | B2 | 3/2014 | Rabinowitz et al. |
| 9,347,100 | B2 | 5/2016 | Shoemaker et al. |
| 9,441,273 | B2 | 9/2016 | Quake et al. |
| 2001/0007749 | A1 | 7/2001 | Feinberg |
| 2001/0051341 | A1 | 12/2001 | Lo et al. |
| 2001/0053958 | A1 | 12/2001 | Ried et al. |
| 2002/0005354 | A1 | 1/2002 | Spence et al. |
| 2002/0006621 | A1 | 1/2002 | Bianchi |
| 2002/0009738 | A1 | 1/2002 | Houghton et al. |
| 2002/0012930 | A1 | 1/2002 | Rothberg et al. |
| 2002/0012931 | A1 | 1/2002 | Waldman et al. |
| 2002/0012933 | A1 | 1/2002 | Rothberg et al. |
| 2002/0016450 | A1 | 2/2002 | Laugharn et al. |
| 2002/0019001 | A1 | 2/2002 | Light |
| 2002/0028431 | A1 | 3/2002 | Julien |
| 2002/0058332 | A1 | 5/2002 | Quake et al. |
| 2002/0076825 | A1 | 6/2002 | Cheng et al. |
| 2002/0086329 | A1 | 7/2002 | Shvets et al. |
| 2002/0090741 | A1 | 7/2002 | Jurgensen et al. |
| 2002/0098535 | A1 | 7/2002 | Wang et al. |
| 2002/0106661 | A1 | 8/2002 | Virtanen |
| 2002/0108859 | A1 | 8/2002 | Wang et al. |
| 2002/0110835 | A1 | 8/2002 | Kumar |
| 2002/0115163 | A1 | 8/2002 | Wang et al. |
| 2002/0115164 | A1 | 8/2002 | Wang et al. |
| 2002/0115201 | A1 | 8/2002 | Barenburg et al. |
| 2002/0119469 | A1 | 8/2002 | Shuber et al. |
| 2002/0123078 | A1 | 9/2002 | Seul et al. |
| 2002/0123112 | A1 | 9/2002 | Wang et al. |
| 2002/0127575 | A1 | 9/2002 | Hoke et al. |
| 2002/0132315 | A1 | 9/2002 | Wang et al. |
| 2002/0132316 | A1 | 9/2002 | Wang et al. |
| 2002/0137088 | A1 | 9/2002 | Bianchi |
| 2002/0160363 | A1 | 10/2002 | McDevitt et al. |
| 2002/0164816 | A1 | 11/2002 | Quake |
| 2002/0164825 | A1 | 11/2002 | Chen |
| 2002/0166760 | A1 | 11/2002 | Prentiss et al. |
| 2002/0172987 | A1 | 11/2002 | Terstappen et al. |
| 2003/0004402 | A1 | 1/2003 | Hitt et al. |
| 2003/0013101 | A1 | 1/2003 | Balasubramanian |
| 2003/0017514 | A1 | 1/2003 | Pachmann et al. |
| 2003/0022207 | A1 | 1/2003 | Balasubramanian |
| 2003/0033091 | A1 | 2/2003 | Opalsky et al. |
| 2003/0044388 | A1 | 3/2003 | Lo et al. |
| 2003/0044832 | A1 | 3/2003 | Blankenstein |
| 2003/0072682 | A1 | 4/2003 | Kikinis |
| 2003/0077292 | A1 | 4/2003 | Hanash et al. |
| 2003/0082566 | A1 | 5/2003 | Sylvan |
| 2003/0096268 | A1 | 5/2003 | Weiner et al. |
| 2003/0100102 | A1 | 5/2003 | Rothberg et al. |
| 2003/0119077 | A1 | 6/2003 | Ts'o et al. |
| 2003/0119724 | A1 | 6/2003 | Ts'o et al. |
| 2003/0129676 | A1 | 7/2003 | Terstappen et al. |
| 2003/0152981 | A1 | 8/2003 | Hulten |
| 2003/0153085 | A1 | 8/2003 | Leary et al. |
| 2003/0159999 | A1 | 8/2003 | Oakey et al. |
| 2003/0165852 | A1 | 9/2003 | Schueler et al. |
| 2003/0170631 | A1 | 9/2003 | Houghton et al. |
| 2003/0170703 | A1 | 9/2003 | Piper et al. |
| 2003/0175990 | A1 | 9/2003 | Heyenga |
| 2003/0178641 | A1 | 9/2003 | Blair et al. |
| 2003/0186255 | A1 | 10/2003 | Williams et al. |

(56) References Cited

U.S. PATENT DOCUMENTS

| | | | |
|---|---|---|---|
| 2003/0190602 | A1 | 10/2003 | Pressman et al. |
| 2003/0199685 | A1 | 10/2003 | Pressman et al. |
| 2003/0204331 | A1 | 10/2003 | Whitney et al. |
| 2003/0206901 | A1 | 11/2003 | Chen |
| 2003/0219765 | A1 | 11/2003 | Costa |
| 2003/0231791 | A1 | 12/2003 | Torre-Bueno et al. |
| 2003/0232350 | A1 | 12/2003 | Afar et al. |
| 2004/0005582 | A1 | 1/2004 | Shipwash |
| 2004/0009471 | A1 | 1/2004 | Cao |
| 2004/0018116 | A1 | 1/2004 | Desmond et al. |
| 2004/0018509 | A1 | 1/2004 | Bianchi |
| 2004/0018525 | A1 | 1/2004 | Wirtz et al. |
| 2004/0018611 | A1 | 1/2004 | Ward et al. |
| 2004/0023222 | A1 | 2/2004 | Russell et al. |
| 2004/0043506 | A1 | 3/2004 | Haussecker et al. |
| 2004/0048360 | A1 | 3/2004 | Wada et al. |
| 2004/0053352 | A1 | 3/2004 | Ouyang et al. |
| 2004/0063162 | A1 | 4/2004 | Dunlay et al. |
| 2004/0072278 | A1 | 4/2004 | Chou et al. |
| 2004/0077105 | A1 | 4/2004 | Wu et al. |
| 2004/0096892 | A1 | 5/2004 | Wang et al. |
| 2004/0121343 | A1 | 6/2004 | Buechler et al. |
| 2004/0137452 | A1 | 7/2004 | Levett et al. |
| 2004/0137470 | A1 | 7/2004 | Dhallan |
| 2004/0142463 | A1 | 7/2004 | Walker et al. |
| 2004/0144651 | A1 | 7/2004 | Huang et al. |
| 2004/0146883 | A1 | 7/2004 | Kennedy |
| 2004/0166555 | A1 | 8/2004 | Braff et al. |
| 2004/0171091 | A1 | 9/2004 | Lesko et al. |
| 2004/0185495 | A1 | 9/2004 | Schueler et al. |
| 2004/0197839 | A1 | 10/2004 | Daniely et al. |
| 2004/0203037 | A1 | 10/2004 | Lo et al. |
| 2004/0209299 | A1 | 10/2004 | Pinter et al. |
| 2004/0214240 | A1 | 10/2004 | Cao |
| 2004/0232074 | A1 | 11/2004 | Peters et al. |
| 2004/0241707 | A1 | 12/2004 | Gao et al. |
| 2004/0245317 | A1 | 12/2004 | Larionov et al. |
| 2005/0003351 | A1 | 1/2005 | Fejgin et al. |
| 2005/0014208 | A1 | 1/2005 | Krehan et al. |
| 2005/0019792 | A1 | 1/2005 | McBride et al. |
| 2005/0037388 | A1 | 2/2005 | Antonarakis et al. |
| 2005/0042623 | A1 | 2/2005 | Ault-Riche et al. |
| 2005/0042685 | A1 | 2/2005 | Albert et al. |
| 2005/0049793 | A1 | 3/2005 | Paterlini-Brechot |
| 2005/0061962 | A1 | 3/2005 | Mueth et al. |
| 2005/0095606 | A1 | 5/2005 | Hoke et al. |
| 2005/0118591 | A1 | 6/2005 | Tamak et al. |
| 2005/0129581 | A1 | 6/2005 | McBride et al. |
| 2005/0142663 | A1 | 6/2005 | Parthasarathy et al. |
| 2005/0145496 | A1 | 7/2005 | Goodsaid et al. |
| 2005/0147977 | A1 | 7/2005 | Koo et al. |
| 2005/0153329 | A1 | 7/2005 | Hakansson et al. |
| 2005/0153342 | A1 | 7/2005 | Chen |
| 2005/0158754 | A1 | 7/2005 | Puffenberger et al. |
| 2005/0164241 | A1 | 7/2005 | Hahn et al. |
| 2005/0170373 | A1 | 8/2005 | Monforte |
| 2005/0175505 | A1 | 8/2005 | Cantor et al. |
| 2005/0175981 | A1 | 8/2005 | Voldman et al. |
| 2005/0175996 | A1 | 8/2005 | Chen |
| 2005/0181353 | A1 | 8/2005 | Rao et al. |
| 2005/0181463 | A1 | 8/2005 | Rao et al. |
| 2005/0196785 | A1 | 9/2005 | Quake et al. |
| 2005/0207940 | A1 | 9/2005 | Butler et al. |
| 2005/0211556 | A1 | 9/2005 | Childers et al. |
| 2005/0214855 | A1 | 9/2005 | Wagner et al. |
| 2005/0221341 | A1 | 10/2005 | Shimkets et al. |
| 2005/0221373 | A1 | 10/2005 | Enzelberger et al. |
| 2005/0239101 | A1 | 10/2005 | Sukumar et al. |
| 2005/0244843 | A1 | 11/2005 | Chen et al. |
| 2005/0250111 | A1 | 11/2005 | Xie et al. |
| 2005/0250147 | A1 | 11/2005 | Macevicz |
| 2005/0250155 | A1 | 11/2005 | Lesko et al. |
| 2005/0250199 | A1 | 11/2005 | Anderson et al. |
| 2005/0252773 | A1 | 11/2005 | McBride et al. |
| 2005/0255001 | A1 | 11/2005 | Padmanabhan et al. |
| 2005/0262577 | A1 | 11/2005 | Guelly et al. |
| 2005/0266433 | A1 | 12/2005 | Kapur et al. |
| 2005/0272103 | A1 | 12/2005 | Chen |
| 2005/0282196 | A1 | 12/2005 | Costa |
| 2005/0282213 | A1 | 12/2005 | Halle |
| 2005/0282220 | A1 | 12/2005 | Prober et al. |
| 2005/0282293 | A1 | 12/2005 | Cosmen et al. |
| 2005/0287611 | A1 | 12/2005 | Nugent et al. |
| 2006/0000772 | A1 | 1/2006 | Sano et al. |
| 2006/0003312 | A1 | 1/2006 | Blau et al. |
| 2006/0008807 | A1 | 1/2006 | O'Hara et al. |
| 2006/0008824 | A1 | 1/2006 | Ronaghi et al. |
| 2006/0019235 | A1 | 1/2006 | Soen et al. |
| 2006/0024756 | A1 | 2/2006 | Tibbe et al. |
| 2006/0040305 | A1 | 2/2006 | Fejgin et al. |
| 2006/0046258 | A1 | 3/2006 | Lapidus et al. |
| 2006/0051265 | A1 | 3/2006 | Mohamed et al. |
| 2006/0051775 | A1 | 3/2006 | Bianchi et al. |
| 2006/0052945 | A1 | 3/2006 | Rabinowitz et al. |
| 2006/0060767 | A1 | 3/2006 | Wang et al. |
| 2006/0072805 | A1 | 4/2006 | Tsipouras et al. |
| 2006/0073125 | A1 | 4/2006 | Clarke et al. |
| 2006/0094109 | A1 | 5/2006 | Trainer |
| 2006/0121452 | A1 | 6/2006 | Dhallan |
| 2006/0121624 | A1 | 6/2006 | Huang et al. |
| 2006/0128006 | A1 | 6/2006 | Gerhardt et al. |
| 2006/0134599 | A1 | 6/2006 | Toner et al. |
| 2006/0160105 | A1 | 7/2006 | Dhallan |
| 2006/0160150 | A1 | 7/2006 | Seilhamer et al. |
| 2006/0160243 | A1 | 7/2006 | Tang et al. |
| 2006/0183886 | A1 | 8/2006 | Ts'o et al. |
| 2006/0205057 | A1 | 9/2006 | Wayner et al. |
| 2006/0223178 | A1 | 10/2006 | Barber et al. |
| 2006/0228721 | A1 | 10/2006 | Leamon et al. |
| 2006/0252054 | A1 | 11/2006 | Lin et al. |
| 2006/0252061 | A1 | 11/2006 | Zabeau et al. |
| 2006/0252068 | A1 | 11/2006 | Lo et al. |
| 2006/0252071 | A1 | 11/2006 | Lo et al. |
| 2006/0252087 | A1 | 11/2006 | Tang et al. |
| 2007/0015171 | A1 | 1/2007 | Bianchi et al. |
| 2007/0017633 | A1 | 1/2007 | Tonkovich et al. |
| 2007/0026381 | A1 | 2/2007 | Huang et al. |
| 2007/0026413 | A1 | 2/2007 | Toner et al. |
| 2007/0026414 | A1 | 2/2007 | Fuchs et al. |
| 2007/0026415 | A1 | 2/2007 | Fuchs et al. |
| 2007/0026416 | A1 | 2/2007 | Fuchs |
| 2007/0026417 | A1 | 2/2007 | Fuchs et al. |
| 2007/0026418 | A1 | 2/2007 | Fuchs et al. |
| 2007/0026419 | A1 | 2/2007 | Fuchs et al. |
| 2007/0026469 | A1 | 2/2007 | Fuchs et al. |
| 2007/0027636 | A1 | 2/2007 | Rabinowitz |
| 2007/0037172 | A1 | 2/2007 | Chiu et al. |
| 2007/0037173 | A1 | 2/2007 | Allard et al. |
| 2007/0037273 | A1 | 2/2007 | Shuler et al. |
| 2007/0037275 | A1 | 2/2007 | Shuler et al. |
| 2007/0042238 | A1 | 2/2007 | Kim et al. |
| 2007/0042339 | A1 | 2/2007 | Toner et al. |
| 2007/0042360 | A1 | 2/2007 | Afar et al. |
| 2007/0042368 | A1 | 2/2007 | Zehentner-Wilkinson et al. |
| 2007/0048750 | A1 | 3/2007 | Peck et al. |
| 2007/0054268 | A1 | 3/2007 | Sutherland et al. |
| 2007/0054287 | A1 | 3/2007 | Bloch |
| 2007/0059680 | A1 | 3/2007 | Kapur et al. |
| 2007/0059683 | A1 | 3/2007 | Barber et al. |
| 2007/0059716 | A1 | 3/2007 | Balis et al. |
| 2007/0059718 | A1 | 3/2007 | Toner et al. |
| 2007/0059719 | A1 | 3/2007 | Grisham et al. |
| 2007/0059737 | A1 | 3/2007 | Baker et al. |
| 2007/0059774 | A1 | 3/2007 | Grisham et al. |
| 2007/0059781 | A1 | 3/2007 | Kapur et al. |
| 2007/0059785 | A1 | 3/2007 | Bacus et al. |
| 2007/0065845 | A1 | 3/2007 | Baker et al. |
| 2007/0065858 | A1 | 3/2007 | Haley |
| 2007/0071762 | A1 | 3/2007 | Ts'o et al. |
| 2007/0072228 | A1 | 3/2007 | Brauch |
| 2007/0072290 | A1 | 3/2007 | Hvichia |
| 2007/0077578 | A1 | 4/2007 | Penning et al. |
| 2007/0092444 | A1 | 4/2007 | Benos et al. |
| 2007/0092881 | A1 | 4/2007 | Ohnishi et al. |

(56) References Cited

U.S. PATENT DOCUMENTS

| | | | |
|---|---|---|---|
| 2007/0092917 | A1 | 4/2007 | Guyon |
| 2007/0099207 | A1 | 5/2007 | Fuchs et al. |
| 2007/0099219 | A1 | 5/2007 | Teverovskiy et al. |
| 2007/0099289 | A1 | 5/2007 | Irimia et al. |
| 2007/0105105 | A1 | 5/2007 | Clelland et al. |
| 2007/0105133 | A1 | 5/2007 | Clark et al. |
| 2007/0110773 | A1 | 5/2007 | Asina et al. |
| 2007/0117158 | A1 | 5/2007 | Coumans et al. |
| 2007/0122856 | A1 | 5/2007 | Georges et al. |
| 2007/0122896 | A1 | 5/2007 | Shuler et al. |
| 2007/0128655 | A1 | 6/2007 | Obata |
| 2007/0131622 | A1 | 6/2007 | Oakey et al. |
| 2007/0134658 | A1 | 6/2007 | Bohmer et al. |
| 2007/0134713 | A1 | 6/2007 | Cao |
| 2007/0135621 | A1 | 6/2007 | Bourel et al. |
| 2007/0141587 | A1 | 6/2007 | Baker et al. |
| 2007/0141588 | A1 | 6/2007 | Baker et al. |
| 2007/0141717 | A1 | 6/2007 | Carpenter et al. |
| 2007/0154928 | A1 | 7/2007 | Mack et al. |
| 2007/0154960 | A1 | 7/2007 | Connelly et al. |
| 2007/0160503 | A1 | 7/2007 | Sethu et al. |
| 2007/0160974 | A1 | 7/2007 | Sidhu et al. |
| 2007/0160984 | A1 | 7/2007 | Huang et al. |
| 2007/0161064 | A1 | 7/2007 | Kinch et al. |
| 2007/0166770 | A1 | 7/2007 | Hsieh et al. |
| 2007/0170811 | A1 | 7/2007 | Rubel |
| 2007/0172903 | A1 | 7/2007 | Toner et al. |
| 2007/0178067 | A1 | 8/2007 | Maier et al. |
| 2007/0178458 | A1 | 8/2007 | O'Brien et al. |
| 2007/0178478 | A1 | 8/2007 | Dhallan et al. |
| 2007/0178501 | A1 | 8/2007 | Rabinowitz et al. |
| 2007/0187250 | A1 | 8/2007 | Huang et al. |
| 2007/0196663 | A1 | 8/2007 | Schwartz et al. |
| 2007/0196820 | A1 | 8/2007 | Kapur et al. |
| 2007/0196840 | A1 | 8/2007 | Roca et al. |
| 2007/0196869 | A1 | 8/2007 | Perez et al. |
| 2007/0202106 | A1 | 8/2007 | Palucka et al. |
| 2007/0202109 | A1 | 8/2007 | Nakamura et al. |
| 2007/0202525 | A1 | 8/2007 | Quake et al. |
| 2007/0202536 | A1 | 8/2007 | Yamanishi et al. |
| 2007/0207351 | A1 | 9/2007 | Christensen et al. |
| 2007/0207466 | A1 | 9/2007 | Cantor et al. |
| 2007/0212689 | A1 | 9/2007 | Bianchi et al. |
| 2007/0212698 | A1 | 9/2007 | Bendele et al. |
| 2007/0212737 | A1 | 9/2007 | Clarke et al. |
| 2007/0212738 | A1 | 9/2007 | Haley et al. |
| 2007/0231851 | A1 | 10/2007 | Toner et al. |
| 2007/0238105 | A1 | 10/2007 | Barrett et al. |
| 2007/0259424 | A1 | 11/2007 | Toner et al. |
| 2007/0264675 | A1 | 11/2007 | Toner et al. |
| 2007/0275402 | A1 | 11/2007 | Lo et al. |
| 2008/0020390 | A1 | 1/2008 | Mitchell et al. |
| 2008/0023399 | A1 | 1/2008 | Inglis et al. |
| 2008/0026390 | A1 | 1/2008 | Stoughton et al. |
| 2008/0038733 | A1 | 2/2008 | Bischoff et al. |
| 2008/0050739 | A1 | 2/2008 | Stoughton et al. |
| 2008/0070792 | A1 | 3/2008 | Stoughton et al. |
| 2008/0071076 | A1 | 3/2008 | Hahn et al. |
| 2008/0090239 | A1 | 4/2008 | Shoemaker et al. |
| 2008/0096216 | A1 | 4/2008 | Quake |
| 2008/0096766 | A1 | 4/2008 | Lee |
| 2008/0113350 | A1 | 5/2008 | Terstappen |
| 2008/0113358 | A1 | 5/2008 | Kapur et al. |
| 2008/0124721 | A1 | 5/2008 | Fuchs |
| 2008/0138809 | A1 | 6/2008 | Kapur et al. |
| 2008/0153090 | A1 | 6/2008 | Lo et al. |
| 2008/0182261 | A1 | 7/2008 | Bianchi |
| 2008/0193927 | A1 | 8/2008 | Mann et al. |
| 2008/0213775 | A1 | 9/2008 | Brody et al. |
| 2008/0220422 | A1 | 9/2008 | Shoemaker et al. |
| 2008/0299562 | A1 | 12/2008 | Oeth et al. |
| 2008/0318235 | A1 | 12/2008 | Handyside |
| 2009/0029377 | A1 | 1/2009 | Lo et al. |
| 2009/0087847 | A1 | 4/2009 | Lo et al. |
| 2009/0170113 | A1 | 7/2009 | Quake et al. |
| 2009/0170114 | A1 | 7/2009 | Quake et al. |
| 2009/0215633 | A1 | 8/2009 | Van Eijk et al. |
| 2009/0280492 | A1 | 11/2009 | Stoughton et al. |
| 2009/0291443 | A1 | 11/2009 | Stoughton et al. |
| 2009/0317798 | A1 | 12/2009 | Heid et al. |
| 2009/0317836 | A1 | 12/2009 | Kuhn et al. |
| 2010/0094562 | A1 | 4/2010 | Shohat et al. |
| 2010/0112575 | A1 | 5/2010 | Fan et al. |
| 2010/0136529 | A1 | 6/2010 | Shoemaker et al. |
| 2010/0169990 | A1 | 7/2010 | Clarke et al. |
| 2010/0216151 | A1 | 8/2010 | Lapidus et al. |
| 2010/0216153 | A1 | 8/2010 | Lapidus et al. |
| 2010/0248358 | A1 | 9/2010 | Yoshioka |
| 2010/0291572 | A1 | 11/2010 | Stoughton et al. |
| 2011/0003293 | A1 | 1/2011 | Stoughton et al. |
| 2011/0015096 | A1 | 1/2011 | Chiu et al. |
| 2013/0253369 | A1 | 9/2013 | Rabinowitz et al. |
| 2013/0324418 | A1 | 12/2013 | Fuchs et al. |
| 2014/0032128 | A1 | 1/2014 | Rabinowitz et al. |
| 2014/0087385 | A1 | 3/2014 | Rabinowitz et al. |
| 2014/0106975 | A1 | 4/2014 | Stoughton et al. |
| 2015/0344956 | A1 | 12/2015 | Kapur et al. |
| 2016/0002737 | A1 | 1/2016 | Fuchs et al. |

FOREIGN PATENT DOCUMENTS

| | | | |
|---|---|---|---|
| CN | 1590563 | A | 3/2005 |
| CN | 1650032 | A | 8/2005 |
| EP | 0057907 | A1 | 8/1982 |
| EP | 0637996 | B1 | 7/1997 |
| EP | 0405972 | B1 | 5/1999 |
| EP | 1221342 | A2 | 7/2002 |
| EP | 1262776 | A2 | 12/2002 |
| EP | 1301630 | A2 | 4/2003 |
| EP | 0994963 | B1 | 5/2003 |
| EP | 0970365 | B1 | 10/2003 |
| EP | 0783694 | B1 | 11/2003 |
| EP | 1262776 | A3 | 1/2004 |
| EP | 1388013 | B1 | 2/2004 |
| EP | 0920627 | B1 | 5/2004 |
| EP | 1418003 | A1 | 5/2004 |
| EP | 0739240 | B1 | 6/2004 |
| EP | 1462800 | A1 | 9/2004 |
| EP | 0919812 | B1 | 10/2004 |
| EP | 1561507 | A1 | 8/2005 |
| EP | 1328803 | B1 | 9/2005 |
| EP | 1409727 | B1 | 11/2005 |
| EP | 1272668 | B1 | 2/2007 |
| EP | 1754788 | A2 | 2/2007 |
| EP | 1757694 | A2 | 2/2007 |
| EP | 1409745 | B1 | 4/2007 |
| EP | 1754788 | A3 | 4/2007 |
| EP | 1770171 | A1 | 4/2007 |
| EP | 1313882 | B1 | 5/2007 |
| EP | 1803822 | A1 | 7/2007 |
| EP | 0951645 | B1 | 8/2007 |
| EP | 1813681 | A2 | 8/2007 |
| EP | 1832661 | A1 | 9/2007 |
| EP | 1757694 | A3 | 2/2008 |
| EP | 2161347 | A2 | 3/2010 |
| EP | 2161347 | A3 | 6/2010 |
| EP | 1597353 | B1 | 11/2010 |
| JP | 2004351309 | A | 12/2004 |
| WO | WO 1990/006509 | A1 | 6/1990 |
| WO | WO 1991/007660 | A1 | 5/1991 |
| WO | WO 1991/016452 | A1 | 10/1991 |
| WO | WO 1993/022053 | A1 | 11/1993 |
| WO | WO 1993/022055 | A2 | 11/1993 |
| WO | WO 1994/029707 | A1 | 12/1994 |
| WO | WO 1995/009245 | A1 | 4/1995 |
| WO | WO 1997/032999 | A1 | 9/1997 |
| WO | WO 1997/046882 | A1 | 12/1997 |
| WO | WO 1998/000231 | A1 | 1/1998 |
| WO | WO 1998/002528 | A1 | 1/1998 |
| WO | WO 1998/010267 | A1 | 3/1998 |
| WO | WO 1998/026284 | A1 | 6/1998 |
| WO | WO 1998/031839 | A2 | 7/1998 |
| WO | WO 1998/039474 | A1 | 9/1998 |
| WO | WO 1998/057159 | A1 | 12/1998 |

(56) References Cited

FOREIGN PATENT DOCUMENTS

| | | | |
|---|---|---|---|
| WO | WO 1999/022868 | A1 | 5/1999 |
| WO | WO 1999/038612 | A1 | 8/1999 |
| WO | WO 1999/044064 | A1 | 9/1999 |
| WO | WO 1999/058972 | A1 | 11/1999 |
| WO | WO 1999/061888 | A2 | 12/1999 |
| WO | WO 2000/006770 | A1 | 2/2000 |
| WO | WO 2000/037163 | A1 | 6/2000 |
| WO | WO 2000/040750 | A1 | 7/2000 |
| WO | WO 2000/062931 | A1 | 10/2000 |
| WO | WO 2001/035071 | A2 | 5/2001 |
| WO | WO 2001/037958 | A2 | 5/2001 |
| WO | WO 2001/051668 | A1 | 7/2001 |
| WO | WO 1999/061888 | A3 | 12/2001 |
| WO | WO 2002/004672 | A2 | 1/2002 |
| WO | WO 2001/035071 | A3 | 2/2002 |
| WO | WO 2002/012896 | A1 | 2/2002 |
| WO | WO 2002/028523 | A2 | 4/2002 |
| WO | WO 2002/030562 | A1 | 4/2002 |
| WO | WO 2002/031506 | A1 | 4/2002 |
| WO | WO 2002/044318 | A1 | 6/2002 |
| WO | WO 2002/061143 | A2 | 8/2002 |
| WO | WO 2002/073204 | A2 | 9/2002 |
| WO | WO 2003/003057 | A2 | 1/2003 |
| WO | WO 2003/018757 | A2 | 3/2003 |
| WO | WO 2003/019141 | A2 | 3/2003 |
| WO | WO 2003/020974 | A2 | 3/2003 |
| WO | WO 2003/020986 | A1 | 3/2003 |
| WO | WO 2003/023057 | A2 | 3/2003 |
| WO | WO 2003/031938 | A2 | 4/2003 |
| WO | WO 2003/035894 | A2 | 5/2003 |
| WO | WO 2003/035895 | A2 | 5/2003 |
| WO | WO 2003/040064 | A2 | 5/2003 |
| WO | WO 2003/044217 | A2 | 5/2003 |
| WO | WO 2003/044224 | A1 | 5/2003 |
| WO | WO 2003/048295 | A1 | 6/2003 |
| WO | WO 2003/069421 | A2 | 8/2003 |
| WO | WO 2003/018757 | A3 | 9/2003 |
| WO | WO 2003/020974 | A3 | 9/2003 |
| WO | WO 2003/074740 | A1 | 9/2003 |
| WO | WO 2003/078972 | A1 | 9/2003 |
| WO | WO 2003/044217 | A3 | 10/2003 |
| WO | WO 2003/085379 | A2 | 10/2003 |
| WO | WO 2003/003057 | A3 | 11/2003 |
| WO | WO 2003/031938 | A3 | 11/2003 |
| WO | WO 2003/093795 | A2 | 11/2003 |
| WO | WO 2003/023057 | A3 | 12/2003 |
| WO | WO 2003/069421 | A3 | 12/2003 |
| WO | WO 2003/085379 | A3 | 12/2003 |
| WO | WO 2003/035895 | A3 | 1/2004 |
| WO | WO 2003/035894 | A3 | 3/2004 |
| WO | WO 2004/025251 | A2 | 3/2004 |
| WO | WO 2003/019141 | A3 | 4/2004 |
| WO | WO 2004/029221 | A2 | 4/2004 |
| WO | WO 2004/029221 | A3 | 5/2004 |
| WO | WO 2004/037374 | A2 | 5/2004 |
| WO | WO 2004/044236 | A1 | 5/2004 |
| WO | WO 2003/040064 | A3 | 6/2004 |
| WO | WO 2004/056978 | A1 | 7/2004 |
| WO | WO 2004/065629 | A1 | 8/2004 |
| WO | WO 2004/076643 | A2 | 9/2004 |
| WO | WO 2003/093795 | A3 | 10/2004 |
| WO | WO 2004/037374 | A3 | 10/2004 |
| WO | WO 2004/088310 | A1 | 10/2004 |
| WO | WO 2004/025251 | A3 | 11/2004 |
| WO | WO 2004/101762 | A2 | 11/2004 |
| WO | WO 2004/113877 | A1 | 12/2004 |
| WO | WO 2004/101762 | A3 | 2/2005 |
| WO | WO 2005/023091 | A2 | 3/2005 |
| WO | WO 2005/028663 | A2 | 3/2005 |
| WO | WO 2005/035725 | A2 | 4/2005 |
| WO | WO 2005/042713 | A2 | 5/2005 |
| WO | WO 2005/043121 | A2 | 5/2005 |
| WO | WO 2005/047529 | A1 | 5/2005 |
| WO | WO 2005/047532 | A1 | 5/2005 |
| WO | WO 2005/023091 | A3 | 6/2005 |
| WO | WO 2005/049168 | A2 | 6/2005 |
| WO | WO 2005/058937 | A2 | 6/2005 |
| WO | WO 2005/061075 | A1 | 7/2005 |
| WO | WO 2005/068503 | A2 | 7/2005 |
| WO | WO 2005/049168 | A3 | 9/2005 |
| WO | WO 2005/084374 | A2 | 9/2005 |
| WO | WO 2005/084380 | A2 | 9/2005 |
| WO | WO 2005/085476 | A1 | 9/2005 |
| WO | WO 2005/085861 | A2 | 9/2005 |
| WO | WO 2005/098046 | A2 | 10/2005 |
| WO | WO 2005/108621 | A1 | 11/2005 |
| WO | WO 2005/108963 | A1 | 11/2005 |
| WO | WO 2005/109238 | A2 | 11/2005 |
| WO | WO 2005/028663 | A3 | 12/2005 |
| WO | WO 2005/098046 | A3 | 12/2005 |
| WO | WO 2005/116264 | A2 | 12/2005 |
| WO | WO 2005/118852 | A2 | 12/2005 |
| WO | WO 2005/121362 | A2 | 12/2005 |
| WO | WO 2005/085861 | A3 | 2/2006 |
| WO | WO 2006/010610 | A2 | 2/2006 |
| WO | WO 2006/020936 | A2 | 2/2006 |
| WO | WO 2005/118852 | A3 | 3/2006 |
| WO | WO 2006/023563 | A2 | 3/2006 |
| WO | WO 2005/121362 | A3 | 4/2006 |
| WO | WO 2006/041453 | A1 | 4/2006 |
| WO | WO 2006/043181 | A2 | 4/2006 |
| WO | WO 2005/109238 | A3 | 6/2006 |
| WO | WO 2006/010610 | A3 | 6/2006 |
| WO | WO 2006/043181 | A3 | 6/2006 |
| WO | WO 2006/076567 | A2 | 7/2006 |
| WO | WO 2006/078470 | A2 | 7/2006 |
| WO | WO 2005/043121 | A3 | 8/2006 |
| WO | WO 2006/020936 | A3 | 9/2006 |
| WO | WO 2006/076567 | A3 | 9/2006 |
| WO | WO 2006/078470 | A3 | 9/2006 |
| WO | WO 2006/097049 | A1 | 9/2006 |
| WO | WO 2006/100366 | A2 | 9/2006 |
| WO | WO 2006/104474 | A2 | 10/2006 |
| WO | WO 2006/104530 | A1 | 10/2006 |
| WO | WO 2006/108087 | A2 | 10/2006 |
| WO | WO 2006/108101 | A2 | 10/2006 |
| WO | WO 2005/042713 | A3 | 11/2006 |
| WO | WO 2006/023563 | A3 | 11/2006 |
| WO | WO 2006/120434 | A1 | 11/2006 |
| WO | WO 2005/084380 | A3 | 12/2006 |
| WO | WO 2005/116264 | A3 | 2/2007 |
| WO | WO 2006/104474 | A3 | 2/2007 |
| WO | WO 2007/020081 | A1 | 2/2007 |
| WO | WO 2004/076643 | A3 | 3/2007 |
| WO | WO 2007/024264 | A2 | 3/2007 |
| WO | WO 2007/028146 | A2 | 3/2007 |
| WO | WO 2007/030949 | A2 | 3/2007 |
| WO | WO 2007/033167 | A2 | 3/2007 |
| WO | WO 2007/034221 | A2 | 3/2007 |
| WO | WO 2007/035414 | A2 | 3/2007 |
| WO | WO 2007/035498 | A2 | 3/2007 |
| WO | WO 2007/035585 | A2 | 3/2007 |
| WO | WO 2007/035586 | A2 | 3/2007 |
| WO | WO 2007/024264 | A3 | 4/2007 |
| WO | WO 2007/036025 | A1 | 4/2007 |
| WO | WO 2007/038264 | A2 | 4/2007 |
| WO | WO 2007/041610 | A2 | 4/2007 |
| WO | WO 2007/044091 | A2 | 4/2007 |
| WO | WO 2007/044690 | A2 | 4/2007 |
| WO | WO 2007/048076 | A2 | 4/2007 |
| WO | WO 2007/030949 | A3 | 5/2007 |
| WO | WO 2007/034221 | A3 | 5/2007 |
| WO | WO 2007/050495 | A2 | 5/2007 |
| WO | WO 2007/053142 | A1 | 5/2007 |
| WO | WO 2007/053245 | A2 | 5/2007 |
| WO | WO 2007/053648 | A2 | 5/2007 |
| WO | WO 2007/053785 | A2 | 5/2007 |
| WO | WO 2007/059430 | A2 | 5/2007 |
| WO | WO 2007/062222 | A2 | 5/2007 |
| WO | WO 2005/058937 | A3 | 6/2007 |
| WO | WO 2007/035586 | A3 | 6/2007 |
| WO | WO 2007/067734 | A2 | 6/2007 |
| WO | WO 2007/048076 | A3 | 7/2007 |
| WO | WO 2007/053648 | A3 | 7/2007 |

(56) References Cited

FOREIGN PATENT DOCUMENTS

| | | |
|---|---|---|
| WO | WO 2007/075836 A2 | 7/2007 |
| WO | WO 2007/075879 A2 | 7/2007 |
| WO | WO 2007/076989 A1 | 7/2007 |
| WO | WO 2007/079229 A2 | 7/2007 |
| WO | WO 2007/079250 A2 | 7/2007 |
| WO | WO 2007/080583 A2 | 7/2007 |
| WO | WO 2007/082144 A2 | 7/2007 |
| WO | WO 2007/082154 A2 | 7/2007 |
| WO | WO 2007/082379 A2 | 7/2007 |
| WO | WO 2007/050495 A3 | 8/2007 |
| WO | WO 2007/075879 A3 | 8/2007 |
| WO | WO 2007/087612 A2 | 8/2007 |
| WO | WO 2007/089880 A2 | 8/2007 |
| WO | WO 2007/089911 A2 | 8/2007 |
| WO | WO 2007/090670 A1 | 8/2007 |
| WO | WO 2007/092473 A2 | 8/2007 |
| WO | WO 2007/092713 A2 | 8/2007 |
| WO | WO 2007/098484 A2 | 8/2007 |
| WO | WO 2006/100366 A3 | 9/2007 |
| WO | WO 2007/100684 A2 | 9/2007 |
| WO | WO 2007/101609 A1 | 9/2007 |
| WO | WO 2007/103910 A2 | 9/2007 |
| WO | WO 2007/033167 A3 | 10/2007 |
| WO | WO 2007/038264 A3 | 10/2007 |
| WO | WO 2007/044690 A3 | 10/2007 |
| WO | WO 2007/053785 A3 | 10/2007 |
| WO | WO 2007/059430 A3 | 10/2007 |
| WO | WO 2005/084374 A3 | 11/2007 |
| WO | WO 2007/035414 A3 | 11/2007 |
| WO | WO 2007/035585 A3 | 11/2007 |
| WO | WO 2007/044091 A3 | 11/2007 |
| WO | WO 2007/053245 A3 | 11/2007 |
| WO | WO 2007/089880 A3 | 11/2007 |
| WO | WO 2007/126938 A2 | 11/2007 |
| WO | WO 2007/132166 A2 | 11/2007 |
| WO | WO 2007/132167 A2 | 11/2007 |
| WO | WO 2007/082379 A3 | 12/2007 |
| WO | WO 2007/098484 A3 | 12/2007 |
| WO | WO 2007/062222 A3 | 1/2008 |
| WO | WO 2007/100684 A3 | 1/2008 |
| WO | WO 2007/075836 A3 | 2/2008 |
| WO | WO 2007/132166 A3 | 2/2008 |
| WO | WO 2008/017871 A1 | 2/2008 |
| WO | WO 2007/089911 A3 | 5/2008 |
| WO | WO 2007/132167 A3 | 5/2008 |
| WO | WO 2007/028146 A3 | 6/2008 |
| WO | WO 2007/067734 A3 | 8/2008 |
| WO | WO 2007/126938 A3 | 10/2008 |
| WO | WO 2007/082154 A3 | 11/2008 |
| WO | WO 2007/087612 A3 | 11/2008 |
| WO | WO 2007/092473 A3 | 11/2008 |
| WO | WO 2007/082144 A3 | 12/2008 |
| WO | WO 2007/092713 A3 | 12/2008 |
| WO | WO 2007/079229 A3 | 1/2009 |
| WO | WO 2009/009769 A2 | 1/2009 |
| WO | WO 2009/013492 A1 | 1/2009 |
| WO | WO 2009/013496 A1 | 1/2009 |
| WO | WO 2007/080583 A3 | 2/2009 |
| WO | WO 2009/019455 A2 | 2/2009 |
| WO | WO 2007/079250 A3 | 3/2009 |
| WO | WO 2007/041610 A3 | 4/2009 |
| WO | WO 2009/019455 A3 | 4/2009 |

OTHER PUBLICATIONS

U.S. Appl. No. 60/949,227, filed Jul. 11, 2007, Kapur.

[No Author Listed] “REPLI-g® Mini and Midi Kits: For highly uniform whole genome amplification from small or precious samples,” Qiagen, Oct. 2005, 4 pages.

[No Author Listed], “Detection of aneuploidy in a single cell using the Ion ReproSeq PGS View Kit,” Iontorrent, 2016, 6 pages.

[No Author Listed], “Rapid Aneuploidy and CNV Detection in Single Cells using the MiSeq System,” Illumina, 2014, 6 pages.

ACMG.Omnibooksonline.com [website], “Quantification of cell-free DNA levels in maternal plasma by STR analysis,” Mar. 2010, retrieved on Apr. 5, 2013, retrieved from URL <http://acmg.omnibooksonline.com/2010/data/papers/398.pdf>, 1 page.

Adinolfi, et al. Gene Amplification to Detect Fetal Nucleated Cells in Pregnant Women. The Lancet. Aug. 5, 1989:328-329.

Adinolfi, et al. Rapid detection of aneuploidies by microsatellite and the quantitative fluorescent polymerase chain reaction. Prenat. Diagn. 1997;17(13):1299-311.

Adinolfi, M. On a Non-Invasive Approach to Prenatel Diagnosis based on the detection of Fetal Nucleated Cells in Maternal Blood Samples. Prenatal Diagnosis. 1991;11:799-804.

Advisory Action for U.S. Appl. No. 12/689,548, dated Mar. 4, 2015, 3 pages.

Aggarwal et al., “A combinatorial approach to the selective capture of circulating malignant epithelial cells by peptide ligands,” Biomaterials, 2005, 26(30):6077-86.

Ahn, et al. A fully integrated micromachined magnetic particle separator. Journal of Microelectromechanical Systems. 1996; 5(3):151-158.

Allard, et al. Tumor cells circulate in the peripheral blood of all major carcinomas but not in healthy subjects or patients with nonmalignant diseases. Clin Cancer Res. Oct. 15, 2004;10(20):6897-904.

Allowed claims dated Dec. 9, 2010 for U.S. Appl. No. 11/701,686, 6 pages.

Amendment to the Claims for U.S. Appl. No. 12/751,940, filed Dec. 5, 2013, 11 pages.

Amendment to the Claims for U.S. Appl. No. 13/831,342, filed Oct. 14, 2014, 7 pages.

Amendment to the Claims for U.S. Appl. No. 13/863,992, filed Jun. 16, 2014, 17 pages.

Andre et al., “Lectin-Mediated Drug Targeting: Selection of Valency, Sugar Type (Gal/Lac), and Spacer Length for Cluster Glycosides as Parameters to Distinguish Ligand Binding to C-Type Asialoglycoprotein Receptors and Galectins,” Pharmaceutical Research, 2000, 17(8):985-990.

Andrews, et al. Enrichment of fetal nucleated cells from maternal blood: model test system using cord blood. Prenatal Diagnosis. 1995; 15:913-919.

Applicant’s Amendment and Response dated Jun. 17, 2009 to Non-Final Office Action of Jan. 28, 2009 re U.S. Appl. No. 11/701,686, 8 pages.

Applicant’s Amendment and Response dated Jun. 24, 2010 to Office Action of Jan. 27, 2010 re U.S. Appl. No. 11/701,686, 31 pages.

Applicant’s Amendment and Response dated Nov. 13, 2009 to Office Action of Sep. 11, 2009 re U.S. Appl. No. 11/701,686, 19 pages.

Applicant’s response dated Jun. 10, 2011 to Office action dated Apr. 25, 2011 for U.S. Appl. No. 12/393,803, 8 pages.

Archer et al., “Cell Reactions to Dielectrophoretic Manipulation,” Biochemical and Biophysical Research Communications, 1999, 257:687-698.

Ariga, et al. Kinetics of fetal cellular and cell-free DNA in the maternal circulation during and after pregnancy: implications for noninvasive prenatal diagnosis. Transfusion. 2001; 41:1524-1530.

Arnould, et al. Agreement between chromogenic in situ hybridisation (CISH) and FISH in the determination of HER2 status in breast cancer. Br J Cancer. 2003; 88(10):1587-91. (Abstract only).

AU Notice of Acceptance in Australian Application No. 2013204127, dated Jul. 7, 2015, 3 pages.

Babochkina, et al. Direct detection of fetal cells in maternal blood: a reappraisal using a combination of two different Y chromosome-specific FISH probes and a single X chromosome- specific probe. Arch Gynecol Obstet. Dec. 2005;273(3):166-9. (Abstract only).

Babochkina, T. I. Ph. D. Dissertation—Fetal cells in maternal circulation: Fetal cell separation and FISH analysis. University of Basel, Switzerland. Dec. 8, 2005. (123 pages).

Bailey et al., “Recent Segmental Duplications in the Human Genome,” Science, Aug. 2002, 297:1003-1007, 6 pages.

(56) References Cited

OTHER PUBLICATIONS

Balko, et al. Gene expression patterns that predict sensitivity to epidermal growth factor receptor tyrosine kinase inhibitors in lung cancer cell lines and human lung tumors. BMC Genomics. Nov. 10, 2006;7:289 (14 pages).
Barrett, et al. Comparative genomic hybridization using oligonucleotide microarrays and total genomic DNA. Proc Natl Acad Sci U S A. 2004; 101(51):17765-70.
Basch, et al. Cell separation using positive immunoselective techniques. Journal of Immunological Methods. 1983;56:269-280.
Bauer, J. Advances in cell separation: recent developments in counterflow centrifugal elutriation and continuous flow cell separation. Journal of Chromatography. 1999;722:55-69.
Becker, et al. Fabrication of Microstructures With High Aspect Ratios and Great Structural Heights by Synchrotron Radiation Lithography, Galvanoforming, and Plastic Moulding (LIGA Process). Microelectronic Engineering. 1986;4:35-56.
Becker, et al. Planar quartz chips with submicron channels for two-dimensional capillary electrophoresis applications. J. Micromech Microeng. 1998;9:24-28.
Beebe et al. Functional Hydrogel Structures for Autonomous Flow Control Inside Microfluidic Channels. Nature. 2000; 404:588-590.
Benincasa et al., "Cell Sorting by One Gravity SPLITT Fractionation," Analytical Chemistry, 2005, 77(16):5294-5301.
Bennett, et al. Toward the 1,000 dollars human genome. Pharmacogenomics. 2005; 6(4):373-82.
Berenson, et al. Cellular Immunoabsorption Using Monoclonal Antibodies. Transplantation, 1984, 38:136-143.
Berenson, et al. Positive selection of viable cell populations using avidin-biotin immunoadsorption. Journal of Immunological Methods. 1986, 91:11-19.
Berg, H. C. Random Walks in Biology, Ch. 4. Princeton University Press. Princeton, NJ. 1993. pp. 48-64.
Berger, et al. Design of a microfabricated magnetic cell separator. Electrophoresis. Oct. 2001;22(18):3883-92.
Bianchi et al., "Large amounts of cell-free fetal DNA are present in amniotic fluid," Clinical Chemistry, 2001, 47(10):1867-1869.
Bianchi, et al. Isolation of fetal DNA from nucleated erythrocytes in maternal blood. Medical Sciences. 1990;87:3279-3283.
Bianchi, et al. Demonstration of fetal gene sequences in nucleated erythrocytes isolated from maternal blood. American Journal of Human Genetics. 1989;45:A252.
Bianchi, et al. Fetal gender and aneuploidy detection using fetal cells in maternal blood: analysis of NIFTY I data. Prenatal Diagnosis. 2002; 22:609-615.
Bianchi, et al. Fetal nucleated erythrocytes (FNRBC) in maternal blood: erythroid-specific antibodies improve detection. The American Journal of Human Genetics. Oct. 1992. Supplemental to vol. 51, No. 4: 996.
Bianchi, et al. Isolation of Male Fetal DNA from Nucleated Erythrocytes (NRBC) in Maternal Blood. The American Pediatric Society and Society for Pediatric Research, (1989) Mar. 1989; 818:139A.
Bianchi, et al. Possible Effects of Gestational Age on the Detection of Fetal Nucleated Erythrocytes in Maternal Blood. Prenatal Diagnosis. 1991;11:523-528.
Bignell, et al. High-resolution analysis of DNA copy number using oligonucleotide microarrays. Genome Research. 2004; 14(2):287-295.
Binladen et al. The Use of Coded PCR Primers Enables High-Throughput Sequencing of Multiple Honnolog Amplification Products by 454 Parallel Sequencing. PLoS ONE, Issue 2, e197. (Year: 2007).
Birner et al., "Evaluation of the United States Food and Drug Administration-approved scoring and test system of HER-2 protein expression in breast cancer," Clin Cancer Res., 2001 7(6):1669-1675.
Bischoff et al., "Cell-free fetal DNA and intact fetal cells in maternal blood circulation: implications for first and second trimester non-invasive prenatal diagnosis," Human Reproduction, 2002, 8(6):493-500.
Bischoff et al., "Intact fetal cell isolation from maternal blood: improved isolation using a simple whole blood progenitor cell enrichment approach (RosetteSep™)," Clin. Genet., 2003, 63:483-489, 9 pages.
Blake, et al. Assessment of multiplex fluorescent PCR for screening single cells for trisomy 21 and single gene defects. Mol. Hum. Reprod. 1999; 5(12):1166-75.
Bode, et al. Mutations in the tyrosine kinase domain of the EGFR gene are rare in synovial sarcoma. Mod Pathol. Apr. 2006;19(4):541-7.
Boehm, et al. Analysis of Defective Dystrophin Genes with cDNA Probes: Rearrangement Polymorphism, Detection of Deletions in Carrier Females, and Lower Than Expected Frequency of Carrier Mothers in Isolated Cases of Delections. Pediatric Research. Apr. 1989: 139A-820.
Bohmer, et al. Differential Development of Fetal and Adult Haemoglobin Profiles in Colony Culture: Isolation of Fetal Nucleated Red Cells by Two-Colour Fluorescence Labelling. Br. J. Haematol. 1998; 103:351-60.
Braslavsky, et al. "Sequence information can be obtained from single DNA molecules," PNAS, Apr. 2003, vol. 100, No. 7, 3960-3964.
Breman et al., "Evidence for feasibility of fetal trophoblastic cell-based noninvasive prenatal testing," Prenatal Diagnosis, 2016, 36:1009-19.
Brison, et al. General Method for Cloning Amplified DNA by Differential Screening with Genomic Probes. Molecular and Cellular Biology. 1982;2:578-587.
Brody, et al. Deformation and Flow of Red Blood Cells in a Synthetic Lattice: Evidence for an Active Cytoskeleton. Biophys. J. 68:2224-2232 (1995).
Brown et al., "Aneuploidy detection in mixed DNA samples by methylation-sensitive amplification and microarray analysis," Clinical Chemistry, 2010, 56(5):805-813, 10 pages.
Brown et al., "Validation of QF-PCR for prenatal aneuploidy screening in the United States," Prenatal Diagnosis, 2006, 26(11):1068-1074.
Bustamante-Aragones, et al. Detection of a Paternally Inherited Fetal Mutation in Maternal Plasma by the Use of Automated Sequencing. Ann. N.Y. Acad. Sci. 1075: 108-117 (2006), pp. 108-117, XP-002652985.
CA Office Action for Canadian Appln. No. 2655272, dated Jan. 26, 2015, 4 pages.
Caggana, M. Microfabricated devices for sparse cell isolation. CNF Project #905-00. Cornell NanoScale Facility. 2003; pp. 38-39.
Caggana, M. Microfabricated devices for sparse cell isolation. CNF Project #905-00. Cornell NanoScale Facility. 2004-2005; pp. 32-33.
Calin, et al. A microRNA signature Associated with prognosis and progression in chronic lymphocytic leukemia. New England Journal of Medicine. 2005; 353:1793-1801.
Cappuzzo, et al. Epidermal growth factor receptor gene and protein and gefitinib sensitivity in non-small-cell lung cancer. J Natl Cancer Inst. May 4, 2005;97(9):643-55.
Cha, The utility of an erythroblast scoring system and gender-independent short tandem repeat (STR) analysis for the detection of aneuploid fetal cells in maternal blood. Prenat. Diagn. 2005; 25(7):586-91.
Chamberlain, et al. Deletion screening of the Duchenne muscular dystrophy locus via multiplex DNA amplification. Nucleic Acids Research. 1988;16:11141-11156.
Chan, et al. "DNA Mapping Using Microfluidic Stretching and Single-Molecule Detection of Fluorescent Site-Specific Tags," Genome Research, 2004, vol. 14, 1137-1146.
Chan, et al. Size distributions of maternal and fetal DNA in maternal plasma. Clin Chem. Jan. 2004;50(1):88-92.
Chang et al., "Assessment of Plasma DNA Levels, Allelic Imbalance, and CA 125 as Diagnostic Tests for Cancer," J. Nat'l Cancer Inst., Nov. 2002, 94(22):1697-1703.
Chang, et al. Biomimetic technique for adhesion-based collection and separation of cells in a microfluidic channel. Lab Chip. 2005; 5:64-73.
Cheung, et al. Development and validation of a CGH microarray for clinical cytogenetic diagnosis. Genet Med. 2005; 7(6):422-32.

(56) References Cited

OTHER PUBLICATIONS

Chim et al., "Detection of the placental epigenetic signature of the maspin gene in maternal plasma," PNAS, 2005, 102(41):14753-14758.
Chiu et al., "Noninvasive prenatal diagnosis by analysis of fetal DNA in maternal plasma," Clinical Applications of PCR, 2006, 101-109.
Chiu et al., "Noninvasive prenatal diagnosis by analysis of fetal DNA in maternal plasma," Methods Mol Biol., 2006, 336:101-109.
Chiu, et al. "Effects of Blood-Processing Protocols on Fetal and Total DNA Quantification in Maternal Plasma," Clinical Chemistry, 2001, vol. 47, No. 9, 1607-1613.
Chiu, et al. Non-invasive prenatal assessment of trisomy 21 by multiplexed maternal plasma DNA sequencing: large scale validity study. BMJ. Jan. 2011, 342:c7401.
Chiu, et al. Noninvasive prenatal diagnosis of fetal chromosomal aneuploidy by massively parallel genomic sequencing of DNA in maternal plasma. Proc Natl Acad Sci U S A. Dec. 23, 2008;105(51):20458-63.
Chiu, et al. Patterned Deposition of Cells and Proteins Onto Surfaces by Using Three-Dimensional Microfluidic Systems. Proceedings of the National Academy of Sciences of the United States of America. 2000; pp. 2408-2413.
Choesmel, et al. Enrichment methods to detect bone marrow micrometastases in breast carcinoma patients: clinical relevance. Breast Cancer Res. 2004;6(5):R556-569.
Choolani, et al. Characterization of First Trimester Fetal Erythroblasts for Non-Invasive Prenatal Diagnosis. Mol. Hum. Reprod. 2003; 9:227-35.
Chou, et al. A Microfabricated Device for Sizing and Sorting DNA Molecules. Proceedings of the National Academy of Sciences of the United States of America. 1999; pp. 11-13.
Chou, et al. Sorting by diffusion: An asymmetric obstacle course for continuous molecular separation. PNAS. 1999; 96(24):13762-13765.
Christel, et al. High aspect ratio silicon microstructures for nucleic acid extraction. Solid-state sensor and actuator workshop. Hilton Head, SC. Jun. 8-11, 1998; 363-366.
Christensen et al., "Sensitivity and specificity of the identification of fetal cells in maternal blood by combined staining with antibodies against beta-, gamma-and epsilon-globin chains," Fetal Diagn. Ther., 2003, 18:479-484.
Christensen, et al. Fetal Cells in Maternal Blood: A Comparison of Methods for Cell Isolation and Identification. Fetal Diagn. Ther. 2005; 20:106-12.
Chueh, et al. Prenatal Diagnosis Using Fetal Cells from the Maternal Circulation. West J. Med. 159:308-311 (1993).
Chueh, et al. Prenatal Diagnosis Using Fetal Cells in the Maternal Circulation. Seminars in Perinatology. 1990;14:471-482.
Chueh, et al. The search for fetal cells in the maternal circulation. J Perinat Med. 1991;19:411-420.
Cirigliano, et al. "Clinical application of multiplex quantitative fluorescent polymerase chain reaction (QF-PCR) for the rapid prenatal detection of common chromosome aneuploidies," Molecular Human Reproduction, 2001, vol. 7, No. 10, 1001-1006.
Claims mailed with RCE Response to Final Rejection dated Dec. 31, 2009 for U.S. Appl. No. 11/763,421, filed Jun. 14, 2007 (6 pages).
Clayton, et al. Fetal Erythrocytes in the Maternal Circulation of Pregnant Women. Obstetrics and Gynecology. 1964;23:915-919.
CN Office Action in Chinese Appln. No. 201711191019.9, dated Oct. 22, 2020, 13 pages (with English translation).
Coble et al., "Characterization of New MiniSTR Loci to Aid Analysis of Degraded Dna," J. Forensic Sci., Jan. 2005, 50(1):43-53.
Collarini, et al. Comparison of methods for erythroblast selection: application to selecting fetal erythroblasts from maternal blood. Cytometry. 2001; 45:267-276.
Cremer, et al. Detection of chromosome aberrations in human interphase nucleus by visualization of specific target DNAs with radioactive and non-radioactive in situ hybridization techniques: diagnosis of trisomy 18 with probe L1.84. Human Genetics. 1986;74:346-352.
Cremer, et al. Detection of chromosome aberaations in metaphase and interphase tumor cells by in situ hybridization using chromosome-specific library probes. Human Genetics. 1988;80:235-246.
Cristofanilli, et al. Circulating tumor cells revisited. JAMA. 2010; 303(11):1092-1093.
Cristofanilli, et al. Circulating tumor cells, disease progression, and survival in metastatic breast cancer. N Engl J Med. Aug. 19, 2004;351(8):781-91.
Dahl et al., "Multigene Amplification and Massively Parallel Sequencing for Cancer Mutation Discovery," PNAS USA, May 2007, 104(22):9387-9392.
Das, et al. Dielectrophoretic segregation of different human cell types on microscope slides. Anal. Chem. 2005; 77:2708-2719.
De Alba, et al. Prenatal diagnosis on fetal cells obtained from maternal peripheral blood: report of 66 cases. Prenat Diagn. Oct. 1999;19(10):934-40.
De Kretser, et al. The Separation of Cell Populations using Monoclonal Antibodies attached to Sepharose. Tissue Antigens. 1980;16:317-325.
De Luca, et al. Detection of circulating tumor cells in carcinoma patients by a novel epidermal growth factor receptor reverse transcription-PCR assay. Clin Cancer Res. Apr. 2000;6(4):1439-44.
Declaration of Atul J. Butte, M.D. Ph.D. in Support of Patent Owner's Response to Inter Partes Review of U.S. Pat. No. 8,318,430, dated Jan. 16, 2014, 88 pages.
Delamarche, et al. Microfluidic Networks for Chemical Patterning of Substrates: Design and Application to Bioassays. Journal of the American Chemical Society. 1998; 120:500-508.
Delamarche, et al. Patterned Delivery of Immunoglobulins to Surfaces Using Microfluidic Networks. Science. 1997; 276:779-781.
Deng, et al. Enumeration and microfluidic chip separation of circulating fetal cells early in pregnancy from maternal blood. American Journal of Obstetrics & Gynecology. Dec. 2008 (vol. 199, Issue 6, p. S134).
Deposition of Dr. Cynthia Casson Morton, dated Dec. 10, 2013, 115 pages.
Deposition of Dr. Robert Nussbaum, dated Dec. 11, 2013, 49 pages.
Deshmukh, et al. Continuous Micromixer With Pulsatile Micropumps. Solid-State Sensor and Actuator Workshop. Hilton Head Island, South Carolina; Jun. 4-8, 2000:73-76.
Deutsch et al., "Detection of aneuploidies by paralogous sequence quantification," J Med Genet., 2004, 41(12):908-15.
Devotek. "Separation of RNA 8 DNA by Gel Filtration Chromatography," Edvotek, 1987. 1-9.
Dhallan et al., "A non-invasive test for prenatal diagnosis based on fetal DNA present in maternal blood: a preliminary study," Lancet, 2007, 369(9560):474-481.
Di Naro, et al. Prenatal diagnosis of beta-thalassaemia using fetal erythroblasts enriched from maternal blood by a novel gradient. Mol Hum Reprod. 2000; 6(6):571-4.
Diehl, et al. Digital quantification of mutant DNA in cancer patients. Curr Opin Oncol. Jan. 2007;19(1):36-42.
Dilella, et al. Screening for Phenylketonuria Mutations by DNA Amplification with the Polymerase Chain Reaction. The Lancet. Mar. 5, 1988:497-499.
Dohm, et al. Substantial biases in ultra-short read data sets from high-throughput DNA sequencing. Nucleic Acids Research. 2008. 36: e105 doi: 10.1093\nark\gkn425.
Doyle, et al. Self-Assembled Magnetic Matrices for DNA Separation Chips. Science 295:2237 (2002).
Dragovich, et al. Anti-EGFR-targeted therapy for exophageal and gastric cancers: an evolving concept. Jornal of Oncology. 2009; vol. 2009, Article ID 804108.
Dressman, et al. "Transforming single DNA molecules into fluorescent magnetic particles for detection and enumeration of genetic variations." PNAS, Jul. 2003, vol. 100. No. 15, 8817-8822.
Eigen, et al. Sorting Single Molecules: Application to Diagnostics and Evolutionary Biotechnology. Proceedings of the National Academy of Sciences of the United States of America. 1994; 91:5740-5747.

(56) References Cited

OTHER PUBLICATIONS

Emanuel, et al. Amplification of Specific Gene Products from Human Serum. GATA, 1993, vol. 10, No. 6, 144-146.
EP Extended European Search Report in Application No. 18170287.9, dated Sep. 19, 2018, 10 pages.
EP Extended European Search Report in Application No. 18171950.1, dated Oct. 15, 2018, 8 pages.
EP Extended European Search Report in European Appln. No. 12175907.0, dated Jan. 2, 2013, 11 pages.
EP Notice of Opposition by Olswang against European Appln. No. 07763674.4, dated Apr. 10, 2014, 23 pages.
EP Notice of Opposition by Premaitha Health PLC against European Appln. No. 07763674.4, dated Jun. 12, 2015, 14 pages.
EP Office action dated Sep. 23, 2009 for EP Application No. EP 07763674.4, 1 page.
EP Office Action in European Appln No. 07784444.7, dated Aug. 2, 2010, 6 pages.
EP Office Action in European Appln. No. 07763674.4, dated Mar. 3, 2009, 3 pages.
EP Office Action in European Appln. No. 07784444.7, dated Apr. 4, 2012, 7 pages.
EP Office Action in European Appln. No. 07798579.4, dated Aug. 22, 2013, 5 pages.
EP Office Action in European Appln. No. 07798579.4, dated May 22, 2015, 5 pages.
EP Office Action in European Appln. No. 18170287, dated Apr. 6, 2020, 8 pages.
EP Office Action in European Appln. No. 18170287, dated Feb. 22, 2021, 7 pages.
EP Office Action in European Appln. No. 18171950.1, dated Apr. 7, 2020, 6 pages.
EP Summons to attend oral proceedings pursuant to Rule 115(1) EPC in European Appln. No. 18171950.1, dated Mar. 3, 2021, 9 pages.
European office action dated Jun. 26, 2012 for EP Application No. 11159371.1, 7 pages.
European office action dated Dec. 18, 2012 for EP Application No. 11159371.1, 8 pages.
European Search Opinion dated Jul. 31, 2009 for EP07763674.4, 5 pages.
European Search Report Office action dated Dec. 21, 2010 for EP07763674.4, 5 pages.
European search report dated Nov. 9, 2009 for Application No. 7784442.1, 9 pages.
European search report dated Dec. 21, 2009 for Application No. 07798579.4, 8 pages.
European search report dated Dec. 22, 2009 for Application No. 07798580.2, 6 pages.
European search report dated Dec. 22, 2009 for Application No. 07784444.7, 9 pages.
European Search Report dated Jul. 31, 2009 for EP07763674.4, 10 pages.
Evans et al., "Digital PCR for noninvasive detection of aneuploidy: power analysis equations for feasibility," Fetal Diagn. Ther., 2012, 31(4):244-247.
Applicant's Response with Allowed Claims dated Dec 2, 2010 issued in U.S. Appl. No. 11/701,686, 17 pages.
Pending Claims filed with the USPTO in U.S. Appl. No. 11/701,686, Jun. 24, 2010, 6 pages.
Notice of Allowance in U.S. Appl. No. 12/393,803, dated Jul. 12, 2011, with allowed claims, 11 pages.
Office Action in U.S. Appl. No. 11/067,102, dated Aug. 1, 2008, 24 pages.
Office Action in U.S. Appl. No. 11/067,102, dated Apr. 13, 2009, 22 pages.
Office Action in U.S. Appl. No. 11/067,102, dated Februrary 4, 2010, 21 pages.
Office Action in U.S. Appl. No. 11/067,102, dated Jun. 15, 2007, 18 pages.
Office Action in U.S. Appl. No. 11/067,102, dated Sep. 17, 2010, 31 pages.
Office Action in U.S. Appl. No. 11/763,426, dated Jun. 14, 2010, 14 pages.
Extended European Search Report for Application No. 11159371 dated Aug. 10, 2011, 10 pages.
Extended European Search Report in European Appln. No. 22174784.3, dated Nov. 16, 2022, 9 pages.
Extended European Search Report in European Appln. No. 22194250.1, dated Feb. 24, 2023, 7 pages.
Falcidia, et al. Fetal Cells in maternal blood: a six-fold increase in women who have undergone mniocentesis and carry a fetus with Down syndrome: a multicenter study. Neuropediatrics. 2004; 35(6):321-324. (Abstract only).
Fan et al., "Highly Parallel Genomic Assays," Nat. Rev. Genet., Aug. 2006, 7(8):632-644.
Fan, et al. Detection of aneuploidy with digital polymerase chain reaction. Anal Chem. Oct. 1, 2007; 79(19):7576-9.
Fan, et al. Highly parallel SNP genotyping. Cold Spring Harb. Symp. Quant. Biol. 2003; 68:69-78.
Fan, et al. Microfluidic digital PCR enables rapid prenatal diagnosis of fetal aneuploidy. Am J Obstet Gynecol. May 2009;200(5):543.e1-7.
Fan, et al. Noninvasive diagnosis of fetal aneuploidy by shotgun sequencing DNA from maternal blood. Proc Natl Acad Sci U S A. Oct. 21, 2008;105(42):16266-71.
Fan, et al. Single cell degenerate oligonucleotide primer—PCR and comparative genomic hybridization with modified control reference. Journal of Ahejian University—Science A. 2001; 2(3):318-321.
Farber, et al. Demonstration of spontaneous XX/XY chimerism by DNA fingerprinting. Human Genetics. 1989;82:197-198.
Farooqui, et al. Microfabrication of Submicron Nozzles in Silicon Nitride. Journal of Microelectromechanical Systems. 1992;1(2):86-88.
FDA.gov [online], "Premarket Approval Decisions for Sep. 1998," available on or before Oct. 16, 1998, via Internet Archive: Wayback Machine URL <http://web.archive.org/web/19990507012424/http://www.fda.gov/cdrh/pma/pmasep98.html>, retrieved on May 28, 2021, URL http://www.fda.gov/cdrh/pma/pmasep98.html>, 12 pages.
Feinberg, et al. A technique for radiolabeling DNA restriction endonuclease fragments to high specific activity. Anal Biochem. Jul. 1, 1983;132(1):6-13.
Fiddler, "Fetal cell based prenatal diagnosis: perspectives on the present and future," J. Clin. Med., 2014, 3:972-985.
Fiedler, et al. Dielectrophoretic Sorting of Particles and Cells in a Microsystem. Analytical Chemistry. 1998; pp. 1909-1915.
Final Office Action for U.S. Appl. No. 12/689,517, dated Aug. 19, 2015, 15 pages.
Final Office Action for U.S. Appl. No. 12/689,517, dated Feb. 5, 2014, 12 pages.
Final Office Action for U.S. Appl. No. 12/689,548, dated Nov. 24, 2014, 33 pages.
Final Office Action for U.S. Appl. No. 12/816,043, dated Aug. 1, 2014, 7 pages.
Final Office Action for U.S. Appl. No. 12/816,043, dated Sep. 18, 2015, 8 pages.
Final Office Action for U.S. Appl. No. 13/794,503, dated Dec. 22, 2015, 37 pages.
Final Office Action for U.S. Appl. No. 13/863,992, dated Aug. 16, 2016, 27 pages.
Final Office Action for U.S. Appl. No. 13/863,992, dated May 11, 2015, 37 pages .
Findlay, et al. Using MF-PCR to diagnose multiple defects from single cells: implications for PGD. Mol Cell Endocrinol. 2001; 183 Suppl 1:S5-12.
Freemantle, M. Downsizing Chemistry. Chemical analysis and synthesis on microchips promise a variety of potential benefits. Chemical & Engineering News. 1999; pp. 27-36.
Fu, et al. An integrated miscrofabricated cell sorter. Anal Chem. 2002;74:2451-2457.
Fu, et al. A Microfabricated Fluorescence-Activated Cell Sorter. Nature Biotechnology. 1999; 17:1109-1111.

(56) References Cited

OTHER PUBLICATIONS

Fuhr, et al. Biological Application of Microstructures. Topics in Current Chemistry. 1997; 194:83-116.
Fullwood, et al. Next Generation DNA sequencin of paired-end tags (PET) for transcriptome and genome analyses. Genome Research. 2009. 19:521-532.
Furdui, et al. Immunomagnetic T cell capture from blood for PCR analysis using microfluidic systems. Lab Chip. Dec. 2004;4(6):614-8.
Ganshirt-Ahlert, et al. Magnetic cell sorting and the transferrin receptor as potential means of prenatal diagnosis from maternal blood. Am J Obstet Gynecol. 1992;166:1350-1355.
Ganshirt-Ahlert, et al. Noninvasive prenatal diagnosis: Triple density gradient, magnetic activated cell sorting and FISH prove to be an efficient and reproducible method for detection of fetal aneuploidies from maternal blood. The American Journal of Human Genetics. Oct. 1992. Supplemental to vol. 51, No. 4: 182.
Geifman-Holtzman et al., "The clinical utility of fetal cell sorting to determine prenatally fetal E/e or e/e Rh genotype from peripheral maternal blood," Am. J. Obstet. Gynecol., 2000, 183:462-468.
GenomeWeb. Immunicon inks biomarker assay, lab services deal with merck serona. Accessed on Sep. 11, 2007, 1 page.
GenomeWeb.com [online], "Following Improvements in Noninvasive Fetal Cell Isolation, First Prenatal Tests Expected in 2016," Nov. 2015, retrieved on Sep. 6, 2017, retrieved from URL <https://www.genomeweb.com/archive/following-improvements-noninvasive-fetal-cell-isolation-first-prenatal-testsexpected-2016>, 4 pages.
Ghia, et al. Ordering of human bone marrow B lymphocyte precursors by single-cell polymerase chain reaction analyses of the rearrangement status of the immunoglobulin H and L chain gene loci. J Exp Med. Dec. 1, 1996;184(6):2217-29.
Giddings, J. C. Chemistry 'Eddy' Diffusion in Chromatography. Nature. 1959;184:357-358.
Giddings, J. C. Field-Flow Fractionation: Analysis of Macromolecular, Colloidal, and Particulate Materials. Science. 1993;260:1456-1465.
Gonzalez, et al. Multiple displacement amplification as a prepolymerase chain reaction (pre-PCR) to process difficult to amplify samples and low copy number sequences from natural environments. Environ Microbiol. 2005; 7(7):1024-8.
Graham. Efficiency comparison of two preparative mechanisms for magnetic separation of erthrocytes from whole blood. J. Appl. Phys. 1981; 52:2578-2580.
Greaves, et al. Expression of the OKT Monoclonal Antibody Defined Antigenic Determinants in Malignancy. Int. J. Immunopharmac. 1981;3:283-299.
Grundevik et al., "Molecular Diagnostics of Aneuploidies", Chalmers University of Technology, Sweden, Department of Molecular Biotechnology, May 17, 2005, 12 pages.
Guetta, et al. Analysis of fetal blood cells in the maternal circulation: challenges, ongoing efforts, and potential solutions. Stem Cells Dev. 2004;13(1):93-9.
Gunderson, et al. A genome-wide scalable SNP genotyping assay using microarray technology. Nat Genet. 2005; 37(5):549-54.
Hahn, et al. "Prenatal Diagnosis Using Fetal Cells and Cell-Free Fetal DNA in Maternal Blood: What is Currently Feasible?" Clinical Obstetrics and Gynecology, Sep. 2002, vol. 45, No. 3, 649-656.
Hahn, et al. Current applications of single-cell PCR. Cell. Mol. Life Sci. 2000; 57(1):96-105. Review.
Hall, "Advanced Sequencing Technologies and their Wider Impact in Microbiology," J. Exp. Biol., 2007, 209:1518-1525.
Hamabe, et al. Molecular study of the Prader-Willi syndrome: deletion, RFLP, and phenotype analyses of 50 patients. Am J Med Genet. Oct. 1, 1991;41(1):54-63.
Han, et al. Separation of Long DNA Molecules in a Microfabricated Entropic Trap Array. Science. 2000;288:1026-1029.
Hardenbol, et al. Highly multiplexed molecular inversion probe genotyping: over 10,000 targeted SNPs genotyped in a single tube assay. Genome Res. 2005;15(2):269-75.
Hardenbol, et al. Multiplexed genotyping with sequence-tagged molecular inversion probes. Nat. Biotechnol. 2003; 21(6):673-8.
Hartmann, et al. Gene expression profiling of single cells on large-scale oligonucleotide arrays. Nucleic Acids Research. 2006; 34(21): e143. (11 pages).
Hatch et al., "A rapid diffusion immunoassay in a T-sensor," Nature Biotechnology, 2001, 19:461-465.
Hatt et al., "A New Marker Set That Identifies Fetal Cells in Maternal Circulation With High Specificity," Prenatal Diagn., 2014, 34:1-7.
Herzenberg, et al. Fetal cells in the blood of pregnant women: Detection and enrichment by flourescence-activated cell sorting. Proc. Natl. Acad. Sci. 1979;76:1453-1455.
Holzgreve, et al. Fetal Cells in the Maternal Circulation. Journal of Reproductive Medicine. 1992;37:410-418.
Hong, et al. A nanoliter-scale nucleic acid processor with parallel architecture. Nat. Biotechnol. 2004; 22(4):435-9.
Hong, et al. Molecular biology on a microfluidic chip. Journal of Physics: Condensed Matter, 2006, vol. 18, S691-S701.
Hosono, et al. Unbiased whole-genome amplification directly from clinical samples. Genome Res. May 2003;13(5):954-64.
Hromadnikova, et al. "Quantitative analysis of DNA levels in maternal plasma in normal and Down syndrome pregnancies." Bio Med Central, May 2002, 1-5.
Hua et al., "Detection of aneuploidy from single fetal nucleated red blood cells using whole genome sequencing," Prenatal Diagnosis, 2014, 34:1-8.
Huang, et al. A DNA prism for high-speed continuous fractionation of large DNA molecules. Nature Biotechnology. 2002;20:1048-1051.
Huang, et al. Continuous Particle Separation Through Deterministic Lateral Displacement. Science 304:987-90 (2004).
Huang, et al. Electric Manipulation of Bioparticles and Macromoledules on Microfabricated Electrodes. Analytical Chemistry. 2001; pp. 1549-1559.
Huang, et al. Role of Molecular Size in Ratchet Fractionation. 2002; 89(17):178301-1-178301-4.
Huh, et al. Gravity-driven microhydrodynamics-based cell sorter (microHYCS) for rapid, inexpensive, and efficient cell separation and size-profiling. 2nd Annual International IEEE-EMBS Special Topic Conference on Microtechnology in Medicine and Biology. Madison, Wisconsin USA; May 2-4, 2002:466-469.
Hviid T. In-Cell PCT method for specific genotyping of genomic DNA from one individual in a micture of cells from two individuals: a model study with specific relevance to prenatal diagnosis based on fetal cells in maternal blood. Molecular Diagnostics and Genetics. 2002; 48:2115-2123.
Hviid, T. In-cell polymerase chain reaction: strategy and diagnostic applications. Methods Mol Biol. 2006;336:45-58.
International preliminary report on patentability dated Oct. 29, 2008 for PCT/US2007/003209, 7 pages.
International Preliminary Report on Patentability in International Appln. No. PCT/US2007/071248, dated Dec. 16, 2008, 7 pages.
International search report and written opinion dated Mar. 16, 2010 for PCT Application No. US2009/57136, 15 pages.
International Search Report and Written Opinion dated Sep. 18, 2008 for PCT/US2007/003209, 8 pages.
International search report dated Jan. 16, 2008 for PCT Application No. US2007/71247, 2 pages.
International search report dated Jan. 25, 2008 for PCT Application No. US2007/71250, 3 pages.
International search report dated Nov. 15, 2007 for PCT Application No. US2007/71149, 1 page.
International search report dated Nov. 26, 2007 for PCT Application No. US2007/71256, 1 page.
International search report dated Feb. 25, 2008 for PCT Application No. US07/71148, 2 pages.
International search report dated Feb. 25, 2008 for PCT Application No. US2007/71248, 2 pages.
Iverson, et al. Detection and Isolation of Fetal Cells From Maternal Blood Using the Flourescence-Activated Cell Sorter (FACS). Prenatal Diagnosis 1981;1:61-73.
Jan, et al. Fetal Erythrocytes Detected and Separated from Maternal Blood by Electronic Fluorescent Cell Sorter. Texas Rep Biol Med. 1973;31:575.

(56) References Cited

OTHER PUBLICATIONS

Jauniaux et al., "Very early prenatal diagnosis on coelomic cells using quantitative fluorescent polymerase chain reaction," Reproductive BioMedicine Online, Jan. 2003, 6: 494-498.
Jayasena, "Aptamers: an emerging class of molecules that rival antibodies in diagnostics," Clin Chem., 1999, 45(9):1628-1650.
Jeon, et al. Generation of Solution and surface Gradients Using Microfluidic Systems. Langmuir. 2000, pp. 8311-8316.
Jiang, et al. Genome amplification of single sperm using multiple displacement amplification. Nucleic Acids Res. 2005; 33(10):e91. (9 pages).
Kaiser, "An earlier look at baby's genes," Science, 2005, 309(5740):1476-1478.
Kamholz, et al. Quantitative Analysis of Molecular Interaction in a Microfluidic Channel: the T- Sensor. Analytical Chemistry. 1999; pp. 5340-5347.
Kan, et al. Concentration of Fetal Red Blood Cells From a Mixture of Maternal and Fetal Blood by Anti-i Serum—An Aid to Prenatal Diagnosis of Hemoglobinopathies. Blood. 1974; 43:411-415.
Kartalov et al.: "Microfluidic device reads up to four consecutive base pairs in DNA sequencing-by-synthesis.", Nucleic Acids Research, 2004, vol. 32, No. 9, 2004, pp. 2873-2879, XP-002652987.
Kasakov, et al. Extracellular DNA in the blood of pregnant women. Tsitologiia. 1995;37(3):232-6. (English translation only).
Kenis, et al. Microfabrication Inside Capillaries Using Multiphase Laminar Flow Patterning. Science. 1999; 285:83-85.
Khattabi et al., "Could Digital PCR Be an Alternative as a Non-Invasive Prenatal Test for Trisomy, 21: A Proof of Concept Study," PloS ONE, 2016, 11(5):e0155009, 13 pages.
Kim et al., "rSW-seq: algorithm for detection of copy number alterations in deep sequencing data," BMC Bioinformatics, 2010, 11:432, 13 pages.
Kim, et al. Polymer microstructures formed by moulding in capillaries. Nature. 1995;376:581-584.
Kimura, et al. Deletional mutant EGFR detected in circulating tumor-derived DNA from lung cancer patients treated with gefitinib. American Association for Cancer Research 96th Annual Meeting. Apr. 16-20, 2005. Abstract 479.
Kimura, et al. The DYRKIA gene, encoded in chromosome 21 Down syndrome critical region, bridges between (β-amyloid production and tau phosphorylation in Alzheimer disease. Human Molecular Genetics, Nov. 29, 2008, vol. 16, No. 1, 15-23.
Klein, C. A. Single cell amplification methods for the study of cancer and cellular ageing. Mech. Ageing Dev. 2005; 126(1):147-51.
Klein, et al. Comparative genomic hybridization, loss of heterozygosity, and DNA sequence analysis of single cells. Proc Natl Acad Sci U S A. 1999; 96(8):4494-9.
Kobayashi, et al. EGFR mutation and resistance of non-small-cell lung cancer to gefitinib. N Engl J Med. Feb. 24, 2005;352(8):786-92.
Kogan, et al. An Improved Method for Prenatal Diagnosis of Genetic Diseases by Analysis of Amplified DNA Sequences, Application to Hemophilia A. The New England Journal of Medicine. 1987;317:985-990.
Koide et al., "Fragmentation of Cell-Free Fetal DNA in Plasma and Urine of Pregnant Women," Prenat. Diagn., 2005, 25(7):604-607.
Korenberg, et al. Down syndrome phenotypes: the consequences of chromosomal imbalance. PNAS 1994; 91:4997-5001.
Krabchi, et al. Quantification of all fetal nucleated cells in maternal blood between the 18th and 22nd weeks of pregnancy using molecular cytogenic techniques. Clin. Genet. 2001; 60:145-150.
Krivacic, et al. A rare-cell detector for cancer. PNAS. 2004;101:10501-10504.
Kulozik, et al. Fetal Cell in the Maternal Circulation: Detection by Direct AFP-Immunoflourescence. Human Genetics. 1982;62:221-224.
Kurg, et al. Arrayed primer extension: solid-phase four-color DNA resequencing and mutation detection technology. Genet Test. 2000;4(1):1-7.
Leary et al., "Digital karyotyping," Nature Protocols, 2007, 2:1973-1986.
Leon et al., "Free DNA in the serum of cancer patients and the effect of therapy," Cancer Res., 1977, 37(3):646-650, 6 pages.
Leutwyler, K. Mapping Chromosome 21. Available at http://www.scientificamerican.com/article.cfm?id=mapping-chromosome-21. Accessed Feb. 3, 2010, 2 pages.
Levett, et al. A large-scale evaluation of amnio-PCR for the rapid prenatal diagnosis of fetal trisomy. Ultrasound Obstet Gynecol. 2001; 17(2):115-8.
Li, et al. Transport, Manipulation, and Reaction of Biological Cells On-Chip Using Electrokinetic Effects. Analytical Chemistry., 1997; pp. 1564-1568.
Li, et al. Amplification and analysis of DNA sequences in single human sperm and diploid cells. Nature. 1988;335:414-417.
Li, et al. Mapping short DNA sequencing reads and calling variants using mapping quality scores. Genome Research. Genome Res. Nov. 2008;18(11):1851-8.
Li, et al. Size separation of circulatory DNA in maternal plasma permits ready detection of fetal DNA polymorphisms. Clin Chem. Jun. 2004;50(6):1002-11.
Lichter , et al. Delineation of individual human chromosomes in metaphase and interphase cells by in situ suppression hyridization using recombinant DNA libraries. Hum Genet. 1988;80:224-234.
Liu et al., "Feasibility Study of Using Fetal DNA in Maternal Plasma for Non-invasive Prenatal Diagnosis," Acta Obstet. Gynecol. Scand., 2007, 86(5):535-541.
Liu, et al. Development and validation of a T7 based linear amplification for genomic Dna. Bmc Genomics. 2003; 4(1):19. (11 pages).
Lo et al., "Increased Fetal DNA Concentrations in the Plasma of Pregnant Women Carrying Fetuses with Trisomy 21," Clin. Chem., 1999, 45(10):1747-1751.
Lo et al., "Rapid Clearance of Fetal DNA from Maternal Plasma," Am. J. Hum. Genet., 1999, 64(1):218-224.
Lo, et al. Detection of fetal RhD sequence from peripheral blood of sensitized RhD-negative pregnant women. British Journalof Haematology, 1994, vol. 87, 658-660.
Lo, et al. Detection of single-copy fetal DNA sequence from maternal blood. The Lancet, Jun. 16, 1990, vol. 335, 1463-1464.
Lo, et al. Digital PCR for the molecular detection of fetal chromosomal aneuploidy. PNAS. Aug. 7, 2007; 104(32):13116-13121.
Lo, et al. Fetal DNA in Maternal Plasma. Ann. N. Y. Acad. Sci, Apr. 2000, vol. 906, 141-147.
Lo, et al. Plasma placental RNA allelic ratio permits noninvasive prenatal chromosomal aneuploidy detection. Nat Med. Feb. 2007;13(2):218-23.
Lo, et al. Prenatal diagnosis: progress through plasma nucleic acids. Nature. Jan. 2007, vol. 8, 71-76.
Lo, et al. Prenatal sex determination by DNA amplification from material peripheral blood. The Lancet.Dec. 9, 1989:1363-1365.
Lo, et al. Presence of fetal DNA in maternal plasma and serum. The Lancet, Aug. 16, 1997, vol. 350, 485-487.
Lo, et al. Quantitative Analysis of Fetal NA in Maternal Plasma and Serum: Implications for Noninvasive Prenatal Diagnosis. Am J. Hum. Genet., 1998, vol. 62, 768-775.
Lo, Y. M. Noninvasive prenatal detection of fetal chromosomal aneuploidies by maternal plasma nucleic acid analysis: a review of the current state of the art. BJOG, 2009, vol. 116, 152-157.
Loken, et al. Flow Cytometric Analysis of Human Bone Marrow: I. Normal Erythroid Development. Blood. 1987;69:255-263.
Lun, et al. Microfluidics Digital PCR Reveals a Higher than Expected Fraction of Fetal DNA in Maternal Plasma. Clinical Chemistry, 2008, vol. 54, No. 10, 1664-1672.
Mahr, et al. Fluorescence in situ hybridization of fetal nucleated red blood cells. The American Journal of Human Genetics. Oct. 1992. Supplemental to vol. 51, No. 4: 1621.
Maloney et al. "Microchimerism of maternal origin persists into adult life," J. Clin. Invest. 104:41-47 (1999).
Mann et al., "Strategies for the rapid prenatal diagnosis of chromosome aneuploidy," European Journal of Human Genetics, 2004, 12(11):907-915.

(56) References Cited

OTHER PUBLICATIONS

Marcus, et al. Microfluidic Single-Cell mRNA Isolation and Analysis. American Chemical Society, Mar. 2006; 76:3084-3089.
Marcus, et al. Parallel Picoliter RT-PCR Assays Using Microfluidics. Analytical Chemistry, Feb. 1, 2006, vol. 78, No. 3, 956-958.
Margulies, et al., "Genome sequencing in microfabricated high-density picolitre reactors," Nature, Sep. 2005, 437(7057):376-380.
Marks, et al. Epidermal growth factor receptor (EGFR) expression in prostatic adenocarcinoma after hormonal therapy: a fluorescense in situ hybridization and immunohistochemical analysis. The Prostate. 2008; 68:919-923.
Martin, et al. "A method for using serum or plasma as a source of NDA for HLA typing," Human Immunology. 1992; 33:108-113.
Mavrou, et al. Identification of nucleated red blood cells in maternal circulation: A second step in screening for fetal aneuploidies and pregnancy complications. Prenat Diagn. 2007; 247:150-153.
Mccabe, et al. DNA microextraction from dried blood spots on filter paper blotters: potential applications to newborn screening. Hum Genet. 1987;75:213-216.
McCarley, et al. Patterning of surface-capture architectures in polymer-based microanalytical devices. In Kutter, et al. Eds. Royal Society of Chemistry Special Publication. 2005;130-132. (Abstract only).
Mehrishi , et al. Electrophoresis of cells and the biological relevance of surface charge. Electrophoresis. 2002;23:1984-1994.
Melville, et al. Direct magnetic separation of red cells from whole blood. Nature. 1975; 255:706.
Meng et al., "HER-2 gene amplification can be acquired as breast cancer progresses," PNAS, 2004, 101:9393-9398.
Meng, et al.: "Design and Synthesis of a Photocleavable Fluorescent Nucleotide 3'-O-Allyl-dGTPPC-Bodipy-FL-510 as a Reversible Terminator for DNA Sequencing by Synthesis", J. Org. Chem. 2006, 71, pp. 3248-3252, XP-002652986.
Mohamed, et al. A Micromachined Sparse Cell Isolation Device: Application in Prenatal Diagnostics. Nanotech 2006 vol. 2; 641-644. (Abstract only).
Mohamed, et al. Biochip for separating fetal cells from maternal circulation. J Chromatogr A. Aug. 31, 2007;1162(2):187-92.
Mohamed, et al. Development of a rare cell fractionation device: application for cancer detection. IEEE Trans Nanobioscience. 2004; 3(4): 251-6.
Moore, et al. Lymphocyte fractionation using immunomagnetic colloid and a dipole magnet flow cell sorter. J Biochem Biophys Methods. 1998;37:11-33.
Moorhead, et al. Optimal genotype determination in highly multiplexed SNP data. Eur. J. Hum. Genet. 2006;14(2):207-15. (published online Nov. 23, 2005).
Mueller , et al. Isolation of fetal trophoblast cells from peripheral blood of pregnant women. The Lancet. 1990;336:197-200.
Muller, et al. Moderately repeated DNA sequences specific for the short arm of the human Y chromosome are present in XX makes and reduced in copy number in an XY female. 1986;14:1325-1340.
Mullis, et al. Specific Enzymatic Amplification of DNA In Vitro: The Polymerase Chain Reaction. Cold Spring Harbor Symposia on Quantitative Biolgy 1986;51:263-273.
Murakami, et al. A novel single cell PCR assay: detection of human T lymphotropic virus type I DNA in lymphocytes of patients with adult T cell leukemia. Leukemia. Oct. 1998;12(10):1645-50.
Murthy, et al. Assessment of multiple displacement amplification for polymorphism discovery and haplotype determination at a highly polymorphic locus, MC1R. Hum. Mutat. 2005; 26(2):145-52.
Nagrath, et al. Isolation of rare circulating tumour cells in cancer patients by microchip technology. Nature. 2007; 450: 1235-1241 (with Supplemental pp. 1-10).
Nelson, et al. Genotyping Fetal DNA by Non-Invasive Means: Extraction From Maternal Plasma. Vox Sang. 2001;80:112-116.
Newcombe, R. G. Two-sided confidence intervals for the single proportion: comparison of seven methods. Statistics in Medicine. 1998; 17:857-872.
Ng, et al. "The Concentration of Circulating Corticotropin-releasing Hormone mRNA in Maternal Plasma Is Increased in Preeclampsia," Clinical Chemistry, 2003, vol. 49, No. 5, 727-731.
Non-Final Office Action for U.S. Appl. No. 12/816,043, dated Mar. 20, 2014, 11 pages.
Non-Final Office Action for U.S. Appl. No. 13/738,268, dated Dec. 12, 2014, 27 pages.
Non-Final Office Action for U.S. Appl. No. 12/689,517, dated Feb. 23, 2015, 16 pages.
Non-Final Office Action for U.S. Appl. No. 12/689,517, dated Sep. 16, 2016, 8 pages.
Non-Final Office Action for U.S. Appl. No. 12/689,548, dated Apr. 28, 2014, 32 pages.
Non-Final Office Action for U.S. Appl. No. 12/689,548, dated Jul. 21, 2015, 31 pages.
Non-Final Office Action for U.S. Appl. No. 12/751,940, dated Dec. 10, 2014, 9 pages.
Non-Final Office Action for U.S. Appl. No. 12/751,940, dated Mar. 15, 2016, 22 pages.
Non-Final Office Action for U.S. Appl. No. 12/815,674, dated Mar. 21, 2014, 32 pages.
Non-final Office Action for U.S. Appl. No. 12/816,043, dated Mar. 14, 2016, 18 pages.
Non-Final Office Action for U.S. Appl. No. 12/816,043, dated May 8, 2015, 13 pages.
Non-Final Office Action for U.S. Appl. No. 13/794,503, dated Apr. 29, 2015, 17 pages.
Non-Final Office Action for U.S. Appl. No. 13/794,503, dated Dec. 1, 2016, 18 pages.
Non-Final Office Action for U.S. Appl. No. 13/831,342, dated Nov. 7, 2014, 21 pages.
Non-Final Office Action for U.S. Appl. No. 13/863,992, dated Mar. 31, 2016, 15 pages.
Non-Final Office Action for U.S. Appl. No. 13/863,992, dated Sep. 17, 2014, 28 pages.
Notice of Allowance and Issue Fee Due Dec. 9, 2010 issued in U.S. Appl. No. 11/701,686, 5 pages.
Notice of Allowance for U.S. Appl. No. 12/816,043, dated Jul. 27, 2016, 13 pages.
Notice of Decision from Post-Prosecution Pilot Program (P3) Conference for U.S. Appl. No. 13/863,992, dated Dec. 27, 2016, 4 pages.
Oakey et al. Laminar Flow-Based Separations at the Microscale. Biotechnology Progress. 2002; pp. 1439-1442.
Office action (Ex parte Quayle) dated May 13, 2011 for U.S. Appl. No. 11/763,421, 5 pages.
Office Action dated Jan. 12, 2009 for U.S. Appl. No. 11/763,133, 8 pages.
Office Action dated Jan. 27, 2010 for U.S. Appl. No. 11/701,686, 44 pages.
Office action dated Jan. 28, 2009 for U.S. Appl. No. 11/701,686, 11 pages.
Office action dated Feb. 4, 2010 for U.S. Appl. No. 11/067,102, 21 pages.
Office action dated Feb. 15, 2011 for U.S. Appl. No. 11/763,426, 10 pages.
Office action dated Mar. 4, 2009 for U.S. Appl. No. 11/228,454, 13 pages.
Office action dated Mar. 11, 2010 for U.S. Appl. No. 11/763,245, 11 pages.
Office action dated Mar. 29, 2011 for U.S. Appl. No. 11/763,245, 16 pages.
Office action dated Apr. 4, 2008 for U.S. Appl. No. 11/067,102, 27 pages.
Office action dated Apr. 13, 2009 for U.S. Appl. No. 11/067,102, 21 pages.
Office action dated Apr. 25, 2011 for U.S. Appl. No. 12/393,803 with pending claims, 20 pages.
Office action dated May 4, 2009 for U.S. Appl. No. 11/763,431, 58 pages.
Office action dated May 6, 2011 for U.S. Appl. No. 11/763,133, 42 pages.

(56) References Cited

OTHER PUBLICATIONS

Office action dated May 12, 2011 for U.S. Appl. No. 12/230,628, 10 pages.
Office action dated May 18, 2011 for U.S. Appl. No. 12/413,467, 32 pages.
Office action dated May 26, 2011 for U.S. Appl. No. 11/762,750, 9 pages.
Office action dated Jun. 4, 2012 for U.S. Appl. No. 11/762,747, 15 pages.
Office action dated Jun. 5, 2012 for U.S. Appl. No. 12/393,833, 10 pages.
Office action dated Jun. 14, 2010 for U.S. Appl. No. 11/763,426, 14 pages.
Office action dated Jun. 15, 2007 for U.S. Appl. No. 11/067,102, 17 pages.
Office action dated Jul. 9, 2012 for U.S. Appl. No. 11/762,750, 8 pages.
Office action dated Jul. 10, 2009 for U.S. Appl. No. 11/763,421, 21 pages.
Office action dated Jul. 26, 2011 for U.S. Appl. No. 11/763,245, 16 pages.
Office action dated Aug. 1, 2008 for U.S. Appl. No. 11/067,102, 24 pages.
Office action dated Aug. 27, 2010 for U.S. Appl. No. 11/762,747, 11 pages.
Office Action dated Sep. 8, 2010 for U.S. Appl. No. 11/701,686, 40 pages.
Office action dated Sep. 10, 2010 for U.S. Appl. No. 11/762,750, 10 pages.
Office Action dated Sep. 11, 2009 for U.S. Appl. No. 11/701,686, 32 pages.
Office action dated Sep. 14, 2012 for U.S. Appl. No. 12/393,833, 7 pages.
Office action dated Sep. 17, 2010 for U.S. Appl. No. 11/067,102, 31 pages.
Office action dated Oct. 24, 2011 for U.S. Appl. No. 11/762,747, 14 pages.
Office action dated Oct. 29, 2010 for U.S. Appl. No. 12/230,628, 19 pages.
Office action dated Nov. 3, 2009 for U.S. Appl. No. 11/763,133, 13 pages.
Office action dated Dec. 1, 2009 for U.S. Appl. No. 11/763,426, 11 pages.
Office action dated Dec. 2, 2008 for U.S. Appl. No. 11/762,747, 8 pages.
Office action dated Dec. 3, 2008 for U.S. Appl. No. 11/763,426, 17 pages.
Office action dated Dec. 31, 2009 for U.S. Appl. No. 11/763,421, 13 pages.
Office action dated Dec. 31, 2009 for U.S. Appl. No. 11/762,750, 11 pages.
Office Action dated for U.S. Appl. No. 13/737,730, dated Mar. 11, 2015, 21 pages.
Office Action in European Appln. No. 18170287.9, dated Dec. 8, 2023, 9 pages.
Olson et al. An In Situ Flow Cytometer for the Optical Analysis of Individual Particles in Seawater. Available at http://www.whoi.edu/science/B/Olsonlab/insitu2001.htm. Accessed Apr. 24, 2006, 7 pages.
Oosterwijk et al. Prenatal diagnosis of trisomy 13 on fetal cells obtained from maternal blood after minor enrichment. Prenat Diagn. 1998;18(10):1082-5.
Ottesen et al. Microfluidic Digital PCR Enables Multigene Analysis of Individual Environmental Bacteria. Science. Dec. 1, 2006; 314(5804):1464-1467. (Abstract only).
Owen et al. High gradient magnetic separation of erythrocytes. Biophys. J. 1978; 22:171-178.
Pallavicini et al. Analysis of fetal cells sorted from maternal blood using fluorescence in situ hybridization. The American Journal of Human Genetics. Oct. 1992. Supplemental to vol. 51, No. 4: 1031.
Parano et al. Fetal Nucleated red blood cell counts in peripheral blood of mothers bearing Down Syndrome fetus. Neuropediatrics. 2001; 32(3):147-149. (Abstract only).
Parano et al. Noninvasive Prenatal Diagnosis of Chromosomal Aneuploidies by Isolation and Analysis of Fetal Cells from Maternal Blood. Am. J. Med. Genet. 101:262-7 (2001).
Paterlini-Brechot et al. Circulating tumor cells (CTC) detection: Clinical impact and future directions. Cancer Letter. 2007. (In press, 25 pages. ) Available at www.sciencedirect.com.
Pathak et al., “Circulating Cell-Free DNA in Plasma/Serum of Lung Cancer Patients as a Potential Screening and Prognostic Tool,” Clin. Chem., 2006, 52(10):1833-1842.
Paul et al. Single-molecule dilution and multiple displacement amplification for molecular haplotyping. Biotechniques. 2005; 38(4):553-4, 556, 558-9.
Pawlik et al. Prodrug Bioactivation and Oncolysis of Diffuse Liver Metastases by a Herpes Simplex Virus 1 Mutant that Expresses the CYP2B1 Transgene. Cancer. 2002;95:1171-81.
Peixoto et al. Quantification of multiple gene expression in individual cells. Genome Res. Oct. 2004;14(10A):1938-47.
Pending Claims and Preliminary Amendment filed Nov. 19, 2010 for U.S. Appl. No. 11/763,133, 6 pages.
Pending claims and preliminary amendment filed Dec. 10, 2010 for U.S. Appl. No. 11/763,245, 11 pages.
Pending claims filed with the USPTO on Apr. 26, 2010 for U.S. Appl. No. 11/067,102, 2 pages.
Peng, et al. Real-time detection of gene expression in cancer cells using molecular beacon imaging: new strategies for cancer research. Cancer Res. 2005; 65(5):1909-17.
Pertl et al. “Fetal DNA in Maternal Plasma: Emerging Clinical Applications,” Obstetrics and Gynecology, Sep. 2001, vol. 98, No. 3, 483-490.
Pertl et al., “Detection of Male and Female fetal DNA in Maternal Plasma by Multiplex Fluorescent Polymerase Chain Reaction Amplification of Short Tandem Repeats,” Hum. Genet., 2000, 106(1):45-49.
Petersen et al. The Promise of Miniaturized Clinical Diagnostic Systems. IVD Technol. 4:43-49 (1998).
Pfaffl, et al. Relative expression software tool (REST) for group-wise comparison and statistical analysis of relative expression results in real-time PCR. Nucleic Acids Res. May 1, 2002;30(9):e36.
Pinkel, et al. Cytogenetic Analysis Using Quantitative, High-sensitivity, Fluorescence Hybridization. Genetics. 1986;83:2934-2938.
Pinkel, et al. Fluorescence in situ Hybridization with Human Chromosome-specific Libraries: Detection of Trisomy 21 and Translocations of Chromosome 4. Genetics. 1988;85:9138-9142.
Pinkel, et al. Detection of structural chromosome abberations in metaphase in metaphase spreads and interphase nuclei by in situ hybridization high complexity probes which stain entire human chromosomes. The American Journal of Human Genetics. Sep. 1988. Supplemental to vol. 43, No. 3: 0471.
Pinzani, et al. Isolation by size of epithelial tumor cells in peripheral blood of patients with breast cancer: correlation with real-time reverse transcriptase-polymerase chain reaction results and feasibility of molecular analysis by laser microdissection. Hum Pathol. 2006; 37(6):711-8.
Pohl et al. Principle and applications of digital PCR. Expert Rev Mol Diagn. Jan. 2004;4(1):41-7.
Poon et al., “Differential DNA methylation between fetus and mother as a strategy for detecting fetal DNA in maternal plasma,” Clinical Chemistry, 2002, 48(1):35-41.
Poon, et al. “Circulating fetal DNA in maternal plasma,” ClinicalChimica Acta, 2001, vol. 313, 151-155.
Potti, et al. Genomic signatures to guide the use of chemotherapeutics. Nat Med. 2006; 12(11):1294-1300.
Price, et al. Prenatal Diagnosis with Fetal Cells Isolated from Maternal Blood by Multiparameter Flow Cytometry. Am. J. Obstet. Gynecol. 1991; 165:1731-7.
Prieto, et al. Isolation of fetal nucleated red blood cells from maternal blood in normal and aneuploid pregnancies. Clin Chem Lab Med. Jul. 2002;40(7):667-72.

(56) References Cited

OTHER PUBLICATIONS

Product literature for GEM, a system for blood testing: GEM Premier 3000. Avaiable at http://www.ilus.com/premier_gem3000_iqm.asp. Accessed Apr. 24, 2006, 3 pages.
Purwosunu, et al. Clinical potential for noninvasive prenatal diagnosis through detection of fetal cells in maternal blood. Taiwan J Obstet Gynecol. Mar. 2006;45(1):10-20.
Raeburn, P. Fetal Cells Isolated In Women's Blood. Associated Press (Jul. 28, 1989) [electronic version], 6 pages.
Rahil, et al. Rapid detection of common autosomal aneuploidies by quantitative fluorescent PCR on uncultured amniocytes, European Journal of Human Genetics, 2002, vol. 10, 462-466.
Request for Continued Examination by applicant with claim set dated Mar. 26, 2010 in Response to Final Office Action dated Nov. 3, 2009 for U.S. Appl. No. 11/763,133, 12 pages.
Request for Continued Examination by applicant with claim set dated Mar. 26, 2010 in Response to Final Office Action dated Dec. 1, 2009 for U.S. Appl. No. 11/763,426, 8 pages.
Response dated Nov. 24, 2010 to Office action dated Jun. 14, 2010 with Pending Claims for U.S. Appl. No. 11/763,426, 7 pages.
Response filed Dec. 26, 2012 with claims for U.S. Appl. No. 12/393,833, 103 pages.
Rickman, et al. Prenatal diagnosis by array-CGH. European Journal of Medical Genetics. 2005; 48:232-240.
Rolle, et al. Increase in number of circulating disseminated epithelia cells after surgery for non-small cell lung cancer monitored by MAINTRAC is a predictor for relapse: a preliminary report. World Journal of Surgical Oncology. 2005; 9 pages.
Ruan, et al. Identification of clinically significant tumor antigens by selecting phage antibody library on tumor cells in situ using laser capture microdissection. Molecular & Cellular Proteomics. 2006; 5(12): 2364-73.
Sakhnini, et al. Magnetic behavior of human erythrocytes at different hemoglobin states. Eur Biophys J. Oct. 2001;30(6):467-70.
Samura, et al. Female fetal cells in maternal blood: use of DNA polymorphisms to prove origin. Hum. Genet. 2000;107(1):28-32.
Samura, et al., "Diagnosis of trisomy 21 in fetal nucleated erythrocytes from maternal blood by use of short tandem repeat sequences," Clin. Chem., 2001, 47(9):1622-6.
Sato, et al. Individual and Mass Operation of Biological Cells Using Micromechanical Silicon Devices. Sensors and Actuators. 1990;A21-A23:948-953.
Schaefer, et al. The Clinical Relevance of Nucleated Red Blood Cells counts. Sysmex Journal International. 2000; 10(2):59-63.
Schröder, et al. Fetal Lymphocytes in the Maternal Blood. The Journal of Hematolog:Blood. 1972;39:153-162.
Scoazec, "Tissue and cell imaging in situ: potential for applications in pathology and endoscopy," Gut, 2003, 52(Suppl 4):iv1-iv6.
Sehnert, et al. Optimal Detection of Fetal Chromosomal Abnormalities by Massively Parallel DNA Sequencing of Cell-Free Fetal DNA from Maternal Blood. Clin Chem. Apr. 25, 2011, 8 pages [Epub ahead of print].
Sekizawa et al., "Recent advances in non-invasive prenatal DNA diagnosis through analysis of maternal blood," J. Obstet. Gynaecol. Res., 2007, 33(6):747-764.
Sequenom, Inc and Sequenom Center for Molecular Medicine LLC's Patent L. R. 3-3 Preliminary Invalidity Contentions for U.S. Pat. No. 7,888,017, U.S. Pat. No. 8,008,018 and U.S. Pat. No. 8,195,415 and Patent L. R. 3-4 Document Production, *Verinata Health* v. *Sequenom,* No. 12-00865 (N.D. Cal. 2012), dated Sep. 28, 2012.
Sequenom, Inc and Sequenom Center for Molecular Medicine LLC's Patent L. R. 4-2 Preliminary Claim Constructions and Extrinsic Evidence, *Verinata Health* v. *Sequenom,* No. 12-00865 (N.D. Cal. 2012), dated Oct. 26, 2012.
Sethu, et al. Continuous Flow Microfluidic Device for Rapid Erythrocyte Lysis. Anal. Chem. 76:6247-6253 (2004).
Shen, et al. High-throughput SNP genotyping on universal bead arrays. Mutat. Res. 2005; 573:70-82.
Shendure, et al. Accurate multiplex polony sequencing of an evolved bacterial genome. Science. 2005; 309:1728-32.
Shendure, et al. Next-generation DNA sequencing. Nature. 2008; 26(10):1135-1145.
Sherlock, et al. Assessment of diagnostic quantitative fluorescent multiplex polymerase chain reaction assays performed on single cells. Ann. Hum. Genet. 1998; 62:9-23.
Sitar, et al. The Use of Non-Physiological Conditions to Isolate Fetal Cells from Maternal Blood. Exp. Cell. Res. 2005; 302:153-61.
Sohda, et al. The Proportion of Fetal Nucleated Red Blood Cells in Maternal Blood: Estimation by FACS Analysis. Prenat. Diagn. 1997; 17:743-52.
Solexa Genome Analysis System. 2006; 1-2.
Solexa, "Protocol for whole genome digital expression profiling using Solexa Technology," Biotechniques, Protocol Guide, 2007, 1 page.
Sparkes, et al. "New Molecular Techniques for the Prenatal Detection of Chromosomal Aneuploidy," JOGC, Jul. 2008, No. 210, 617-621.
Stipp, D. IG Labs Licenses New Technology for Fetal Testing. The Wall Street Journal. Aug. 10, 1990:B5.
Stoecklein, et al. SCOMP is superior to degenerated oligonucleotide primed-polymerase chain reaction for global amplification of minute amounts of DNA from microdissected archival tissue samples. Am J Pathol. 2002; 161(1):43-51.
Stoughton, et al. Data-adaptive algorithms for calling alleles in repeat polymorphisms. Electrophoresis. 1997;18(1):1-5.
Su et al., "Human Urine Contains Small, 150 to 250 Nucleotide-Sized, Soluble DNA Derived from the Circulation and May Be Useful in the Detection of Colorectal Cancer," J. Mol. Diagn., May 2004, 6(2):101-107.
Sun, et al. Whole-genome amplification: relative efficiencies of the current methods. Leg Med. 2005; 7(5):279-86.
Swarup et al., "Circulating (cell free) nucleic acids—A promising, non-invasive tool for early detection of several human diseases," FEBS Letters, 2007, 581:795-799.
Sykes, et al. Quantitation of targets for PCR by use of limiting dilution. Biotechniques. Sep. 1992;13(3):444-9.
Tanaka, et al. "Genome-wide expression profiling of mid-gestation placenta and embryo using a 15,000 mouse developmental cDNA microarray," PNAS, Aug. 2000, vol. 97, No. 16, 9127-9132.
Tettelin, et al. The nucleotide sequence of Saccharomyces cerevisiae chromosome VII. Nature. May 29, 1997;387(6632 Suppl):81-4.
Thomas et al., "Sensitive Mutation Detection in Heterogeneous Cancer Specimens by Massively Parallel Picoliter Reactor Sequencing," Nature Medicine, Jul. 2006, 12(7):852-855, 5 pages.
Thomas, et al. Specific Binding and Release of Cells from Beads Using Cleavable Tettrametric Antibody Complexes. Journal of Immunological Methods 1989;120:221-231.
Tibbe, et al. Statistical considerations for enumeration of circulating tumor cells. Cytometry A. Mar. 2007;71(3):154-62.
Toner, et al. Blood-on-a-Chip. Annu. Rev. Biomed. Eng. 7:77-103, C1-C3 (2005).
Tong et al., "Noninvasive prenatal detection of fetal trisomy 18 by epigenetic allelic ratio analysis in maternal plasma: theoretical and empirical considerations," Clinical Chemistry, 2006, 52(12):2194-2202, 9 pages.
Trask, et al. Detection of DNA Sequences and Nuclei in Suspension by In Situ Hybridization and Dual Beam Flow Cytometry. Science. 1985;230:1401-1403.
Troeger, et al. Approximately half of the erythroblasts in maternal blood are of fetal origin. Mol Hum Reprod. 1999; 5(12):1162-5.
Tufan, et al., Analysis of Cell-Free Fetal DNA from Maternal Plasma and Serum Using a Conventional Multiplex PCR: Factors Influencing Success. 2005. Turk. J. Med. Sci. 35:85-92.
Uitto, et al. Probing the fetal genome: progress in non-invasive prenatal diagnosis. Trends Mol Med. Aug. 2003;9(8):339-43.
Van Raamsdonk, et al. Optimizing the detection of nascent transcripts by RNA fluorescence in situ hybridization. Nucl. Acids. Res. 2001; 29(8):e42.
Voelkerding, et al. Digital fetal aneuploidy diagnosis by next-generation sequencing. Clin Chem. Mar. 2010;56(3):336-8.

(56) References Cited

OTHER PUBLICATIONS

Vogelstein et al., "Allelotype of colorectal carcinomas," Science, 1989, 244(4):207-211.
Vogelstein, et al. "Digital PCR." Proc Natl. Acad Sci. USA, Aug. 1999, vol. 96., 9236-9241.
Voldberg, et al. Epidermal growth factor receptor (EGFR) and EGFR mutations, function and possible role in clinical trials. Ann Oncol. Dec. 1997;8(12):1197-206.
Voldman et al., "Holding Forces of Single-Particle Dielectrophoretic Traps," Biophysical Journal, 2001, 80:531-541.
Volkmuth, et al. DNA electrophoresis in microlithographic arrays. Nature. 1992; 358:600-602.
Volkmuth, et al. Observation of Electrophoresis of Single DNA Molecules in Nanofabricated Arrays. Presentation at joint annual meeting of Biophysical Society and the American Society for Biochemistry and Molecular Biology. Feb. 9-13, 1992, A223.
Von Eggeling, et al. Determination of the origin of single nucleated cells in maternal circulation by means of random PCR and a set of length polymorphisms. Hum Genet. Feb. 1997;99(2):266-70.
Vona et al., "Enrichment, immunomorphological, and genetic characterization of fetal cells circulating in maternal blood," Am. J. Pathol., vol. 160, pp. 51-58 (2002).
Vona et al., "Isolation by size of epthelieal tumor cells," American Journal of Pathology, 2000, 156:57-63.
Voullaire, et al. Detection of aneuploidy in single cells using comparative genomic hybridization. Prenat Diagn. 1999; 19(9):846-51.
Vrettou, et al. Real-time PCR for single-cell genotyping in sickle cell and thalassemia syndromes as a rapid, accurate, reliable, and widely applicable protocol for preimplantation genetic diagnosis. Human Mutation. 2004; 23(5):513-21.
Wachtel, et al. Fetal Cells in the Maternal Circulation: Isolation by Multiparameter Flow Cytometry and Confirmation by Polymerase Chain Reaction. Human Reproduction. 1991;6:1466-1469.
Wang et al., "Advances and applications of single-cell sequencing technologies," Mol. Cell, 2015, 58:598-609.
Wang et al., "Digital karyotyping," PNAS, Dec 2002, 99:16156-16161.
Wang, et al. Allele quantification using molecular inversion probes (MIP). Nucleic Acids Research. 2005; 33(21); e183 (14 pages).
Wapner, et al. First-trimester screening for trisomies 21 and 18. N. Engl. J. Med. 2003; 349:1405-1413.
Warren, et al. Transcription factor profiling in individual hematopoietic progenitors by digital RT-PCR. PNAS. Nov. 21, 2006; 103(47):17807-17812.
Washizu, et al. Handling Biological Cells Utilizing a Fluid Integrated Circuit. IEEE Industry Applications Society Annual Meeting Presentations. Oct. 2-7, 1988;: 1735-40.
Washizu, et al. Handling Biological Cells Utilizing a Fluid Integrated Circuit. IEEE Transactions of Industry Applications. 1990; 26: 352-8.
Weigl, et al. Microfluidic Diffusion-Based Separation and Detection. Science. 1999; pp. 346-347.
White, et al. Digital PCR provides sensitive and absolute calibration for high throughput sequencing. BMC Genomics. Mar. 19, 2009;10:116.
Williams, et al. Comparison of cell separation methods to entrich the proportion of fetal cells in material blood samples. The American Journal of Human Genetics. Oct. 1992. Supplemental to vol. 51, No. 4: 1049.
Wong et al., "Circulating placental RNA in maternal plasma is associated with a preponderance of 5' mRNA fragments: implications for noninvasive prenatal diagnosis and monitoring," Clinical Chemistry, Oct. 2005, 51(10):1786-1795.
Wright et al., "The use of cell-free fetal nucleic acids in maternal blood for noninvasive prenatal diagnosis," Hum. Reprod. Update, 2009, 15(1):139-151.
Xiong, et al. "A simple, rapid, high-fidelity and cost-effective PCR-based two-step DNA synthesis method for long gene sequences," Nucleic Acids Research, Apr. 19, 2004, vol. 32, No. 12, e98.
Xu et al., "Dielectrophoresis of human red cells in microchips," Electrophoresis, 1999, 20:1829-1831.
Yang et al., "Prenatal diagnosis of trisomy 21 with fetal cells i maternal blood using comparative genomic hybridization," Fetal Diagn Ther., 2006, 21:125-133.
Yang, et al. Rapid Prenatal Diagnosis of Trisomy 21 by Real-time Quantitative Polymerase Chain Reaction with Amplification of Small Tandem Repeats and S100B in Chromosome 21. Yonsei Medical Journal, 2005, vol. 46, No. 2, 193-197.
Yu et al., "Size-based molecular diagnostics using plasma DNA for noninvasive prenatal testing," PNAS, 2014, 111(23):8583-8588.
Yu, et al. Objective Aneuploidy Detection for Fetal and Neonatal Screening Using Comparative Genomic Hybridization (CGH). Cytometry. 1997; 28(3): 191-197. (Abstract).
Zavala, et al. Genomic GC content prediction in prokaryotes from a sample of genes. Gene. Sep. 12, 2005;357(2):137-43.
Zborowski et al., "Red Blood Cell Magnetophoresis," Biophys. J., 2003, 84:2638-2645.
Zhang et al., "Whole genome amplification from a single cell: Implications for genetic analysis," PNAS, 1992, 89:5847-5851.
Zhang et al., "Whole genome amplification from a single cell: implications for genetic analysis," Proc Natl Acad Sci USA, Jul. 1992, 89(13):5847-5851.
Zhao et al., "Enrichment of fetal cells from maternal blood by magnetic activated cell sorting (MACS) with fetal cell specific antibodies: One-step versus two-step MACS," Congen. Anomal., 2002, 42:120-124.
Zhen, et al. Poly-FISH: a technique of repeated hybridizations that improves cytogenetic analysis of fetal cells in maternal blood. Prenat Diagn. 1998; 18(11):1181-5.
Zheng, et al. Fetal cell identifiers: results of microscope slide-based immunocytochemical studies as a function of gestational age and abnormality. Am J Obstet Gynecol. May 1999;180(5):1234-9.
Zhou et al., "Counting alleles reveals a connection between chromosome 18q loss and vascular invasion," Nature Biotechnology, 2001, 19(1):78-81.
Zhou et al., "Counting alleles to predict recurrence of early-stage colorectal cancers," The Lancet, 2002, 359(9302):219-225.
Zhu, et al. Single molecule profiling of alternative pre-mRNA splicing. Science. Aug. 8, 2003;301(5634):836-8.
Zimmerman et al., "Digital PCR: a powerful new tool for noninvasive prenatal diagnosis?" Prenat. Diagn., 2008, 28:1087-1093.
Zimmerman, et al. Novel real-time quantitative PCR test for trisomy 21. Jan. 1, 2002. Clinical Chemistry, American Association for Clinical Chemistry. 48:(2) 362-363.
Zimmermann, Bernhard. "Molecular Diagnosis in Prenatal Medicine," Ph.D. Thesis, 2004, 166 pages.
Zuska, P. Microtechnology Opens Doors to the Universe of Small Space, MD&DI Jan. 1997, p. 131.
Office Action in U.S. Appl. No. 17/850,599, mailed on Nov. 29, 2024, 20 pages.
Qian et al., "A comparison of DP-TOF Mass Spectroscopy (MS) and Next Generation Sequencing (NGS) methods for detecting molecular mutations in thyroid nodules fine needle aspiration biopsies," Front Endocrinol. (Lausanne), Aug. 2022, 13:928788, 8 pages.
Xu et al., "Cross-platform comparison of next-generation sequencing and matrix-assisted laser desorption/ionization time-of-flight mass spectrometry for detecting KRAS/NRAS/BRAF/PIK3CA mutations in cfDNA from metastatic colorectal cancer patients," J Clin Lab Anal., Sep. 2021, 35(9):e23818, 9 pages.

40-plex MIP assay performed for each of the 500 wells

Cross-section

2AR
A DISINTEGRIN
ACTIVATOR OF THYROID AND RETINOIC ACID RECEPTOR (ACTR)
ADAM 11
ADIPOGENESIS INHIBITORY FACTOR (ADIF)
ALPHA 6 INTEGRIN SUBUNIT
ALPHA V INTEGRIN SUBUNIT
ALPHA-CATENIN
AMPLIFIED IN BREAST CANCER 1 (AIB1)
AMPLIFIED IN BREAST CANCER 3 (AIB3)
AMPLIFIED IN BREAST CANCER 4 (AIB4)
AMYLOID PRECURSOR PROTEIN SECRETASE (APPS)
AP-2 GAMMA
APPS
ATP-BINDING CASSETTE TRANSPORTER (ABCT)
PLACENTA-SPECIFIC (ABCP)
ATP-BINDING CASSETTE SUBFAMILY C MEMBER (ABCC1)
BAG-1
BASIGIN (BSG)
BCEI
B-CELL DIFFERENTIATION FACTOR (BCDF)
B-CELL LEUKEMIA 2 (BCL-2)
B-CELL STIMULATORY FACTOR-2 (BSF-2)
BCL-1
BCL-2-ASSOCIATED X PROTEIN (BAX)
BCRP
BETA 1 INTEGRIN SUBUNIT
BETA 3 INTEGRIN SUBUNIT
BETA 5 INTEGRIN SUBUNIT
BETA-2 INTERFERON
BETA-CATENIN
BETA-CATENIN
BONE SIALOPROTEIN (BSP)
BREAST CANCER ESTROGEN-INDUCIBLE SEQUENCE (BCEI)
BREAST CANCER RESISTANCE PROTEIN (BCRP)
BREAST CANCER TYPE 1 (BRCA1)
BREAST CANCER TYPE 2 (BRCA2)
BREAST CARCINOMA AMPLIFIED SEQUENCE 2 (BCAS2)
CADHERIN
EPITHELIAL CADHERIN-11
CADHERIN-ASSOCIATED PROTEIN
CALCITONIN RECEPTOR (CTR)
CALCIUM PLACENTAL PROTEIN (CAPL)
CALCYCLIN
CALLA
CAM5
CAPL
CARCINOEMBRYONIC ANTIGEN (CEA)
CATENIN
ALPHA 1
CATHEPSIN B
CATHEPSIN D
CATHEPSIN K
CATHEPSIN L2
CATHEPSIN O
CATHEPSIN O1
CATHEPSIN V
CD10
CD146
CD147
CD24
CD29
CD44
CD51
CD54
CD61
CD66e
CD82
CD87
CD9
CEA
CELLULAR RETINOL-BINDING PROTEIN 1 (CRBP1)
c-ERBB-2
CK7
CK8
CK18
CK19
CK20
CLAUDIN-7
c-MET
COLLAGENASE
FIBROBLAST
COLLAGENASE
INTERSTITIAL
COLLAGENASE-3
COMMON ACUTE LYMPHOCYTIC LEUKEMIA ANTIGEN (CALLA)
CONNEXIN 26 (Cx26)
CONNEXIN 43 (Cx43)
CORTACTIN
COX-2
CTLA-8
CTR
CTSD
CYCLIN D1
CYCLOOXYGENASE-2
CYTOKERATIN 18
CYTOKERATIN 19
CYTOKERATIN 8
CYTOTOXIC T-LYMPHOCYTE-ASSOCIATED SERINE ESTERASE 8 (CTLA-8)
DIFFERENTIATION-INHIBITING ACTIVITY (DIA)
DNA AMPLIFIED IN MAMMARY CARCINOMA 1 (DAM1)
DNA TOPOISOMERASE II ALPHA
DR-NM23
E-CADHERIN
EMMPRIN
EMS1

FIG. 10A

ENDOTHELIAL CELL GROWTH FACTOR (ECGR)
PLATELET-DERIVED (PD-ECGF)
ENKEPHALINASE
EPIDERMAL GROWTH FACTOR RECEPTOR (EGFR)
EPISIALIN
EPITHELIAL MEMBRANE ANTIGEN (EMA)
ER-ALPHA
ERBB2
ERBB4
ER-BETA
ERF-1
ERYTHROID-POTENTIATING ACTIVITY (EPA)
ESR1
ESTROGEN RECEPTOR-ALPHA
ESTROGEN RECEPTOR-BETA
ETS-1
EXTRACELLULAR MATRIX METALLOPROTEINASE INDUCER (EMMPRIN)
FIBRONECTIN RECEPTOR
BETA POLYPEPTIDE (FNRB)
FIBRONECTIN RECEPTOR BETA SUBUNIT (FNRB)
FLK-1
GA15.3
GA733.2
GALECTIN-3
GAMMA-CATENIN
GAP JUNCTION PROTEIN (26 kDa)
GAP JUNCTION PROTEIN (43 kDa)
GAP JUNCTION PROTEIN ALPHA-1 (GJA1)
GAP JUNCTION PROTEIN BETA-2 (GJB2)
GCP1
GELATINASE A
GELATINASE B
GELATINASE (72 kDa)
GELATINASE (92 kDa)
GLIOSTATIN

GLUCOCORTICOID RECEPTOR INTERACTING PROTEIN 1 (GRIP1)
GLUTATHIONE S-TRANSFERASE p
GM-CSF
GRANULOCYTE CHEMOTACTIC PROTEIN 1 (GCP1)
GRANULOCYTE-MACROPHAGE-COLONY STIMULATING FACTOR
GROWTH FACTOR RECEPTOR BOUND-7 (GRB-7)
GSTp
HAP
HEAT-SHOCK COGNATE PROTEIN 70 (HSC70)
HEAT-STABLE ANTIGEN
HEPATOCYTE GROWTH FACTOR (HGF)
HEPATOCYTE GROWTH FACTOR RECEPTOR (HGFR)
HEPATOCYTE-STIMULATING FACTOR III (HSF III)
HER-2
HER2/NEU
HERMES ANTIGEN
HET
HHM
HUMORAL HYPERCALCEMIA OF MALIGNANCY (HHM)
ICERE-1
INT-1
INTERCELLULAR ADHESION MOLECULE-1 (ICAM-1)
INTERFERON-GAMMA-INDUCING FACTOR (IGIF)
INTERLEUKIN-1 ALPHA (IL-1A)
INTERLEUKIN-1 BETA (IL-1B)
INTERLEUKIN-11 (IL-11)
INTERLEUKIN-17 (IL-17)
INTERLEUKIN-18 (IL-18)
INTERLEUKIN-6 (IL-6)
INTERLEUKIN-8 (IL-8)
INVERSELY CORRELATED WITH ESTROGEN RECEPTOR EXPRESSION-1 (ICERE-1)
KAI1

KDR
KERATIN 8
KERATIN 18
KERATIN 19
KISS-1
LEUKEMIA INHIBITORY FACTOR (LIF)
LIF
LOST IN INFLAMMATORY BREAST CANCER (LIBC)
LOT ("LOST ON TRANSFORMATION")
LYMPHOCYTE HOMING RECEPTOR
MACROPHAGE-COLONY STIMULATING FACTOR
MAGE-3
MAMMAGLOBIN
MASPIN
MC56
M-CSF
MDC
MDNCF
MDR
MELANOMA CELL ADHESION MOLECULE (MCAM)
MEMBRANE METALLOENDOPEPTIDASE (MME)
MEMBRANE-ASSOCIATED NEUTRAL ENDOPEPTIDASE (NEP)
CYSTEINE-RICH PROTEIN (MDC)
METASTASIN (MTS-1)
MLN64
MMP1
MMP2
MMP3
MMP7
MMP9
MMP11
MMP13
MMP14
MMP15
MMP16
MMP17
MOESIN
MONOCYTE ARGININE-SERPIN

FIG. 10B

MONOCYTE-DERIVED NEUTROPHIL CHEMOTACTIC FACTOR
MONOCYTE-DERIVED PLASMINOGEN ACTIVATOR INHIBITOR
MTS-1
MUC-1
MUC18
MUCIN LIKE CANCER ASSOCIATED ANTIGEN (MCA)
MUCIN
MUC-1
MULTIDRUG RESISTANCE PROTEIN 1 (MDR, MDR1)
MULTIDRUG RESISTANCE RELATED PROTEIN-1 (MRP, MRP-1)
N-CADHERIN
NEP
NEU
NEUTRAL ENDOPEPTIDASE
NEUTROPHIL-ACTIVATING PEPTIDE 1 (NAP1)
NM23-H1
NM23-H2
NME1
NME2
NUCLEAR RECEPTOR COACTIVATOR-1 (NCoA-1)
NUCLEAR RECEPTOR COACTIVATOR-2 (NCoA-2)
NUCLEAR RECEPTOR COACTIVATOR-3 (NCoA-3)
NUCLEOSIDE DIPHOSPHATE KINASE A (NDPKA)
NUCLEOSIDE DIPHOSPHATE KINASE B (NDPKB)
ONCOSTATIN M (OSM)
ORNITHINE DECARBOXYLASE (ODC)
OSTEOCLAST DIFFERENTIATION FACTOR (ODF)
OSTEOCLAST DIFFERENTIATION FACTOR RECEPTOR (ODFR)
OSTEONECTIN (OSN, ON)
OSTEOPONTIN (OPN)
OXYTOCIN RECEPTOR (OXTR)

p27/kip1
p300/CBP COINTEGRATOR ASSOCIATE PROTEIN (p/CIP)
p53
p9Ka
PAI-1
PAI-2
PARATHYROID ADENOMATOSIS 1 (PRAD1)
PARATHYROID HORMONE-LIKE HORMONE (PTHLH)
PARATHYROID HORMONE-RELATED PEPTIDE (PTHrP)
P-CADHERIN
PD-ECGF
PDGF-[illegible]
PEANUT-REACTIVE URINARY MUCIN (PUM)
P-GLYCOPROTEIN (P-GP)
PGP-1
PHGS-2
PHS-2
PIP
PLAKOGLOBIN
PLASMINOGEN ACTIVATOR INHIBITOR (TYPE 1)
PLASMINOGEN ACTIVATOR INHIBITOR (TYPE 2)
PLASMINOGEN ACTIVATOR (TISSUE-TYPE)
PLASMINOGEN ACTIVATOR (UROKINASE-TYPE)
PLATELET GLYCOPROTEIN IIIa (GP3A)
PLAU
PLEOMORPHIC ADENOMA GENE-LIKE 1 (PLAGL1)
POLYMORPHIC EPITHELIAL MUCIN (PEM)
PRAD1
PROGESTERONE RECEPTOR (PgR)
PROGESTERONE RESISTANCE
PROSTAGLANDIN ENDOPEROXIDE SYNTHASE-2
PROSTAGLANDIN G/H SYNTHASE-2

PROSTAGLANDIN H SYNTHASE-2
pS2
PS6K
PSORIASIN
PTHLH
PTHrP
RAD51
RAD52
RAD54
RAP46
RECEPTOR-ASSOCIATED COACTIVATOR 3 (RAC3)
REPRESSOR OF ESTROGEN RECEPTOR ACTIVITY (REA)
S100A4
S100A6
S100A7
S6K
SART-1
SCAFFOLD ATTACHMENT FACTOR B (SAF-B)
SCATTER FACTOR (SF)
SECRETED PHOSPHOPROTEIN-1 (SPP-1)
SECRETED PROTEIN
ACIDIC AND RICH IN CYSTEINE (SPARC)
STANNICALCIN
STEROID RECEPTOR COACTIVATOR-1 (SRC-1)
STEROID RECEPTOR COACTIVATOR-2 (SRC-2)
STEROID RECEPTOR COACTIVATOR-3 (SRC-3)
STEROID RECEPTOR RNA ACTIVATOR (SRA)
STROMELYSIN-1
STROMELYSIN-3
TENASCIN-C (TN-C)
TESTES-SPECIFIC PROTEASE 50
THROMBOSPONDIN I
THROMBOSPONDIN II
THYMIDINE PHOSPHORYLASE (TP)
THYROID HORMONE RECEPTOR ACTIVATOR MOLECULE 1 (TRAM-1)

FIG. 10C

TIGHT JUNCTION PROTEIN 1 (TJP1)
TIMP1
TIMP2
TIMP3
TIMP4
TISSUE-TYPE PLASMINOGEN ACTIVATOR
TN-C
TP53
tPA
TRANSCRIPTIONAL INTERMEDIARY FACTOR 2 (TIF2)
TREFOIL FACTOR 1 (TFF1)
TSG101
TSP-1
TSP1
TSP-2

TSP2
TSP50
TUMOR CELL COLLAGENASE STIMULATING FACTOR (TCSF)
TUMOR-ASSOCIATED EPITHELIAL MUCIN
uPA
uPAR
UROKINASE
UROKINASE-TYPE PLASMINOGEN ACTIVATOR
UROKINASE-TYPE PLASMINOGEN ACTIVATOR RECEPTOR (uPAR)
UVOMORULIN
VASCULAR ENDOTHELIAL GROWTH FACTOR
VASCULAR ENDOTHELIAL GROWTH FACTOR RECEPTOR-2 (VEGFR2)

VASCULAR ENDOTHELIAL GROWTH FACTOR-A
VASCULAR PERMEABILITY FACTOR
VEGFR2
VERY LATE T-CELL ANTIGEN BETA (VLA-BETA)
VIMENTIN
VITRONECTIN RECEPTOR ALPHA POLYPEPTIDE (VNRA)
VITRONECTIN RECEPTOR
VON WILLEBRAND FACTOR
VPF
VWF
WNT-1
ZAC
ZO-1
ZONULA OCCLUDENS-1

FIG. 10D

| Name | SEQ ID NO | Sequence (5' to 3') | Exon | Amplicon Size |
|---|---|---|---|---|
| NXK-ex18.1(+) | 11 | TCAGAGCCTGTGTTTCTACCAA | 18 | 534 |
| NXK-ex18.2(-) | 12 | TGGTCTCACAGGACCACTGATT | 18 | |
| NXK-ex18.3(+) | 13 | TCCAAATGAGCTGGCAAGTG | 18 | 397 |
| NXK-ex18.4(-) | 14 | TCCCAAACACTCAGTGAAACAAA | 18 | |
| NXK-ex19.1(+) | 15 | AAATAATCAGTGTGATTCGTGGAG | 19 | 495 |
| NXK-ex19.2(-) | 16 | GAGGCCAGTGCTGTCTCTAAGG | 19 | |
| NXK-ex19.3(+) | 17 | GTGCATCGCTGGTAACATCC | 19 | 298 |
| NXK-ex19.4(-) | 18 | TGTGGAGATGAGCAGGGTCT | 19 | |
| NXK-ex20.1(+) | 19 | ACTTCACAGCCCTGCGTAAAC | 20 | 555 |
| NXK-ex20.2(-) | 20 | ATGGGACAGGCACTGATTTGT | 20 | |
| NXK-ex20.3(+) | 21 | ATCGCATTCATGCGTCTTCA | 20 | 379 |
| NXK-ex20.4(-) | 22 | ATCCCCATGGCAAACTCTTG | 20 | |
| NXK-ex21.1(+) | 23 | GCAGCGGGTTACATCTTCTTTC | 21 | 526 |
| NXK-ex21.2(-) | 24 | CAGCTCTGGCTCACACTACCAG | 21 | |
| NXK-ex21.3(+) | 25 | GCAGCGGGTTACATCTTCTTTC | 21 | 349 |
| NXK-ex21.4(-) | 26 | CATCCTCCCCTGCATGTGT | 21 | |

FIG. 11

FIG. 13A
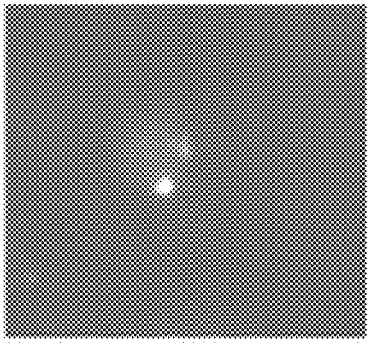
FIG. 13B
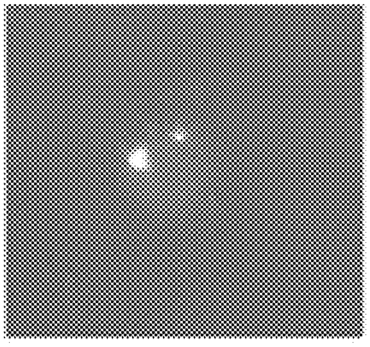
FIG. 13C
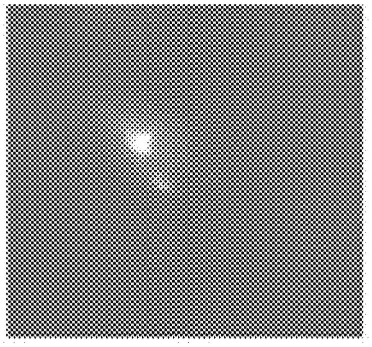
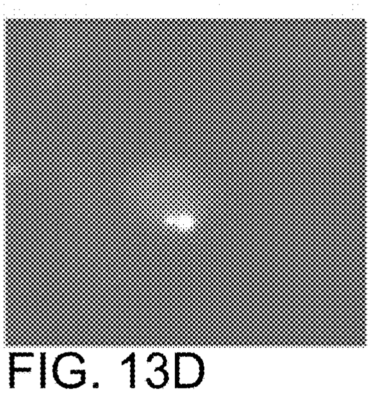
FIG. 13D
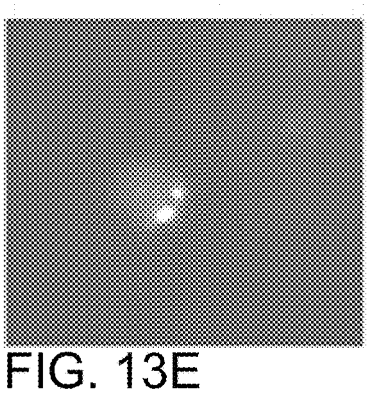
FIG. 13E
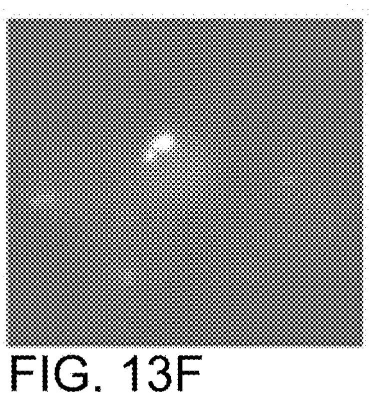
FIG. 13F

| | | Version 1 | Version 2 | Version 3 |
|---|---|---|---|---|
| Inlet Channel Width (Blood) | 50 | 50 | 100 | 100 |
| Inlet Channel Width (Buffer) | 55 | 55 | 110 | 110 |
| Outlet Channel Width (Product) | 49 | 49 | 98 | 98 |
| Outlet Channel Width (Waste) | 50 | 50 | 100 | 100 |
| Gap Size / Deflect Cell Size | | | | |
| Post Section 1 | 18/9 | 36/18 | 44/22 | 50/25 |
| Post Section 2 | 12/6 | 24/12 | 30/15 | 36/18 |
| Post Section 3 | 8/4 | 16/8 | 20/10 | 24/12 |
| Number of Parallel Sections | 14 | 14 | 14 | 14 |
| Etch Depth | 150 | 150 | 150 | 150 |
| Product Cell Size (Cut Off) | 4 | 8 | 10 | 12 |
| Estimated Flow Rate, ml/hr | 5 | 10 | 20 | 30 |

FIG. 19B

CAA→CAG (Silent) at 2361
ACG→ATG (T790M) at 2369

CTG→CGG (L828R) at 2573

ACC→ACT (Silent) at 2709

| | | | | | | | | | | | | | |
|---|---|---|---|---|---|---|---|---|---|---|---|---|---|
| WBC cDNA | - | + | - | - | + | - | - | + | - | - | + | - | Size Standards |
| H1650 cDNA | - | - | + | - | - | + | - | - | + | - | - | + | |
| Target mRNA | BCKD | | | CD45 | | | EpCaM | | | EGFR | | | |

| Tissue | Ct | [mRNA] |
|---|---|---|
| 1 Renal Blood Vessel | 24.02 | 25,916 |
| 2 Blood Mononuclear Cells (PBMC) | >40 | 0 |
| 3 Colon | 24.28 | 21,968 |
| 4 Primary Lung Bronchus | 24.49 | 19,224 |

RARE CELL ANALYSIS USING SAMPLE SPLITTING AND DNA TAGS

CROSS-REFERENCE

This application is a continuation of Ser. No. 16/193,916, filed on Nov. 16, 2018 and claims priority under 35 U.S.C. § 120 to U.S. application Ser. No. 14/697,372, filed on Apr. 27, 2015, now U.S. Pat. No. 10,155,984, which is a continuation of U.S. application Ser. No. 13/835,926, filed on Mar. 15, 2013, now U.S. Pat. No. 9,017,942, which is a continuation of U.S. application Ser. No. 13/306,640, filed on Nov. 29, 2011, now abandoned, which is a continuation of U.S. application Ser. No. 12/230,628, filed on Sep. 2, 2008, now U.S. Pat. No. 8,168,389, which is a continuation of and claims priority to U.S. application Ser. No. 11/763,421, filed on Jun. 14, 2007, now U.S. Pat. No. 8,372,584, which claims the benefit of U.S. Provisional Application Ser. No. 60/804,819, filed on Jun. 14, 2006 and U.S. Provisional Application Ser. No. 60/820,778, filed on Jul. 28, 2006, the entire disclosures of which are incorporated herein by reference.

SEQUENCE LISTING

This application contains a Sequence Listing that has been submitted electronically as an XML file named 26101-0025010_SL_ST26.xml. The XML file, created on Sep. 1, 2023, is 62,615 bytes in size. The material in the XML file is hereby incorporated by reference in its entirety.

BACKGROUND OF THE INVENTION

Analysis of specific cells can give insight into a variety of diseases. These analyses can provide non-invasive tests for detection, diagnosis and prognosis of diseases such as cancer or fetal disorders, thereby eliminating the risk of invasive diagnosis. Regarding fetal disorders, current prenatal diagnosis, such as amniocentesis and chorionic villus sampling (CVS), are potentially harmful to the mother and to the fetus. The rate of miscarriage for pregnant women undergoing amniocentesis is increased by 0.5-1%, and that figure is slightly higher for CVS. Because of the inherent risks posed by amniocentesis and CVS, these procedures are offered primarily to older women, e.g., those over 35 years of age, who have a statistically greater probability of bearing children with congenital defects. As a result, a pregnant woman at the age of 35 has to balance an average risk of 0.5-1% to induce an abortion by amniocentesis against an age related probability for trisomy 21 of less than 0.3%.

Regarding prenatal diagnostics, some non-invasive methods have already been developed to screen for fetuses at higher risk of having specific congenital defects. For example, maternal serum alpha-fetoprotein, and levels of unconjugated estriol and human chorionic gonadotropin can be used to identify a proportion of fetuses with Down's syndrome. However, these tests suffer from many false positive. Similarly, ultrasonography is used to determine congenital defects involving neural tube defects and limb abnormalities, but such methods are limited to time periods after fifteen weeks of gestation and are present unreliable results.

The presence of fetal cells within the blood of pregnant women offers the opportunity to develop a prenatal diagnostic that replaces amniocentesis and thereby eliminates the risk of today's invasive diagnosis. However, fetal cells represent a small number of cells against the background of a large number of maternal cells in the blood which make the analysis time consuming and prone to error.

With respect to cancer diagnosis, early detection is of paramount importance. Cancer is a disease marked by the uncontrolled proliferation of abnormal cells. In normal tissue, cells divide and organize within the tissue in response to signals from surrounding cells. Cancer cells do not respond in the same way to these signals, causing them to proliferate and, in many organs, form a tumor. As the growth of a tumor continues, genetic alterations may accumulate, manifesting as a more aggressive growth phenotype of the cancer cells. If left untreated, metastasis, the spread of cancer cells to distant areas of the body by way of the lymph system or bloodstream, may ensue. Metastasis results in the formation of secondary tumors at multiple sites, damaging healthy tissue. Most cancer death is caused by such secondary tumors. Despite decades of advances in cancer diagnosis and therapy, many cancers continue to go undetected until late in their development. As one example, most early-stage lung cancers are asymptomatic and are not detected in time for curative treatment, resulting in an overall five-year survival rate for patients with lung cancer of less than 15%. However, in those instances in which lung cancer is detected and treated at an early stage, the prognosis is much more favorable.

The methods of the present invention allow for the detection of fetal cells and fetal abnormalities when fetal cells are mixed with a population of maternal cells, even when the maternal cells dominate the mixture. In addition, the methods of the present invention can also be utilized to detect or diagnose cancer.

SUMMARY OF THE INVENTION

The present invention relates to methods for the detection of fetal cells or cancer cells in a mixed sample. In one embodiment, the present invention provides methods for determining fetal abnormalities in a sample comprising fetal cells that are mixed with a population of maternal cells. In some embodiments, determining the presence of fetal cells and fetal abnormalities comprises labeling one or more regions of genomic DNA in each cell from a mixed sample comprising at least one fetal cell with different labels wherein each label is specific to each cell. In some embodiments, the genomic DNA to be labeled comprises one or more polymorphisms, particularly STRs or SNPs In some embodiments, the methods of the invention allow for simultaneously detecting the presence of fetal cells and fetal abnormalities when fetal cells are mixed with a population of maternal cells, even when the maternal cells dominate the mixture. In some embodiments, the sample is enriched to contain at least one fetal and one non fetal cell, and in other embodiments, the cells of the enriched population can be divided between two or more discrete locations that can be used as addressable locations. Examples of addressable locations include wells, bins, sieves, pores, geometric sites, slides, matrixes, membranes, electric traps, gaps, obstacles or in-situ within a cell or nuclear membrane.

In some embodiments, the methods comprise labeling one or more regions of genomic DNA in each cell in the enriched sample with different labels, wherein each label is specific to each cell, and quantifying the labeled DNA regions. The labeling methods can comprise adding a unique tag sequence for each cell in the mixed sample. In some embodiments, the unique tag sequence identifies the presence or absence of a DNA polymorphism in each cell from the mixed sample. Labels are added to the cells/DNA using an amplification reaction, which can be performed by PCR methods. For example, amplification can be achieved by multiplex PCR. In some embodiments, a further PCR amplification is performed using nested primers for the genomic DNA region(s).

In some embodiments, the DNA regions can be amplified prior to being quantified. The labeled DNA can be quantified using sequencing methods, which, in some embodiments, can precede amplifying the DNA regions. The amplified DNA region(s) can be analyzed by sequencing methods. For example, ultra deep sequencing can be used to provide an accurate and quantitative measurement of the allele abundances for each STR or SNP. In other embodiments, quantitative genotyping can be used to declare the presence of fetal cells and to determine the copy numbers of the fetal chromosomes. Preferably, quantitative genotyping is performed using molecular inversion probes.

The invention also relates to methods of identifying cells from a mixed sample with non-maternal genomic DNA and identifying said cells with non-maternal genomic DNA as fetal cells. In some embodiments, the ratio of maternal to paternal alleles is compared on the identified fetal cells in the mixed sample.

In one embodiment, the invention provides for a method for determining a fetal abnormality in a maternal sample that comprises at least one fetal and one non fetal cell. The sample can be enriched to contain at least one fetal cell, and the enriched maternal sample can be arrayed into a plurality of discrete sites. In some embodiments, each discrete site comprises no more than one cell.

In some embodiments, the invention comprises labeling one or more regions of genomic DNA from the arrayed samples using primers that are specific to each DNA region or location, amplifying the DNA region(s), and quantifying the labeled DNA region. The labeling of the DNA region(s) can comprise labeling each region with a unique tag sequence, which can be used to identify the presence or absence of a DNA polymorphism on arrayed cells and the distinct location of the cells.

The step of determining can comprise identifying non-maternal alleles at the distinct locations, which can result from comparing the ratio of maternal to paternal alleles at the location. In some embodiments, the method of identifying a fetal abnormality in an arrayed sample can further comprise amplifying the genomic DNA regions. The genomic DNA regions can comprise one or more polymorphisms e.g. STRs and SNPs, which can be amplified using PCR methods including multiplex PCR. An additional amplification step can be performed using nested primers.

The amplified DNA region(s) can be analyzed by sequencing methods. For example, ultra deep sequencing can be used to provide an accurate and quantitative measurement of the allele abundances for each STR or SNP. In other embodiments, quantitative genotyping can be sued to declare the presence of fetal cells and to determine the copy numbers of the fetal chromosomes. Preferably, quantitative genotyping is performed using molecular inversion probes.

In one embodiment, the invention provides methods for diagnosing a cancer and giving a prognosis by obtaining and enriching a blood sample from a patient for epithelial cells, splitting the enriched sample into discrete locations, and performing one or more molecular and/or morphological analyses on the enriched and split sample. The molecular analyses can include detecting the level of expression or a mutation of gene disclosed in FIG. 10. Preferably, the method comprises performing molecular analyses on EGFR, EpCAM, GA733-2, MUC-1, HER-2, or Claudin-7 in each arrayed cell. The morphological analyses can include identifying, quantifying and/or characterizing mitochondrial DNA, telomerase, or nuclear matrix proteins.

In some embodiments, the sample can be enriched for epithelial cells by at least 10,000 fold, and the diagnosis and prognosis can be provided prior to treating the patient for the cancer. Preferably, the blood samples are obtained from a patient at regular intervals such as daily, or every 2, 3 or 4 days, weekly, bimonthly, monthly, bi-yearly or yearly.

In some embodiments, the step of enriching a patient's blood sample for epithelial cells involves flowing the sample through a first array of obstacles that selectively directs cells that are larger than a predetermined size to a first outlet and cells that are smaller than a predetermined size to a second outlet. Optionally, the sample can be subjected to further enrichment by flowing the sample through a second array of obstacles, which can be coated with antibodies that selectively bind to white blood cells or epithelial cells. For example, the obstacles of the second array can be coated with anti-EpCAM antibodies.

Splitting the sample of cells of the enriched population can comprises splitting the enriched sample to locate individual cells at discrete sites that can be addressable sites. Examples of addressable locations include wells, bins, sieves, pores, geometric sites, slides, matrixes, membranes, electric traps, gaps, obstacles or in-situ within a cell or nuclear membrane.

In some embodiments there are provided kits comprising devices for enriching the sample and the devices and reagents needed to perform the genetic analysis. The kits may contain the arrays for size-based separation, reagents for uniquely labeling the cells, devices for splitting the cells into individual addressable locations and reagents for the genetic analysis.

SUMMARY OF THE DRAWINGS

FIG. 7A shows these steps. FIG. 7C illustrates an overview of the use of nucleic acid tags.

FIGS. 10A-D illustrate genes whose expression or mutations can be associated with cancer or another condition diagnosed herein.

FIG. 11 illustrates primers useful in the methods herein.

FIGS. 13A-F illustrate isolated fetal cells confirmed by the reliable presence of male cells.

FIGS. 19A-C illustrate one embodiment of a flow-through size-based separation module adapted to separate epithelial cells from blood and alternative parameters that can be used with such device.

INCORPORATION BY REFERENCE

Figure 1A:
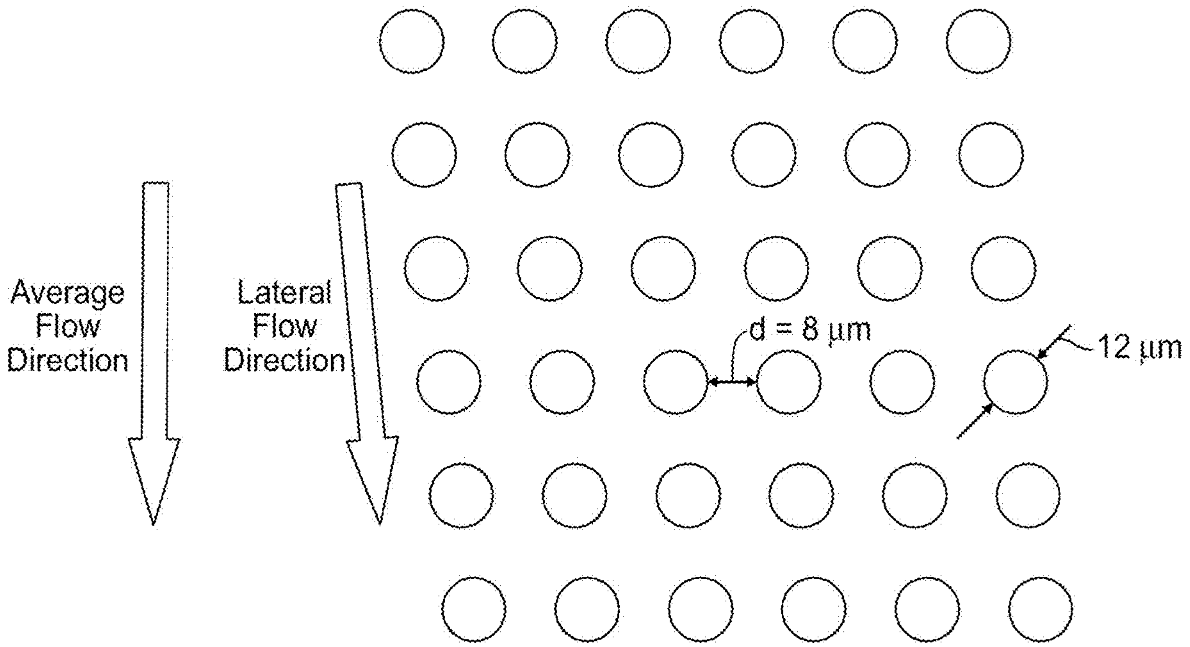
FIGS. 1A-1D illustrate various embodiments of a size-based separation module.

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention provides systems, apparatus, and methods to detect the presence of or abnormalities of rare analytes or cells, such as hematopoietic bone marrow progenitor cells, endothelial cells, fetal cells, epithelial cells, or circulating tumor cells in a sample of a mixed analyte or cell population (e.g., maternal peripheral blood samples).

I. Sample Collection/Preparation

Samples containing rare cells can be obtained from any animal in need of a diagnosis or prognosis or from an animal pregnant with a fetus in need of a diagnosis or prognosis. In one example, a sample can be obtained from animal suspected of being pregnant, pregnant, or that has been pregnant to detect the presence of a fetus or fetal abnormality. In another example, a sample is obtained from an animal suspected of having, having, or an animal that had a disease or condition (e.g. cancer). Such condition can be diagnosed, prognosed, monitored and therapy can be determined based on the methods and systems herein. Animal of the present invention can be a human or a domesticated animals such as a cow, chicken, pig, horse, rabbit, dogs, cat, or goat. Samples derived from an animal or human can include, e.g., whole blood, sweat, tears, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid.

To obtain a blood sample, any technique known in the art may be used, e.g. a syringe or other vacuum suction device. A blood sample can be optionally pre-treated or processed prior to enrichment. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a cross-linking reagent.

When a blood sample is obtained, a preservative such an anti-coagulation agent and/or a stabilizer is often added to the sample prior to enrichment. This allows for extended time for analysis/detection. Thus, a sample, such as a blood sample, can be enriched and/or analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained.

In some embodiments, a blood sample can be combined with an agent that selectively lyses one or more cells or components in a blood sample. For example, fetal cells can be selectively lysed releasing their nuclei when a blood sample including fetal cells is combined with deionized water. Such selective lysis allows for the subsequent enrichment of fetal nuclei using, e.g., size or affinity based separation. In another example platelets and/or enucleated red blood cells are selectively lysed to generate a sample enriched in nucleated cells, such as fetal nucleated red blood cells (fnRBC's), maternal nucleated blood cells (mnBC), epithelial cells and circulating tumor cells. fnRBC's can be subsequently separated from mnBC's using, e.g., antigen-i affinity or differences in hemoglobin When obtaining a sample from an animal (e.g., blood sample), the amount can vary depending upon animal size, its gestation period, and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

To detect fetal abnormality, a blood sample can be obtained from a pregnant animal or human within 36, 24, 22, 20, 18, 16, 14, 12, 10, 8, 6 or 4 weeks of gestation.

II. Enrichment

A sample (e.g. blood sample) can be enriched for rare analytes or rare cells (e.g. fetal cells, epithelial cells or circulating tumor cells) using one or more any methods known in the art (e.g. Guetta, E M et al. Stem Cells Dev, 13(1):93-9 (2004)) or described herein. The enrichment increases the concentration of rare cells or ratio of rare cells to non-rare cells in the sample. For example, enrichment can increase concentration of an analyte of interest such as a fetal cell or epithelial cell or CTC by a factor of at least 2, 4, 6, 8, 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 50,000,000, 100,000,000, 200,000,000, 500,000,000, 1,000,000,000, 2,000,000,000, or 5,000,000,000 fold over its concentration in the original sample. In particular, when enriching fetal cells from a maternal peripheral venous blood sample, the initial concentration of the fetal cells may be about 1:50,000,000 and it may be increased to at least 1:5,000 or 1:500. Enrichment can also increase concentration of rare cells in volume of rare cells/total volume of sample (removal of fluid). A fluid sample (e.g., a blood sample) of greater than 10, 15, 20, 50, or 100 mL total volume comprising rare components of interest, and it can be concentrated such that the rare component of interest into a concentrated solution of less than 0.5, 1, 2, 3, 5, or 10 mL total volume.

Enrichment can occur using one or more types of separation modules. Several different modules are described herein, all of which can be fluidly coupled with one another in the series for enhanced performance.

In some embodiments, enrichment occurs by selective lysis as described above.

In one embodiment, enrichment of rare cells occurs using one or more size-based separation modules. Examples of size-based separation modules include filtration modules, sieves, matrixes, etc. Examples of size-based separation modules contemplated by the present invention include those disclosed in International Publication No. WO 2004/113877. Other size based separation modules are disclosed in International Publication No. WO 2004/0144651.

In some embodiments, a size-based separation module comprises one or more arrays of obstacles forming a network of gaps. The obstacles are configured to direct particles as they flow through the array/network of gaps into different directions or outlets based on the particle's hydrodynamic size. For example, as a blood sample flows through an array of obstacles, nucleated cells or cells having a hydrodynamic size larger than a predetermined certain size such as a cutoff or predetermined size, e.g., 8 microns, are directed to a first outlet located on the opposite side of the array of obstacles from the fluid flow inlet, while the enucleated cells or cells having a hydrodynamic size smaller than a predetermined size, e.g., 8 microns, are directed to a second outlet also located on the opposite side of the array of obstacles from the fluid flow inlet.

An array can be configured to separate cells smaller or larger than a predetermined size by adjusting the size of the gaps, obstacles, and offset in the period between each successive row of obstacles. For example, in some embodiments, obstacles or gaps between obstacles can be up to 10, 20, 50, 70, 100, 120, 150, 170, or 200 microns in length or about 2, 4, 6, 8 or 10 microns in length. In some embodiments, an array for size-based separation includes more than 100, 500, 1,000, 5,000, 10,000, 50,000 or 100,000 obstacles that are arranged into more than 10, 20, 50, 100, 200, 500, or 1000 rows. Preferably, obstacles in a first row of obstacles are offset from a previous (upstream) row of obstacles by up to 50% the period of the previous row of obstacles. In some embodiments, obstacles in a first row of obstacles are offset from a previous row of obstacles by up to 45, 40, 35, 30, 25, 20, 15 or 10% the period of the previous row of obstacles. Furthermore, the distance between a first row of obstacles and a second row of obstacles can be up to 10, 20, 50, 70, 100, 120, 150, 170 or 200 microns. A particular offset can be continuous (repeating for multiple rows) or non-continuous. In some embodiments, a separation module includes multiple discrete arrays of obstacles fluidly coupled such that they are in series with one another. Each array of obstacles has a continuous offset. But each subsequent (downstream) array of obstacles has an offset that is different from the previous (upstream) offset. Preferably, each subsequent array of obstacles has a smaller offset that the previous array of obstacles. This allows for a refinement in the separation process as cells migrate through the array of obstacles. Thus, a plurality of arrays can be fluidly coupled in series or in parallel, (e.g., more than 2, 4, 6, 8, 10, 20, 30, 40, 50). Fluidly coupling separation modules (e.g., arrays) in parallel allows for high-throughput analysis of the sample, such that at least 1, 2, 5, 10, 20, 50, 100, 200, or 500 mL per hour flows through the enrichment modules or at least 1, 5, 10, or 50 million cells per hour are sorted or flow through the device.

FIG. 1A illustrates an example of a size-based separation module. Obstacles (which may be of any shape) are coupled to a flat substrate to form an array of gaps. A transparent cover or lid may be used to cover the array. The obstacles form a two-dimensional array with each successive row shifted horizontally with respect to the previous row of obstacles, where the array of obstacles directs component having a hydrodynamic size smaller than a predetermined size in a first direction and component having a hydrodynamic size larger that a predetermined size in a second direction. For enriching epithelial or circulating tumor cells from enucleated, the predetermined size of an array of obstacles can be get at 6-12 μm or 6-8 μm. For enriching fetal cells from a mixed sample (e.g. maternal blood sample) the predetermined size of an array of obstacles can be between 4-10 μm or 6-8 μm. The flow of sample into the array of obstacles can be aligned at a small angle (flow angle) with respect to a line-of-sight of the array. Optionally, the array is coupled to an infusion pump to perfuse the sample through the obstacles. The flow conditions of the size-based separation module described herein are such that cells are sorted by the array with minimal damage. This allows for downstream analysis of intact cells and intact nuclei to be more efficient and reliable.

Figure 1B:
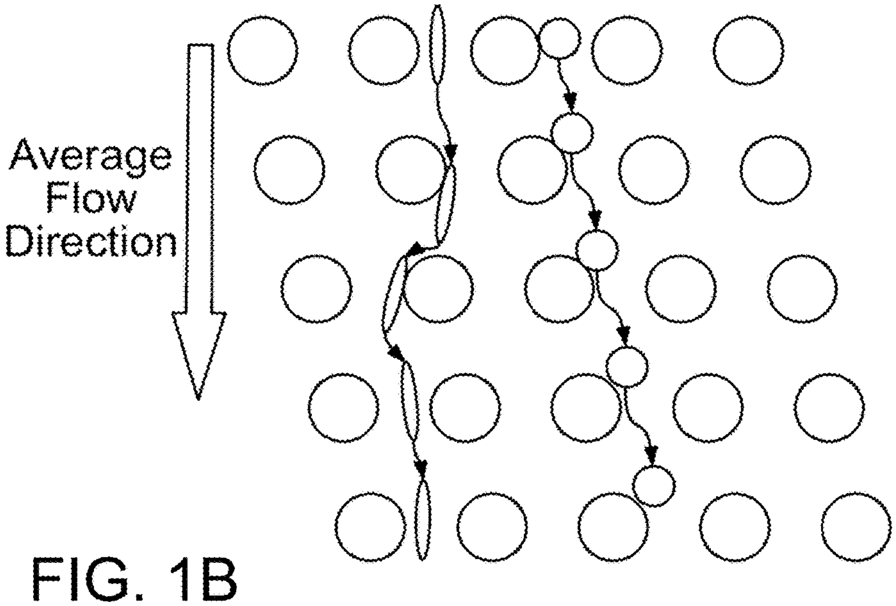
Figure 1C:
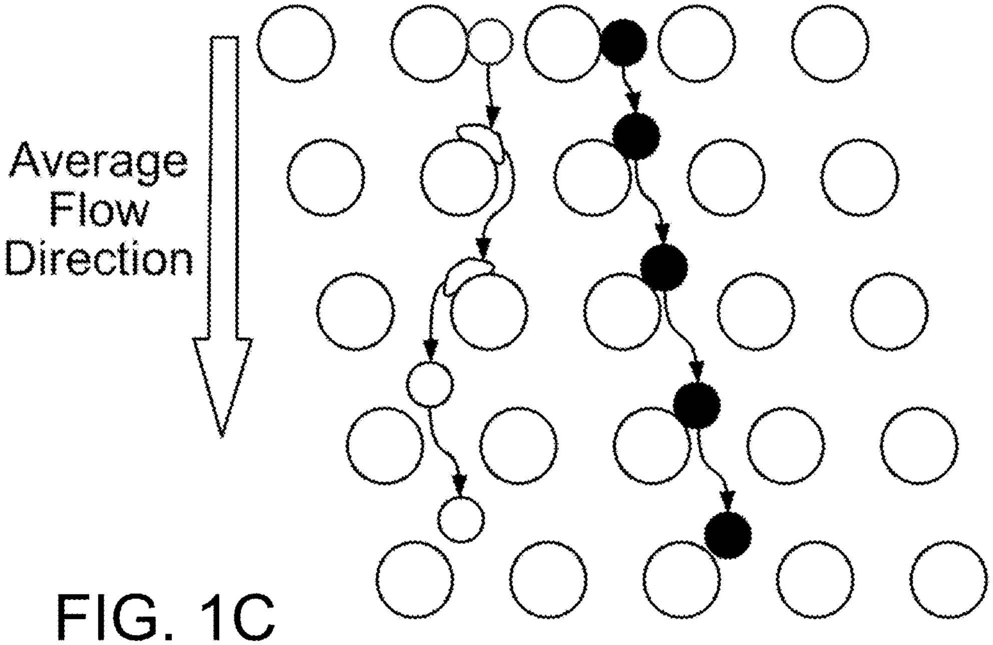
Figure 1D:
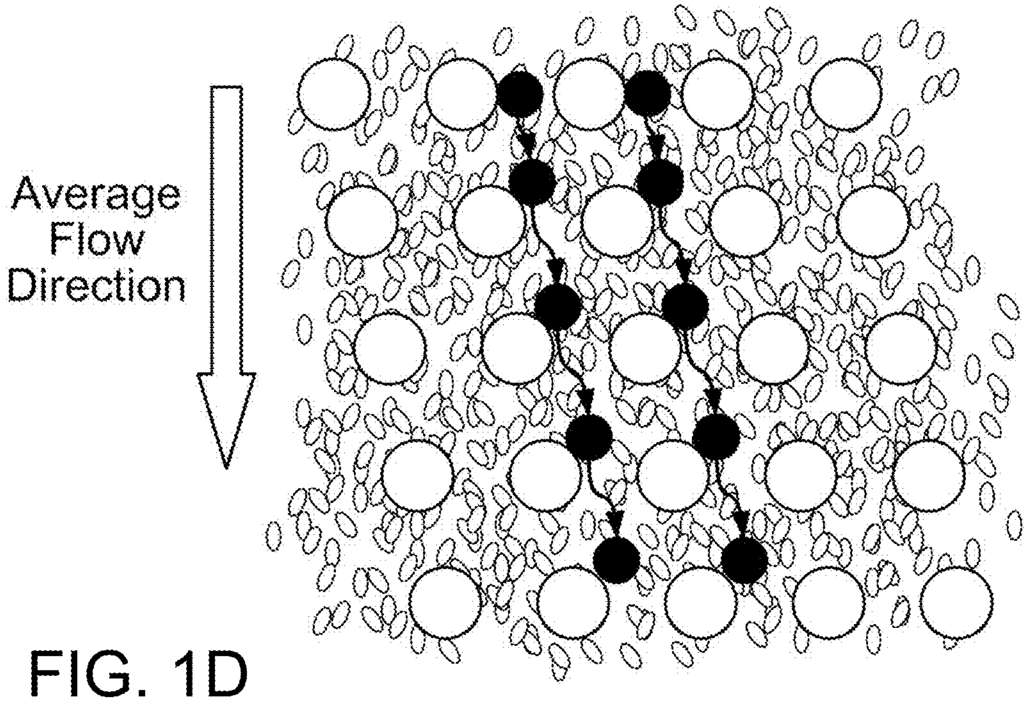

In some embodiments, a size-based separation module comprises an array of obstacles configured to direct cells larger than a predetermined size to migrate along a line-of-sight within the array (e.g. towards a first outlet or bypass channel leading to a first outlet), while directing cells and analytes smaller than a predetermined size to migrate through the array of obstacles in a different direction than the larger cells (e.g. towards a second outlet). Such embodiments are illustrated in part in FIGS. 1B-1D.

A variety of enrichment protocols may be utilized although gentle handling of the cells is needed to reduce any mechanical damage to the cells or their DNA. This gentle handling also preserves the small number of fetal or rare cells in the sample. Integrity of the nucleic acid being evaluated is an important feature to permit the distinction between the genomic material from the fetal or rare cells and other cells in the sample. In particular, the enrichment and separation of the fetal or rare cells using the arrays of obstacles produces gentle treatment which minimizes cellular damage and maximizes nucleic acid integrity permitting exceptional levels of separation and the ability to subsequently utilize various formats to very accurately analyze the genome of the cells which are present in the sample in extremely low numbers.

In some embodiments, enrichment of rare cells (e.g. fetal cells, epithelial cells or circulating tumor cells (CTCs)) occurs using one or more capture modules that selectively inhibit the mobility of one or more cells of interest. Preferable a capture module is fluidly coupled downstream to a size-based separation module. Capture modules can include a substrate having multiple obstacles that restrict the movement of cells or analytes greater than a predetermined size. Examples of capture modules that inhibit the migration of cells based on size are disclosed in U.S. Pat. Nos. 5,837,115 and 6,692,952.

In some embodiments, a capture module includes a two dimensional array of obstacles that selectively filters or captures cells or analytes having a hydrodynamic size greater than a particular gap size (predetermined size), International Publication No. WO 2004/113877.

In some cases a capture module captures analytes (e.g., cells of interest or not of interest) based on their affinity. For example, an affinity-based separation module that can capture cells or analytes can include an array of obstacles adapted for permitting sample flow through, but for the fact that the obstacles are covered with binding moieties that selectively bind one or more analytes (e.g., cell populations) of interest (e.g., red blood cells, fetal cells, epithelial cells or nucleated cells) or analytes not-of-interest (e.g., white blood cells). Arrays of obstacles adapted for separation by capture can include obstacles having one or more shapes and can be arranged in a uniform or non-uniform order. In some embodiments, a two-dimensional array of obstacles is staggered such that each subsequent row of obstacles is offset from the previous row of obstacles to increase the number of interactions between the analytes being sorted (separated) and the obstacles.

Binding moieties coupled to the obstacles can include e.g., proteins (e.g., ligands/receptors), nucleic acids having complementary counterparts in retained analytes, antibodies, etc. In some embodiments, an affinity-based separation module comprises a two-dimensional array of obstacles covered with one or more antibodies selected from the group consisting of: anti-CD71, anti-CD235a, anti-CD36, anti-carbohydrates, anti-selectin, anti-CD45, anti-GPA, anti-antigen-i, anti-EpCAM, anti-E-cadherin, and anti-Muc-1.

Figure 2A:
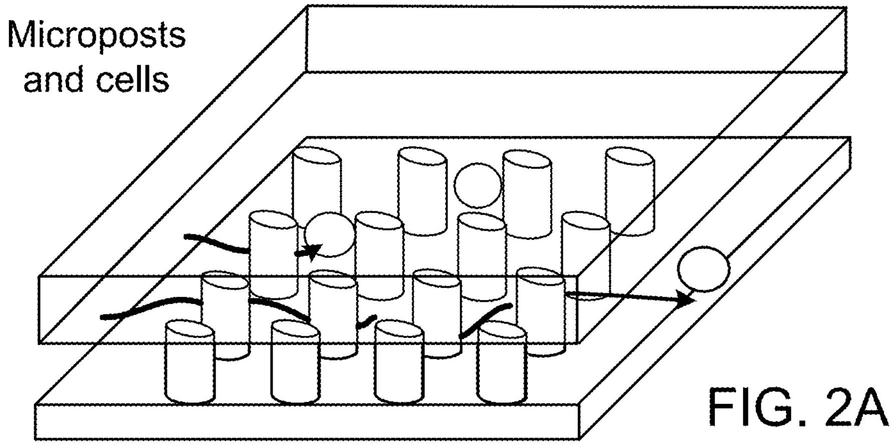
FIGS. 2A-2C illustrate one embodiment of an affinity separation module.
Figure 2B:
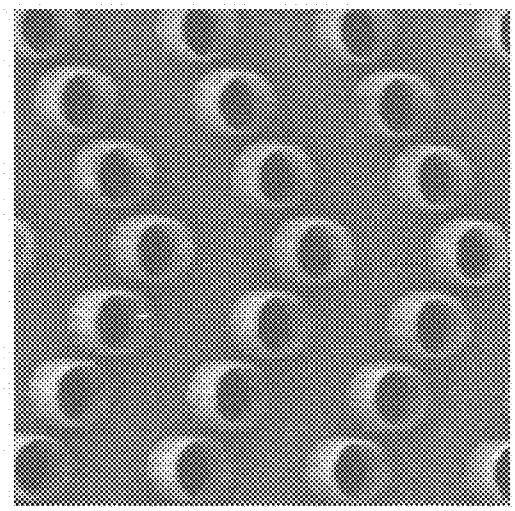
Figure 2C:
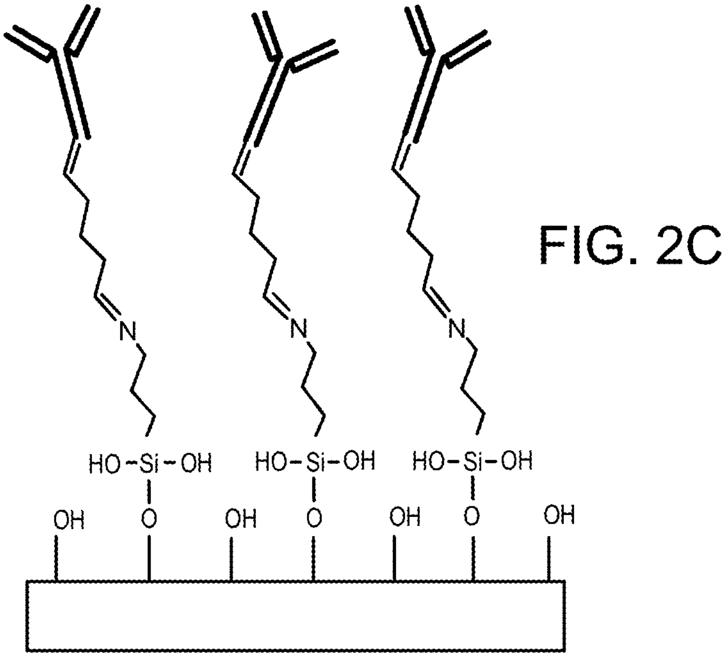

FIG. 2A illustrates a path of a first analyte through an array of posts wherein an analyte that does not specifically bind to a post continues to migrate through the array, while an analyte that does bind a post is captured by the array. FIG. 2B is a picture of antibody coated posts. FIG. 2C illustrates coupling of antibodies to a substrate (e.g., obstacles, side walls, etc.) as contemplated by the present invention. Examples of such affinity-based separation modules are described in International Publication No. WO 2004/029221.

In some embodiments, a capture module utilizes a magnetic field to separate and/or enrich one or more analytes (cells) based on a magnetic property or magnetic potential in such analyte of interest or an analyte not of interest. For example, red blood cells which are slightly diamagnetic (repelled by magnetic field) in physiological conditions can be made paramagnetic (attributed by magnetic field) by deoxygenation of the hemoglobin into methemoglobin. This magnetic property can be achieved through physical or chemical treatment of the red blood cells. Thus, a sample containing one or more red blood cells and one or more white blood cells can be enriched for the red blood cells by first inducing a magnetic property in the red blood cells and then separating the red blood cells from the white blood cells by flowing the sample through a magnetic field (uniform or non-uniform).

For example, a maternal blood sample can flow first through a size-based separation module to remove enucleated cells and cellular components (e.g., analytes having a hydrodynamic size less than 6 μms) based on size. Subsequently, the enriched nucleated cells (e.g., analytes having a hydrodynamic size greater than 6 ums) white blood cells and nucleated red blood cells are treated with a reagent, such as $CO_2$, $N_2$, or $NaNO_2$, that changes the magnetic property of the red blood cells' hemoglobin. The treated sample then flows through a magnetic field (e.g., a column coupled to an external magnet), such that the paramagnetic analytes (e.g., red blood cells) will be captured by the magnetic field while the white blood cells and any other non-red blood cells will flow through the device to result in a sample enriched in nucleated red blood cells (including fetal nucleated red blood cells or fnRBC's). Additional examples of magnetic separation modules are described in U.S. application Ser. No. 11/323,971, filed Dec. 29, 2005 entitled "Devices and Methods for Magnetic Enrichment of Cells and Other Particles" and U.S. application Ser. No. 11/227,904, filed Sep. 15, 2005, entitled "Devices and Methods for Enrichment and Alteration of Cells and Other Particles".

Subsequent enrichment steps can be used to separate the rare cells (e.g. fnRBC's) from the non-rare cells maternal nucleated red blood cells. In some embodiments, a sample enriched by size-based separation followed by affinity/magnetic separation is further enriched for rare cells using fluorescence activated cell sorting (FACS) or selective lysis of a subset of the cells.

In some embodiments, enrichment involves detection and/or isolation of rare cells or rare DNA (e.g. fetal cells or fetal DNA) by selectively initiating apoptosis in the rare cells. This can be accomplished, for example, by subjecting a sample that includes rare cells (e.g. a mixed sample) to hyperbaric pressure (increased levels of $CO_2$; e.g. 4% $CO_2$). This will selectively initiate apoptosis in the rare or fragile cells in the sample (e.g. fetal cells). Once the rare cells (e.g. fetal cells) begin apoptosis, their nuclei will condense and optionally be ejected from the rare cells. At that point, the rare cells or nuclei can be detected using any technique known in the art to detect condensed nuclei, including DNA gel electrophoresis, in situ labeling of DNA nick using terminal deoxynucleotidyl transferase (TdT)-mediated dUTP in situ nick labeling (TUNEL) (Gavrieli, Y., et al. J. Cell Biol. 119:493-501 (1992)), and ligation of DNA strand breaks having one or two-base 3' overhangs (Taq polymerase-based in situ ligation). (Didenko V., et al. J. Cell Biol. 135:1369-76 (1996)).

In some embodiments ejected nuclei can further be detected using a size based separation module adapted to selectively enrich nuclei and other analytes smaller than a predetermined size (e.g. 6 microns) and isolate them from cells and analytes having a hydrodynamic diameter larger than 6 microns. Thus, in one embodiment, the present invention contemplated detecting fetal cells/fetal DNA and optionally using such fetal DNA to diagnose or prognose a condition in a fetus. Such detection and diagnosis can occur by obtaining a blood sample from the female pregnant with the fetus, enriching the sample for cells and analytes larger than 8 microns using, for example, an array of obstacles adapted for size-base separation where the predetermined size of the separation is 8 microns (e.g. the gap between obstacles is up to 8 microns). Then, the enriched product is further enriched for red blood cells (RBC's) by oxidizing the sample to make the hemoglobin puramagnetic and flowing the sample through one or more magnetic regions. This selectively captures the RBC's and removes other cells (e.g. white blood cells) from the sample. Subsequently, the fnRBC's can be enriched from mnRBC's in the second enriched product by subjecting the second enriched product to hyperbaric pressure or other stimulus that selectively causes the fetal cells to begin apoptosis and condense/eject their nuclei. Such condensed nuclei are then identified/isolated using e.g. laser capture microdissection or a size based separation module that separates components smaller than 3, 4, 5 or 6 microns from a sample. Such fetal nuclei can then by analyzed using any method known in the art or described herein.

In some embodiments, when the analyte desired to be separated (e.g., red blood cells or white blood cells) is not ferromagnetic or does not have a potential magnetic property, a magnetic particle (e.g., a bead) or compound (e.g., $Fe^{3+}$) can be coupled to the analyte to give it a magnetic property. In some embodiments, a bead coupled to an antibody that selectively binds to an analyte of interest can be decorated with an antibody elected from the group of anti CD71 or CD75. In some embodiments a magnetic compound, such as $Fe^{3+}$, can be couple to an antibody such as those described above. The magnetic particles or magnetic antibodies herein may be coupled to any one or more of the devices herein prior to contact with a sample or may be mixed with the sample prior to delivery of the sample to the device(s). Magnetic particles can also be used to decorate one or more analytes (cells of interest or not of interest) to increase the size prior to performing size-based separation.

Magnetic field used to separate analytes/cells in any of the embodiments herein can uniform or non-uniform as well as external or internal to the device(s) herein. An external magnetic field is one whose source is outside a device herein (e.g., container, channel, obstacles). An internal magnetic field is one whose source is within a device contemplated herein. An example of an internal magnetic field is one where magnetic particles may be attached to obstacles present in the device (or manipulated to create obstacles) to increase surface area for analytes to interact with to increase the likelihood of binding. Analytes captured by a magnetic field can be released by demagnetizing the magnetic regions retaining the magnetic particles. For selective release of analytes from regions, the demagnetization can be limited to selected obstacles or regions. For example, the magnetic field can be designed to be electromagnetic, enabling turn-on and turn-off off the magnetic fields for each individual region or obstacle at will.

Figure 3:
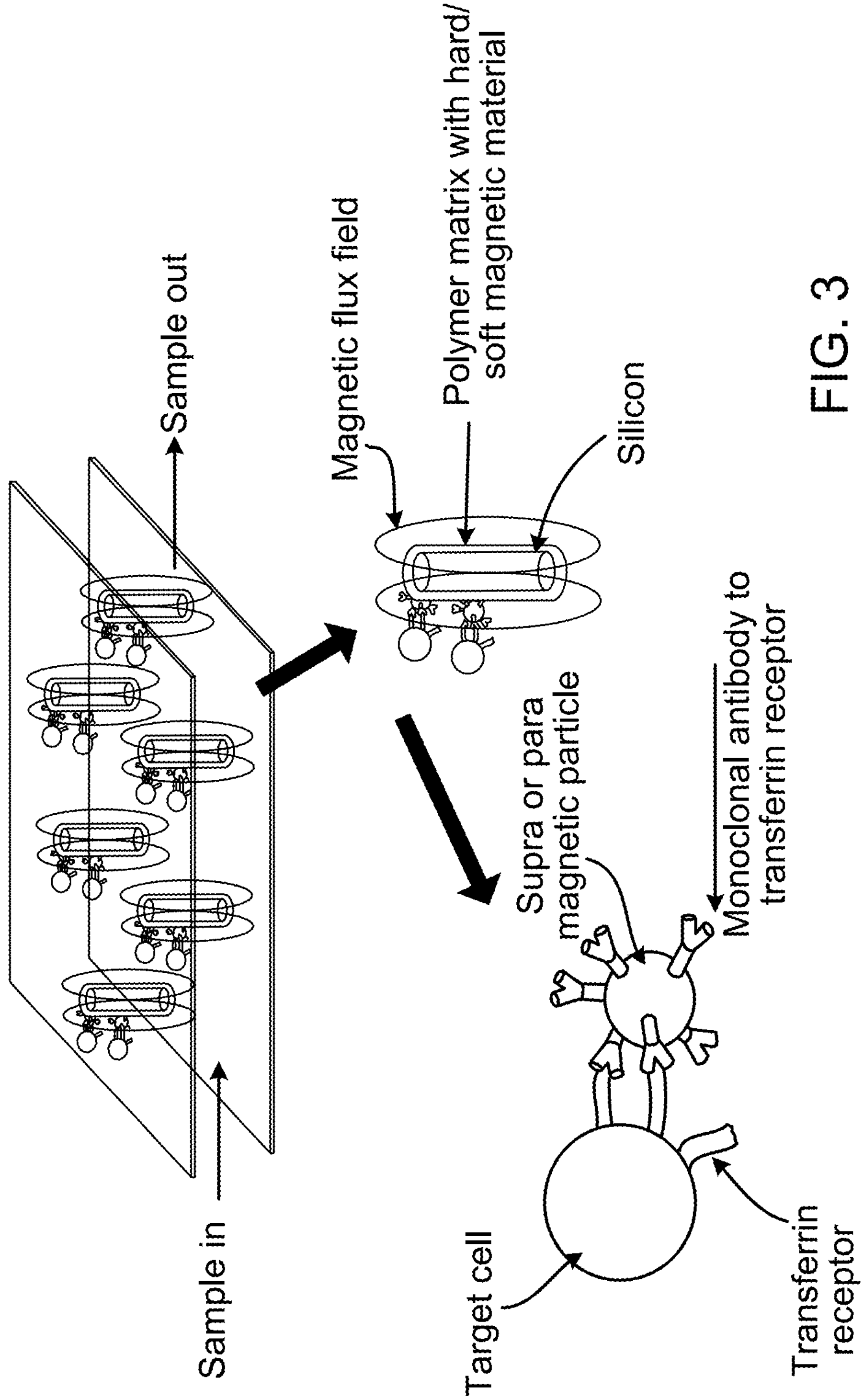
FIG. 3 illustrates one embodiment of a magnetic separation module.

FIG. 3 illustrates an embodiment of a device configured for capture and isolation of cells expressing the transferrin receptor from a complex mixture. Monoclonal antibodies to CD71 receptor are readily available off-the-shelf and can be covalently coupled to magnetic materials comprising any conventional ferroparticles, such as, but not limited to ferrous doped polystyrene and ferroparticles or ferro-colloids (e.g., from Miltenyi and Dynal). The anti CD71 bound to magnetic particles is flowed into the device. The antibody coated particles are drawn to the obstacles (e.g., posts), floor, and walls and are retained by the strength of the magnetic field interaction between the particles and the magnetic field. The particles between the obstacles and those loosely retained with the sphere of influence of the local magnetic fields away from the obstacles are removed by a rinse.

One or more of the enrichment modules herein (e.g., size-based separation module(s) and capture module(s)) may be fluidly coupled in series or in parallel with one another. For example a first outlet from a separation module can be fluidly coupled to a capture module. In some embodiments, the separation module and capture module are integrated such that a plurality of obstacles acts both to deflect certain analytes according to size and direct them in a path different than the direction of analyte(s) of interest, and also as a capture module to capture, retain, or bind certain analytes based on size, affinity, magnetism or other physical property.

In any of the embodiments herein, the enrichment steps performed have a specificity and/or sensitivity greater than 50, 60, 70, 80, 90, 95, 96, 97, 98, 99, 99.1, 99.2, 99.3, 99.4, 99.5, 99.6, 99.7, 99.8, 99.9 or 99.95% The retention rate of the enrichment module(s) herein is such that ≥50, 60, 70, 80, 90, 91, 92, 93, 94, 95, 96, 97, 98, 99, or 99.9% of the analytes or cells of interest (e.g., nucleated cells or nucleated red blood cells or nucleated from red blood cells) are retained. Simultaneously, the enrichment modules are configured to remove ≥50, 60, 70, 80, 85, 90, 91, 92, 93, 94, 95, 96, 97, 98, 99, or 99.9% of all unwanted analytes (e.g., red blood-platelet enriched cells) from a sample.

Any of the enrichment methods herein may be further supplemented by splitting the enriched sample into aliquots or sub-samples. In some embodiments, an enriched sample is split into at least 2, 5, 10, 20, 50, 100, 200, 500, or 1000 sub-samples. Thus when an enriched sample comprises about 500 cells and is split into 500 or 1000 different sub-samples, each sub-sample will have 1 or 0 cells.

In some cases a sample is split or arranged such that each sub-sample is in a unique or distinct location (e.g., well). Such location may be addressable. Each site can further comprise a capture mechanism to capture cell(s) to the site of interest and/or release mechanism for selectively releasing cells from the site of interest. In some cases, the well is configured to hold a single cell.

III. Sample Analysis

In some embodiments, the methods herein are used for detecting the presence or conditions of rare cells that are in a mixed sample (optionally even after enrichment) at a concentration of up to 90%, 80%, 70%, 60%, 50%, 40%, 30%, 20%, 10%, 5% or 1% of all cells in the mixed sample, or at a concentration of less than 1:2, 1:4, 1:10, 1:50, 1:100, 1:200, 1:500, 1:1000, 1:2000, 1:5000, 1:10,000, 1:20,000, 1:50,000, 1:100,000, 1:200,000, 1:1,000,000, 1:2,000,000, 1:5,000,000, 1:10,000,000, 1:20,000,000, 1:50,000,000 or 1:100,000,000 of all cells in the sample, or at a concentration of less than $1\times10^{-3}$, $1\times10^{-4}$, $1\times10^{-5}$, $1\times10^{-6}$, or $1\times10^{-7}$ cells/μL of a fluid sample. In some embodiments, the mixed sample has a total of up to 2, 3, 4, 5, 6, 7, 8, 9, 10, 15, 20, 30, 40, 50, or 100 rare cells (e.g. fetal cells or epithelial cells).

Figure 34:
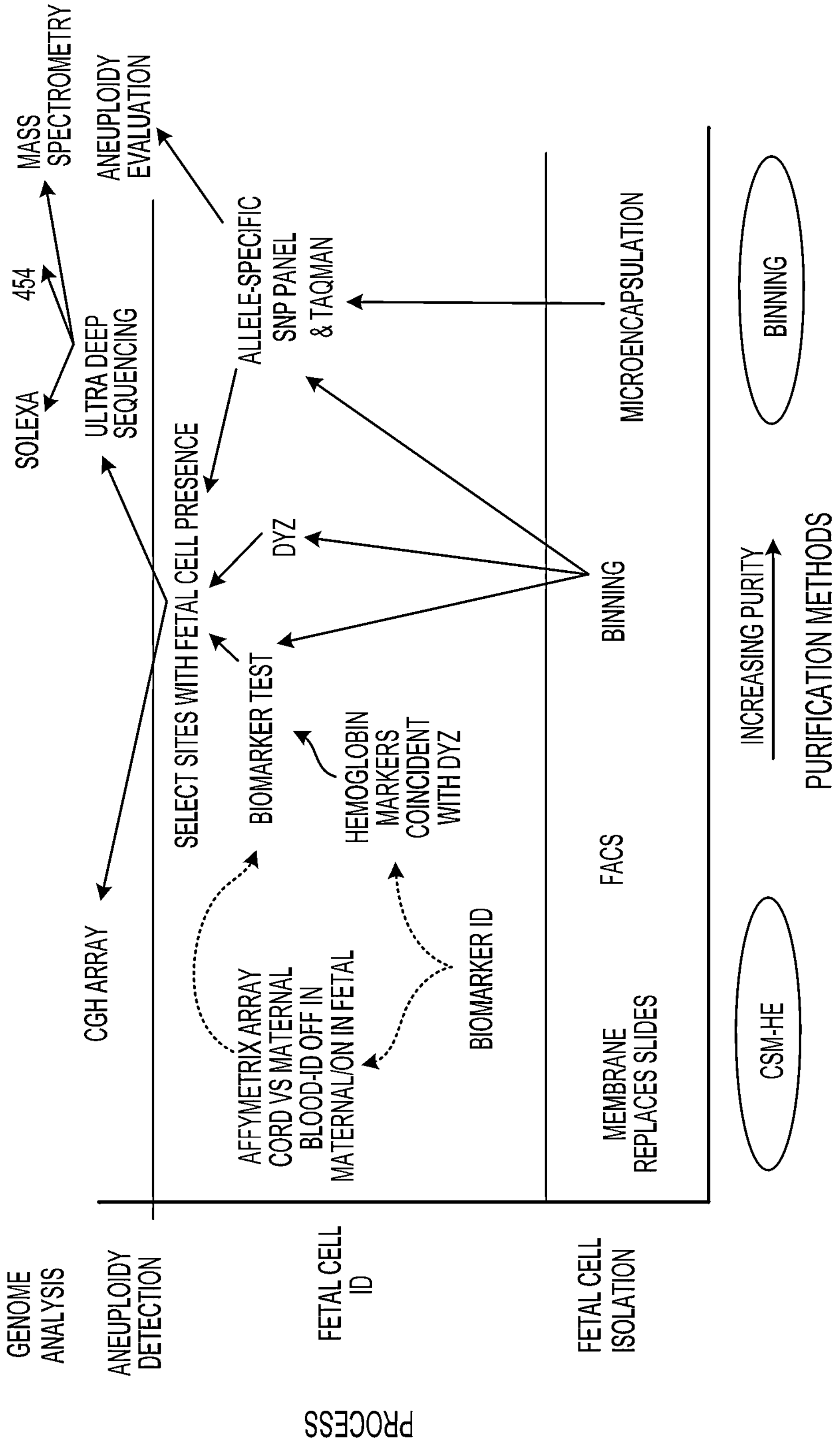
FIG. 34 illustrates methods of fetal diagnostic assays. Fetal cells are isolated by CSM-HE enrichment of target cells from blood. The designation of the fetal cells may be confirmed using techniques comprising FISH staining (using slides or membranes and optionally an automated detector), FACS, and/or binning. Binning may comprise distribution of enriched cells across wells in a plate (such as a 96 or 384 well plate), microencapsulation of cells in droplets that are separated in an emulsion, or by introduction of cells into microarrays of nanofluidic bins. Fetal cells are then identified using methods that may comprise the use of biomarkers (such as fetal (gamma) hemoglobin), allele-specific SNP panels that could detect fetal genome DNA, detection of differentially expressed maternal and fetal transcripts (such as Affymetrix chips), or primers and probes directed to fetal specific loci (such as the multi-repeat DYZ locus on the Y-chromosome). Binning sites that contain fetal cells are then be analyzed for aneuploidy and/or other genetic defects using a technique such as CGH array detection, ultra deep sequencing (such as Solexa, 454, or mass spectrometry), STR analysis, or SNP detection.
Figure 35:
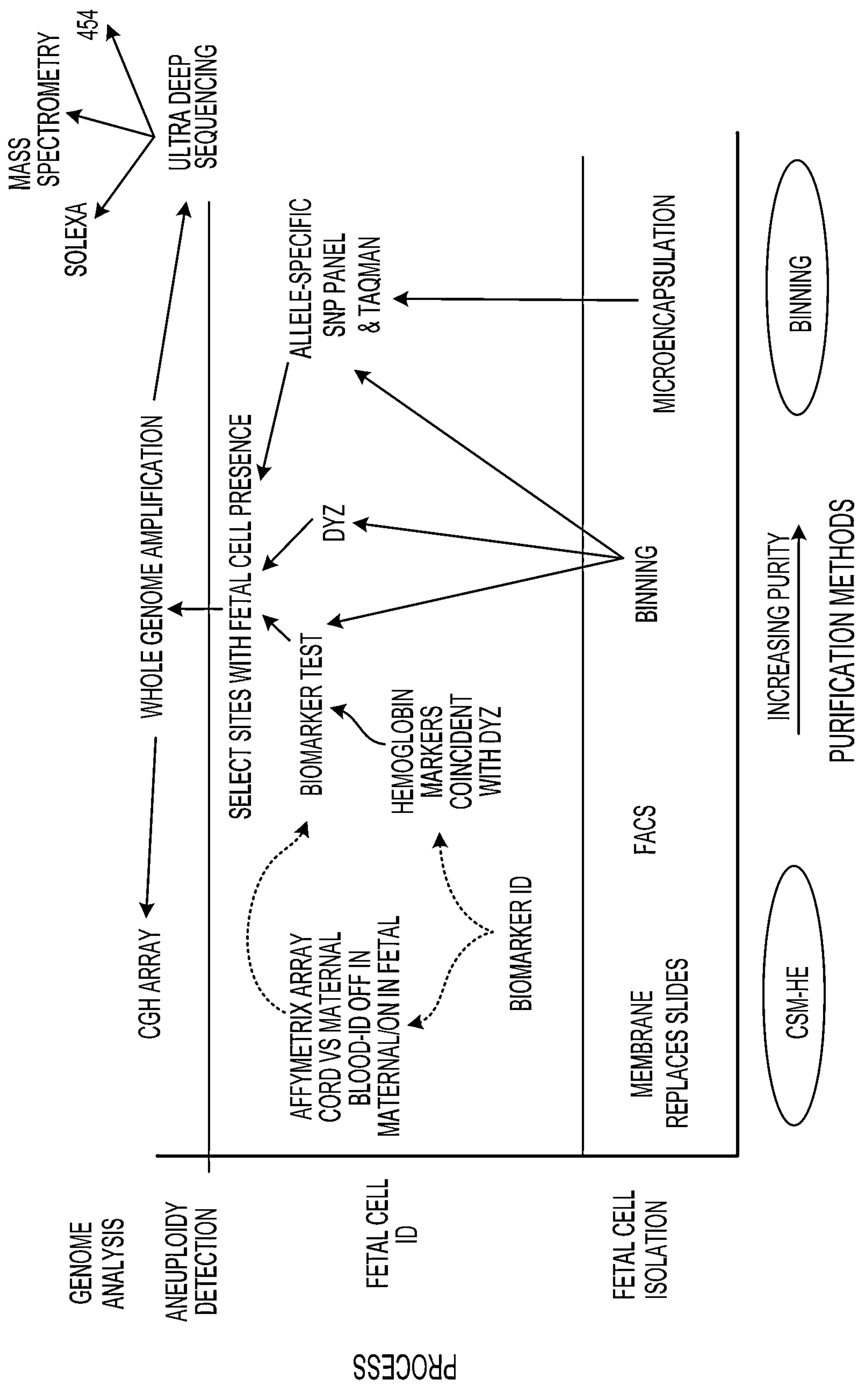
FIG. 35 illustrates methods of fetal diagnostic assays, further comprising the step of whole genome amplification prior to analysis of aneuploidy and/or other genetic defects.

Enriched target cells (e.g., fnRBC) may be "binned" prior to further analysis of the enriched cells (FIGS. 34 & 35). Binning is any process which results in the reduction of complexity and/or total cell number of the enriched cell output. Binning may be performed by any method known in the art or described herein. One method of binning is by serial dilution. Such dilution may be carried out using any appropriate platform (e.g., PCR wells, microtiter plates) and appropriate buffers. Other methods include nanofluidic systems which can separate samples into droplets (e.g., BioTrove, Raindance, Fluidigm). Such nanofluidic systems may result in the presence of a single cell present in a nanodroplet.

Binning may be preceded by positive selection for target cells including, but not limited to, affinity binding (e.g. using anti-CD71 antibodies). Alternately, negative selection of non-target cells may precede binning. For example, output from a size-based separation module may be passed through a magnetic hemoglobin enrichment module (MHEM) which selectively removes WBCs from the enriched sample by attracting magnetized hemoglobin-containing cells.

For example, the possible cellular content of output from enriched maternal blood which has been passed through a size-based separation module (with or without further enrichment by passing the enriched sample through a MHEM) may consist of: 1) approximately 20 fnRBC; 2) 1,500 mnRBC; 3) 4,000-40,000 WBC; 4) $15\times10^{6}$ RBC. If this sample is separated into 100 bins (PCR wells or other acceptable binning platform), each bin would be expected to contain: 1) 80 negative bins and 20 bins positive for one fnRBC; 2) 150 mnRBC; 3) 400-4,000 WBC; 4) $15\times10^{4}$ RBC. If separated into 10,000 bins, each bin would be expected to contain: 1) 9,980 negative bins and 20 bins positive for one fnRBC; 2) 8,500 negative bins and 1,500 bins positive for one mnRBC; 3) <1-4 WBC; 4) $15\times10^{2}$ RBC. One of skill in the art will recognize that the number of bins may be increased or decreased depending on experimental design and/or the platform used for binning. Reduced complexity of the binned cell populations may facilitate further genetic and/or cellular analysis of the target cells by reducing the number of non-target cells in an individual bin.

Analysis may be performed on individual bins to confirm the presence of target cells (e.g. fnRBC) in the individual bin. Such analysis may consist of any method known in the art including, but not limited to, FISH, PCR, STR detection, SNP analysis, biomarker detection, and sequence analysis (FIGS. 34 & 35).

For example, a peripheral maternal venous blood sample enriched by the methods herein can be analyzed to determine pregnancy or a condition of a fetus (e.g., sex of fetus or aneuploidy). The analysis step for fetal cells may further involves comparing the ratio of maternal to paternal genomic DNA on the identified fetal cells.

IV. Fetal Biomarkers

In some embodiments fetal biomarkers may be used to detect and/or isolate fetal cells, after enrichment or after detection of fetal abnormality or lack thereof. For example, this may be performed by distinguishing between fetal and maternal nRBCs based on relative expression of a gene (e.g., DYS1, DYZ, CD-71, ε- and ζ-globin) that is differentially expressed during fetal development. In preferred embodiments, biomarker genes are differentially expressed in the first and/or second trimester. "Differentially expressed," as applied to nucleotide sequences or polypeptide sequences in a cell or cell nuclei, refers to differences in over/under-expression of that sequence when compared to the level of expression of the same sequence in another sample, a control or a reference sample. In some embodiments, expression differences can be temporal and/or cell-specific. For example, for cell-specific expression of biomarkers, differential expression of one or more biomarkers in the cell(s) of interest can be higher or lower relative to background cell populations. Detection of such difference in expression of the biomarker may indicate the presence of a rare cell (e.g., fnRBC) versus other cells in a mixed sample (e.g., background cell populations). In other embodiments, a ratio of two or more such biomarkers that are differentially expressed can be measured and used to detect rare cells.

In one embodiment, fetal biomarkers comprise differentially expressed hemoglobins. Erythroblasts (nRBCs) are very abundant in the early fetal circulation, virtually absent in normal adult blood and by having a short finite lifespan, there is no risk of obtaining fnRBC which may persist from a previous pregnancy. Furthermore, unlike trophoblast cells, fetal erythroblasts are not prone to mosaic characteristics.

Yolk sac erythroblasts synthesize ε-, ζ-, γ- and α-globins, these combine to form the embryonic hemoglobins. Between six and eight weeks, the primary site of erythropoiesis shifts from the yolk sac to the liver, the three embryonic hemoglobins are replaced by fetal hemoglobin (HbF) as the predominant oxygen transport system, and ε- and ζ-globin production gives way to γ-, α- and β-globin production within definitive erythrocytes (Peschle et al., 1985). HbF remains the principal hemoglobin until birth, when the second globin switch occurs and β-globin production accelerates.

Hemoglobin (Hb) is a heterodimer composed of two identical α globin chains and two copies of a second globin. Due to differential gene expression during fetal development, the composition of the second chain changes from ε globin during early embryonic development (1 to 4 weeks of gestation) to γ globin during fetal development (6 to 8 weeks of gestation) to β globin in neonates and adults as illustrated in (Table 1).

TABLE 1

Relative expression of ε, γ and β in maternal and fetal RBCs.

| | | ε | γ | B |
|---|---|---|---|---|
| 1st trimester | Fetal | ++ | ++ | − |
| | Maternal | − | +/− | ++ |
| 2nd trimester | Fetal | − | ++ | +/− |
| | Maternal | − | +/− | ++ |

In the late-first trimester, the earliest time that fetal cells may be sampled by CVS, fnRBCs contain, in addition to α globin, primarily ε and γ globin. In the early to mid second trimester, when amniocentesis is typically performed, fnRBCs contain primarily γ globin with some adult β globin. Maternal cells contain almost exclusively α and β globin, with traces of γ detectable in some samples. Therefore, by measuring the relative expression of the ε, γ and β genes in RBCs purified from maternal blood samples, the presence of fetal cells in the sample can be determined. Furthermore, positive controls can be utilized to assess failure of the FISH analysis itself.

In various embodiments, fetal cells are distinguished from maternal cells based on the differential expression of hemoglobins β, γ or ε. Expression levels or RNA levels can be determined in the cytoplasm or in the nucleus of cells. Thus in some embodiments, the methods herein involve determining levels of messenger RNA (mRNA), ribosomal RNA (rRNA), or nuclear RNA (nRNA).

In some embodiments, identification of fnRBCs can be achieved by measuring the levels of at least two hemoglobins in the cytoplasm or nucleus of a cell. In various embodiments, identification and assay is from 1, 2, 3, 4, 5, 6, 7, 8, 9, 10, 15 or 20 fetal nuclei. Furthermore, total nuclei arrayed on one or more slides can number from about 100, 200, 300, 400, 500, 700, 800, 5000, 10,000, 100,000, 1,000,000, 2,000,000 to about 3,000,000. In some embodiments, a ratio for γ/β or ε/β is used to determine the presence of fetal cells, where a number less than one indicates that a fnRBC(s) is not present. In some embodiments, the relative expression of γ/β or ε/β provides a fnRBC index ("FNI"), as measured by γ or ε relative to β. In some embodiments, a FNI for γ/β greater than 5, 10, 15, 20, 25, 30, 35, 40, 45, 90, 180, 360, 720, 975, 1020, 1024, 1250 to about 1250, indicate that a fnRBC(s) is present. In yet other embodiments, a FNI for γ/β of less than about 1 indicates that a fnRBC(s) is not present. Preferably, the above FNI is determined from a sample obtained during a first trimester. However, similar ratios can be used during second trimester and third trimester.

In some embodiments, the expression levels are determined by measuring nuclear RNA transcripts including, nascent or unprocessed transcripts. In another embodiment, expression levels are determined by measuring mRNA, including ribosomal RNA. There are many methods known in the art for imaging (e.g., measuring) nucleic acids or RNA including, but not limited to, using expression arrays from Affymetrix, Inc. or Illumina, Inc.

RT-PCR primers can be designed by targeting the globin variable regions, selecting the amplicon size, and adjusting the primers annealing temperature to achieve equal PCR amplification efficiency. Thus TaqMan probes can be designed for each of the amplicons with well-separated fluorescent dyes, Alexa Fluor®-355 for ε, Alexa Fluor®-488 for γ, and Alexa Fluor-555 for β. The specificity of these primers can be first verified using ε, γ, and β cDNA as templates. The primer sets that give the best specificity can be selected for further assay development. As an alternative, the primers can be selected from two exons spanning an intron sequence to amplify only the mRNA to eliminate the genomic DNA contamination.

The primers selected can be tested first in a duplex format to verify their specificity, limit of detection, and amplification efficiency using target cDNA templates. The best combinations of primers can be further tested in a triplex format for its amplification efficiency, detection dynamic range, and limit of detection.

Various commercially available reagents are available for RT-PCR, such as One-step RT-PCR reagents, including Qiagen One-Step RT-PCR Kit and Applied Biosystems TaqMan® One-Step RT-PCR Master Mix Reagents kit. Such reagents can be used to establish the expression ratio of ε, γ, and β using purified RNA from enriched samples. Forward primers can be labeled for each of the targets, using Alexa fluor-355 for ε, Alexa fluor-488 for γ, and Alexa fluor-555 for β. Enriched cells can be deposited by cytospinning onto glass slides. Additionally, cytospinning the enriched cells can be performed after in situ RT-PCR. Thereafter, the presence of the fluorescent-labeled amplicons can be visualized by fluorescence microscopy. The reverse transcription time and PCR cycle can be optimized to maximize the amplicon signal:background ratio to have maximal separation of fetal over maternal signature. Preferably, signal:background ratio is greater than 5, 10, 50 or 100 and the overall cell loss during the process is less than 50, 10 or 5%.

V. Fetal Cell Analysis

Figure 4:
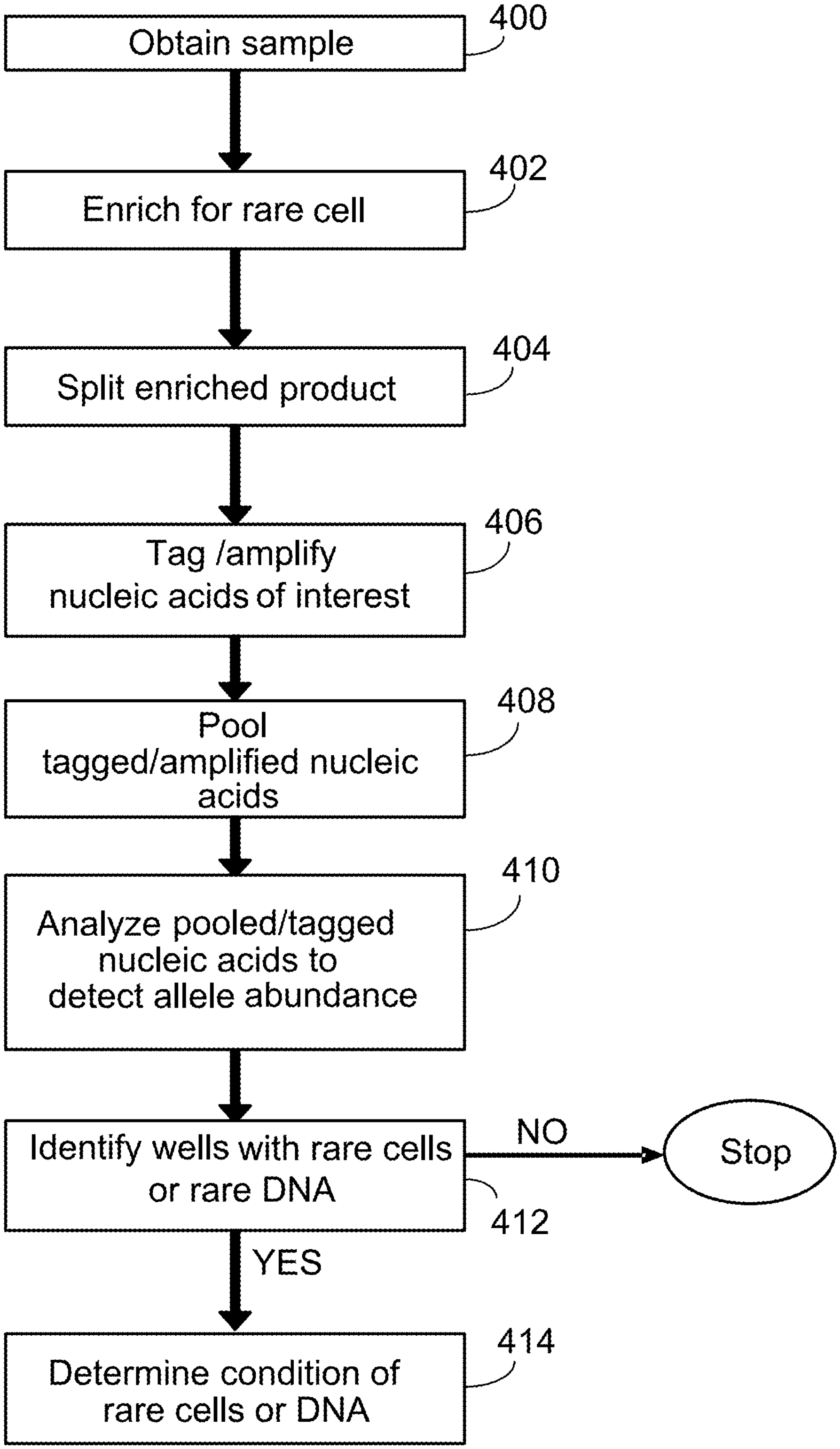
FIG. 4 illustrates an overview for diagnosing, prognosing, or monitoring a prenatal condition in a fetus.

FIG. 4 illustrates an overview of some embodiments of the present invention.

Aneuploidy means the condition of having less than or more than the normal diploid number of chromosomes. In other words, it is any deviation from euploidy. Aneuploidy includes conditions such as monosomy (the presence of only one chromosome of a pair in a cell's nucleus), trisomy (having three chromosomes of a particular type in a cell's nucleus), tetrasomy (having four chromosomes of a particular type in a cell's nucleus), pentasomy (having five chromosomes of a particular type in a cell's nucleus), triploidy (having three of every chromosome in a cell's nucleus), and tetraploidy (having four of every chromosome in a cell's nucleus). Birth of a live triploid is extraordinarily rare and such individuals are quite abnormal, however triploidy occurs in about 2-3% of all human pregnancies and appears to be a factor in about 15% of all miscarriages. Tetraploidy occurs in approximately 8% of all miscarriages. (emedicine-.com/med/topic3241).

In step 400, a sample is obtained from an animal, such as a human. In some embodiments, animal or human is pregnant, suspected of being pregnant, or may have been pregnant, and, the systems and methods herein are used to diagnose pregnancy and/or conditions of the fetus (e.g. trisomy). In some embodiments, the animal or human is suspected of having a condition, has a condition, or had a condition (e.g., cancer) and, the systems and methods herein are used to diagnose the condition, determine appropriate therapy, and/or monitor for recurrence.

In both scenarios a sample obtained from the animal can be a blood sample e.g., of up to 50, 40, 30, 20, or 15 mL. In some cases multiple samples are obtained from the same animal at different points in time (e.g. before therapy, during therapy, and after therapy, or during 1$^{st}$ trimester, 2$^{nd}$ trimester, and 3$^{rd}$ trimester of pregnancy).

In optional step 402, rare cells (e.g., fetal cells or epithelial cells) or DNA of such rare cells are enriched using one or more methods known in the art or described herein. For example, to enrich fetal cells from a maternal blood sample, the sample can be applied to a size-base separation module (e.g., two-dimensional array of obstacles) configured to direct cells or particles in the sample greater than 8 microns to a first outlet and cells or particles in the sample smaller than 8 microns to a second outlet. The fetal cells can subsequently be further enriched from maternal white blood cells (which are also greater than 8 microns) based on their potential magnetic property. For example, $N_2$ or anti-CD71 coated magnetic beads is added to the first enriched product to make the hemoglobin in the red blood cells (maternal and fetal) paramagnetic. The enriched sample is then flowed through a column coupled to an external magnet. This captures both the fnRBC's and mnRBC's creating a second enriched product. The sample can then be subjected to hyperbaric pressure or other stimulus to initiate apoptosis in the fetal cells. Fetal cells/nuclei can then be enriched using microdissection, for example. It should be noted that even an enriched product can be dominated (>50%) by cells not of interest (e.g. maternal red blood cells). In some cases an enriched sample has the rare cells (or rare genomes) consisting of up to 0.01, 0.02, 0.05, 0.1, 0.2, 0.5, 1, 2, 5, 10, 20, or 50% of all cells (or genomes) in the enriched sample. For example, using the systems herein, a maternal blood sample of 20 mL from a pregnant human can be enriched for fetal cells such that the enriched sample has a total of about 500 cells, 2% of which are fetal and the rest are maternal.

In step 404, the enriched product is split between two or more discrete locations. In some embodiments, a sample is split into at least 2, 10, 20, 50, 100, 200, 300, 400, 500, 600, 700, 800, 900, 1000, 2000, 3,000, 4,000, 5000, or 10,000 total different discrete sites or about 100, 200, 500, 1000, 1200, 1500 sites. In some embodiments, output from an enrichment module is serially divided into wells of a 1536 microwell plate (FIG. 8). This can result in one cell or genome per location or 0 or 1 cell or genome per location. In some embodiments, cell splitting results in more than 1, 2, 3, 4, 5, 6, 7, 8, 9, 10, 20, 50, 100, 200, 500, 1000, 2000, 5000, 10,000, 20,000, 50,000, 100,000, 200,000, or 500,000 cells or genomes per location. When splitting a sample enriched for epithelial cells, endothelial cells, or CTC's, the load at each discrete location (e.g., well) can include several leukocytes, while one only some of the loads includes one or more CTC's. When splitting a sample enriched for fetal cells preferably each site includes 0 or 1 fetal cells.

Examples of discrete locations which could be used as addressable locations include, but are not limited to, wells, bins, sieves, pores, geometric sites, slides, matrixes, membranes, electric traps, gaps, obstacles, or in-situ within a cell or nuclear membrane. In some embodiments, the discrete cells are addressable such that one can correlate a cell or cell sample with a particular location.

Examples of methods for splitting a sample into discrete addressable locations include, but are not limited to, fluorescent activated cell sorting (FACS) (Sherlock, J V et al. Ann. Hum. Genet. 62 (Pt. 1): 9-23 (1998)), micromanipulation (Samura, O., Ct al Hum. Genet. 107(1):28-32 (2000)) and dilution strategies (Findlay, I. et al. Mol. Cell. Endocrinol. 183 Suppl 1: S5-12 (2001)). Other methods for sample splitting cell sorting and splitting methods known in the art may also be used. For example, samples can be split by affinity sorting techniques using affinity agents (e.g. antibodies) bound to any immobilized or mobilized substrate (Samura O., et al., Hum. Genet. 107(1):28-32 (2000)). Such affinity agents can be specific to a cell type e.g. RBC's fetal cells epithelial cells including those specifically binding EpCAM, antigen-i, or CD-71.

In some embodiments, a sample or enriched sample is transferred to a cell sorting device that includes an array of discrete locations for capturing cells traveling along a fluid flow. The discrete locations can be arranged in a defined pattern across a surface such that the discrete sites are also addressable. In some embodiments, the sorting device is coupled to any of the enrichment devices known in the art or disclosed herein. Examples of cell sorting devices included are described in International Publication No. WO 01/35071. Examples of surfaces that may be used for creating arrays of cells in discrete addressable sites include, but are not limited to, cellulose, cellulose acetate, nitrocellulose, glass, quartz or other crystalline substrates such as gallium arsenide, silicones, metals, semiconductors, various plastics and plastic copolymers, cyclo-olefin polymers, various membranes and gels, microspheres, beads and paramagnetic or supramagnetic microparticles.

In some embodiments, a sorting device comprises an array of wells or discrete locations wherein each well or discrete location is configured to hold up to 1 cell. Each well or discrete addressable location may have a capture mechanism adapted for retention of such cell (e.g. gravity, suction, etc.) and optionally a release mechanism for selectively releasing a cell of interest from a specific well or site (e.g. bubble actuation). Figure B illustrates such an embodiment.

In step 406, nucleic acids of interest from each cell or nuclei arrayed are tagged by amplification. Preferably, the amplified/tagged nucleic acids include at least 1, 2, 3, 4, 5, 6, 7, 8, 9, 10, 20, 30, 40, 50, 60, 70, 90, 90 or 100 polymorphic genomic DNA regions such as short tandem repeats (STRs) or variable number of tandem repeats ("VNTR"). When the amplified DNA regions include one or more STR/s/, the STR/s/ are selected for high heterozygosity (variety of alleles) such that the paternal allele of any fetal cell is more likely to be distinct in length from the maternal allele. This results in improved power to detect the presence of fetal cells in a mixed sample and any potential of fetal abnormalities in such cells. In some embodiment, STR(s) amplified are selected for their association with a particular condition. For example, to determine fetal abnormality an STR sequence comprising a mutation associated with fetal abnormality or condition is amplified. Examples of STRs that can be amplified/analyzed by the methods herein include, but are not limited to D21S1414, D21S1411, D21S1412, D21S11 MBP, D13S634, D13S631, D18S535, AmgXY and XHPRT. Additional STRs that can be amplified/analyzed by the methods herein include, but are not limited to, those at locus F13B (1:q31-q32); TPOX (2:p23-2pter); FIBRA (FGA) (4:q28); CSFIPO (5:q33.3-q34); FI3A (6:p24-p25); THOI (11:p15-15.5); VWA (12:p12-pter); CDU (12p12-pter); D14S1434 (14:q32.13); CYAR04 (p450) (15:q21.1) D21S11 (21:q11-q21) and D22S1045 (22:q12.3). In some cases, STR loci are chosen on a chromosome suspected of trisomy and on a control chromosome. Examples of chromosomes that are often trisomic include chromosomes 21, 18, 13, and X. In some cases, 1 or more than 1, 2, 3, 4, 5, 6, 7, 8, 9, 10, 15, or 20 STRs are amplified per chromosome tested (Samura, O. et al., Clin. Chem. 47(9):1622-6 (2001)). For example amplification can be used to generate amplicons of up to 20, up to 30, up to 40, up to 50, up to 60, up to 70, up to 80, up to 90, up to 100, up to 150, up to 200, up to 300, up to 400, up to 500 or up to 1000 nucleotides in length. Di-, tri-, tetra-, or penta-nucleotide repeat STR loci can be used in the methods described herein.

To amplify and tag genomic DNA region(s) of interest, PCR primers can include: (i) a primer element, (ii) a sequencing element, and (iii) a locator element.

The primer element is configured to amplify the genomic DNA region of interest (e.g. STR). The primer element includes, when necessary, the upstream and downstream primers for the amplification reactions. Primer elements can be chosen which are multiplexible with other primer pairs from other tags in the same amplification reaction (e.g. fairly uniform melting temperature, absence of cross-priming on the human genome, and absence of primer-primer interaction based on sequence analysis). The primer element can have at least 4, 5, 6, 7, 8, 9, 10, 15, 20, 25, 30, 40 or 50 nucleotide bases, which are designed to specifically hybridize with and amplify the genomic DNA region of interest.

The sequencing element can be located on the 5' end of each primer element or nucleic acid tag. The sequencing element is adapted to cloning and/or sequencing of the amplicons. (Margulies, M., Nature 437 (7057)(2005): 376-80) The sequencing element can be about 4, 6, 8, 10, 18, 20, 28, 36, 46 or 50 nucleotide bases in length.

The locator element (also known as a unique tag sequence), which is often incorporated into the middle part of the upstream primer, can include a short DNA or nucleic acid sequence between 4-20 bp in length (e.g., about 4, 6, 8, 10, or 20 nucleotide bases). The locator element makes it possible to pool the amplicons from all discrete addressable locations following the amplification step and analyze the amplicons in parallel. In some embodiments each locator element is specific for a single addressable location.

Tags are added to the cells/DNA at each discrete location using an amplification reaction. Amplification can be performed using PCR or by a variety of methods including, but not limited to, singleplex PCR, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR, multiple strand displacement amplification (MDA), and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Additional examples of amplification techniques using PCR primers are described in, U.S. Pat. Nos. 5,242,794, 5,494,810, 4,988,617 and 6,582,938.

In some embodiments, a further PCR amplification is performed using nested primers for the one or more genomic DNA regions of interest to ensure optimal performance of the multiplex amplification. The nested PCR amplification generates sufficient genomic DNA starting material for further analysis such as in the parallel sequencing procedures below.

In step 408, genomic DNA regions tagged/amplified are pooled and purified prior to further processing. Methods for pooling and purifying genomic DNA are known in the art.

In step 410, pooled genomic DNA/amplicons are analyzed to measure, e.g. allele abundance of genomic DNA regions (e.g. STRs amplified). In some embodiments such analysis involves the use of capillary gel electrophoresis (CGE). In other embodiments, such analysis involves sequencing or ultra deep sequencing.

Sequencing can be performed using the classic Sanger sequencing method or any other method known in the art.

For example, sequencing can occur by sequencing-by-synthesis, which involves inferring the sequence of the template by synthesizing a strand complementary to the target nucleic acid sequence. Sequence-by-synthesis can be initiated using sequencing primers complementary to the sequencing element on the nucleic acid tags. The method involves detecting the identity of each nucleotide immediately after (substantially real-time) or upon (real-time) the incorporation of a labeled nucleotide or nucleotide analog into a growing strand of a complementary nucleic acid sequence in a polymerase reaction. After the successful incorporation of a label nucleotide, a signal is measured and then nulled by methods known in the art. Examples of sequence-by-synthesis methods are described in U.S. Application Publication Nos. 2003/0044781, 2006/0024711, 2006/0024678 and 2005/0100932. Examples of labels that can be used to label nucleotide or nucleotide analogs for sequencing-by-synthesis include, but are not limited to, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, and electrochemical detection moieties. Sequencing-by-synthesis can generate at least 1,000, at least 5,000, at least 10,000, at least 20,000, 30,000, at least 40,000, at least 50,000, at least 100,000 or at least 500,000 reads per hour. Such reads can have at least 50, at least 60, at least 70, at least 80, at least 90, at least 100, at least 120 or at least 150 bases per read.

Another sequencing method involves hybridizing the amplified genomic region of interest to a primer complementary to it. This hybridization complex is incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined.

Yet another sequencing method involves a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer:nonamer complexes are stripped and a new cycle begins. Methods to image sequence information after performing ligation are known in the art.

Preferably, analysis involves the use of ultra-deep sequencing, such as described in Margulies et al., Nature 437 (7057): 376-80 (2005). Briefly, the amplicons are diluted and mixed with beads such that each bead captures a single molecule of the amplified material. The DNA molecule on each bead is then amplified to generate millions of copies of the sequence which all remain bound to the bead. Such amplification can occur by PCR. Each bead can be placed in a separate well, which can be a (optionally addressable) picolitre-sized well. In some embodiments, each bead is captured within a droplet of a PCR-reaction-mixture-in-oil-emulsion and PCR amplification occurs within each droplet. The amplification on the bead results in each bead carrying at least one million, at least 5 million, or at least 10 million copies of the original amplicon coupled to it. Finally, the beads are placed into a highly parallel sequencing by synthesis machine which generates over 400,000 reads (~100 bp per read) in a single 4 hour run.

Other methods for ultra-deep sequencing that can be used are described in Hong, S. et al. Nat. Biotechnol. 22(4):435-9 (2004); Bennett, B. et al. Pharmacogenomics 6(4):373-82 (2005); Shendure, P. et al. Science 309 (5741):1728-32 (2005).

The role of the ultra-deep sequencing is to provide an accurate and quantitative way to measure the allele abundances for each of the STRs. The total required number of reads for each of the aliquot wells is determined by the number of STRs, the error rates of the multiplex PCR, and the Poisson sampling statistics associated with the sequencing procedures.

In one example, the enrichment output from step 402 results in approximately 500 cells of which 98% are maternal cells and 2% are fetal cells. Such enriched cells are subsequently split into 500 discrete locations (e.g., wells) in a microtiter plate such that each well contains 1 cell. PCR is used to amplify STR's (~3-10 STR loci) on each chromosome of interest. Based on the above example, as the fetal/maternal ratio goes down, the aneuploidy signal becomes diluted and more loci are needed to average out measurement errors associated with variable DNA amplification efficiencies from locus to locus. The sample division into wells containing ~1 cell proposed in the methods described herein achieves pure or highly enriched fetal/maternal ratios in some wells, alleviating the requirements for averaging of PCR errors over many loci.

In one example, let 'f' be the fetal/maternal DNA copy ratio in a particular PCR reaction. Trisomy increases the ratio of maternal to paternal alleles by a factor 1+f/2. PCR efficiencies vary from allele to allele within a locus by a mean square error in the logarithm given by $_{allele}{}^2$, and vary from locus to locus by $_{locus}{}^2$, where this second variance is apt to be larger due to differences in primer efficiency. $N_a$ is the loci per suspected aneuploid chromosome and $N_c$ is the control loci. If the mean of the two maternal allele strengths at any locus is 'm' and the paternal allele strength is 'p,' then the squared error expected is the mean of the ln(ratio(m/p)), where this mean is taken over N loci is given by $$2(\sigma_{allele}^2)/N.$$

When taking the difference of this mean of ln(ratio(m/p)) between a suspected aneuploidy region and a control region, the error in the difference is given by $$\sigma_{diff}^2 = 2(\sigma_{allele}^2)/N_a + 2(\sigma_{allele}^2)/N_c \tag{1}$$

For a robust detection of aneuploidy we require $$3\sigma_{diff} < f/2.$$

For simplicity, assuming $N_a=N_c=N$ in Equation 1, this gives the requirement $$6\sigma_{allele}/N^{1/2} < f/2, \tag{3}$$

or a minimum N of $$N = 144(\sigma_{allele}/f)^2 \tag{4}$$

In the context of trisomy detection, the suspected aneuploidy region is usually the entire chromosome and N denotes the number of loci per chromosome. For reference, Equation 3 is evaluated for N in the following Table 2 for various values of $\sigma_{allele}$ and f.

TABLE 2

Required number of loci per chromosome as a function $\sigma_{allele}$ and f.

| | f | | |
|---|---|---|---|
| $\sigma_{allele}$ | 0.1 | 0.3 | 1.0 |
| 0.1 | 144 | 16 | 1 |
| 0.3 | 1296 | 144 | 13 |
| 1.0 | 14400 | 1600 | 144 |

Since sample splitting decreases the number of starting genome copies which increases σallele at the same time that it increases the value of f in some wells, the methods herein are based on the assumption that the overall effect of splitting is favorable; i.e., that the PCR errors do not increase too fast with decreasing starting number of genome copies to offset the benefit of having some wells with large f. The required number of loci can be somewhat larger because for many loci the paternal allele is not distinct from the maternal alleles, and this incidence depends on the heterozygosity of the loci. In the case of highly polymorphic STRs, this amounts to an approximate doubling of N.

The role of the sequencing is to measure the allele abundances output from the amplification step. It is desirable to do this without adding significantly more error due to the Poisson statistics of selecting only a finite number of amplicons for sequencing. The rms error in the ln(abundance) due to Poisson statistics is approximately $(N_{reads})^{-1/2}$. It is desirable to keep this value less than or equal to the PCR error $\sigma_{allele}$. Thus, a typical paternal allele needs to be allocated at least $(\sigma_{allele})^{-2}$ reads. The maternal alleles, being more abundant, do not add appreciably to this error when forming the ratio estimate for m/p. The mixture input to sequencing contains amplicons from $N_{loci}$ loci of which roughly an abundance fraction f/2 are paternal alleles. Thus, the total required number of reads for each of the aliquot wells is given approximately by $2N_{loci}/(f\ \sigma_{allele}^{2})$. Combining this result with Equation 4, it is found a total number of reads over all the wells given approximately by $$N_{reads} = 288\ N_{wells} f^{-3}. \tag{5}$$

When performing sample splitting, a rough approximation is to stipulate that the sample splitting causes f to approach unity in at least a few wells. If the sample splitting is to have advantages, then it must be these wells which dominate the information content in the final result. Therefore, Equation (5) with f=1 is adopted, which suggests a minimum of about 300 reads per well. For 500 wells, this gives a minimum requirement for ~150,000 sequence reads. Allowing for the limited heterozygosity of the loci tends to increase the requirements (by a factor of ~2 in the case of STRs), while the effect of reinforcement of data from multiple wells tends to relax the requirements with respect to this result (in the baseline case examined above it is assumed that ~10 wells have a pure fetal cell). Thus the required total number of reads per patient is expected to be in the range 100,000-300,000.

In step 412, wells with rare cells/alleles (e.g., fetal alleles) are identified. The locator elements of each tag can be used to sort the reads (~200,000 sequence reads) into 'bins' which correspond to the individual wells of the microtiter plates (~500 bins). The sequence reads from each of the bins (~400 reads per bin) are then separated into the different genomic DNA region groups, (e.g. STR loci,) using standard sequence alignment algorithms. The aligned sequences from each of the bins are used to identify rare (e.g., non-maternal) alleles. It is estimated that on average a 15 ml blood sample from a pregnant human will result in ~10 bins having a single fetal cell each.

The following are two examples by which rare alleles can be identified. In a first approach, an independent blood sample fraction known to contain only maternal cells can be analyzed as described above in order to obtain maternal alleles. This sample can be a white blood cell fraction or simply a dilution of the original sample before enrichment. In a second approach, the sequences or genotypes for all the wells can be similarity-clustered to identify the dominant pattern associated with maternal cells. In either approach, the detection of non-maternal alleles determines which discrete location (e.g. well) contained fetal cells. Determining the number of bins with non-maternal alleles relative to the total number of bins provides an estimate of the number of fetal cells that were present in the original cell population or enriched sample. Bins containing fetal cells are identified with high levels of confidence because the non-maternal alleles are detected by multiple independent polymorphic DNA regions, e.g. STR loci.

In step 414, condition of rare cells or DNA is determined. This can be accomplished by determining abundance of selected alleles (polymorphic genomic DNA regions) in bin(s) with rare cells/DNA. In some embodiments, allele abundance is used to determine aneuploidy, e.g. chromosomes 13, 18 and 21. Abundance of alleles can be determined by comparing ratio of maternal to paternal alleles for each genomic region amplified (e.g., ~12 STR's). For example, if 12 STRs are analyzed, for each bin there are 33 sequence reads for each of the STRs. In a normal fetus, a given STR will have 1:1 ratio of the maternal to paternal alleles with approximately 16 sequence reads corresponding to each allele (normal diallelic). In a trisomic fetus, three doses of an STR marker will be detected either as three alleles with a 1:1:1 ratio (trisomic triallelic) or two alleles with a ratio of 2:1 (trisomic diallelic). (Adinolfi, P. et al., Prenat. Diagn, 17(13):1299-311 (1997)). In rare instances all three alleles may coincide and the locus will not be informative for that individual patient. In some embodiments, the information from the different DNA regions on each chromosome are combined to increase the confidence of a given aneuploidy call. In some embodiments, the information from the independent bins containing fetal cells can also be combined to further increase the confidence of the call.

In some embodiments allele abundance is used to determine segmental aneuploidy. Normal diploid cells have two copies of each chromosome and thus two alleles of each gene or loci. Changes in the allele abundance for a particular chromosomal region may be indicative of a chromosomal rearrangement, such as a deletion, duplication or translocation event. In some embodiments, the information from the different DNA regions on each chromosome are combined to increase the confidence of a given segmental aneuploidy call. In some embodiments, the information from the independent bins containing fetal cells can also be combined to further increase the confidence of the call.

The determination of fetal trisomy can be used to diagnose conditions such as abnormal fetal genotypes, including, trisomy 13, trisomy 18, trisomy 21 (Down syndrome) and Klinefelter Syndrome (XXY). Other examples of abnormal fetal genotypes include, but are not limited to, aneuploidy such as, monosomy of one or more chromosomes (X chromosome monosomy, also known as Turner's syndrome), trisomy of one or more chromosomes (13, 18, 21, and X), tetrasomy and pentasomy of one or more chromosomes (which in humans is most commonly observed in the sex chromosomes, e.g. XXXX, XXYY, XXXY, XYYY, XXXXX, XXXXY, XXXYY, XYYYY and XXYYY), triploidy (three of every chromosome, e.g. 69 chromosomes in humans), tetraploidy (four of every chromosome, e.g. 92 chromosomes in humans) and multiploidy. In some embodiments, an abnormal fetal genotype is a segmental aneuploidy. Examples of segmental aneuploidy include, but are not limited to, 1p36 duplication, dup(17)(p11.2p11.2) syndrome, Down syndrome, Pelizaeus-Merzbacher disease, dup (22)(q11.2q11.2) syndrome, and cat-eye syndrome. In some cases, an abnormal fetal genotype is due to one or more deletions of sex or autosomal chromosomes, which may result in a condition such as Cri-du-chat syndrome, Wolf-Hirschhorn, Williams-Beuren syndrome, Charcot-Marie-Tooth disease, Hereditary neuropathy with liability to pressure palsies, Smith-Magenis syndrome, Neurofibromatosis, Alagille syndrome, Velocardiofacial syndrome, DiGeorge syndrome, Steroid sulfatase deficiency, Kallmann syndrome, Microphthalmia with linear skin defects, Adrenal hypoplasia, Glycerol kinase deficiency, Pelizaeus-Merzbacher disease, Testis-determining factor on Y, Azoospermia (factor a), Azoospermia (factor b), Azoospermia (factor c), or 1p36 deletion. In some embodiments, a decrease in chromosomal number results in an XO syndrome.

In one embodiment, the methods of the invention allow for the determination of maternal or paternal trisomy. In some embodiments, the methods of the invention allow for the determination of trisomy or other conditions in fetal cells in a mixed maternal sample arising from more than one fetus.

In another aspect of the invention, standard quantitative genotyping technology is used to declare the presence of fetal cells and to determine the copy numbers (ploidies) of the fetal chromosomes. Several groups have demonstrated that quantitative genotyping approaches can be used to detect copy number changes (Wang, Moorhead et al. 2005). However, these approaches do not perform well on mixtures of cells and typically require a relatively large number of input cells (~10,000). The current invention addresses the complexity issue by performing the quantitative genotyping reactions on individual cells. In addition, multiplex PCR and DNA tags are used to perform the thousands of genotyping reaction on single cells in highly parallel fashion.

Figure 5:
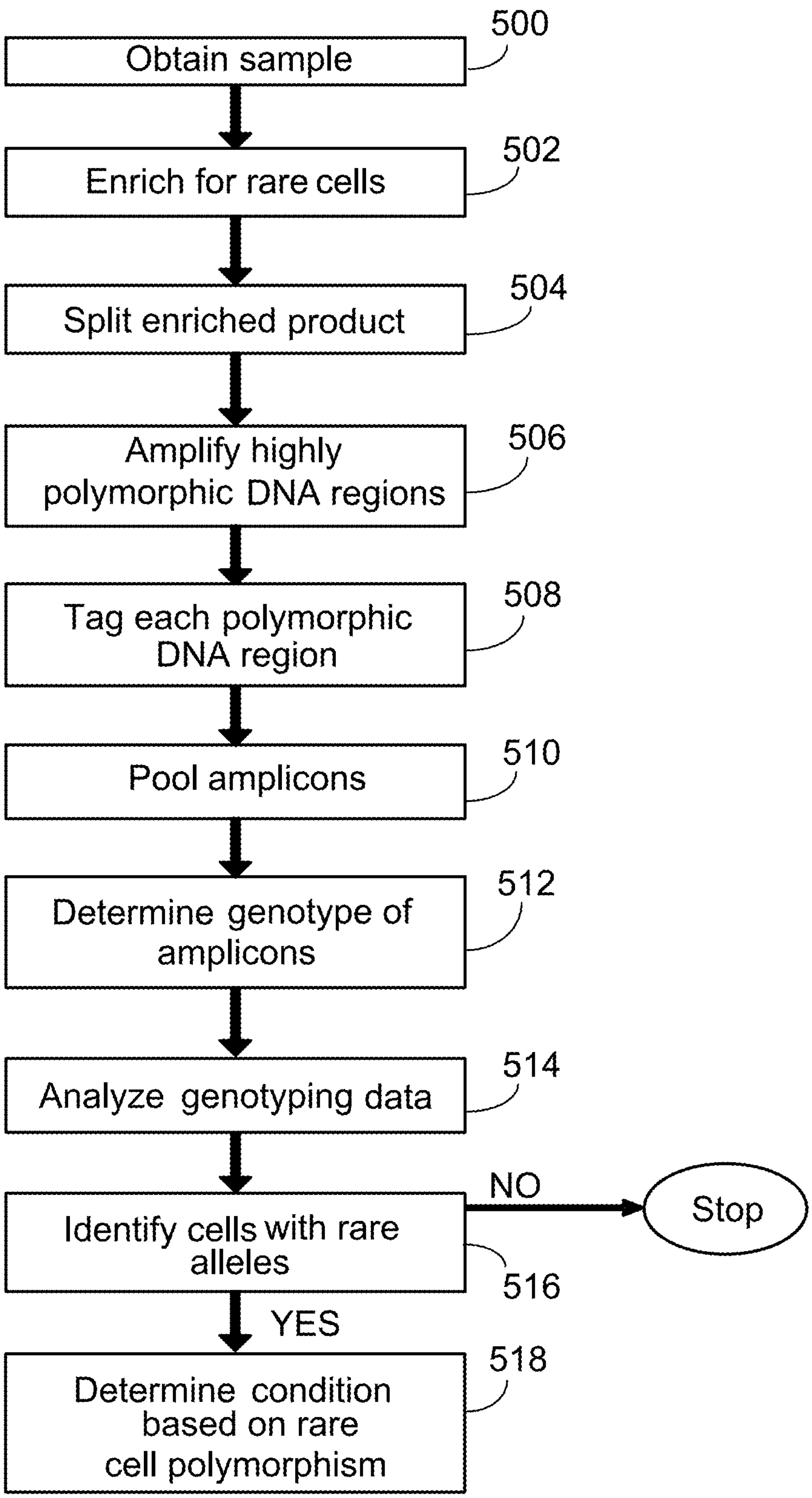
FIG. 5 illustrates an overview for diagnosing, prognosing, or monitoring a prenatal condition in a fetus.

An overview of this embodiment is illustrated in FIG. 5.

In step 500, a sample (e.g., a mixed sample of rare and non-rare cells) is obtained from an animal or a human. See, e.g., step 400 of FIG. 4. Preferably, the sample is a peripheral maternal blood sample.

In step 502, the sample is enriched for rare cells (e.g., fetal cells) by any method known in the art or described herein. See, e.g., step 402 of FIG. 4.

In step 504, the enriched product is split into multiple distinct sites (e.g., wells). See, e.g., step 404 of FIG. 4.

In step 506, PCR primer pairs for amplifying multiple (e.g., 2-100) highly polymorphic genomic DNA regions (e.g., SNPs) are added to each discrete site or well in the array or microtiter plate. For example, PCR primer pairs for amplifying SNPs along chromosome 13, 18, 21 and/or X can be designed to detect the most frequent aneuploidies. Other PCR primer pairs can be designed to amplify SNPs along control regions of the genome where aneuploidy is not expected. The genomic loci (e.g., SNPs) in the aneuploidy region or aneuploidy suspect region are selected for high polymorphism such that the paternal alleles of the fetal cells are more likely to be distinct from the maternal alleles. This improves the power to detect the presence of fetal cells in a mixed sample as well as fetal conditions or abnormalities. SNPs can also be selected for their association with a particular condition to be detected in a fetus. In some cases, one or more than one, 2, 3, 4, 5, 6, 7, 8, 9, 10, 20, 30, 40, 50, 60, 70, 80, 90, or 100 SNPs are analyzed per target chromosome (e.g., 13, 18, 21, and/or X). The increase in number of SNPs interrogated per chromosome ensures accurate results. PCR primers are chosen to be multiplexible with other pairs (fairly uniform melting temperature, absence of cross-priming on the human genome, and absence of primer-primer interaction based on sequence analysis). The primers are designed to generate amplicons 10-200, 20-180, 40-160, 60-140 or 70-100 bp in size to increase the performance of the multiplex PCR.

A second of round of PCR using nested primers may be performed to ensure optimal performance of the multiplex amplification. The multiplex amplification of single cells is helpful to generate sufficient starting material for the parallel genotyping procedure. Multiplex PCT can be performed on single cells with minimal levels of allele dropout and preferential amplification. See Sherlock, J., et al. Ann. Hum. Genet. 61 (Pt 1): 9-23 (1998); and Findlay, I., et al. Mol. Cell. Endocrinol. 183 Suppl. 1: S5-12 (2001).

In step 508, amplified polymorphic DNA region(s) of interest (e.g., SNPs) are tagged e.g., with nucleic acid tags. Preferably, the nucleic acid tags serve two roles: to determine the identity of the different SNPs and to determine the identity of the bin from which the genotype was derived. Nucleic acid tags can comprise primers that allow for allele-specific amplification and/or detection. The nucleic acid tags can be of a variety of sizes including up to 10 base pairs, 10-40, 15-30, 18-25 or ~22 base pair long.

Figure 7A:
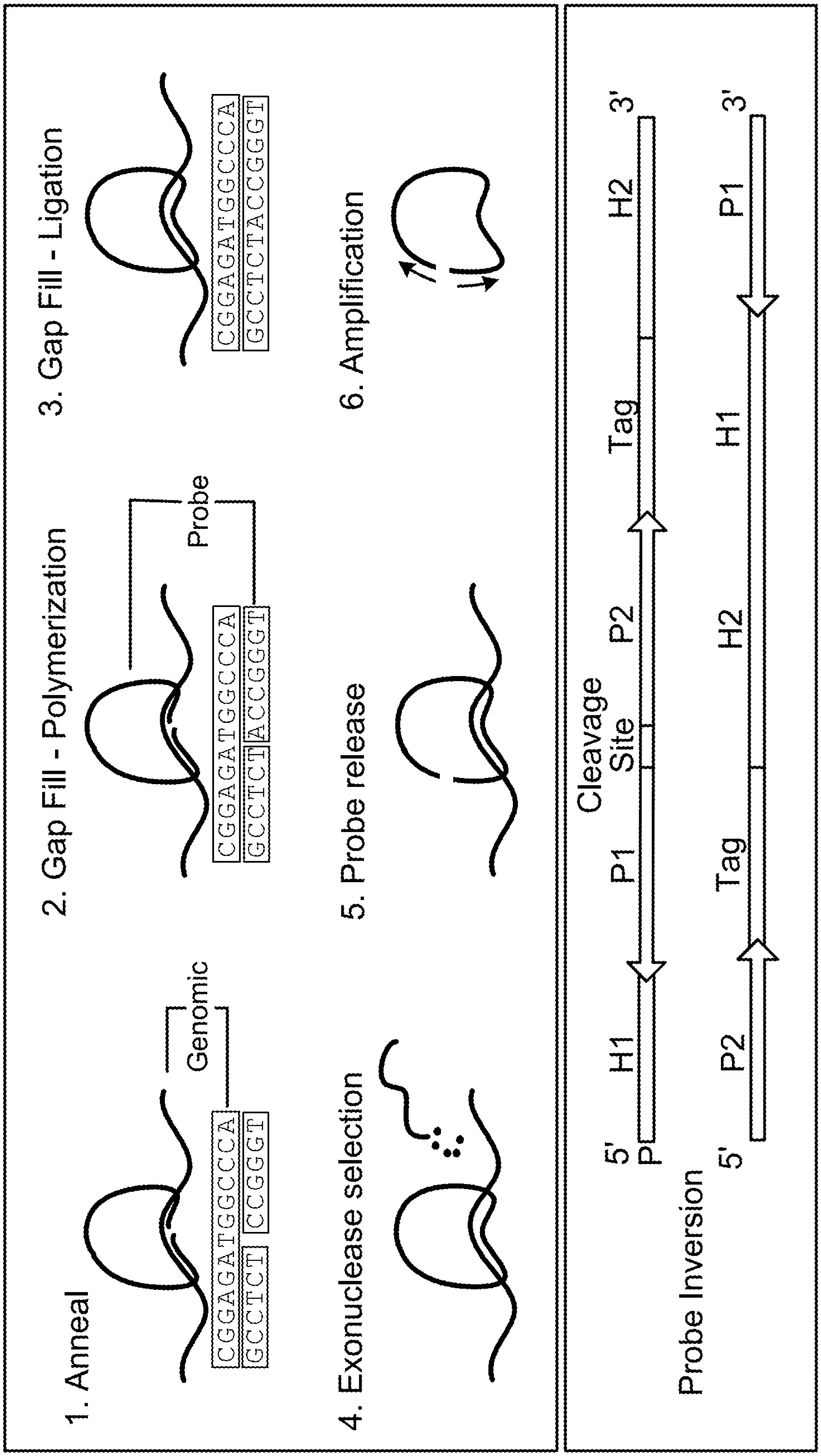
FIGS. 7A-7C illustrate an assay using molecular inversion probes SEQ ID NO: 67 (top nucleotide sequence of each double-stranded nucleotide sequence shown in FIGS. 7A.1, 7A.2, and 7A.3) and SEQ ID NO: 71 (bottom nucleotide sequence of each double-stranded nucleotide sequence shown in FIGS. 7A.2 and 7A.3). Molecular Inversion Probes are so named because the oligonucleotide probe central to the process undergoes a unimolecular rearrangement from a molecule that cannot be amplified (step 1), to a molecule that can be amplified (step 6). This rearrangement is mediated by hybridization to genomic DNA (step 2) and an enzymatic "gap fill" process that occurs in an allele-specific manner (step 3). The resulting circularized probe can be separated from cross-reacted or unreacted probes by a simple exonuclease reaction (step 4).
Figure 7B:
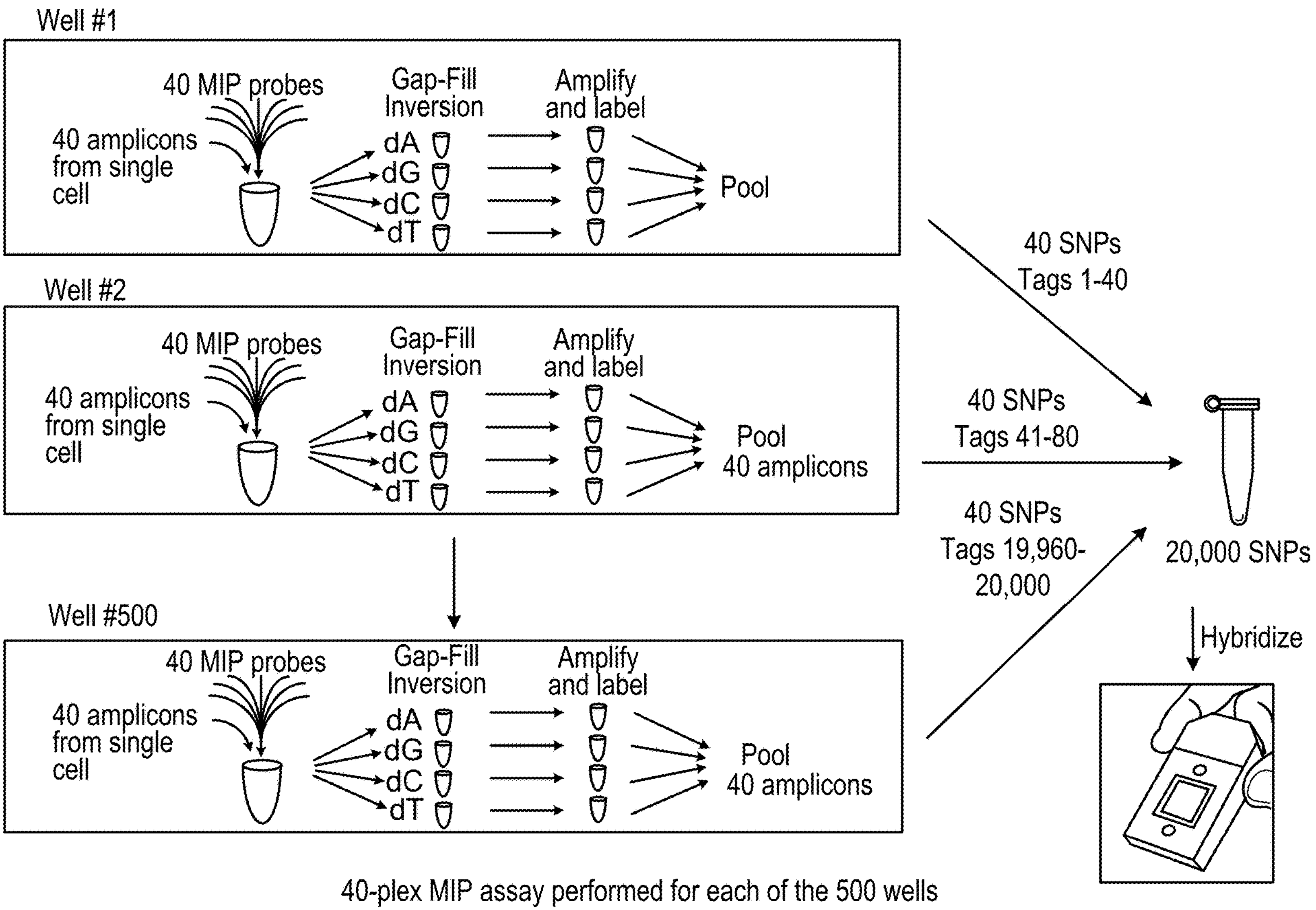

In some embodiments, a nucleic acid tag comprises a molecular inversion probe (MIP). Examples of MIPs and their uses are described in Hardenbol, P., et al., Nat. Biotechnol. 21(6):673-8 (2003); Hardenbol, P., et al., Genome Res. 15(2):269-75 (2005); and Wang, Y., et al., Nucleic Acids Res. 33(21):e183 (2005). FIG. 7A illustrates one example of a MIP assay used herein. The MIP tag can include a locator element to determine the identity of the bin from which the genotype was derived. For example, when output from an enrichment procedure results in about 500 cells, the enriched product/cells can be split into a microliter plate containing 500 wells such that each cell is in a different distinct well. FIG. 7B illustrates a microtiter plate with 500 wells each of which contains a single cell. Each cell is interrogated at 10 different SNPs per chromosome, on 4 chromosomes (e.g., chromosomes 13, 18, 21 and X). This analysis requires 40 MIPs per cell/well for a total of 20,000 tags per 500 wells (i.e., 4 chromosomes×10 SNPs×500 wells). The tagging step can also include amplification of the MIPs after their rearrangement or enzymatic "gap fill".

In one embodiment, a nucleic acid tag comprises a unique property, such as a difference in mass or chemical properties from other tags. In another embodiments a nucleic acid tag comprises a photoactivatable label, so that it crosslinks where it binds. In another embodiment a nucleic acid tag can be used as a linker for ultra deep sequencing. In another embodiment a nucleic acid tag can be used as a linker for arrays. In another embodiment a nucleic acid tag comprises a unique fluorescent label, (Such as FAM, JOE, ROX, NED, HEX, SYBR, PET, TAMRA, VIC, CY-3, CY-5, dR6G, DS-33, LIZ, DS-02, dR110, and Texas Red) which can be used to differentiate individual DNA fragments. In another embodiment a nucleic acid tag can serve as primer or hybridization site for a probe, to facilitate signal amplification or detection from a single cell by using a tractable marker. In some embodiments the labeled nucleic acid tag can be analyzed using a system coupled to a light source, such as an ABI 377, 310, 3700 or any other system which can detect fluorescently labeled DNA.

In step 510, the tagged amplicons are pooled together for further analysis.

In step 512, the genotype at each polymorphic site is determined and/or quantified using any technique known in the art. In one embodiment, genotyping occurs by hybridization of the MIP tags to a microarray containing probes complementary to the sequences of each MIP tag. See U.S. Pat. No. 6,858,412.

Using the example described above with the MIP probes, the 20,000 tags are hybridized to a single tag array containing complementary sequences to each of the tagged MIP probes. Microarrays (e.g. tag arrays) can include a plurality of nucleic acid probes immobilized to discrete spots (e.g., defined locations or assigned positions) on a substrate surface. For example, a microarray can have at least 5, 10, 20, 30, 40, 50, 60, 70, 80, 90, 100, 500, 1,000, 5,000, 10,000, 15,000, 20,000, 30,000, 40,000, 50,000, 60,000, 70,000, 80,000, 90,000, or 100,000 different probes complementary to MIP tagged probes. Methods to prepare microarrays capable to monitor several genes according to the methods of the invention are well known in the art. Examples of microarrays that can be used in nucleic acid analysis that may be used are described in U.S. Pat. Nos. 6,300,063, 5,837,832, 6,969,589, 6,040,138, 6,858,412, US Publication No. 2005/0100893, US Publication No. 2004/0018491, US Publication No. 2003/0215821 and US Publication No. 2003/0207295.

In step 516, bins with rare alleles (e.g., fetal alleles) are identified. Using the example described above, rare allele identification can be accomplished by first using the 22 bp tags to sort the 20,000 genotypes into 500 bins which correspond to the individual wells of the original microtiter plates. Then, one can identify bins containing non-maternal alleles which correspond to wells that contained fetal cells. Determining the number bins with non-maternal alleles relative to the total number of its provides an accurate estimate of the number of fnRBCs that were present in the original enriched cell population. When a fetal cell is identified in a given bin, the non-maternal alleles can be detected by 40 independent SNPS s which provide an extremely high level of confidence in the result.

In step 518, a condition such as trisomy is determined based on the rare cell polymorphism. For example, after identifying the ~10 bins that contain fetal cells, one can determine the ploidy of chromosomes 13, 18, 21 and X of such cells by comparing the ratio of maternal to paternal alleles for each of ~10 SNPs on each chromosome (X, 13, 18, 21). The ratios for the multiple SNPs on each chromosome can be combined (averaged) to increase the confidence of the aneuploidy call for that chromosome. In addition, the information from the ~10 independent bins containing fetal cells can also be combined to further increase the confidence of the call.

As described above, an enriched maternal sample with 500 cells can be split into 500 discrete locations such that each location contains one cell. If ten SNPs are analyzed in each of four different chromosomes, forty tagged MIP probes are added per discrete location to analyze forty different SNPs per cell. The forty SNPs are then amplified in each location using the primer element in the MIP probe as described above. All the amplicons from all the discrete locations are then pooled and analyzed using quantitative genotyping as describe above. In this example a total of 20,000 probes in a microarray are required to genotype the same 40 SNPs in each of the 500 discrete locations (4 chromosomes×10 SNPs×500 discrete locations).

The above embodiment can also be modified to provide for genotyping by hybridizing the nucleic acid tags to bead arrays as are commercially available by Illumina, Inc. and as described in U.S. Pat. Nos. 7,040,959; 7,035,740; 7,033,754; 7,025,935, 6,998,274; 6,942,968; 6,913,884; 6,890,764; 6,890,741; 6,858,394; 6,846,460; 6,812,005; 6,770,441; 6,663,832; 6,620,584; 6,544,732; 6,429,027; 6,396,995; 6,355,431 and US Publication Application Nos. 20060019258; 20050266432; 20050244870; 20050216207; 20050181394; 20050164246; 20040224353; 20040185482; 20030198573; 20030175773; 20030003490; 20020187515; and 20020177141; as well as Shen, R., et al. Mutation Research 573 70-82 (2005).

Figure 7C:
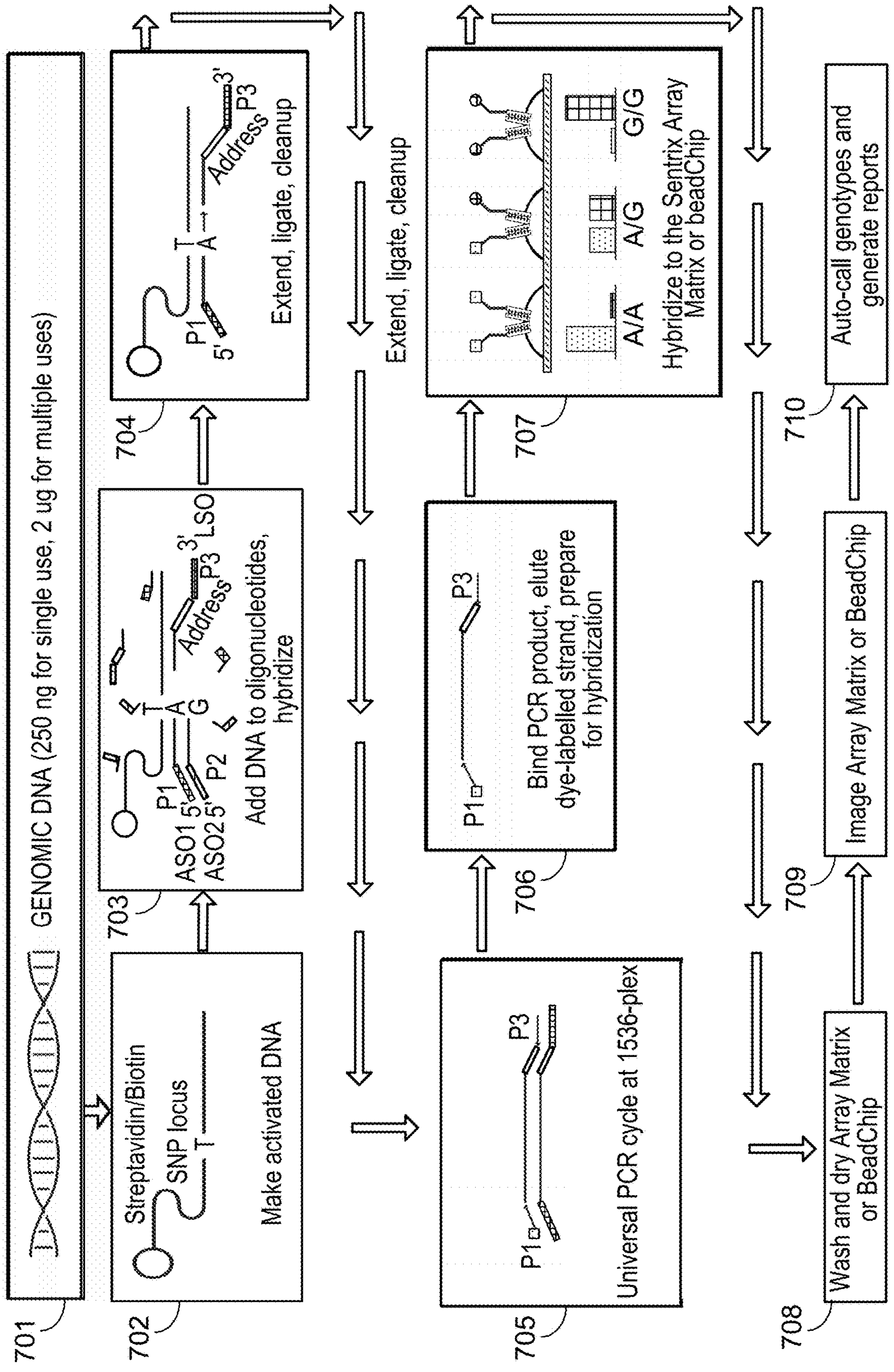

An overview of the use of nucleic acid tags is described in FIG. 7C. After enrichment and amplification as described above, target genomic DNA regions are activated in step 702 such that they may bind paramagnetic particles. In step 703 assay oligonucleotides, hybridization buffer, and paramagnetic particles are combined with the activated DNA and allowed to hybridize (hybridization step). In some cases, three oligonucleotides are added for each SNP to be detected. Two of the three oligos are specific for each of the two alleles at a SNP position and are referred to as Allele-Specific Oligos (ASOs). A third oligo hybridizes several bases downstream from the SNP site and is referred to as the Locus-Specific Oligo (LSO). All three oligos contain regions of genomic complementarity (C1, C2, and C3) and universal PCR primer sites (P1, P2 and P3). The LSO also contains a unique address sequence (Address) that targets a particular bead type. In some cases, up to 1,536 SNPs may be interrogated in this manner. During the primer hybridization process, the assay oligonucleotides hybridize to the genomic DNA sample bound to paramagnetic particles. Because hybridization occurs prior to any amplification steps, no amplification bias is introduced into the assay. The above primers can further be modified to serve the two roles of determining the identity of the different SNPs and to determining the identity of the bin from which the genotype was derived. In step 704, following the hybridization step, several wash steps are performed reducing noise by removing excess and mis-hybridized oligonucleotides. Extension of the appropriate ASO and ligation of the extended product to the LSO joins information about the genotype present at the SNP site to the address sequence on the LSO. In step 705, the joined, full-length products provide a template for performing PCR reactions using universal PCR primers P1, P2, and P3. Universal primers P1 and P2 are labeled with two different labels (e.g., Cy3 and Cy5). Other labels that can be used include, chromophores, fluorescent moieties, enzymes, antigens, heavy metal, magnetic probes, dyes, phosphorescent groups, radioactive materials, chemiluminescent moieties, scattering or fluorescent nanoparticles, Raman signal generating moieties, or electrochemical detection moieties. In step 706, the single-stranded, labeled DNAs are eluted and prepared for hybridization. In step 707, the single-stranded, labeled DNAs are hybridized to their complement bead type through their unique address sequence. Hybridization of the GoldenGate Assay products onto the Array Matrix of Beadchip allows for separation of the assay products in solution, onto a solid surface for individual SNP genotype readout. In step 708, the array is washed and dried. In step 709, a reader such as the BeadArray Reader is used to analyze signals from the label. For example, when the labels are dye labels such as Cy3 and Cy5, the reader can analyze the fluorescence signal on the Sentrix Array Matrix or BeadChip. In step 710, a computer readable medium having a computer executable logic recorded on it can be used in a computer to perform receive data from one or more quantified DNA genomic regions to automate genotyping clusters and callings. Expression detection and analysis using microarrays is described in part in Valk, P. J. et al. New England Journal of Medicine 350(16), 1617-28, 2004; Modlich, O. et al. Clinical Cancer Research 10(10), 3410-21, 2004; Onken, Michael D. et al. Cancer Res. 64(20), 7205-7209, 2004; Gardian, et al. J. Biol. Chem. 280(1), 556-563, 2005; Becker, M. et al. Mol. Cancer Ther. 4(1), 151-170, 2005; and Flechner, S M et al. Am J Transplant 4(9), 1475-89, 2004; as well as in U.S. Pat. Nos. 5,445,934; 5,700,637; 5,744,305; 5,945,334; 6,054,270; 6,140,044; 6,261,776; 6,291,183; 6,346,413; 6,399,365; 6,420,169; 6,551,817; 6,610,482; 6,733,977; and EP 619 321; 323 203.

In any of the embodiments herein, preferably, more than 1000, 5,000, 10,000, 50,000, 100,000, 500,000, or 1,000,000 SNPs are interrogated in parallel.

Figure 6:
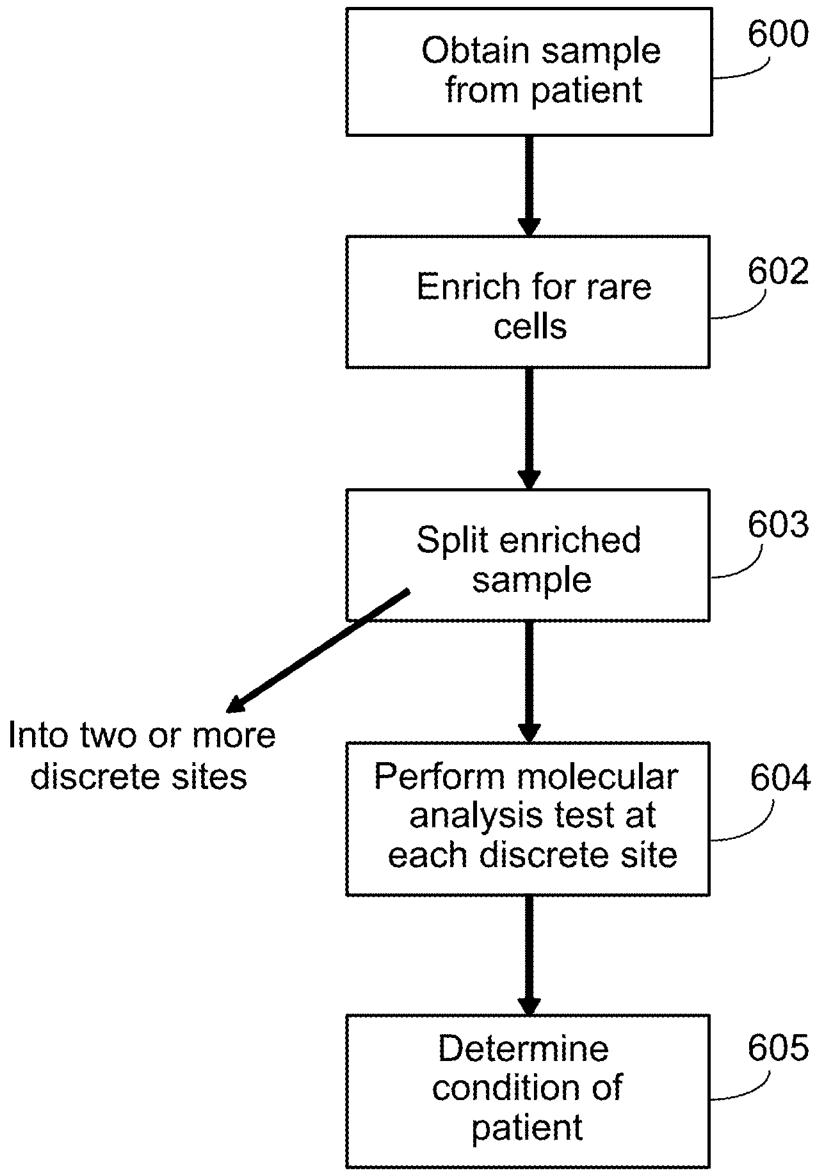
FIG. 6 illustrates an overview for diagnosing, prognosing or monitoring cancer in a patient.

In another aspect of the invention, illustrated in part by FIG. 6, the systems and methods herein can be used to diagnose, prognose, and monitor neoplastic conditions such as cancer in a patient. Examples of neoplastic conditions contemplated herein include acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, and Wilm's tumor.

Cancers such as breast, colon, liver, ovary, prostate, and lung as well as other tumors exfoliate epithelial cells into the bloodstream. The presence of an increased number epithelial cells is associated with an active tumor or other neoplastic condition, tumor progression and spread, poor response to therapy, relapse of disease, and/or decreased survival over a period of several years. Therefore, enumerating and/or analyzing epithelial cells and CTC's in the bloodstream can be used to diagnose, prognose, and/or monitor neoplastic conditions.

In step 600, a sample is obtained from an animal such as a human. The human can be suspected of having cancer or cancer recurrence or may have cancer and is in need of therapy selection. The sample obtained is a mixed sample comprising normal cells as well as one or more CTCs, epithelial cells, endothelial cells, stem cells, or other cells indicative of cancer. In some cases, the sample is a blood sample. In some cases multiple samples are obtained from the animal at different points in time (e.g., regular intervals such as daily, or every 2, 3 or 4 days, weekly, bimonthly, monthly, bi-yearly or yearly.

In step 602, the mixed sample is then enriched for epithelial cells or CTC's or other cell indicative of cancer. Epithelial cells that are exfoliated from solid tumors have been found in very low concentrations in the circulation of patients with advanced cancers of the breast, colon, liver, ovary, prostate, and lung, and the presence or relative number of these cells in blood has been correlated with overall prognosis and response to therapy. These epithelial cells which are in fact CTCs can be used as an early indicator of tumor expansion or metastasis before the appearance of clinical symptoms.

CTCs are generally larger than most blood cells. Therefore, one useful approach for obtaining CTCs in blood is to enrich them based on size, resulting in a cell population enriched in CTCs. Another way to enrich CTCs is by affinity separation, using antibodies specific for particular cell surface markers may be used. Useful endothelial cell surface markers include CD105, CD106, CD144, and CD146; useful tumor endothelial cell surface markers include TEM1, TEM5, and TEM8 (see, e.g., Carson-Walter et al., Cancer Res. 61:6649-6655 (2001)); and useful mesenchymal cell surface markers include CD133. Antibodies to these or other markers may be obtained from, e.g., Chemicon, Abcam, and R&D Systems.

In one example, a size-based separation module that enriches CTC's from a fluid sample (e.g., blood) comprises an array of obstacles that selectively deflect particles having a hydrodynamic size larger than 10 μm into a first outlet and particles having a hydrodynamic size smaller than 10 μm into a second outlet is used to enrich epithelial cells and CTC's from the sample.

Figure 9:
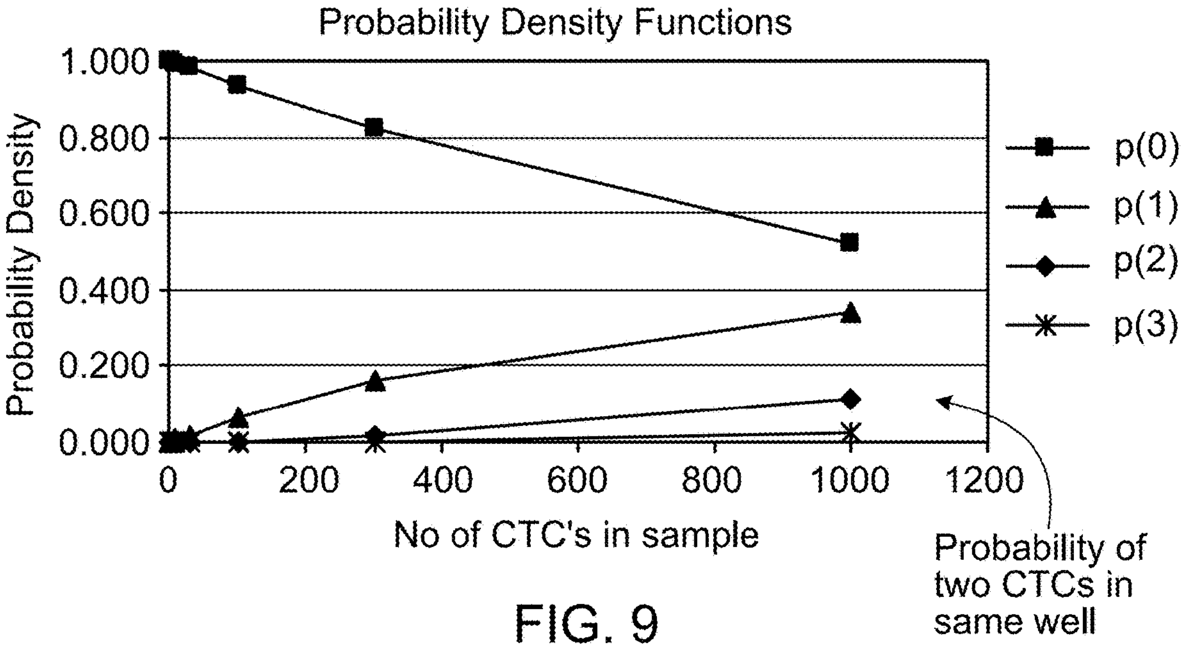
FIG. 9 illustrates the probability of having 2 or more CTC's loaded into a single sample well.

In step 603, the enriched product is split into a plurality of discrete sites, such as microwells. Examples of microwells that can be used in the present invention include microplates having 1536 wells as well as those of lesser density (e.g., 96 and 384 wells). Microwell plate design contemplated herein include those having 14 outputs that can be automatically dispensed at the same time, as well as those with 16, 24, or 32 outputs such that e.g., 32 outputs can be dispensed simultaneously. FIG. 9 illustrates one embodiment of a microwell plate contemplated herein.

Dispensing of the cells into the various discrete sites is preferably automated. In some cases, about 1, 5, 10, or 15 μL of enriched sample is dispensed into each well. Preferably, the size of the well and volume dispensed into each well is such that only 1 cell is dispensed per well and only 1-5 or less than 3 cells can fit in each well.

Figure 8A:
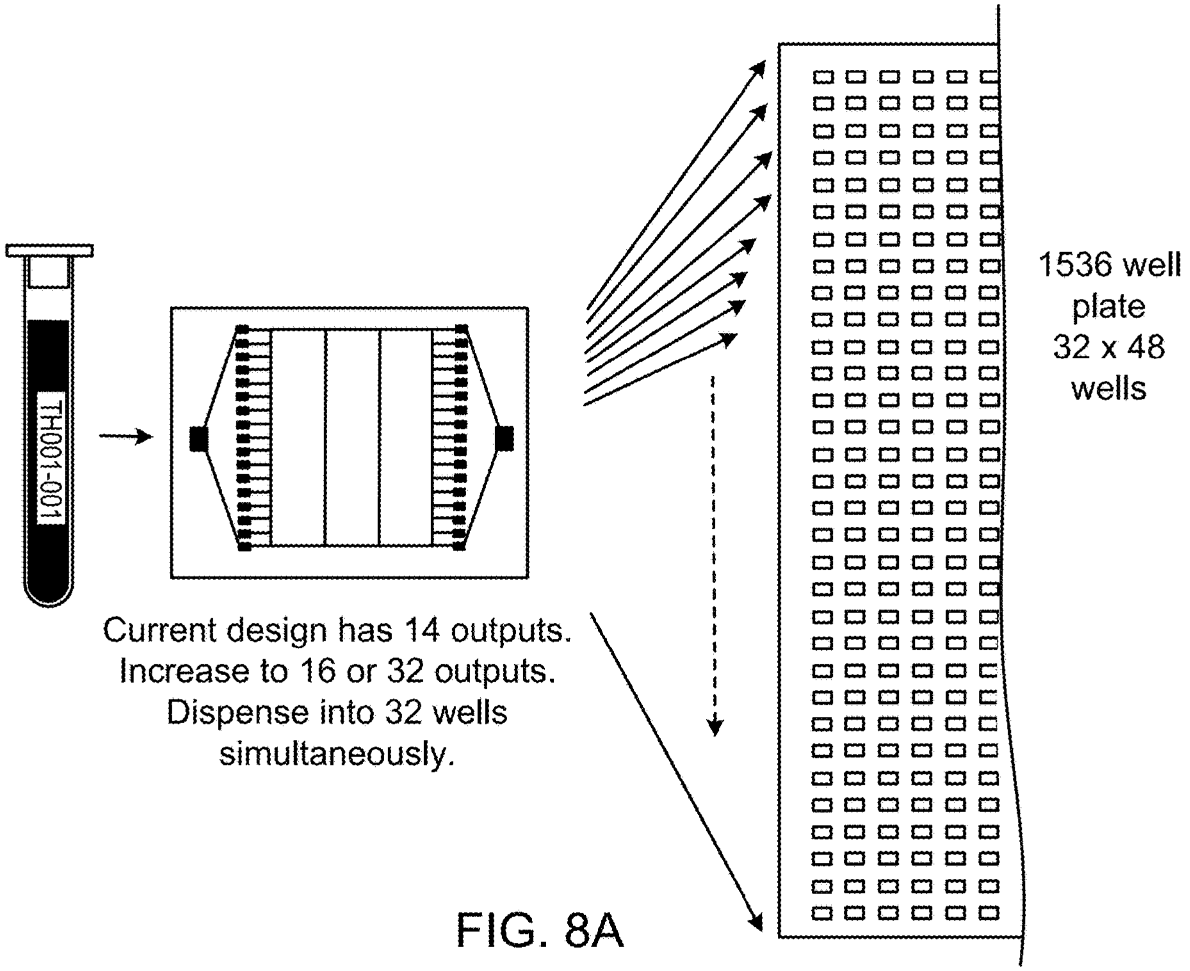
FIGS. 8A-8C illustrate one example of a sample splitting apparatus.
Figure 8B:
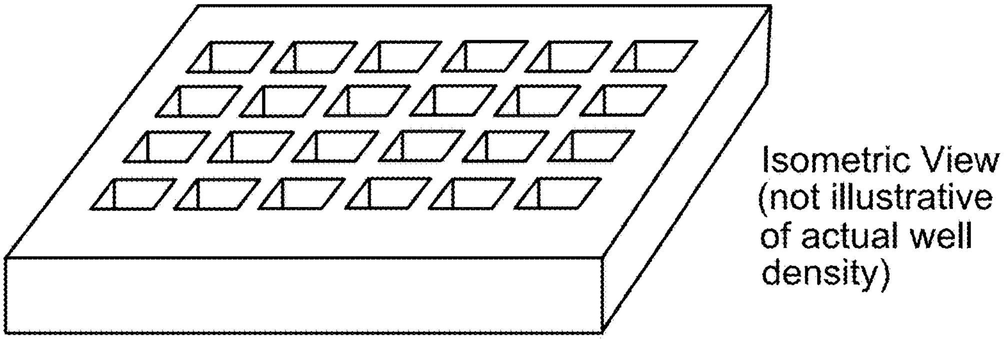

An exemplary array for sample splitting is illustrated in FIG. 8A. FIG. 8B illustrates an isometric view and FIG. 8B illustrates a top view and cross sectional view of such an array. A square array of wells is arranged such that each subsequent row or column of wells is identical to the previous row or column of wells, respectively. In some embodiments, an array of wells is configured in a substrate or plate that about 2.0 $cm^2$, 2.5 $cm^2$, 3 $cm^2$ or larger. The wells can be of any shape, e.g., round, square, or oval. The height or width of each well can be between 5-50 μm, 10-40 μm, or about 25 μm. The depth of each well can be up to 100, 80, 60, or 40 μm; and the radius between the centers of two wells in one column is between 10-60 μm, 20-50 μm, or about 35 μm. Using these configurations, an array of wells of area 2.5 $cm^2$ can have a at least $0.1\times10^6$ wells, $0.2\times10^6$ wells, $0.3\times10^6$ wells, $0.4\times10^6$ wells, or $0.5\times10^6$ wells.

Figure 8C:
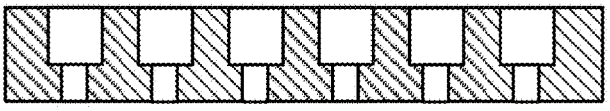

In some embodiments, such as those illustrated in FIG. 8C each well may have an opening at the bottom. The bottom opening is preferably smaller in size than the cells of interest. In this case, if the average radius of a CTC is about 10 μm, the bottom opening of each well can have a radius of up to 8, 7, 6, 5, 4, 3, 2 or 1 μm. The bottom opening allows for cells non-of interest and other components smaller than the cell of interest to be removed from the well using flow pressure, leaving the cells of interest behind in the well for further processing. Methods and systems for actuating removal of cells from discrete predetermined sites are disclosed in U.S. Pat. No. 6,692,952 and U.S. application Ser. No. 11/146,581.

In some cases, the array of wells can be a micro-electro-mechanical system (MEMS) such that it integrates mechanical elements, sensors, actuators, and electronics on a common silicon substrate through microfabrication technology. Any electronics in the system can be fabricated using integrated circuit (IC) process sequences (e.g., CMOS, Bipolar, or BICMOS processes), while the micromechanical components are fabricated using compatible micromachining processes that selectively etch away parts of the silicon wafer or add new structural layers to form the mechanical and electromechanical devices. One example of a MEMS array of wells includes a MEMS isolation element within each well. The MEMS isolation element can create a flow using pressure and/or vacuum to increase pressure on cells and particles not of interest to escape the well through the well opening. In any of the embodiments herein, the array of wells can be coupled to a microscope slide or other substrate that allows for convenient and rapid optical scanning of all chambers (i.e. discrete sites) under a microscope. In some embodiments, a 1536-well microtiter plate is used for enhanced convenience of reagent addition and other manipulations.

In some cases, the enriched product can be split into wells such that each well is loaded with a plurality of leukocytes (e.g., more than 100, 200, 500, 1000, 2000, or 5000). In some cases, about 2500 leukocytes are dispensed per well, while random wells will have a single epithelial CTC or up to 2, 3, 4, or 5 epithelial cells or CTC's. Preferably, the probability of getting a single epithelial cell or CTC into a well is calculated such that no more than 1 CTC is loaded per well. The probability of dispensing CTC's from a sample into wells can be calculated using Poisson statistics. When dispensing a 15 mL sample into 1536 wellplate at 10 μL per well, it is not until the number of CTC's in the sample is >100 that there is more than negligible probability of two or more CTC's being loaded into the sample well. FIG. 9 illustrates the probability density function of loading two CTC's into the same plate.

In step 604, rare cells (e.g. epithelial cells or CTC's) or rare DNA is detected and/or analyzed in each well.

In some embodiments, detection and analysis includes enumerating epithelial cells and/or CTC's. CTCs typically have a short half-life of approximately one day, and their presence generally indicates a recent influx from a proliferating tumor. Therefore, CTCs represent a dynamic process that may reflect the current clinical status of patient disease and therapeutic response. Thus, in some embodiments, step 604 involves enumerating CTC and/or epithelial cells in a sample (array of wells) and determining based on their number if a patient has cancer, severity of condition, therapy to be used, or effectiveness of therapy administered.

In some cases, the method herein involve making a series of measurements, optionally made at regular intervals such as one day, two days, three days, one week, two weeks, one month, two months, three months, six months, or one year, one may track the level of epithelial cells present in a patient's bloodstream as a function of time. In the case of existing cancer patients, this provides a useful indication of the progression of the disease and assists medical practitioners in making appropriate therapeutic choices based on the increase, decrease, or lack of change in epithelial cells, e.g., CTCs, in the patient's bloodstream. For those at risk of cancer, a sudden increase in the number of cells detected may provide an early warning that the patient has developed a tumor. This early diagnosis, coupled with subsequent therapeutic intervention, is likely to result in an improved patient outcome in comparison to an absence of diagnostic information.

In some cases, more than one type of cell (e.g., epithelial, endothelial, etc.) can be enumerated and a determination of a ratio of numbers of cells or profile of various cells can be obtained to generate the diagnosis or prognosis.

Alternatively, detection of rare cells or rare DNA (e.g. epithelial cells or CTC's) can be made by detecting one or more cancer biomarkers, e.g., any of those listed in FIG. 10 in one or more cells in the array. Detection of cancer biomarkers can be accomplished using, e.g., an antibody specific to the marker or by detecting a nucleic acid encoding a cancer biomarker, e.g., listed in FIG. 9.

In some cases single cell analysis techniques are used to analyze individual cells in each well. For example, single cell PCR may be performed on a single cell in a discrete location to detect one or more mutant alleles in the cell (Thornhill A R, J. Mol. Diag; (4) 11-29 (2002)) or a mutation in a gene listed in FIG. 9. In-cell PCR, gene expression analysis can be performed even when the number of cells per well is very low (e.g. 1 cell per well) using techniques known in the art. (Giordano et al., Am. J. Pathol. 159:1231-1238 (2001), and Buckhaults et al., Cancer Res. 63:4144-4149 (2003)). In some cases, single cell expression analysis can be performed to detect expression of one or more genes of interest (Liss B., Nucleic Acids Res., 30 (2002)) including those listed in FIG. 9. Furthermore, ultra-deep sequencing can be performed on single cells using methods such as those described in Margulies M., et al. Nature, "Genome sequencing in microfabricated high-density picolitre reactors." DOI 10.1038, in which whole genomes are fragmented, fragments are captured using common adapters on their own beads and within droplets of an emulsion, clonally amplified. Such ultra-deep sequencing can also be used to detect mutations in genes associated with cancer, such as those listed in FIG. 9. In addition, fluorescence in-situ hybridization can be used, e.g., to determine the tissue or tissues of origin of the cells being analyzed.

In some cases, morphological analyses are performed on the cells in each well. Morphological analyses include identification, quantification and characterization of mitochondrial DNA, telomerase, or nuclear matrix proteins. Parrella et al., Cancer Res. 61:7623-7626 (2001); Jones et al., Cancer Res. 61:1299-1304 (2001); Fliss et al., Science 287:2017-2019 (2000); and Soria et al., Clin. Cancer Res. 5:971-975 (1999). In particular, in some cases, the molecular analyses involve determining whether any mitochondrial abnormalities or whether perinuclear compartments are present. Carew et al., Mol. Cancer 1:9 (2002); and Wallace, Science 283:1482-1488 (1999).

A variety of cellular characteristics may be measured using any technique known in the art, including: protein phosphorylation, protein glycosylation, DNA methylation (Das et al., J. Clin. Oncol. 22:4632-4642 (2004)), microRNA levels (He et al., Nature 435:828-833 (2005), Lu et al., Nature 435:834-838 (2005), O'Donnell et al., Nature 435:839-843 (2005), and Calin et al., N. Engl. J. Med. 353:1793-1801 (2005)), cell morphology or other structural characteristics, e.g., pleomorphisms, adhesion, migration, binding, division, level of gene expression, and presence of a somatic mutation. This analysis may be performed on any number of cells, including a single cell of interest, e.g., a cancer cell.

In one embodiment, the cell(s) (such as fetal, maternal, epithelial or CTCs) in each well are lysed and RNA is extracted using any means known in the art. For example, The Quiagen RNeasy™ 96 bioRobot™ 8000 system can be used to automate high-throughput isolation of total RNA from each discrete site. Once the RNA is extracted reverse transcriptase reactions can be performed to generate cDNA sequences, which can then be used for performing multiplex PCR reactions on target genes. For example, 1 or more than 1, 2, 3, 4, 5, 6, 7, 8, 9, 10, 15, or 20 target genes can be amplified in the same reaction. When more than one target genes are used in the same amplification reaction, primers are chosen to be multiplexable (fairly uniform melting temperature, absence of cross-priming on the human genome, and absence of primer-primer interaction based on sequence analysis) with other pairs of primers. Multiple dyes and multi-color fluorescence readout may be used to increase the multiplexing capacity. Examples of dyes that can be used to label primers for amplification include, but are not limited to, chromophores, fluorescent moieties, enzymes, antigens, heavy metal, magnetic probes, dyes, phosphorescent groups, radioactive materials, chemiluminescent moeities, scattering or fluorescent nanoparticles, Raman signal generating moieties, and electrochemical detection moieties.

In another embodiment, fetal or maternal cells or nuclei are enriched using one or more methods disclosed herein. Preferably, fetal cells are enriched by flowing the sample through an array of obstacles that selectively directs particles or cells of different hydrodynamic sizes into different outlets such that fetal cells and cells larger than fetal cells are directed into a first outlet and one or more cells or particles smaller than the rare cells are directed into a second outlet.

Total RNA or poly-A mRNA is then obtained from enriched cell(s) (fetal or maternal cells) using purification techniques known in the art. Generally, about 1 μg-2 μg of total RNA is sufficient. Next, a first-strand complementary DNA (cDNA) is synthesized using reverse transcriptase and a single T7-oligo(dT) primer. Next, a second-strand cDNA is synthesized using DNA ligase, DNA polymerase, and RNase enzyme. Next, the double stranded cDNA (ds-cDNA) is purified.

In another embodiment, total RNA is extracted from enriched cells (fetal cells or maternal cells). Next a, two one-quarter scale Message Amp II reactions (Ambion, Austin, Texas) are performed for each RNA extraction using 200 ng of total RNA. MessageAmp is a procedure based on antisense RNA (aRNA) amplification, and involves a series of enzymatic reactions resulting in linear amplification of exceedingly small amounts of RNA for use in array analysis. Unlike exponential RNA amplification methods, such as NASBA and RT-PCR, aRNA amplification maintains representation of the starting mRNA population. The procedure begins with total or poly(A) RNA that is reverse transcribed using a primer containing both oligo(dT) and a T7 RNA polymerase promoter sequence. After first-strand synthesis, the reaction is treated with RNase H to cleave the mRNA into small fragments. These small RNA fragments serve as primers during a second-strand synthesis reaction that produces a double-stranded cDNA template.

In some embodiments, cDNAs, which are reverse transcribed from mRNAs obtained from fetal or maternal cells, are tagged and sequenced. The type and abundance of the cDNAs can be used to determine whether a cell is a fetal cell (such as by the presence of Y chromosome specific transcripts) or whether the fetal cell has a genetic abnormality (such as aneuploidy, abundance or type of alternative transcripts or problems with DNA methylation or imprinting).

In one embodiment, PCR amplification can be performed on genes that are expressed in epithelial cells and not in normal cells, e.g., white blood cells or other cells remaining in an enriched product. Exemplary genes that can be analyzed according to the methods herein include EGFR, EpCAM, GA733-2, MUC-1, HER-2, Claudin-7 and any other gene identified in FIG. 10.

For example, analysis of the expression level or pattern of such a polypeptide or nucleic acid, e.g., cell surface markers, genomic DNA, RNA, or microRNA, may result in a diagnosis or prognosis of cancer.

In some embodiments, cDNAs, which are reverse transcribed from mRNAs obtained from fetal or maternal cells, are tagged and sequenced. The type and abundance of the cDNAs can be used to determine whether a cell is a fetal cell (such as by the presence of Y chromosome specific transcripts) or whether the fetal cell has a genetic abnormality (such as aneuploidy, or problems with DNA methylation or imprinting).

In some embodiments, analysis step 604 involves identifying cells from a mixed sample that express genes which are not expressed in the non-rare cells (e.g. EGFR or EpCAM). For example, an important indicator for circulating tumor cells is the presence/expression of EGFR or EGF at high levels wherein non-cancerous epithelial cells will express EGFR or EGF at smaller amounts if at all.

In addition, for lung cancer and other cancers, the presence or absence of certain mutations in EGFR can be associated with diagnosis and/or prognosis of the cancer as well and can also be used to select a more effective treatment (see, e.g., International Publication WO 2005/094357). For example, many non-small cell lung tumors with EGFR mutations respond to small molecule EGFR inhibitors, such as gefitinib (Iressa; AstraZeneca), but often eventually acquire secondary mutations that make them drug resistant. In some embodiments, one can determine a therapy treatment for a patient by enriching epithelial cells and/or CTC's using the methods herein, splitting sample of cells (preferably so no more than 1 CTC is in a discrete location), and detecting one or more mutations in the EGFR gene of such cells. Exemplary mutations that can be analyzed include those clustered around the ATP-binding pocket of the EGFR TK domain, which are known to make cells susceptible to gefitinib inhibition. Thus, presence of such mutations supports a diagnosis of cancer that is likely to respond to treatment using gefitinib.

Many patients who respond to gefitinib eventually develop a second mutation, often a methionine-to-threonine substitution at position 790 in exon 20 of the TK domain. This type of mutation renders such patients resistant to gefitinib. Therefore, the present invention contemplates testing for this mutation as well to provide further diagnostic information.

Since many EGFR mutations, including all EGFR mutations in NSC lung cancer reported to date that are known to confer sensitivity or resistance to gefitinib, lie within the coding regions of exons 18 to 21, this region of the EGFR gene may be emphasized in the development of assays for the presence of mutations. Examples of primers that can be used to detect mutations in EGFR include those listed in FIG. 11.

In step 605, a determination is made as to the condition of a patient based on analysis made above. In some cases the patient can be diagnosed with cancer or lack thereof. In some cases, the patient can be prognosed with a particular type of cancer. In cases where the patient has cancer, therapy may be determined based on the types of mutations detected.

In another embodiment, cancer cells may be detected in a mixed sample (e.g. circulating tumor cells and circulating normal cells) using one or more of the sequencing methods described herein. Briefly, RNA is extracted from cells in each location and converted to cDNA as described above. Target genes are then amplified and high throughput ultra deep sequencing is performed to detect a mutation expression level associated with cancer.

VI. Computer Executable Logic

Any of the steps herein can be performed using computer program product that comprises a computer executable logic recorded on a computer readable medium. For example, the computer program can use data from target genomic DNA regions to determine the presence or absence of fetal cells in a sample and to determine fetal abnormalit(ies) in cells detected. In some embodiments, computer executable logic uses data input on STR or SNP intensities to determine the presence of fetal cells in a test sample and determine fetal abnormalities and/or conditions in said cells.

The computer program may be specially designed and configured to support and execute some or all of the functions for determining the presence of rare cells such as fetal cells or epithelial/CTC's in a mixed sample and abnormalities and/or conditions associated with such rare cells or their DNA including the acts of (i) controlling the splitting or sorting of cells or DNA into discrete locations (ii) amplifying one or more regions of genomic DNA e.g. trisomic region(s) and non-trisomic region(s) (particularly DNA polymorphisms such as STR and SNP) in cells from a mixed sample and optionally control sample, (iii) receiving data from the one or more genomic DNA regions analyzed (e.g. sequencing or genotyping data); (iv) identifying bins with rare (e.g. non-maternal) alleles, (v) identifying bins with rare (e.g. non-maternal) alleles as bins containing fetal cells or epithelial cells, (vi) determining number of rare cells (e.g. fetal cells or epithelial cells) in the mixed sample, (vii) detecting the levels of maternal and non-maternal alleles in identified fetal cells, (viii) detecting a fetal abnormality or condition in said fetal cells and/or (ix) detecting a neoplastic condition and information concerning such condition such as its prevalence, origin, susceptibility to drug treatment(s), etc. In particular, the program can fit data of the quantity of allele abundance for each polymorphism into one or more data models. One example of a data model provides for a determination of the presence or absence of aneuploidy using data of amplified polymorphisms present at loci in DNA from samples that are highly enriched for fetal cells. The determination of presence of fetal cells in the mixed sample and fetal abnormalities and/or conditions in said cells can be made by the computer program or by a user.

In one example, let 'f' be the fetal/maternal DNA copy ratio in a particular PCR reaction. Trisomy increases the ratio of maternal to paternal alleles by a factor 1+f/2. PCR efficiencies vary from allele to allele within a locus by a mean square error in the logarithm given by $\sigma_{allele}^2$, and vary from locus to locus by ($\sigma_{locus}^2$, where this second variance is apt to be larger due to differences in primer efficiency. $N_a$ is the loci per suspected aneuploid chromosome and $N_c$ is the control loci. If the mean of the two maternal allele strengths at any locus is 'm' and the paternal allele strength is 'p,' then the squared error expected is the mean of the ln(ratio(m/p)), where this mean is taken over N loci is given by $2(\sigma_{allele}^2)/N$. When taking the difference of this mean of ln(ratio(m/p)) between a suspected aneuploidy region and a control region, the error in the difference is given by $$\sigma_{diff}^2 = 2(\sigma_{allele}^2)/N_a + 2(\sigma_{allele}^2)/N_c \quad (1)$$

For a robust detection of aneuploidy we require $$3\sigma_{diff} < f/2.$$

For simplicity, assuming $N_a=N_c=N$ in Equation 1, this gives the requirement $$6\sigma_{allele}/N^{1/2} < f/2, \quad (3)$$

or a minimum N of $$N = 144(\sigma_{allele}/f)^2 \quad (4)$$

In the context of trisomy detection, the suspected aneuploidy region is usually the entire chromosome and N denotes the number of loci per chromosome. For reference, Equation 3 is evaluated for N in Table 2 for various values of $\sigma_{allele}$ and f.

The role of the sequencing is to measure the allele abundances output from the amplification step. It is desirable to do this without adding significantly more error due to the Poisson statistics of selecting only a finite number of amplicons for sequencing. The rms error in the ln(abundance) due to Poisson statistics is approximately $(N_{reads})^{-1/2}$. It is desirable to keep this value less than or equal to the PCR error $\sigma_{allele}$. Thus, a typical paternal allele needs to be allocated at least $(\sigma_{allele})^{-2}$ reads. The maternal alleles, being more abundant, do not add appreciably to this error when forming the ratio estimate for m/p. The mixture input to sequencing contains amplicons from $N_{loci}$ loci of which roughly an abundance fraction f/2 are paternal alleles. Thus, the total required number of reads for each of the aliquot wells is given approximately by $2N_{loci}/(f(\sigma_{allele}^2)$. Combining this result with Equation 4, it is found a total number of reads over all the wells given approximately by $N_{reads}=288\ N_{wells}f^{-3}$. Thus, the program can determine the total number of reads that need to be obtained for determining the presence or absence of aneuploidy in a patient sample.

The computer program can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

In one embodiment, the computer executing the computer logic of the invention may also include a digital input device such as a scanner. The digital input device can provide an image of the target genomic DNA regions (e.g. DNA polymorphism, preferably STRs or SNPs) according to method of the invention. For instance, the scanner can provide an image by detecting fluorescent, radioactive, or other emissions; by detecting transmitted, reflected, or scattered radiation; by detecting electromagnetic properties or characteristics; or by other techniques. Various detection schemes are employed depending on the type of emissions and other factors. The data typically are stored in a memory device, such as the system memory described above, in the form of a data file.

In one embodiment, the scanner may identify one or more labeled targets. For instance, in the genotyping analysis described herein a first DNA polymorphism may be labeled with a first dye that fluoresces at a particular characteristic frequency, or narrow band of frequencies, in response to an excitation source of a particular frequency. A second DNA polymorphisms may be labeled with a second dye that fluoresces at a different characteristic frequency. The excitation sources for the second dye may, but need not, have a different excitation frequency than the source that excites the first dye, e.g., the excitation sources could be the same, or different, lasers.

In one embodiment, a human being may inspect a printed or displayed image constructed from the data in an image file and may identify the data (e.g. fluorescence from microarray) that are suitable for analysis according to the method of the invention. In another embodiment, the information is provided in an automated, quantifiable, and repeatable way that is compatible with various image processing and/or analysis techniques.

Another aspect of the invention is kits which permit the enrichment and analysis of the rare cells present in small qualities in the samples. Such kits may include any materials or combination of materials described for the individual steps or the combination of steps ranging from the enrichment through the genetic analysis of the genomic material. Thus, the kits may include the arrays used for size-based separation or enrichment, labels for uniquely labeling each cell, the devices utilized for splitting the cells into individual addressable locations and the reagents for the genetic analysis. For example, a kit might contain the arrays for size-based separation, unique labels for the cells and reagents for detecting polymorphisms including STRs or SNPs, such as reagents for performing PCR.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1. Separation of Fetal Cord Blood

FIG. 1E shows a schematic of the device used to separate nucleated cells from fetal cord blood.

Dimensions: 100 mm×28 mm×1 mm

Array design: 3 stages, gap size=18, 12 and 8 μm for the first, second and third stage, respectively.

Device fabrication: The arrays and channels were fabricated in silicon using standard photolithography and deep silicon reactive etching techniques. The etch depth is 140 μm. Through holes for fluid access are made using KOH wet etching. The silicon substrate was sealed on the etched face to form enclosed fluidic channels using a blood compatible pressure sensitive adhesive (9795, 3M, St Paul, MN).

Device packaging: The device was mechanically mated to a plastic manifold with external fluidic reservoirs to deliver blood and buffer to the device and extract the generated fractions.

Device operation: An external pressure source was used to apply a pressure of 2.0 PSI to the buffer and blood reservoirs to modulate fluidic delivery and extraction from the packaged device.

Experimental conditions: Human fetal cord blood was drawn into phosphate buffered saline containing Acid Citrate Dextrose anticoagulants. 1 mL of blood was processed at 3 mL/hr using the device described above at room temperature and within 48 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, CA) containing 1% Bovine Serum Albumin (BSA) (A8412-100ML, Sigma-Aldrich, St Louis, MO) and 2 mM EDTA (15575-020, Invitrogen, Carlsbad, CA).

Figure 12A:
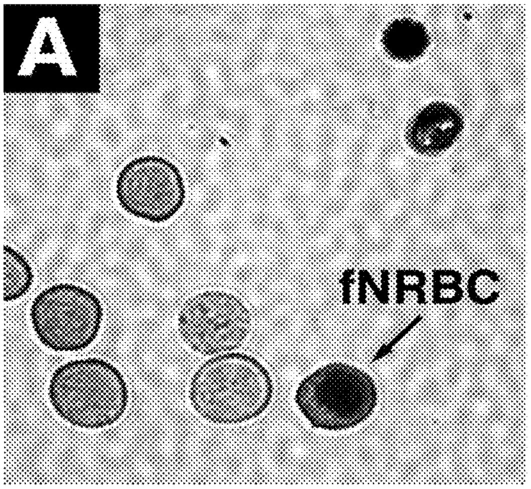
FIGS. 12A-B illustrate cell smears of the product and waste fractions.

Measurement techniques: Cell smears of the product and waste fractions (FIGS. 12A-12B) were prepared and stained with modified Wright-Giemsa (WG16, Sigma Aldrich, St. Louis, MO).

Figure 12B:
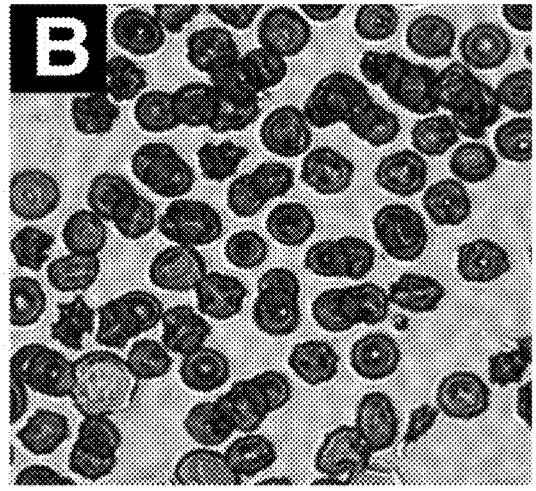

Performance: Fetal nucleated red blood cells were observed in the product fraction (FIG. 12A) and absent from the waste fraction (FIG. 12B).

Example 2. Isolation of Fetal Cells from Maternal Blood

The device and process described in detail in Example 1 were used in combination with immunomagnetic affinity enrichment techniques to demonstrate the feasibility of isolating fetal cells from maternal blood.

Experimental conditions: blood from consenting maternal donors carrying male fetuses was collected into $K_2$EDTA vacutainers (366643, Becton Dickinson, Franklin Lakes, NJ) immediately following elective termination of pregnancy. The undiluted blood was processed using the device described in Example 1 at room temperature and within 9 hrs of draw. Nucleated cells from the blood were separated from enucleated cells (red blood cells and platelets), and plasma delivered into a buffer stream of calcium and magnesium-free Dulbecco's Phosphate Buffered Saline (14190-144, Invitrogen, Carlsbad, CA) containing 1% Bovine Serum Albumin (BSA) (A8412-100ML, Sigma-Aldrich, St Louis, MO). Subsequently, the nucleated cell fraction was labeled with anti-CD71 microbeads (130-046-201, Miltenyi Biotech Inc., Auburn, CA) and enriched using the MiniMACS™ MS column (130-042-201, Miltenyi Biotech Inc., Auburn, CA) according to the manufacturer's specifications. Finally, the CD71-positive fraction was spotted onto glass slides.

Measurement techniques: Spotted slides were stained using fluorescence in situ hybridization (FISH) techniques according to the manufacturer's specifications using Vysis probes (Abbott Laboratories, Downer's Grove, IL). Samples were stained from the presence of X and Y chromosomes. In one case, a sample prepared from a known Trisomy 21 pregnancy was also stained for chromosome 21.

Performance: Isolation of fetal cells was confirmed by the reliable presence of male cells in the CD71-positive population prepared from the nucleated cell fractions (FIGS.

Figure 14:
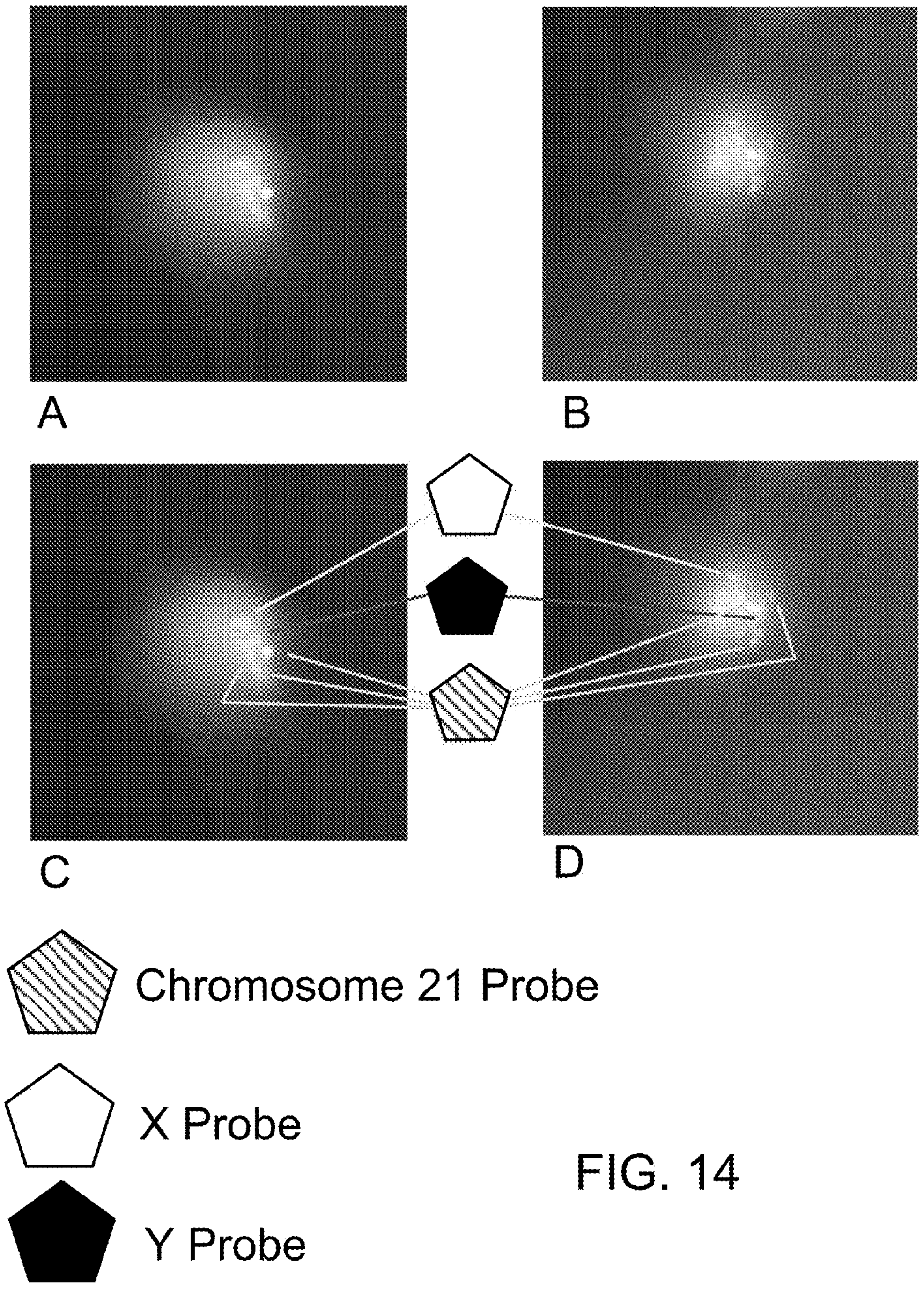
FIG. 14 illustrates cells with abnormal trisomy 21 pathology.

13A-13F). In the single abnormal case tested, the trisomy 21 pathology was also identified (FIG. 14).

Example 3. Confirmation of the Presence of Male Fetal Cells in Enriched Samples

Confirmation of the presence of a male fetal cell in an enriched sample is performed using qPCR with primers specific for DYZ, a marker repeated in high copy number on the Y chromosome. After enrichment of fnRBC by any of the methods described herein, the resulting enriched fnRBC are binned by dividing the sample into 100 PCR wells. Prior to binning, enriched samples may be screened by FISH to determine the presence of any fnRBC containing an aneuploidy of interest. Because of the low number of fnRBC in maternal blood, only a portion of the wells will contain a single fnRBC (the other wells are expected to be negative for fnRBC). The cells are fixed in 2% Paraformaldehyde and stored at 4° C. Cells in each bin are pelleted and resuspended in 5 μl PBS plus 1 μl 20 mg/ml Proteinase K (Sigma #P-2308). Cells are lysed by incubation at 65° C. for 60 minutes followed by inactivation of the Proteinase K by incubation for 15 minutes at 95° C. For each reaction, primer sets (DYZ forward primer TCGAGTGCATTCCATTCCG (SEQ ID NO: 57); DYZ reverse primer ATGGAATGGCATCAAACGGAA (SEQ ID NO: 58); and DYZ Taqman Probe 6FAM-TGGCTGTCCATTCCA-MGBNFQ (SEQ ID NO: 59)), TaqMan Universal PCR master mix, No AmpErase and water are added. The samples are run and analysis is performed on an ABI 7300: 2 minutes at 50° C., 10 minutes 95° C. followed by 40 cycles of 95° C. (15 seconds) and 60° C. (1 minute). Following confirmation of the presence of male fetal cells, further analysis of bins containing fnRBC is performed. Positive bins may be pooled prior to further analysis.

Figure 30:
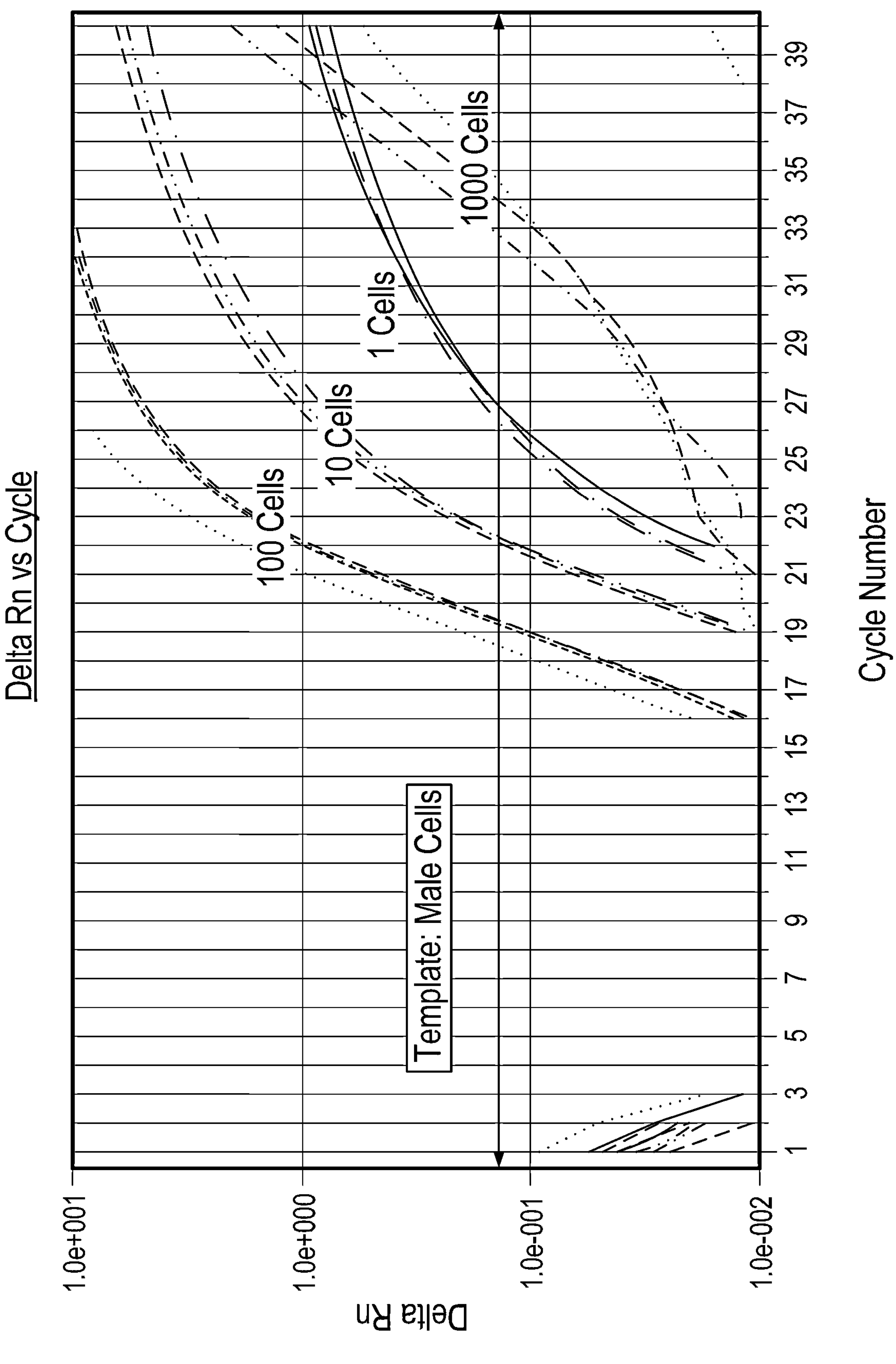
FIG. 30 illustrates the detection of single copies of a fetal cell genome by qPCR.

FIG. 30 shows the results expected from such an experiment. The data in FIG. 30 was collected by the following protocol. Nucleated red blood cells were enriched from cord cell blood of a male fetus by sucrose gradient two Heme Extractions (HE). The cells were fixed in 2% paraformaldehyde and stored at 4° C. Approximately 10×1000 cells were pelleted and resuspended each in 5 μl PBS plus 1 μl 20 mg/ml Proteinase K (Sigma #P-2308). Cells were lysed by incubation at 65° C. for 60 minutes followed by a inactivation of the Proteinase K by 15 minute at 95° C. Cells were combined and serially diluted 10-fold in PBS for 100, 10 and 1 cell per 6 μl final concentration were obtained. Six μl of each dilution was assayed in quadruplicate in 96 well format. For each reaction, primer sets (0.9 uM DYZ forward primer TCGAGTGCATTCCATTCCG (SEQ ID NO: 57); 0.9 uM DYZ reverse primer ATGGAATGGCATCAAACGGAA (SEQ ID NO: 58); and 0.5 uM DYZ TaqMan Probe 6FAM-TGGCTGTCCATTCCA-MGBNFQ (SEQ ID NO: 59)), TaqMan Universal PCR master mix, No AmpErase and water were added to a final volume of 25 μl per reaction. Plates were run and analyzed on an ABI 7300: 2 minutes at 50° C., 10 minutes 95° C. followed by 40 cycles of 95° C. (15 seconds) and 60° C. (1 minute). These results show that detection of a single fnRBC in a bin is possible using this method.

Example 4. Confirmation of the Presence of Fetal Cells in Enriched Samples by STR Analysis Maternal blood is processed through a size-based separation module, with or without subsequent MHEM enhancement of fnRBCs. The enhanced sample is then subjected to FISH analysis using probes specific to the aneuploidy of interest (e.g., trisomy 13, trisomy 18, and XYY). Individual positive cells are isolated by "plucking" individual positive cells from the enhanced sample using standard micromanipulation techniques. Using a nested PCR protocol, STR marker sets are amplified and analyzed to confirm that the FISH-positive aneuploid cell(s) are of fetal origin. For this analysis, comparison to the maternal genotype is typical. An example of a potential resulting data set is shown in Table 3. Non-maternal alleles may be proven to be paternal alleles by paternal genotyping or genotyping of known fetal tissue samples. As can be seen, the presence of paternal alleles in the resulting cells, demonstrates that the cell is of fetal origin (cells #1, 2, 9, and 10). Positive cells may be pooled for further analysis to diagnose aneuploidy of the fetus, or may be further analyzed individually.

TABLE 3

STR locus alleles in maternal and fetal cells

| DNA Source | STR locus D14S | STR locus D16S | STR locus D8S | STR locus F13B | STR locus vWA |
|---|---|---|---|---|---|
| Maternal alleles | 14, 17 | 11, 12 | 12, 14 | 9, 9 | 16, 17 |
| Cell #1 alleles | | 8 | | | 19 |
| Cell #2 alleles | 17 | | 15 | | |
| Cell #3 alleles | | | 14 | | |
| Cell #4 alleles | | | | | |
| Cell #5 alleles | 17 | 12 | | 9 | |
| Cell #6 alleles | | | | | |
| Cell #7 alleles | | | | | 19 |
| Cell #8 alleles | | | | | |
| Cell #9 alleles | 17 | | 14 | 7, 9 | 17, 19 |
| Cell #10 alleles | | | 15 | | |

Example 5. Confirmation of the Presence of Fetal Cells in Enriched Samples by SNP Analysis Maternal blood is processed through a size-based separation module, with or without subsequent MHEM enhancement of fnRBCs. The enhanced sample is then subjected to FISH analysis using probes specific to the aneuploidy of interest (e.g., triploidy 13, triploidy 18, and XYY). Samples testing positive with FISH analysis are then binned into 96 microtiter wells, each well containing 15 μl of the enhanced sample. Of the 96 wells, 5-10 are expected to contain a single fnRBC and each well should contain approximately 1000 nucleated maternal cells (both WBC and mnRBC). Cells are pelleted and resuspended in 5 μl PBS plus 1 μl 20 mg/ml Proteinase K (Sigma #P-2308). Cells are lysed by incubation at 65° C. for 60 minutes followed by a inactivation of the Proteinase K by 15 minute at 95° C.

In this example, the maternal genotype (BB) and fetal genotype (AB) for a particular set of SNPs is known. The genotypes A and B encompass all three SNPs and differ from each other at all three SNPs. The following sequence from chromosome 7 contains these three SNPs (rs7795605, rs7795611 and rs7795233 indicated in brackets, respectively):

(SEQ ID NO: 60)
(ATGCAGCAAGGCACAGACTAA[G/A]CAAGGAGA[G/C]GCAAAATTT

TC[A/G]TAGGGGAGAGAAATGGGTCATT).

In the first round of PCR, genomic DNA from binned enriched cells is amplified using primers specific to the outer portion of the fetal-specific allele A and which flank the interior SNP (forward primer ATGCAGCAAGGCACA-GACTACG (SEQ ID NO: 61); reverse primer AGAGGG-GAGAGAAATGGGTCATT (SEQ ID NO: 62)). In the second round of PCR, amplification using real time SYBR Green PCR is performed with primers specific to the inner portion of allele A and which encompass the interior SNP (forward primer CAAGGCACA-GACTAAGCAAGGAGAG (SEQ ID NO: 63); reverse primer GGCAAAATTTTCATAGGG-GAGAGAAATGGGTCATT (SEQ ID NO: 64)).

Figure 31:
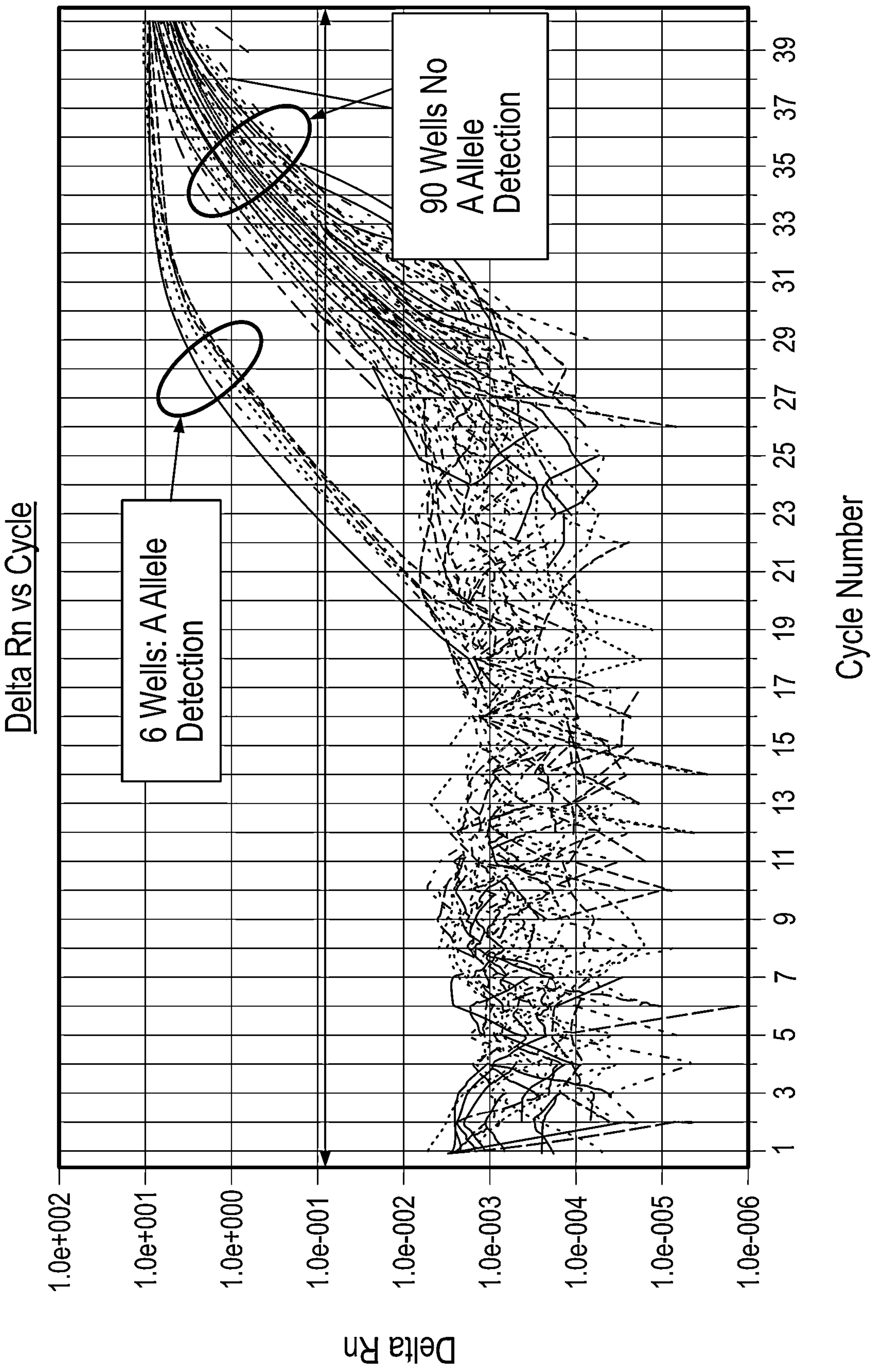
FIG. 31 illustrates detection of single fetal cells in binned samples by SNP analysis.
Figure 32:
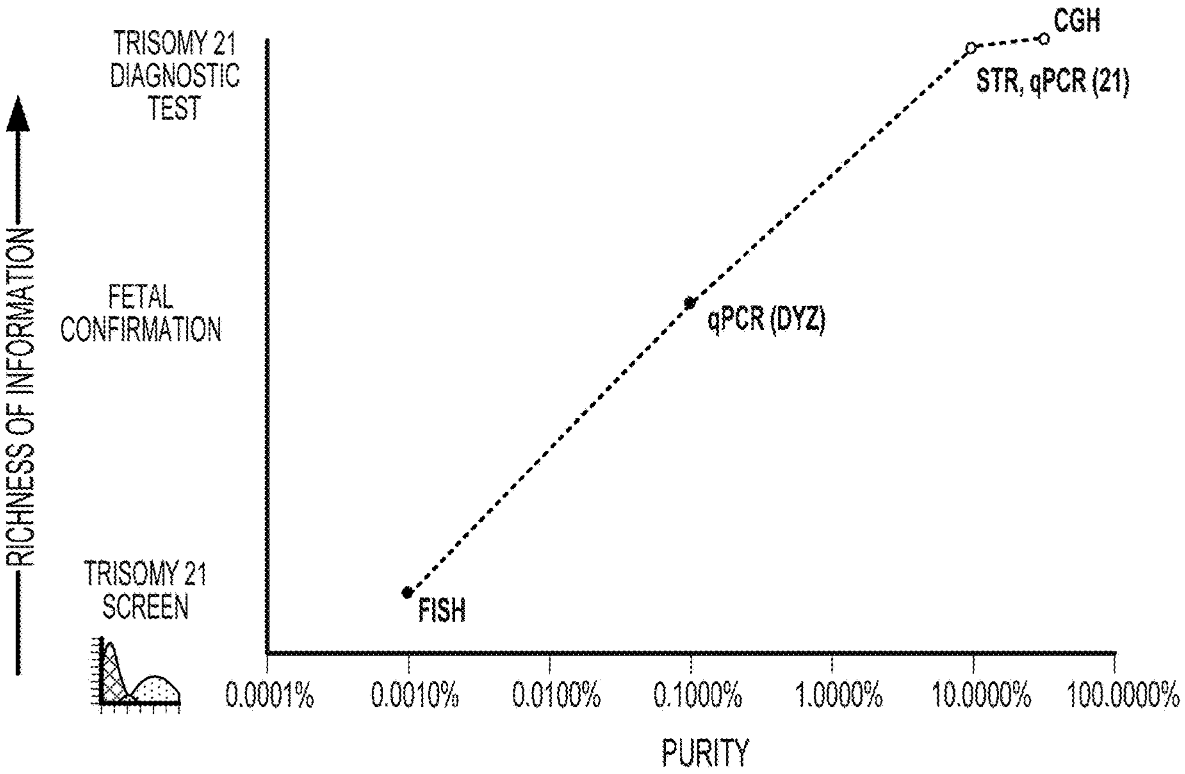
FIG. 32 illustrates a method of trisomy testing. The trisomy 21 screen is based on scoring of target cells obtained from maternal blood. Blood is processed using a cell separation module for hemoglobin enrichment (CSM-HE). Enriched cells are transferred to slides that are first stained and subsequently probed by FISH. Images are acquired, such as from bright field or fluorescent microscopy, and scored. The proportion of trisomic cells of certain classes serves as a classifier for risk of fetal trisomy 21. Fetal genome identification can performed using assays such as: (1) STR markers; (2) qPCR using primers and probes directed to loci, such as the multi-repeat DYZ locus on the Y-chromosome; (3) SNP detection; and (4) CGH (comparative genome hybridization) array detection.
Figure 33:
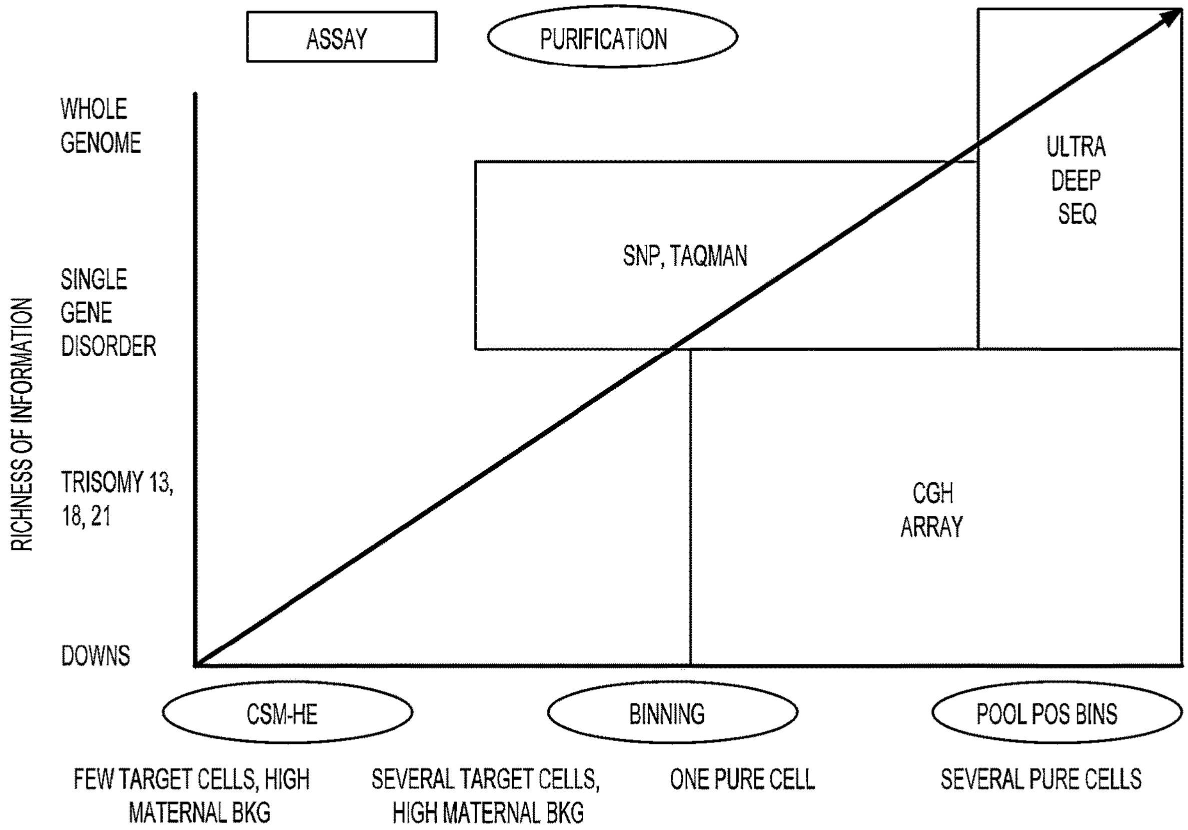
FIG. 33 illustrates assays that can produce information on the presence of aneuploidy and other genetic disorders in target cells. Information on aneuploidy and other genetic disorders in target cells may be acquired using technologies such as: (1) a CGH array established for chromosome counting, which can be used for aneuploidy determination and/or detection of intra-chromosomal deletions; (2) SNP/taqman assays, which can be used for detection of single nucleotide polymorphisms; and (3) ultra-deep sequencing, which can be used to produce partial or complete genome sequences for analysis.

Expected results are shown in FIG. 31. Here, six of the 96 wells test positive for allele A, confirming the presence of cells of fetal origin, because the maternal genotype (BB) is known and cannot be positive for allele A. DNA from positive wells may be pooled for further analysis or analyzed individually.

Example 6. Quantitative Genotyping Using Molecular Inversion Probes for Trisomy Diagnosis on Fetal Cells Fetal cells or nuclei can be isolated as described in the enrichment section or as described in example 1. Quantitative genotyping can then be used to detect chromosome copy number changes. FIG. 5 depicts a flow chart depicting the major steps involved in detecting chromosome copy number changes using the methods described herein. For example, the enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. The output of the enrichment procedure would be divided into separate wells of a microtiter plate with the number of wells chosen so no more than one cell or genome copy is located per well, and where some wells may have no cell or genome copy at all.

Perform multiplex PCR and nested PCR: PCR primer pairs for multiple (40-100) highly polymorphic SNPs can then be added to each well in the microtiter plate. For example, SNPs primers can be designed along chromosomes 13, 18, 21 and X to detect the most frequent aneuploidies, and along control regions of the genome where aneuploidy is not expected. Multiple (~10) SNPs would be designed for each chromosome of interest to allow for non-informative genotypes and to ensure accurate results. The SNPs listed in the Table below can be used to performed analysis and associated PCR primers can be designed as described below.

SNPs that can be used for fetal cell analysis

| Chromosome 13 | Chromosome 18 | Chromosome 21 | Chromosome X |
|---|---|---|---|
| refSNP rs9510053 | refSNP rs584853 | refSNP rs469000 | refSNP rs6608727 |
| refSNP rs7339372 | refSNP rs2345588 | refSNP rs7278903 | refSNP rs2015487 |
| refSNP rs9580269 | refSNP rs9973072 | refSNP rs1004044 | refSNP rs5953330 |
| refSNP rs724946 | refSNP rs7504787 | refSNP rs11910419 | refSNP rs5953330 |
| refSNP rs11842845 | refSNP rs4303617 | refSNP rs2832890 | refSNP rs1984695 |
| refSNP rs7490040 | refSNP rs9947441 | refSNP rs1785477 | refSNP rs5906775 |
| refSNP rs12430585 | refSNP rs2912334 | refSNP rs2250226 | refSNP rs5951325 |
| refSNP rs713280 | refSNP rs11659665 | refSNP rs2243594 | refSNP rs11798710 |
| refSNP rs202090 | refSNP rs8098249 | refSNP rs10483087 | refSNP rs4898352 |
| refSNP rs5000966 | refSNP rs12968582 | refSNP rs855262 | refSNP rs5987079 |

PCR primers would be chosen to be multiplexible with other pairs (fairly uniform melting temperature, absence of cross-priming on the human genome, and absence of primer-primer interaction based on sequence analysis). The primers would be designed to generate amplicons 70-100 bp in size to increase the performance of the multiplex PCR. The primers would contain a 22 bp tag on the 5' which is used in the genotyping analysis. Multiplex PCR protocols can be performed as described in Findlay et al. Molecular Cell Endocrinology 183 (2001) S5-S12. Primer concentrations can vary from 0.7 pmoles to 60 pmoles per reaction. Briefly, PCRs are performed in a total volume of 25 l per well, Taq polymerase buffer (Perkin-Elmer), 200 μM dNTPs, primer, 1.5 mM MgCl2 and 0.6 units AmpliTaq (Perkin-Elmer). After denaturation at 95° C. for 5 min, 41 cycles at 94, 60 and 72° C. for 45 s are performed in a MJ DNA engine thermal cycler. The amplification can be run with an annealing temperature different that 60° C. depending on the primer pair being amplified. Final extension can be for 10 min.

A second of round of PCR using nested primers may be performed to ensure optimal performance of the multiplex amplification. Two ul aliquot of each PCR reaction is diluted 40 fold (to 80 ul total) with nuclease free water from the PCR kit. A no template or negative control is generated to test for contamination. The amplification with the nested PCR primers is run with an annealing temperature of 60° C.-68° C. depending on the primer pair being amplified.

| Nested PCR cycle | | |
|---|---|---|
| Step | Temp (C.) | Time (mins) |
| 1.0 | 95 | 0.5 |
| 2.0 | 94 | 0.5 |
| 3.0 | X | 1.5 |
| 4.0 | 72 | 1.5 |
| 5.0 | cycle to step 2, 44 times | |
| 6.0 | 72 | 10 |

| Master mix for nested primers | | |
|---|---|---|
| | 1 rxn | 9 rxns |
| 2X Q Mix | 12.5 | |
| | 112.5 | |
| titanium | 0.5 | 4.5 |
| Q | 2.5 | |
| | 22.5 | |
| water | 3.3 | |
| | 29.3 | |
| 5 uM primers | 1.3 | |
| 40× diluted template | 5.0 | |
| | 45.0 | |
| | 25.0 | |
| | 213.8 | |

Genotyping using MIP technology with bin specific tags: The Molecular Inversion Probe (MIP) technology developed by Affymetrix (Santa Clara, CA) can genotype 20,000 SNPs or more in a single reaction. In the typical MIP assay, each SNP would be assigned a 22 bp DNA tag which allows the SNP to be uniquely identified during the highly parallel genotyping assay. In this example, the DNA tags serve two roles: (1) determine the identity of the different SNPs and (2) determine the identity of the well from which the genotype was derived. For example, a total of 20,000 tags would be required to genotype the same 40 SNPs in 500 wells different wells (4 chromosomes×10 SNPs×500 wells)

The tagged MIP probes would be combined with the amplicons from the initial multiplex single-cell PCR (or nested PCR) and the genotyping reactions would be performed. The probe/template mix would be divided into 4 tubes each containing a different nucleotide (e.g. G, A, T or C). Following an extension and ligation step, the mixture would be treated with exonuclease to remove all linear molecules and the tags of the surviving circular molecules would be amplified using PCR. The amplified tags form all of the bins would then be pooled and hybridized to a single DNA microarray containing the complementary sequences to each of the 20,000 tags.

Identify bins with non-maternal alleles (e.g. fetal cells): The first step in the data analysis procedure would be to use the 22 bp tags to sort the 20,000 genotypes into bins which correspond to the individual wells of the original microtiter plates. The second step would be to identify bins contain non-maternal alleles which correspond to wells that contained fetal cells. Determining the number bins with non-maternal alleles relative to the total number of bins would provide an accurate estimate of the number of fnRBCs that were present in the original enriched cell population. When a fetal cell is identified in a given bin, the non-maternal alleles would be detected by 40 independent SNPs which provide an extremely high level of confidence in the result.

Detect ploidy for chromosomes 13, 18, and 21: After identifying approximately 10 bins that contain fetal cells, the next step would be to determine the ploidy of chromosomes 13, 18, 21 and X by comparing ratio of maternal to paternal alleles for each of the 10 SNPs on each chromosome. The ratios for the multiple SNPs on each chromosome can be combined (averaged) to increase the confidence of the aneuploidy call for that chromosome. In addition, the information from the approximate 10 independent bins containing fetal cells can also be combined to further increase the confidence of the call.

Example 7. Ultra-Deep Sequencing for Trisomy Diagnosis on Fetal Cells

Fetal cells or nuclei can be isolated as described in the enrichment section or as described in example 1. The enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. The output of the enrichment procedure would be divided into separate wells of a microtiter plate with the number of wells chosen so no more than one cell or genome copy is located per well, and where some wells may have no cell or genome copy at all.

Perform multiplex PCR and Ultra-Deep Sequencing with bin specific tags: PCR primer pairs for highly polymorphic STR loci (multiple loci per chromosome of interest) are then added to each well in the microtiter plate. The polymorphic STRs listed in the Table below can be used to performed analysis and associated PCR primers can be designed.

STR loci that can be used for fetal cell analysis

| MARKER | CHROMOSOME LOCATION |
|---|---|
| D21S1414 | 21q21 |
| MBP | 18q23-ter |
| D13S634 | 13q14.3-22 |
| D13S631 | 13q31-32 |
| D18S535 | 18q12.2-12.3 |
| D21S1412 | 21(S171-S198) |
| D21S1411 | 21q22.3 |
| D21S11 | 21q21 |
| D18S386 | 18q22.1-18q22.2 |
| D13S258 | 13q21.2-13q31 |
| D13S303 | 13q22-13q31 |
| D18S1002 | 18q11 |

The primers for each STR will have two important features. First, each of the primers will contain a common ~18 bp sequence on the 5' end which is used for the subsequent DNA cloning and sequencing procedures. Second, each well in the microtiter plate is assigned a unique ~6 bp DNA tag sequence which is incorporated into the middle part of the upstream primer for each of the different STRs. The DNA tags make it possible to pool all of the STR amplicons following the multiplex PCR which makes it possible to analyze the amplicons in parallel more cost effectively during the ultra-deep sequencing procedure. DNA tags of length ~6 bp provide a compromise between information content (4096 potential bins) and the cost of synthesizing primers.

Multiplex PCR protocols can be performed as described in Findlay et al. Molecular Cell Endocrinology 183 (2001) S5-S12. Primer concentrations can vary from 0.7 pmoles to 60 pmoles per reaction. Briefly, PCRs are performed in a total volume of 25 μl per well, Taq polymerase buffer (Perkin-Elmer), 200 μM dNTPs, primer, 1.5 mM MgCl2 and 0.6 units AmpliTaq (Perkin-Elmer). After denaturation at 95° C. for 5 min, 41 cycles at 94, 60 and 72° C. for 45 s are performed in a MJ DNA engine thermal cycler. The amplification can be run with an annealing temperature different that 60° C. depending on the primer pair being amplified. Final extension can be for 10 min.

Following PCR, the amplicons from each of the wells in the microtiter plate are pooled, purified and analyzed using a single-molecule sequencing strategy as described in Margulies et al. Nature, 437:376-380 (2005). Briefly, the amplicons are diluted and mixed with beads such that each bead captures a single molecule of the amplified material. The DNA-carrying beads are isolated in separate 100 um aqueous droplets made through the creation of a PCR-reaction-mixture-in-oil emulsion. The DNA molecule on each bead is then amplified to generate millions of copies of the sequence, which all remain bound to the bead. Finally, the beads are placed into a highly parallel sequencing-by-synthesis machine which can generate over 400,000 sequence reads (~100 bp per read) in a single 4 hour run.

Ultra-deep sequencing provides an accurate and quantitative way to measure the allele abundances for each of the STRs. The total required number of reads for each of the aliquot wells is determined by the number of STRs and the error rates of the multiplex PCR and the Poisson sampling statistics associated with the sequencing procedures. Statistical models which may account for variables in amplification can be used to detect ploidy changes with high levels of confidence. Using this statistical model it can be predicted that ~100,000 to 300,000 sequence reads will be required to analyze each patient, with ~3 to 10 STR loci per chromosome. Specifically, ~33 reads for each of 12 STRs in each of the individual wells of the microtiter plate will be read (33 reads×12 STRs per well×500 wells=200,000 reads).

Identify bins with non-maternal alleles (e.g. fetal cells): The first step in the data analysis procedure would be to use the 6 bp DNA tags to sort the 200,000 sequence reads into bins which correspond to the individual wells of the microtiter plates. The ~400 sequence reads from each of the bins would then be separated into the different STR groups using standard sequence alignment algorithms. The aligned sequences from each of the bins would then be analyzed to identify non-maternal alleles. These can be identified in one of two ways. First, an independent blood sample fraction known to contain only maternal cells can be analyzed as described above. This sample can be a white blood cell fraction (which will contain only negligible numbers of fetal cells), or simply a dilution of the original sample before enrichment. Alternatively, the genotype profiles for all the wells can be similarity-clustered to identify the dominant pattern associated with maternal cells. In either approach, the detection of non-maternal alleles then determines which wells in the initial microtiter plate contained fetal cells. Determining the number bins with non-maternal alleles relative to the total number of bins provides an estimate of the number of fetal cells that were present in the original enriched cell population. Bins containing fetal cells would be identified with high levels of confidence because the non-maternal alleles are detected by multiple independent STRs.

Detect ploidy for chromosomes 13, 18, and 21: After identifying the bins that contained fetal cells, the next step would be to determine the ploidy of chromosomes 13, 18 and 21 by comparing the ratio of maternal to paternal alleles for each of the STRs. Again, for each bin there will be ~33 sequence reads for each of the 12 STRs. In a normal fetus, a given STR will have 1:1 ratio of the maternal to paternal alleles with approximately 16 sequence reads corresponding to each allele (normal diallelic). In a trisomic fetus, three doses of an STR marker can be detected either as three alleles with a 1:1:1 ratio (trisomic triallelic) or two alleles with a ratio of 2:1 (trisomic diallelic). In rare instances all three alleles may coincide and the locus will not be informative for that individual patient. The information from the different STRs on each chromosome can be combined to increase the confidence of a given aneuploidy call. In addition, the information from the independent bins containing fetal cells can also be combined to further increase the confidence of the call.

Example 8. Sequencing for Trisomy Diagnosis on Fetal Cells

Fetal cells or nuclei can be isolated as described in the enrichment section or as described in example 1 and 2. Sequencing methods can then be used to detect chromosome copy number changes. FIG. 4 depicts a flow chart depicting the major steps involved in detecting chromosome copy number changes using the methods described herein. For example, the enrichment process described in example 1 may generate a final mixture containing approximately 500 maternal white blood cells (WBCs), approximately 100 maternal nuclear red blood cells (mnBCs), and a minimum of approximately 10 fetal nucleated red blood cells (fnRBCs) starting from an initial 20 ml blood sample taken late in the first trimester. The output of the enrichment procedure would be divided into separate wells of a microtiter plate with the number of wells chosen so no more than one cell or genome copy is located per well, and where some wells may have no cell or genome copy at all.

Perform Multiplex PCR and Sequencing with Bin Specific Tags:

PCR primer pairs for highly polymorphic STR loci (multiple loci per chromosome of interest) can be added to each well in the microtiter plate. For example, STRs could be designed along chromosomes 13, 18, 21 and X to detect the most frequent aneuploidies, and along control regions of the genome where aneuploidy is not expected. Typically, four or more STRs should be analyzed per chromosome of interest to ensure accurate detection of aneuploidy.

The primers for each STR can be designed with two important features. First, each primer can contain a common ~18 bp sequence on the 5' end which can be used for the subsequent DNA cloning and sequencing procedures. Second, each well in the microtiter plate can be assigned a unique ~6 bp DNA tag sequence which can be incorporated into the middle part of the upstream primer for each of the different STRs. The DNA tags make it possible to pool all of the STR amplicons following the multiplex PCR, which makes possible to analyze the amplicons in parallel during the ultra-deep sequencing procedure. Furthermore, nested PCR strategies for the STR amplification can achieve higher reliability of amplification from single cells.

Sequencing can be performed using the classic Sanger sequencing method or any other method known in the art.

For example, sequencing can occur by sequencing-by-synthesis, which involves inferring the sequence of the template by synthesizing a strand complementary to the target nucleic acid sequence. Sequence-by-synthesis can be initiated using sequencing primers complementary to the sequencing element on the nucleic acid tags. The method involves detecting the identity of each nucleotide immediately after (substantially real-time) or upon (real-time) the incorporation of a labeled nucleotide or nucleotide analog into a growing strand of a complementary nucleic acid sequence in a polymerase reaction. After the successful incorporation of a label nucleotide, a signal is measured and then nulled by methods known in the art. Examples of sequence-by-synthesis methods are described in U.S. Application Publication Nos. 2003/0044781, 2006/0024711, 2006/0024678 and 2005/0100932. Examples of labels that can be used to label nucleotide or nucleotide analogs for sequencing-by-synthesis include, but are not limited to, chromophores, fluorescent moieties, enzymes, antigens, heavy metal, magnetic probes, dyes, phosphorescent groups, radioactive materials, chemiluminescent moeities, scattering or fluorescent nanoparticles, Raman signal generating moieties, and electrochemical detection moieties. Sequencing-by-synthesis can generate at least 1,000, at least 5,000, at least 10,000, at least 20,000, 30,000, at least 40,000, at least 50,000, at least 100,000 or at least 500,000 reads per hour. Such reads can have at least 50, at least 60, at least 70, at least 80, at least 90, at least 100, at least 120 or at least 150 bases per read.

Another sequencing method involves hybridizing the amplified genomic region of interest to a primer complementary to it. This hybridization complex is incubated with a polymerase, ATP sulfurylase, luciferase, apyrase, and the substrates luciferin and adenosine 5' phosphosulfate. Next, deoxynucleotide triphosphates corresponding to the bases A, C, G, and T (U) are added sequentially. Each base incorporation is accompanied by release of pyrophosphate, converted to ATP by sulfurylase, which drives synthesis of oxyluciferin and the release of visible light. Since pyrophosphate release is equimolar with the number of incorporated bases, the light given off is proportional to the number of nucleotides adding in any one step. The process is repeated until the entire sequence is determined.

Yet another sequencing method involves a four-color sequencing by ligation scheme (degenerate ligation), which involves hybridizing an anchor primer to one of four positions. Then an enzymatic ligation reaction of the anchor primer to a population of degenerate nonamers that are labeled with fluorescent dyes is performed. At any given cycle, the population of nonamers that is used is structure such that the identity of one of its positions is correlated with the identity of the fluorophore attached to that nonamer. To the extent that the ligase discriminates for complementarily at that queried position, the fluorescent signal allows the inference of the identity of the base. After performing the ligation and four-color imaging, the anchor primer:nonamer complexes are stripped and a new cycle begins.

Identify bins with non-maternal alleles (e.g. fetal cells): The first step in the data analysis procedure would be to use the 6 bp DNA tags to sort the 200,000 sequence reads into bins which correspond to the individual wells of the microtiter plates. The ~400 sequence reads from each of the bins would then be separated into the different STR groups using standard sequence alignment algorithms. The aligned sequences from each of the bins would then be analyzed to identify non-maternal alleles. These can be identified in one of two ways. First, an independent blood sample fraction known to contain only maternal cells can be analyzed as described above. This sample can be a white blood cell fraction (which will contain only negligible numbers of fetal cells), or simply a dilution of the original sample before enrichment. Alternatively, the genotype profiles for all the wells can be similarity-clustered to identify the dominant pattern associated with maternal cells. In either approach, the detection of non-maternal alleles then determines which wells in the initial microtiter plate contained fetal cells. Determining the number bins with non-maternal alleles relative to the total number of bins provides an estimate of the number of fetal cells that were present in the original enriched cell population. Bins containing fetal cells would be identified with high levels of confidence because the non-maternal alleles are detected by multiple independent STRs.

Detect ploidy for chromosomes 13, 18, and 21: After identifying the bins that contained fetal cells, the next step would be to determine the ploidy of chromosomes 13, 18 and 21 by comparing the ratio of maternal to paternal alleles for each of the STRs. Again, for each bin there will be ~33 sequence reads for each of the 12 STRs. In a normal fetus, a given STR will have 1:1 ratio of the maternal to paternal alleles with approximately 16 sequence reads corresponding to each allele (normal diallelic). In a trisomic fetus, three doses of an STR marker can be detected either as three alleles with a 1:1:1 ratio (trisomic triallelic) or two alleles with a ratio of 2:1 (trisomic diallelic). In rare instances all three alleles may coincide and the locus will not be informative for that individual patient. The information from the different STRs on each chromosome can be combined to increase the confidence of a given aneuploidy call. In addition, the information from the independent bins containing fetal cells can also be combined to further increase the confidence of the call.

Example 9. Device Embodiment

Figure 15:
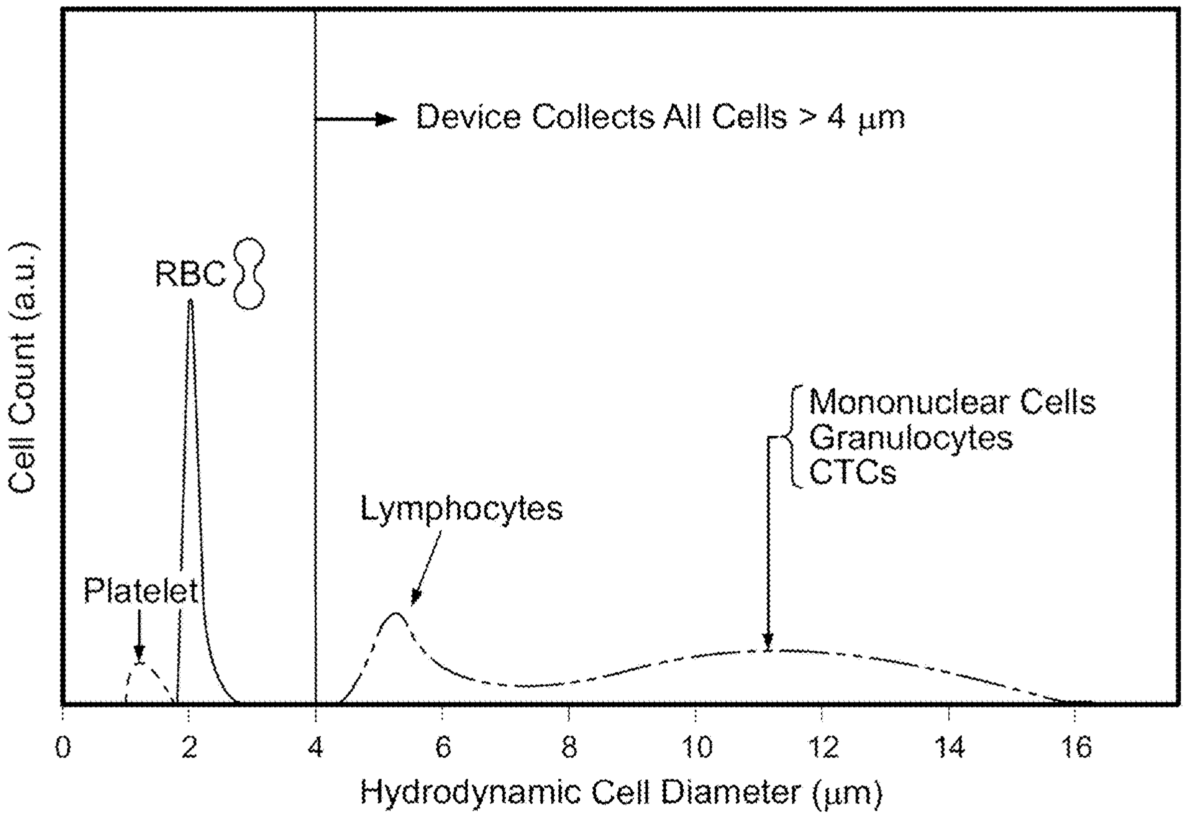
FIG. 15 illustrates performance of a size-based separation module.
Figure 16:
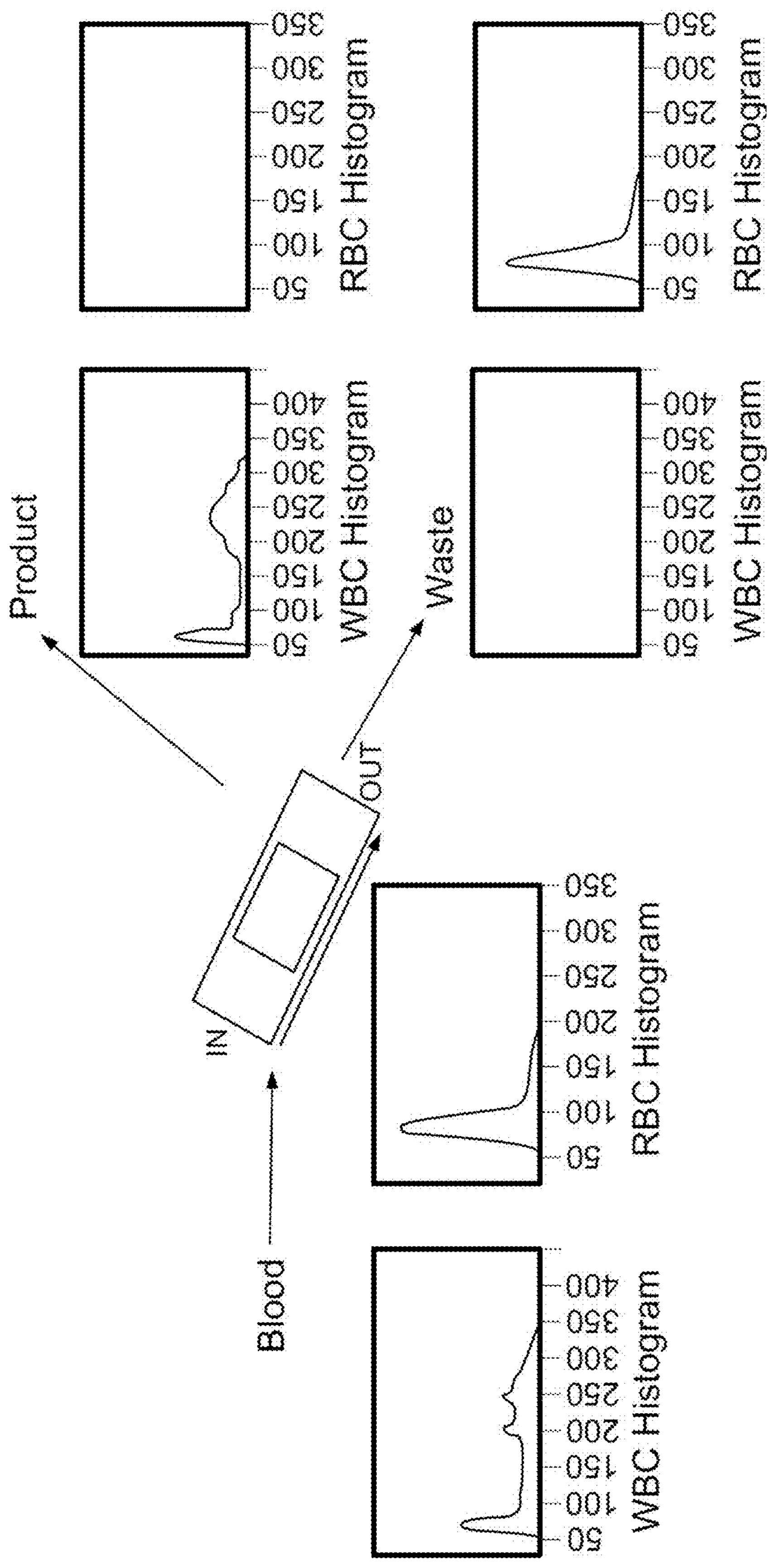
FIG. 16 illustrates histograms of these cell fractions resulting from a size-based separation module.
Figure 17:
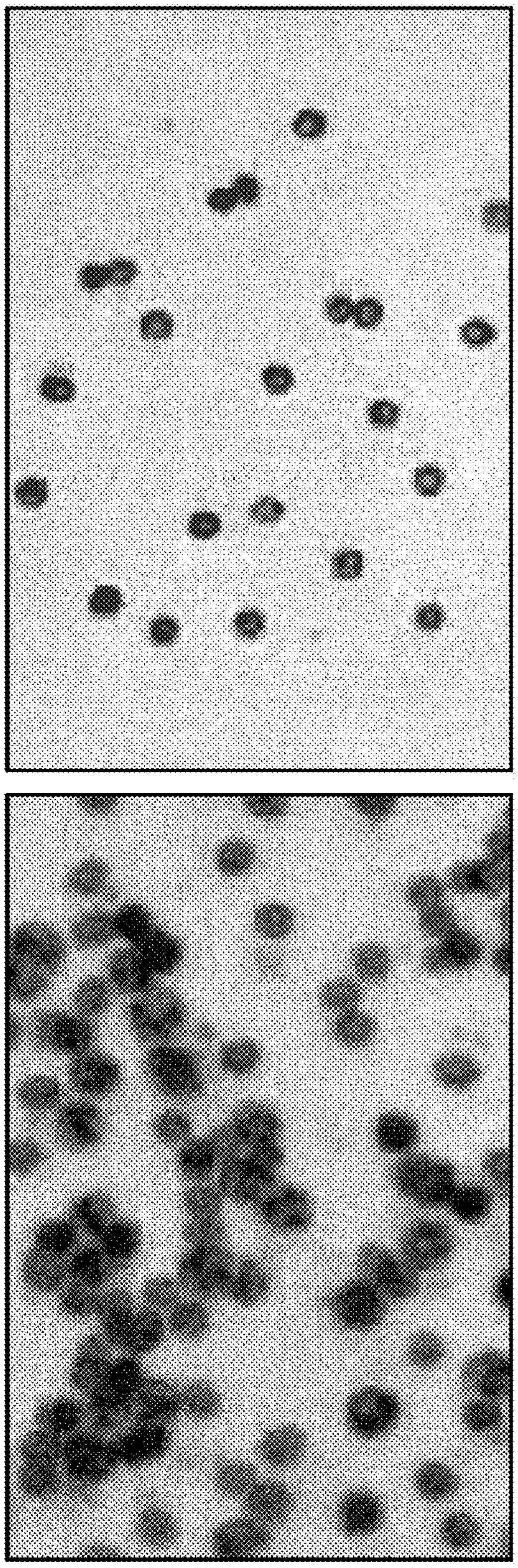
FIG. 17 illustrates a first output and a second output of a size-based separation module.

Microfluidic devices of the invention were designed by computer-aided design (CAD) and microfabricated by photolithography. A two-step process was developed in which a blood sample is first debulked to remove the large population of small cells, and then the rare target epithelial cells target cells are recovered by immunoaffinity capture. The devices were defined by photolithography and etched into a silicon substrate based on the CAD-generated design. The cell enrichment module, which is approximately the size of a standard microscope slide, contains 14 parallel sample processing sections and associated sample handling channels that connect to common sample and buffer inlets and product and waste outlets. Each section contains an array of microfabricated obstacles that is optimized to enrich the target cell type by hydrodynamic size via displacement of the larger cells into the product stream. In this example, the microchip was designed to separate red blood cells (RBCs) and platelets from the larger leukocytes and CTCs. Enriched populations of target cells were recovered from whole blood passed through the device. Performance of the cell enrichment microchip was evaluated by separating RBCs and platelets from white blood cells (WBCs) in normal whole blood (FIG. 15). In cancer patients, CTCs are found in the larger WBC fraction. Blood was minimally diluted (30%), and a 6 ml sample was processed at a flow rate of up to 6 ml/hr. The product and waste stream were evaluated in a Coulter Model "$A^C$-T diff" clinical blood analyzer, which automatically distinguishes, sizes, and counts different blood cell populations. The enrichment chip achieved separation of RBCs from WBCs, in which the WBC fraction had >99% retention of nucleated cells, >99% depletion of RBCs, and >97% depletion of platelets. Representative histograms of these cell fractions are shown in FIG. 16. Routine cytology confirmed the high degree of enrichment of the WBC and RBC fractions (FIG. 17).

Next, epithelial cells were recovered by affinity capture in a microfluidic module that is functionalized with immobilized antibody. A capture module with a single chamber containing a regular array of antibody-coated microfabricated obstacles was designed. These obstacles are disposed to maximize cell capture by increasing the capture area approximately four-fold, and by slowing the flow of cells under laminar flow adjacent to the obstacles to increase the contact time between the cells and the immobilized antibody. The capture modules may be operated under conditions of relatively high flow rate but low shear to protect cells against damage. The surface of the capture module was functionalized by sequential treatment with 10% silane, 0.5% gluteraldehyde, and avidin, followed by biotinylated anti-EpCAM. Active sites were blocked with 3% bovine serum albumin in PBS, quenched with dilute Tris HCl, and stabilized with dilute L-histidine. Modules were washed in PBS after each stage and finally dried and stored at room temperature. Capture performance was measured with the human advanced lung cancer cell line NCI-H1650 (ATCC Number CRL-5883). This cell line has a heterozygous 15 bp in-frame deletion in exon 19 of EGFR that renders it susceptible to gefitinib. Cells from confluent cultures were harvested with trypsin, stained with the vital dye Cell Tracker Orange (CMRA reagent, Molecular Probes, Eugene, OR), resuspended in fresh whole blood, and fractionated in the microfluidic chip at various flow rates. In these initial feasibility experiments, cell suspensions were processed directly in the capture modules without prior fractionation in the cell enrichment module to debulk the red blood cells; hence, the sample stream contained normal blood red cells and leukocytes as well as tumor cells. After the cells were processed in the capture module, the device was washed with buffer at a higher flow rate (3 ml/hr) to remove the nonspecifically bound cells. The adhesive top was removed and the adherent cells were fixed on the chip with paraformaldehyde and observed by fluorescence microscopy. Cell recovery was calculated from hemacytometer counts; representative capture results are shown in Table 4. Initial yields in reconstitution studies with unfractionated blood were greater than 60% with less than 5% of non-specific binding.

TABLE 4

| Run number | Avg. flow rate | Length of run | No. cells processed | No. cells captured | Yield |
|---|---|---|---|---|---|
| 1 | 3.0 | 1 hr | 150,000 | 38,012 | 25% |
| 2 | 1.5 | 2 hr | 150,000 | 30,000/ml | 60% |
| 3 | 0.08 | 2 hr | 108,000 | 68,661 | 64% |
| 4 | 1.21 | 2 hr | 121,000 | 75,491 | 62% |

Figure 18:
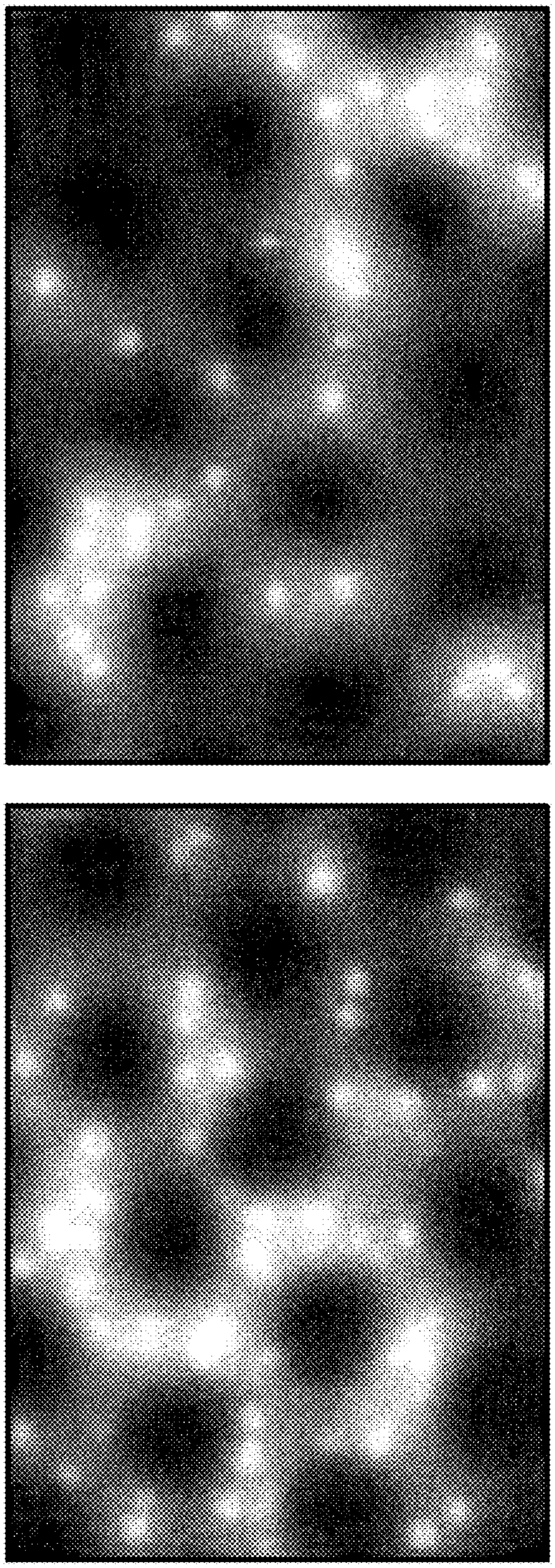
FIG. 18 illustrates epithelial cells bound to a capture module of an array of obstacles coated with anti-EpCAM.

Next, NCI-H1650 cells that were spiked into whole blood and recovered by size fractionation and affinity capture as described above were successfully analyzed in situ. In a trial run to distinguish epithelial cells from leukocytes, 0.5 ml of a stock solution of fluorescein-labeled CD45 pan-leukocyte monoclonal antibody were passed into the capture module and incubated at room temperature for 30 minutes. The module was washed with buffer to remove unbound antibody, and the cells were fixed on the chip with 1% paraformaldehyde and observed by fluorescence microscopy. As shown in FIG. 18, the epithelial cells were bound to the obstacles and floor of the capture module. Background staining of the flow passages with CD45 pan-leukocyte antibody is visible, as are several stained leukocytes, apparently because of a low level of non-specific capture.

Example 10: Device Embodiments

Figure 19A:
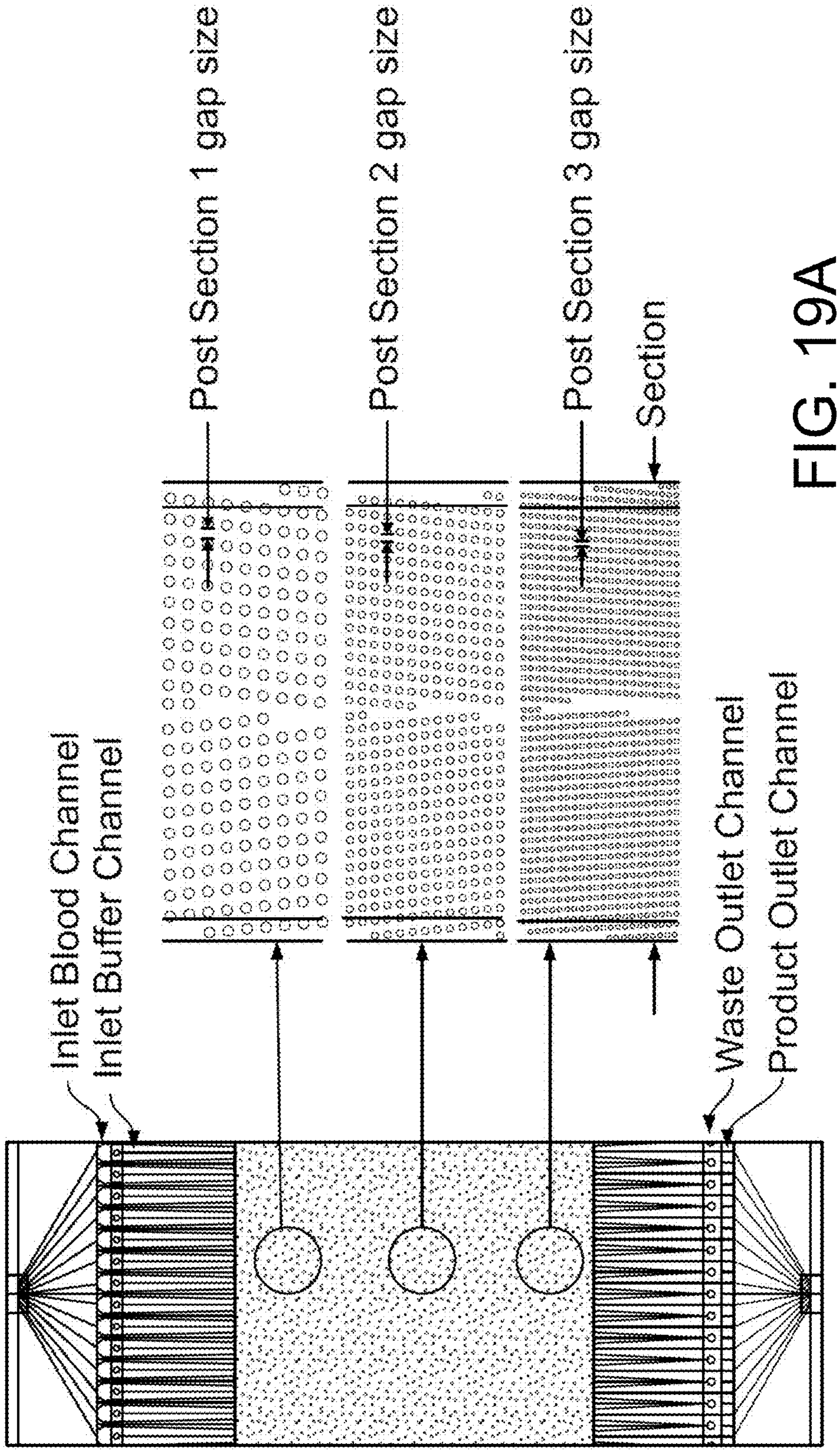
Figure 19C:
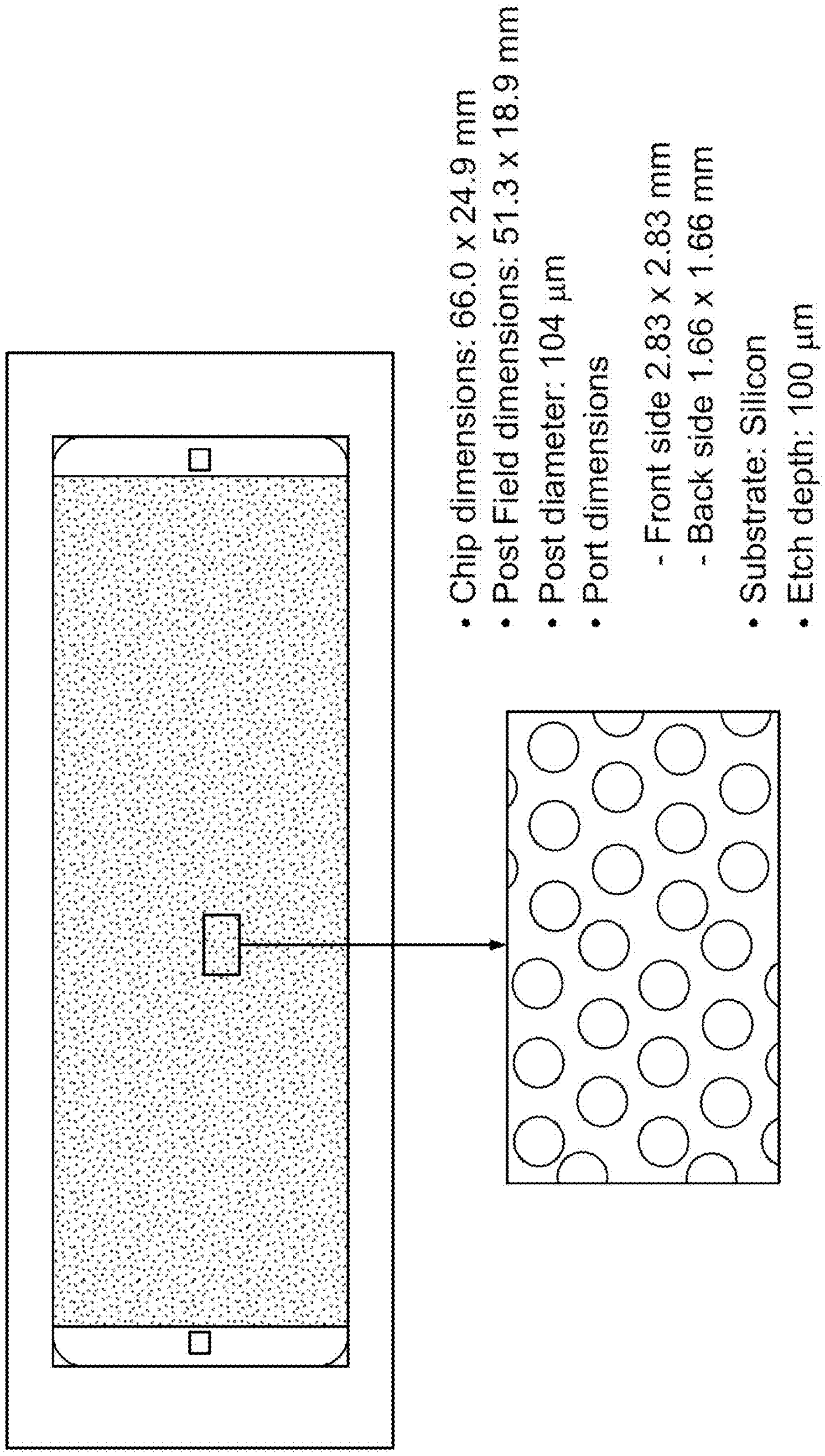
Figure 20A:
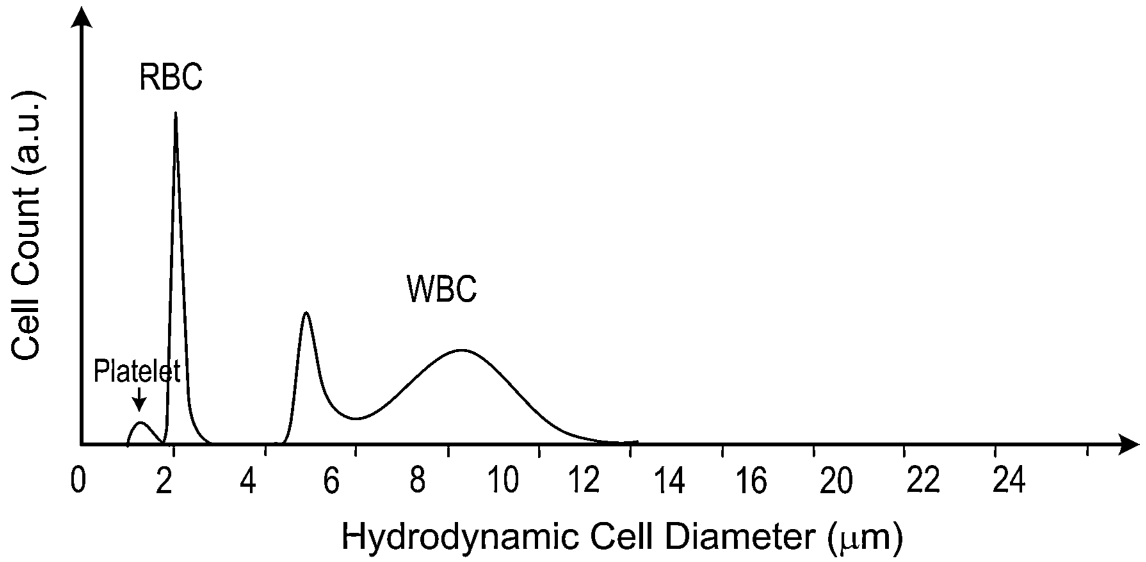
FIGS. 20A-D illustrate various targeted subpopulations of cells that can be isolated using size-based separation and various cut-off sizes that can be used to separate such targeted subpopulations.
Figure 20B:
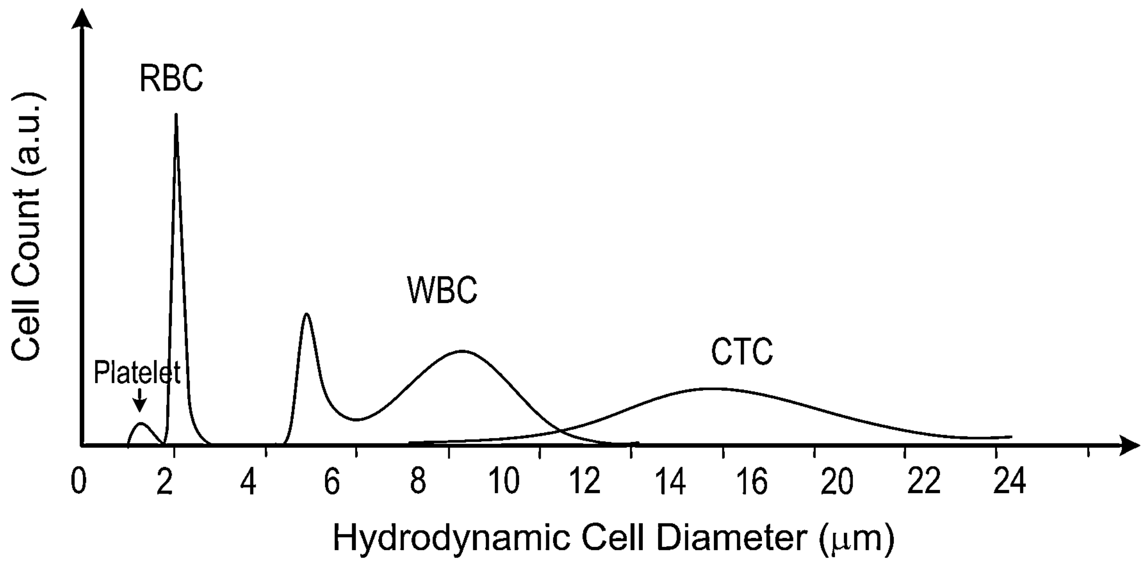
Figure 20C:
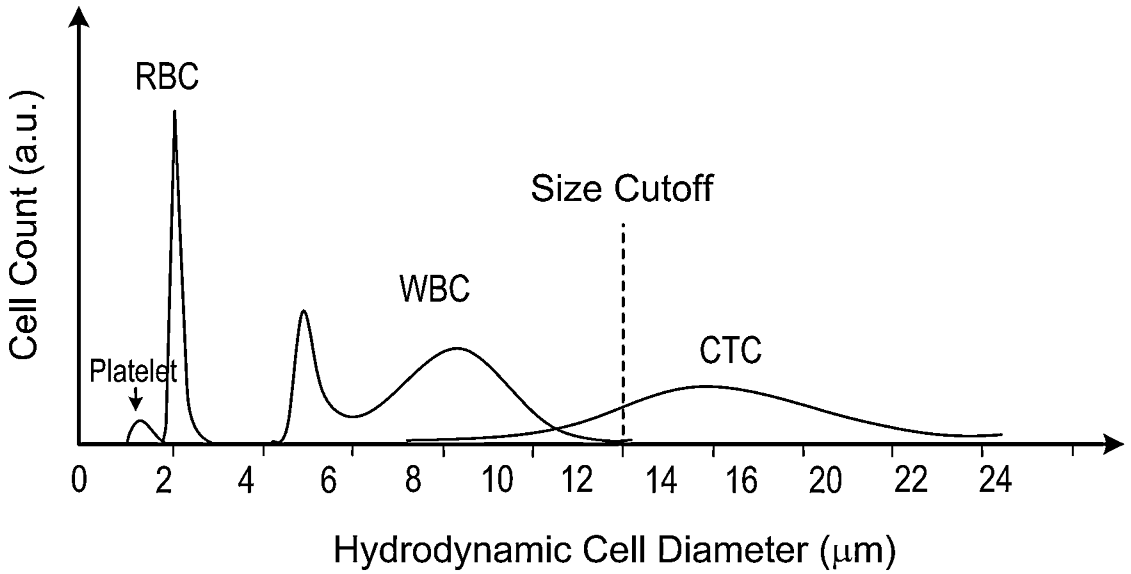
Figure 20D:
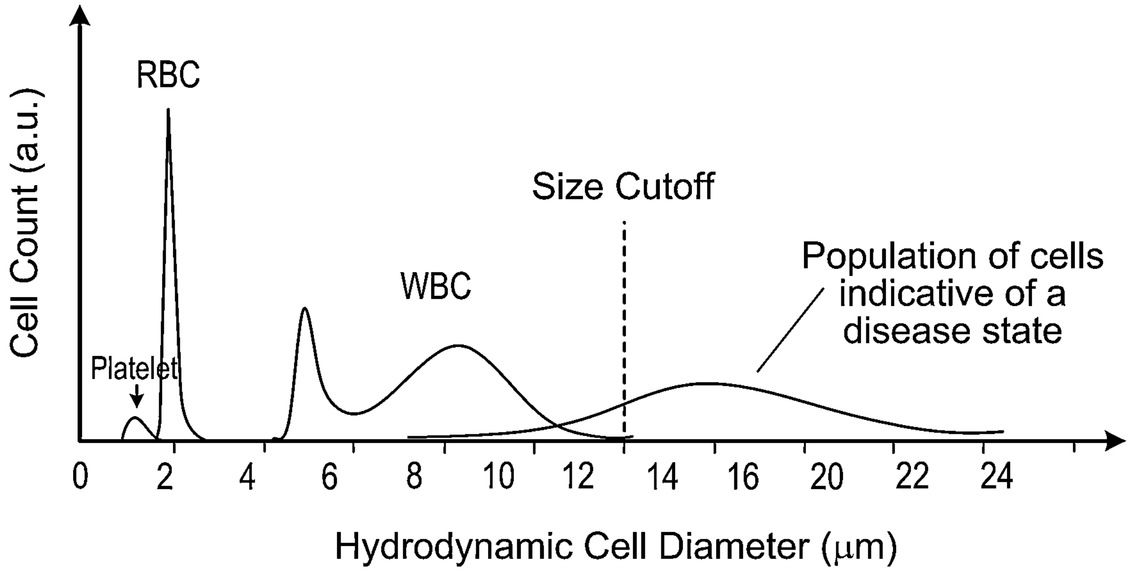

A design for preferred device embodiments of the invention is shown in FIG. 19A, and parameters corresponding to three preferred device embodiments associated with this design are shown in FIGS. 19B and 19C. These embodiments are particularly useful for enrich epithelial cells from blood.

Example 11: Determining Counts for Large Cell Types

Using the methods of the invention, a diagnosis of the absence, presence, or progression of cancer may be based on the number of cells in a cellular sample that are larger than a particular cutoff size. For example, cells with a hydrodynamic size of 14 microns or larger may be selected. This cutoff size would eliminate most leukocytes. The nature of these cells may then be determined by downstream molecular or cytological analysis.

Cell types other than epithelial cells that would be useful to analyze include endothelial cells, endothelial progenitor cells, endometrial cells, or trophoblasts indicative of a disease state. Furthermore, determining separate counts for epithelial cells, e.g., cancer cells, and other cell types, e.g., endothelial cells, followed by a determination of the ratios between the number of epithelial cells and the number of other cell types, may provide useful diagnostic information.

A device of the invention may be configured to isolate targeted subpopulations of cells such as those described above, as shown in FIGS. 20A-D. A size cutoff may be selected such that most native blood cells, including red blood cells, white blood cells, and platelets, flow to waste, while non-native cells, which could include endothelial cells, endothelial progenitor cells, endometrial cells, or trophoblasts, are collected in an enriched sample. This enriched sample may be further analyzed.

Figure 21:
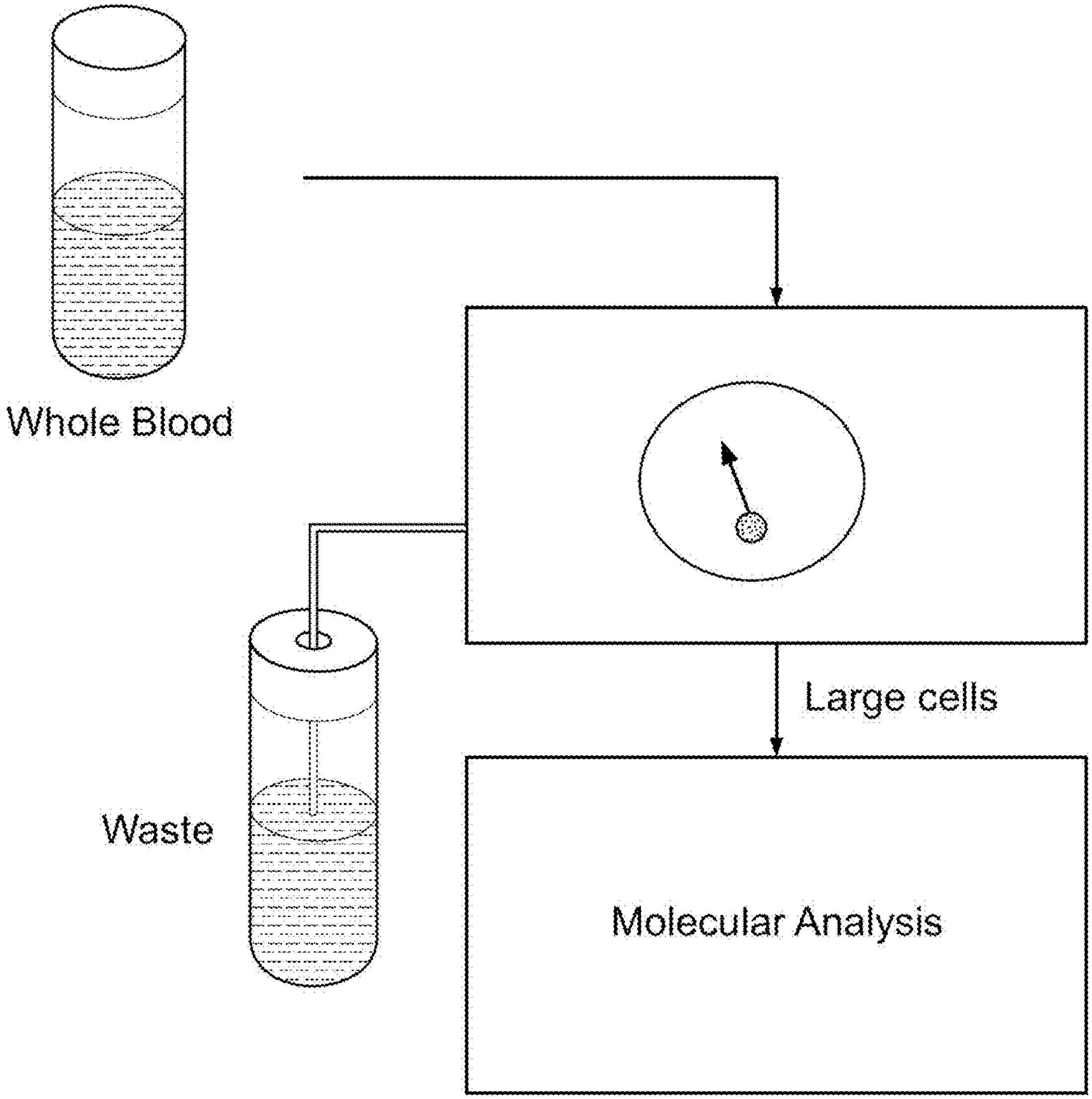
FIG. 21 illustrates a device of the invention with counting means to determine the number of cells in the enriched sample.

Using a device of the invention, therefore, it is possible to isolate a subpopulation of cells from blood or other bodily fluids based on size, which conveniently allows for the elimination of a large proportion of native blood cells when large cell types are targeted. As shown schematically in FIG. 21, a device of the invention may include counting means to determine the number of cells in the enriched sample, or the number of cells of a particular type, e.g., cancer cells, within the enriched sample, and further analysis of the cells in the enriched sample may provide additional information that is useful for diagnostic or other purposes.

Example 12: Method for Detection of EGFR Mutations

Figure 22:
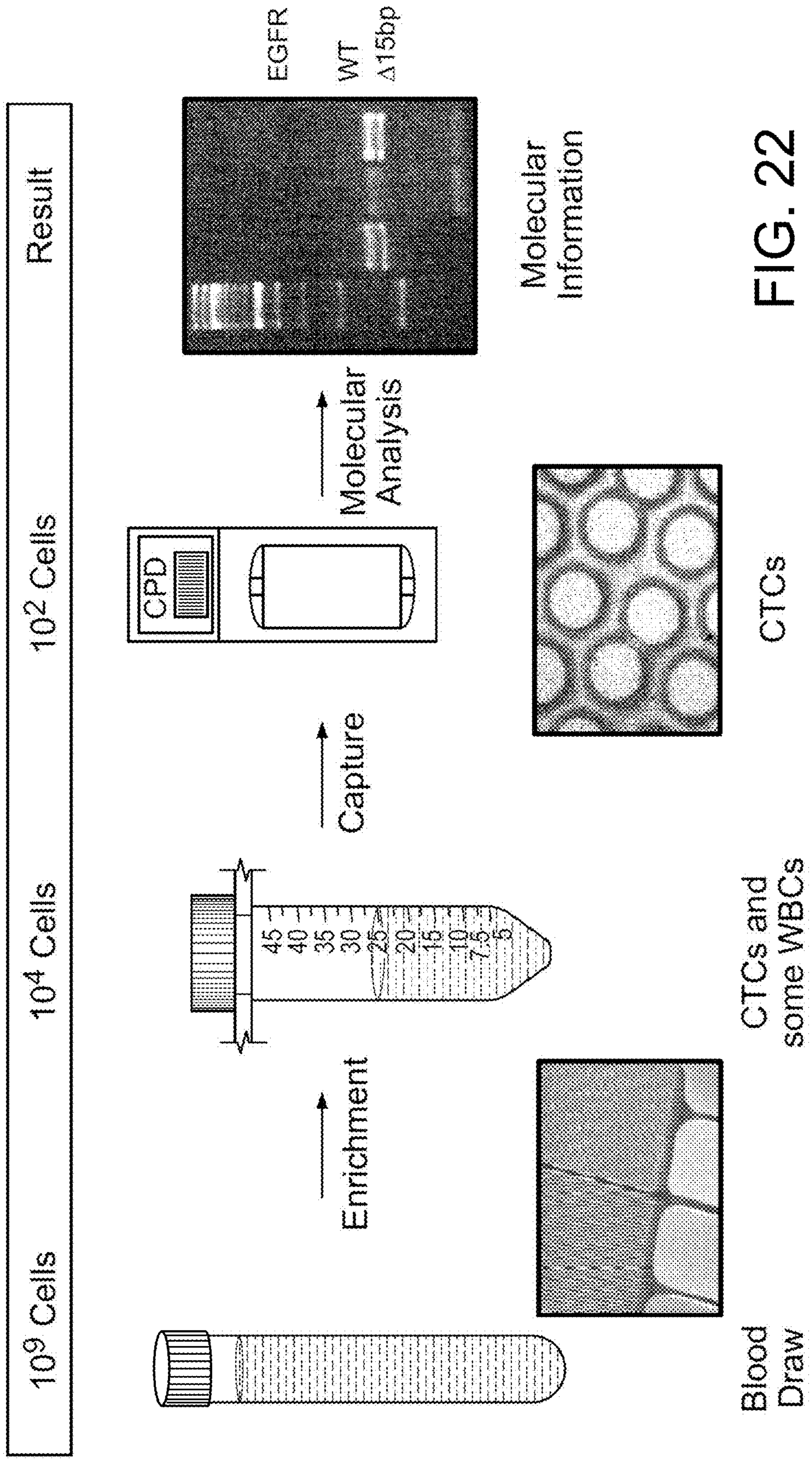
FIG. 22 illustrates an overview of one aspect of the invention for diagnosing, prognosing, or monitoring cancer in a patient.

A blood sample from a cancer patient is processed and analyzed using the devices and methods of the invention, resulting in an enriched sample of epithelial cells containing CTCs. This sample is then analyzed to identify potential EGFR mutations. The method permits both identification of known, clinically relevant EGFR mutations as well as discovery of novel mutations. An overview of this process is shown in FIG. 22.

Below is an outline of the strategy for detection and confirmation of EGFR mutations:

1) Sequence CTC EGFR mRNA
   - a) Purify CTCs from blood sample;
   - b) Purify total RNA from CTCs;
   - c) Convert RNA to cDNA using reverse transcriptase;
   - d) Use resultant cDNA to perform first and second PCR reactions for generating sequencing templates; and
   - e) Purify the nested PCR amplicon and use as a sequencing template to sequence EGFR exons 18-21.
2) Confirm RNA Sequence Using CTC Genomic DNA
   - a) Purify CTCs from blood sample;
   - b) Purify genomic DNA (gDNA) from CTCs;
   - c) Amplify exons 18, 19, 20, and or 21 via PCR reactions; and
   - d) Use the resulting PCR amplicon(s) in real-time quantitative allele-specific PCR reactions in order to confirm the sequence of mutations discovered via RNA sequencing.

Further details for each step outlined above are as follows.

Figure 23:
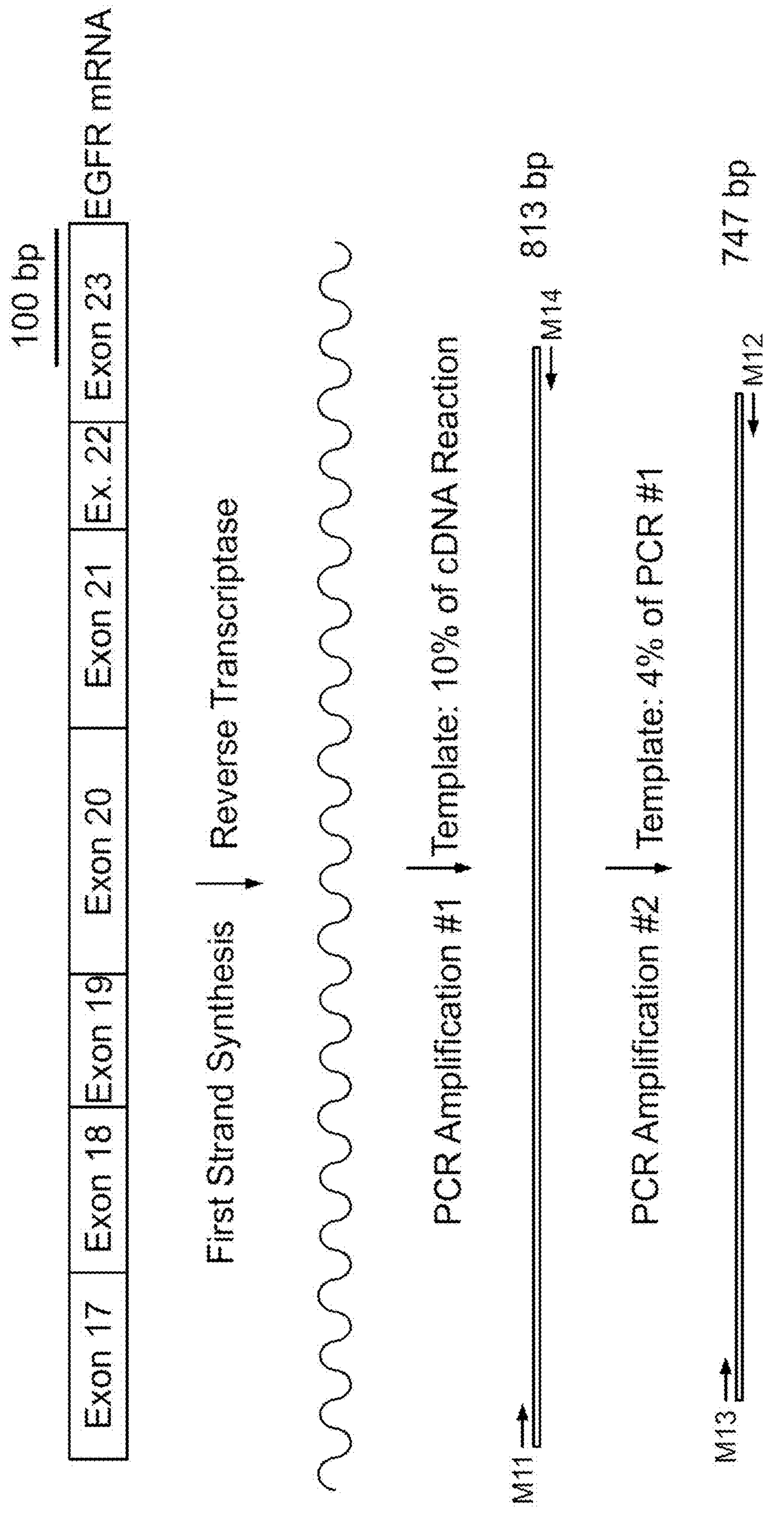
FIG. 23 illustrates the use of EGFR mRNA for generating sequencing templates.

1) Sequence CTC EGFR mRNA
   - a) Purify CTCs from blood sample. CTCs are isolated using any of the size-based enrichment and/or affinity purification devices of the invention.
   - b) Purify total RNA from CTCs. Total RNA is then purified from isolated CTC populations using, e.g., the Qiagen Micro RNeasy kit, or a similar total RNA purification protocol from another manufacturer; alternatively, standard RNA purification protocols such as guanidium isothiocyanate homogenization followed by phenol/chloroform extraction and ethanol precipitation may be used. One such method is described in "Molecular Cloning—A Laboratory Manual, Second Edition" (1989) by J. Sambrook, E. F. Fritch and T. Maniatis, p. 7.24.
   - c) Convert RNA to cDNA using reverse transcriptase. cDNA reactions are carried out based on the protocols of the supplier of reverse transcriptase. Typically, the amount of input RNA into the cDNA reactions is in the range of 10 picograms (pg) to 2 micrograms (μg) total RNA. First-strand DNA synthesis is carried out by hybridizing random 7mer DNA primers, or oligo-dT primers, or gene-specific primers, to RNA templates at 65° C. followed by snap-chilling on ice. cDNA synthesis is initiated by the addition of iScript Reverse Transcriptase (BioRad) or SuperScript Reverse Transcriptase (Invitrogen) or a reverse transcriptase from another commercial vendor along with the appropriate enzyme reaction buffer. For iScript, reverse transcriptase reactions are carried out at 42° C. for 30-45 minutes, followed by enzyme inactivation for 5 minutes at 85° C. cDNA is stored at −20° C. until use or used immediately in PCR reactions. Typically, cDNA reactions are carried out in a final volume of 20 μl, and 10% (2 μl) of the resultant cDNA is used in subsequent PCR reactions.
   - d) Use resultant cDNA to perform first and second PCR reactions for generating sequencing templates. cDNA from the reverse transcriptase reactions is mixed with DNA primers specific for the region of interest (FIG. 23). See Table 5 for sets of primers that may be used for amplification of exons 18-21. In Table 5, primer set M13(+)/M12(−) is internal to primer set M11(+)/M14(−). Thus primers M13(+) and M12(−) may be used in the nested round of amplification, if primers M11(+) and M14(−) were used in the first round of expansion. Similarly, primer set M11(+)/M14(−) is internal to primer set M15(+)/M16(−), and primer set M23(+)/M24(−) is internal to primer set M21(+)/M22(−). Hot Start PCR reactions are performed using Qiagen Hot-Star Taq Polymerase kit, or Applied Biosystems Hot-Start TaqMan polymerase, or other Hot Start thermostable polymerase, or without a hot start using Promega GoTaq Green Taq Polymerase master mix, TaqMan DNA polymerase, or other thermostable DNA polymerase. Typically, reaction volumes are 50 μl, nucleotide triphosphates are present at a final concentration of 200 M for each nucleotide, $MgCl_2$ is present at a final concentration of 1-4 mM, and oligo primers are at a final concentration of 0.5 μM. Hot start protocols begin with a 10-15 minute incubation at 95° C., followed by 40 cycles of 94° C. for one minute (denaturation), 52° C. for one minute (annealing), and 72° C. for one minute (extension). A 10 minute terminal extension at 72° C. is performed before samples are stored at 4° C. until they are either used as template in the second (nested) round of PCRs, or purified using QiaQuick Spin Columns (Qiagen) prior to sequencing. If a hot-start protocol is not used, the initial incubation at 95° C. is omitted. If a PCR product is to be used in a second round of PCRs, 2 μl (4%) of the initial PCR product is used as template in the second round reactions, and the identical reagent concentrations and cycling parameters are used.

TABLE 5

Primer Sets for expanding EGFR mRNA around Exons 18-21

| Name | SEQ ID NO | Sequence (5' to 3') | cDNA Coordinates | Amplicon Size |
|---|---|---|---|---|
| NXK-M11(+) | 1 | TTGCTGCTGGTGGTGGC | (+)1966-1982 | 813 |
| NXK-M14(-) | 2 | CAGGGATTCCGTCATATGGC | (-)2778-2759 | |
| NXK-M13(+) | 3 | GATCGGCCTCTTCATGCG | (+)1989-2006 | 747 |
| NXK M12(-) | 4 | GATCCAAAGGTCATCAACTCCC | (-)2735-2714 | |
| NXK-M15(+) | 5 | GCTGTCCAACGAATGGGC | (+)1904-1921 | 894 |
| NXK-M16(-) | 6 | GGCGTTCTCCTTTCTCCAGG | (-)2797-2778 | |
| NXK-M21(+) | 7 | ATGCACTGGGCCAGGTCTT | (+)1881-1899 | 944 |
| NXK-M22(-) | 8 | CGATGGTACATATGGGTGGCT | (-)2824-2804 | |
| NXK-M23(+) | 9 | AGGCTGTCCAACGAATGGG | (+)1902-1920 | 904 |
| NXK-M24(-) | 10 | CTGAGGGAGGCGTTCTCCT | (-)2805-2787 | |

e) Purify the nested PCR amplicon and use as a sequencing template to sequence EGFR exons 18-21. Sequencing is performed by ABI automated fluorescent sequencing machines and fluorescence-labeled DNA sequencing ladders generated via Sanger-style sequencing reactions using fluorescent dideoxynucleotide mixtures. PCR products are purified using Qiagen QuickSpin columns, the Agencourt AMPure PCR Purification System, or PCR product purification kits obtained from other vendors. After PCR products are purified, the nucleotide concentration and purity is determined with a Nanodrop 7000 spectrophotometer, and the PCR product concentration is brought to a concentration of 25 ng/μl. As a quality control measure, only PCR products that have a UV-light absorbance ratio ($A_{260}/A_{280}$) greater than 1.8 are used for sequencing. Sequencing primers are brought to a concentration of 3.2 pmol/μl.

2) Confirm RNA Sequence Using CTC Genomic DNA a) Purify CTCs from blood sample. As above, CTCs are isolated using any of the size-based enrichment and/or affinity purification devices of the invention.

b) Purify genomic DNA (gDNA) from CTCs. Genomic DNA is purified using the Qiagen DNeasy Mini kit, the Invitrogen ChargeSwitch gDNA kit, or another commercial kit, or via the following protocol:

1. Cell pellets are either lysed fresh or stored at −80° C. and are thawed immediately before lysis.
2. Add 500 μl 50 mM Tris pH 7.9/100 mM EDTA/0.5% SDS (TES buffer).
3. Add 12.5 μl Proteinase K (IBI5406, 20 mg/ml), generating a final [ProtK]=0.5 mg/ml.
4. Incubate at 55° C. overnight in rotating incubator.
5. Add 20 μl of RNase cocktail (500 U/ml RNase A+20,000 U/ml RNase T1, Ambion #2288) and incubate four hours at 37° C.
6. Extract with Phenol (Kodak, Tris pH 8 equilibrated), shake to mix, spin 5 min. in tabletop centrifuge.
7. Transfer aqueous phase to fresh tube.
8. Extract with Phenol/Chloroform/Isoamyl alcohol (EMD, 25:24:1 ratio, Tris pH 8 equilibrated), shake to mix, spin five minutes in tabletop centrifuge.
9. Add 50 μl 3M NaOAc pH=6.
10. Add 500 μl EtOH.
11. Shake to mix. Strings of precipitated DNA may be visible. If anticipated DNA concentration is very low, add carrier nucleotide (usually yeast tRNA).
12. Spin one minute at max speed in tabletop centrifuge.
13. Remove supernatant.
14. Add 500 μl 70% EtOH, Room Temperature (RT)
15. Shake to mix.
16. Spin one minute at max speed in tabletop centrifuge.
17. Air dry 10-20 minutes before adding TE.
18. Resuspend in 400 μl TE. Incubate at 65° C. for 10 minutes, then leave at RT overnight before quantitation on Nanodrop.

c) Amplify exons 18, 19, 20, and or 21 via PCR reactions. Hot start nested PCR amplification is carried out as described above in step 1d, except that there is no nested round of amplification. The initial PCR step may be stopped during the log phase in order to minimize possible loss of allele-specific information during amplification. The primer sets used for expansion of EGFR exons 18-21 are listed in Table 6 (see also Paez et al., Science 304:1497-1500 (Supplementary Material) (2004)).

TABLE 6

Primer sets for expanding EGFR genomic DNA

| Name | SEQ ID NO | Sequence (5' to 3') | Exon | Amplicon Size |
|---|---|---|---|---|
| NXK-ex18.1(+) | 11 | TCAGAGCCTGTGTTTCTACCAA | 18 | 534 |
| NXK-ex18.2(-) | 12 | TGGTCTCACAGGACCACTGATT | 18 | |
| NXK-ex18.3(+) | 13 | TCCAAATGAGCTGGCAAGTG | 18 | 397 |
| NXK-ex18.4(-) | 14 | TCCCAAACACTCAGTGAAACAAA | 18 | |
| NXK-ex19.1(+) | 15 | AAATAATCAGTGTGATTCGTGGAG | 19 | 495 |
| NXK-ex19.2(-) | 16 | GAGGCCAGTGCTGTCTCTAAGG | 19 | |
| NXK-ex19.3(+) | 17 | GTGCATCGCTGGTAACATCC | 19 | 298 |
| NXK-ex19.4(-) | 18 | TGTGGAGATGAGCAGGGTCT | 19 | |
| NXK-ex20.1(+) | 19 | ACTTCACAGCCCTGCGTAAAC | 20 | 555 |

TABLE 6-continued

Primer sets for expanding EGFR genomic DNA

Figure 24:
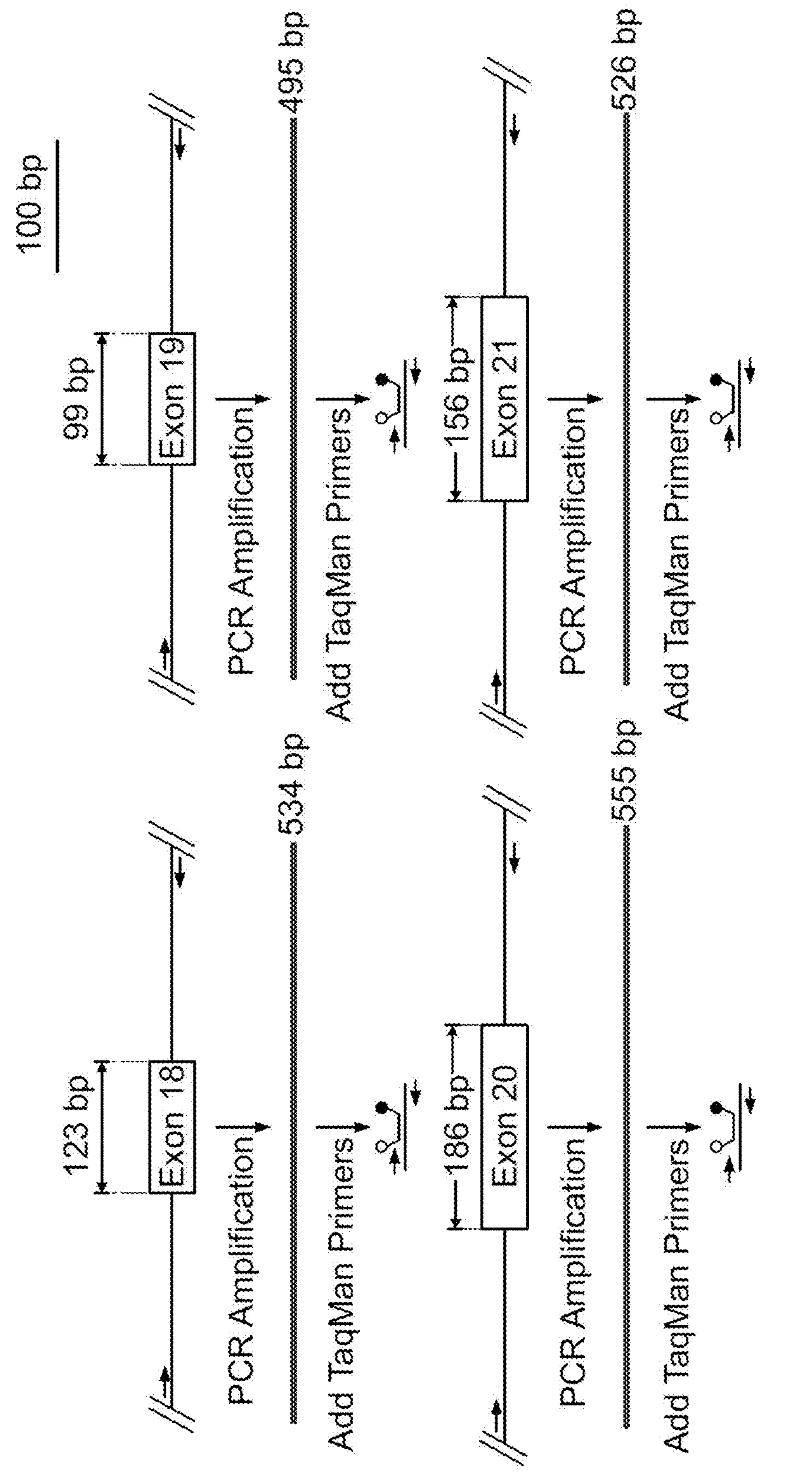
FIG. 24 illustrates performing real-time quantitative allele-specific PCR reactions to confirm the sequence of mutations in EGFR mRNA.

| Name | SEQ ID NO | Sequence (5' to 3') | Exon | Amplicon Size |
|---|---|---|---|---|
| NXK-ex20.2(-) | 20 | ATGGGACAGGCACTGATTTGT | 20 | |
| NXK-ex20.3(+) | 21 | ATCGCATTCATGCGTCTTCA | 20 | 379 |
| NXK-ex20.4(-) | 22 | ATCCCCATGGCAAACTCTTG | 20 | |
| NXK-ex21.1(+) | 23 | GCAGCGGGTTACATCTTCTTTC | 21 | 526 |
| NXK-ex21.2(-) | 24 | CAGCTCTGGCTCACACTACCAG | 21 | |
| NXK-ex21.3(+) | 25 | GCAGCGGGTTACATCTTCTTTC | 21 | 349 |
| NXK-ex21.4(-) | 26 | CATCCTCCCCTGCATGTGT | 21 | |

d) Use the resulting PCR amplicon(s) in real-time quantitative allele-specific PCR reactions in order to confirm the sequence of mutations discovered via RNA sequencing. An aliquot of the PCR amplicons is used as template in a multiplexed allele-specific quantitative PCR reaction using TaqMan PCR 5' Nuclease assays with an Applied Biosystems model 7500 Real Time PCR machine (FIG. 24). This round of PCR amplifies subregions of the initial PCR product specific to each mutation of interest. Given the very high sensitivity of Real Time PCR, it is possible to obtain complete information on the mutation status of the EGFR gene even if as few as 10 CTCs are isolated. Real Time PCR provides quantification of allelic sequences over 8 logs of input DNA concentrations; thus, even heterozygous mutations in impure populations are easily detected using this method.

Probe and primer sets are designed for all known mutations that affect gefitinib responsiveness in NSCLC patients, including over 40 such somatic mutations, including point mutations, deletions, and insertions, that have been reported in the medical literature. For illustrative purposes, examples of primer and probe sets for five of the point mutations are listed in Table 7. In general, oligonucleotides may be designed using the primer optimization software program Primer Express (Applied Biosystems), with hybridization conditions optimized to distinguish the wild type EGFR DNA sequence from mutant alleles. EGFR genomic DNA amplified from lung cancer cell lines that are known to carry EGFR mutations, such as H358 (wild type), H1650 (15-bp deletion, Δ2235-2249), and H1975 (two point mutations, 2369 C→T, 2573 T→G), is used to optimize the allele-specific Real Time PCR reactions. Using the TaqMan 5' nuclease assay, allele-specific labeled probes specific for wild type sequence or for known EGFR mutations are developed. The oligonucleotides are designed to have melting temperatures that easily distinguish a match from a mismatch, and the Real Time PCR conditions are optimized to distinguish wild type and mutant alleles. All Real Time PCR reactions are carried out in triplicate.

Initially, labeled probes containing wild type sequence are multiplexed in the same reaction with a single mutant probe. Expressing the results as a ratio of one mutant allele sequence versus wild type sequence may identify samples containing or lacking a given mutation. After conditions are optimized for a given probe set, it is then possible to multiplex probes for all of the mutant alleles within a given exon within the same Real Time PCR assay, increasing the ease of use of this analytical tool in clinical settings.

Figure 25:
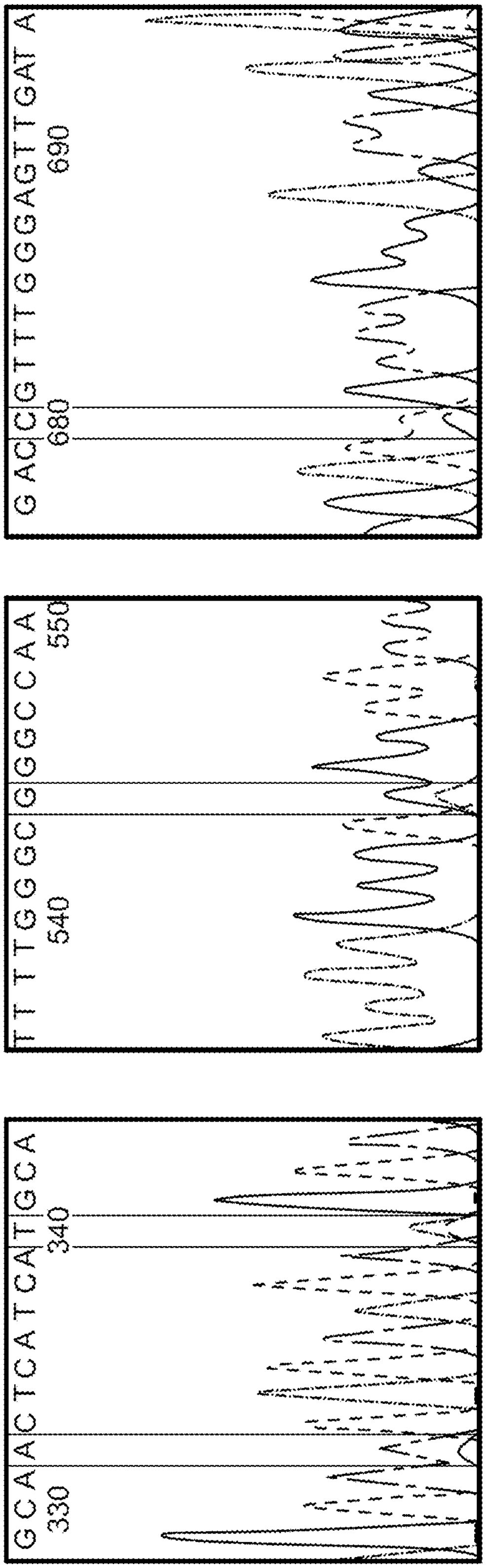
FIG. 25 illustrates confirmation of the presence of a mutation is when the signal from a mutant allele probe rises above the background level of fluorescence.

A unique probe is designed for each wild type allele and mutant allele sequence. Wild-type sequences are marked with the fluorescent dye VIC at the 5' end, and mutant sequences with the fluorophore FAM. A fluorescence quencher and Minor Groove Binding moiety are attached to the 3' ends of the probes. ROX is used as a passive reference dye for normalization purposes. A standard curve is generated for wild type sequences and is used for relative quantitation. Precise quantitation of mutant signal is not required, as the input cell population is of unknown, and varying, purity. The assay is set up as described by ABI product literature, and the presence of a mutation is confirmed when the signal from a mutant allele probe rises above the background level of fluorescence (FIG. 25), and this threshold cycle gives the relative frequency of the mutant allele in the input sample.

TABLE 7

Probes and Primers for Allele-Specific qPCR

| Name | SEQ ID NO | Sequence (5' to 3', mutated position in bold) | EMBL Chromosome 7 Genomic Coordinates | Description | Mutation |
|---|---|---|---|---|---|
| NXK-M01 | 27 | CCGCAGCATGTCAAGATCAC | (+)55,033,694-55,033,713 | (+)primer | L858R |
| NXK-M02 | 28 | TCCTTCTGCATGGTATTCTTTCTCT | (-)55,033,769-55,033,745 | (-)primer | |
| Pwt-L858R | 29 | VIC-TTTGGGCTGGCCAA-MGB | (+)55,033,699-55,033,712 | WT allele probe | |
| Pmut-L858R | 30 | FAM-TTTTGGGCGGGCCA-MGB | (+)55,033,698-55,033,711 | Mutant allele probe | |
| NXK-M03 | 31 | ATGGCCAGCGTGGACAA | (+)55,023,207-55,023,224 | (+)primer | T790M |
| NXK-M04 | 32 | AGCAGGTACTGGGAGCCAATATT | (-)55,023,355-55,023,333 | (-)primer | |
| Pwt-T790M | 33 | VIC-ATGAGCTGCGTGATGA-MGB | (-)55,023,290-55,023,275 | WT allele probe | |
| Pmut-T790M | 34 | FAM-ATGAGCTGCATGATGA-MGB | (-)55,023,290-55,023,275 | Mutant allele probe | |

TABLE 7-continued

Probes and Primers for Allele-Specific qPCR

| Name | SEQ ID NO | Sequence (5' to 3', mutated position in bold) | EMBL Chromosome 7 Genomic Coordinates | Description | Mutation |
|---|---|---|---|---|---|
| NXK-M05 | 35 | GCCTCTTACACCCAGTGGAGAA | (+)55,015,831-55,015,852 | (+)primer | G719S, C |
| NXK-ex18.5 | 36 | GCCTGTGCCAGGGACCTT | (-)55,015,965-55,015,948 | (-)primer | |
| Pwt-G719SC | 37 | VIC-ACCGGAGCCCAGCA-MGB | (-)55,015,924-55,015,911 | WT allele probe | |
| Pmut-G719S | 38 | FAM-ACCGGAGCTCAGCA-MGB | (-)55,015,924-55,015,911 | Mutant allele probe | |
| mut-G719C | 39 | FAM-ACCGGAGCACAGCA-MGB | (-)55,015,924-55,015,911 | Mutant allele probe | |
| NXK-ex21.5 | 40 | ACAGCAGGGTCTTCTCTGTTTCAG | (+)55,033,597-55,033,620 | (+)primer | H835L |
| NXK-M10 | 41 | ATCTTGACATGCTGCGGTGTT | (-)55,033,710 55,033,690 | (-)primer | |
| Pwt-H835L | 42 | VIC-TTGGTGCACCGCGA-MGB | (+)55,033,803-55,033,816 | WT allele probe | |
| Pmut-H835L | 43 | FAM-TGGTGCTCCGCGAC-MGB | (+)55,033,803-55,033,816 | Mutant allele probe | |
| NXK-M07 | 52 | TGGATCCCAGAAGGTGAGAAA | (+)55,016,630-55,016,650 | (+)primer | delE746-A750 |
| NXK-ex19.5 | 53 | AGCAGAAACTCACATCGAGGATTT | (-)55,016,735-55,016,712 | (-)primer | |
| Pwt-delE746-A750 | 54 | AAGGAATTAAGAGAAGCAA | (+)55,016,681-55,016,699 | WT allele probe | |
| Pmut-delE746-A750var1 | 55 | CTATCAAAACATCTCC | (+)55,016,676-55,016,691 | Mutant allele probe, variant 1 | |
| Pmut-delE746-A750var1 | 56 | CTATCAAGACATCTCC | (+)55,016,676-55,016,691 | Mutant allele probe, variant 2 | |

Example 13: Absence of EGFR Expression in Leukocytes

To test whether EGFR mRNA is present in leukocytes, several PCR experiments were performed. Four sets of primers, shown in Table 8, were designed to amplify four corresponding genes:

1) BCKDK (branched-chain a-ketoacid dehydrogenase complex kinase)—a "housekeeping" gene expressed in all types of cells, a positive control for both leukocytes and tumor cells;

2) CD45—specifically expressed in leukocytes, a positive control for leukocytes and a negative control for tumor cells;

3) EpCaM—specifically expressed in epithelial cells, a negative control for leukocytes and a positive control for tumor cells; and 4) EGFR—the target mRNA to be examined.

TABLE 8

| Name | SEQ ID NO | Sequence (5' to 3') | Description | Amplicon Size |
|---|---|---|---|---|
| BCKD_1 | 44 | AGTCAGGACCCATGCACGG | BCKDK (+) primer | 273 |
| BCKD_2 | 45 | ACCCAAGATGCAGCAGTGTG | BCKDK (-) primer | |

TABLE 8-continued

| Name | SEQ ID NO | Sequence (5' to 3') | Description | Amplicon Size |
|---|---|---|---|---|
| CD45_1 | 46 | GATGTCCTCCTTGTTCTACTC | CD45 (+) primer | 263 |
| CD45_2 | 47 | TACAGGGAATAATCGAGCATGC | CD45 (-) primer | |
| EpCAM_1 | 48 | GAAGGGAAATAGCAAATGGACA | EpCAM (+) primer | 222 |
| EpCAM_2 | 49 | CGATGGAGTCCAAGTTCTGG | EpCAM (-) primer | |
| EGFR_1 | 50 | AGCACTTACAGCTCTGGCCA | EGFR (+) primer | 371 |
| EGFR_2 | 51 | GACTGAACATAACTGTAGGCTG | EGFR (-) primer | |

Figure 26A:
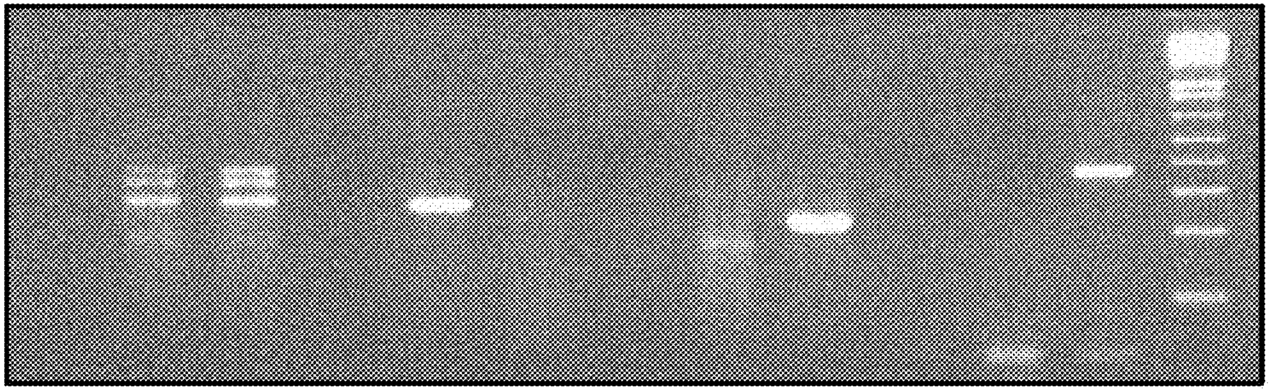
FIGS. 26A-B illustrate the presence of EGFR mRNA in epithelia cells but not leukocytes.
Figure 26B:
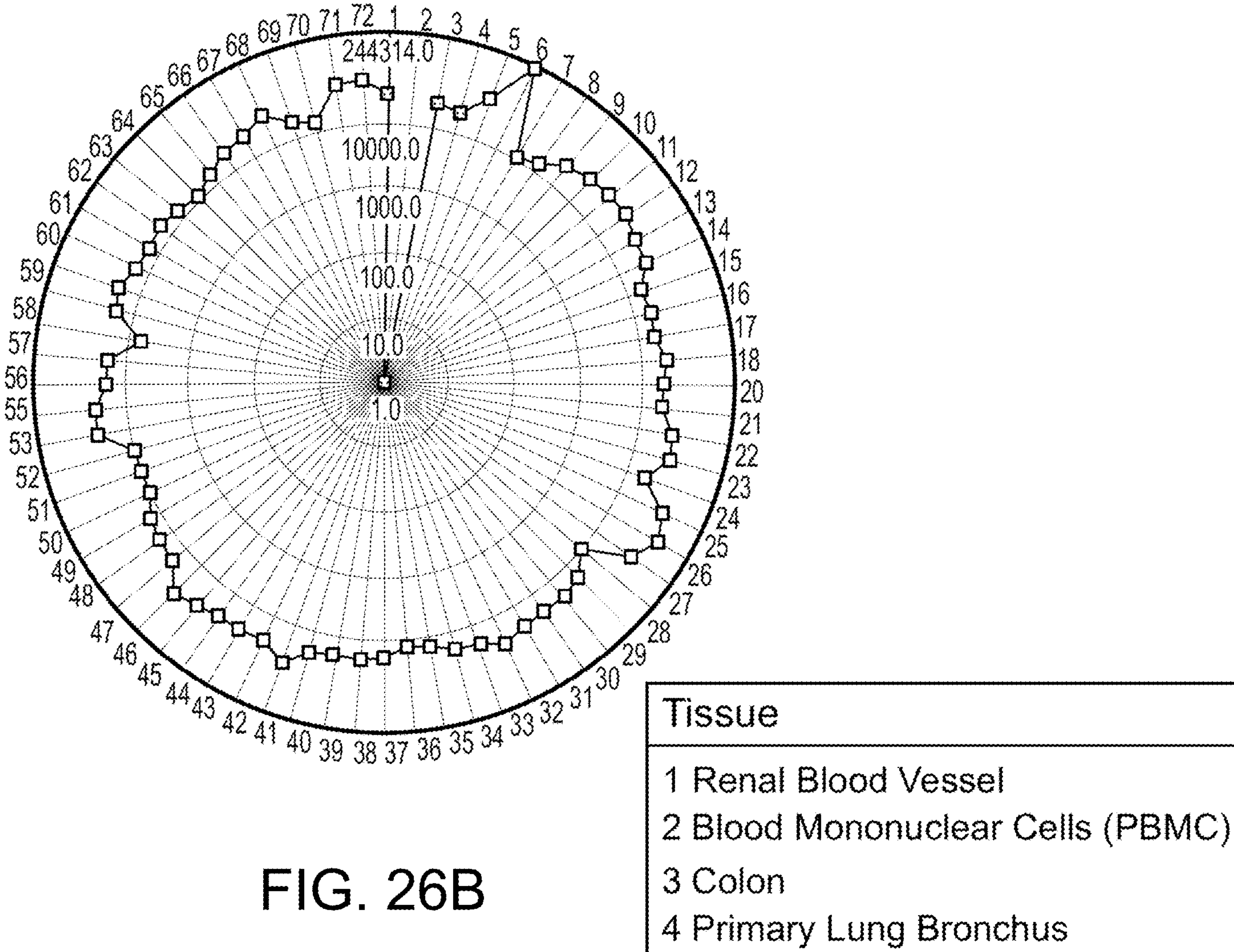

Total RNAs of approximately $9\times10^6$ leukocytes isolated using a cell enrichment device of the invention (cutoff size 4 μm) and $5\times10^6$ H1650 cells were isolated by using RNeasy mini kit (Qiagen). Two micrograms of total RNAs from leukocytes and H1650 cells were reverse transcribed to obtain first strand cDNAs using 100 pmol random hexamer (Roche) and 200 U Superscript II (Invitrogen) in a 20 μl reaction. The subsequent PCR was carried out using 0.5 μl of the first strand cDNA reaction and 10 pmol of forward and reverse primers in total 25 μl of mixture. The PCR was run for 40 cycles of 95° C. for 20 seconds, 56° C. for 20 seconds, and 70° C. for 30 seconds. The amplified products were separated on a 1% agarose gel. As shown in FIG. 26A, BCKDK was found to be expressed in both leukocytes and H1650 cells; CD45 was expressed only in leukocytes; and both EpCAM and EGFR were expressed only in H1650 cells. These results, which are fully consistent with the profile of EGFR expression shown in FIG. 26B, confirmed that EGFR is a particularly useful target for assaying mixtures of cells that include both leukocytes and cancer cells, because only the cancer cells will be expected to produce a signal.

Figure 27:
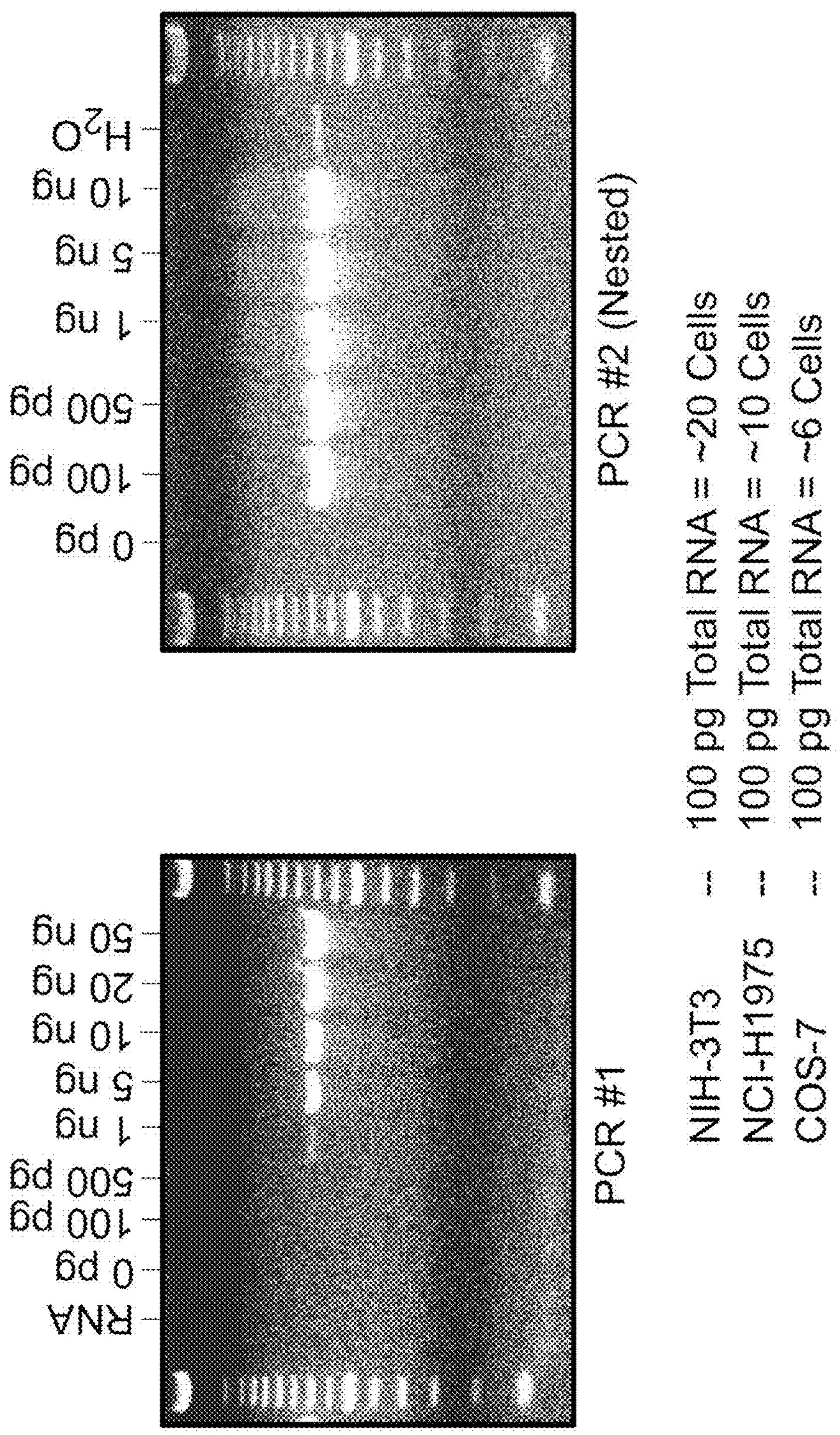
FIG. 27 illustrates results of the first and second EGFR PCR reactions.

Example 14: EGFR Assay with Low Quantities of Target RNA or High Quantities of Background RNA In order to determine the sensitivity of the assay described in Example 12 various quantities of input NSCLC cell line total RNA were tested, ranging from 100 pg to 50 ng. The results of the first and second EGFR PCR reactions (step 1d, Example 12) are shown in FIG. 27. The first PCR reaction was shown to be sufficiently sensitive to detect 1 ng of input RNA, while the second round increased the sensitivity to 100 pg or less of input RNA. This corresponds to 7-10 cells, demonstrating that even extremely dilute samples may generate detectable signals using this assay.

Figure 28A:
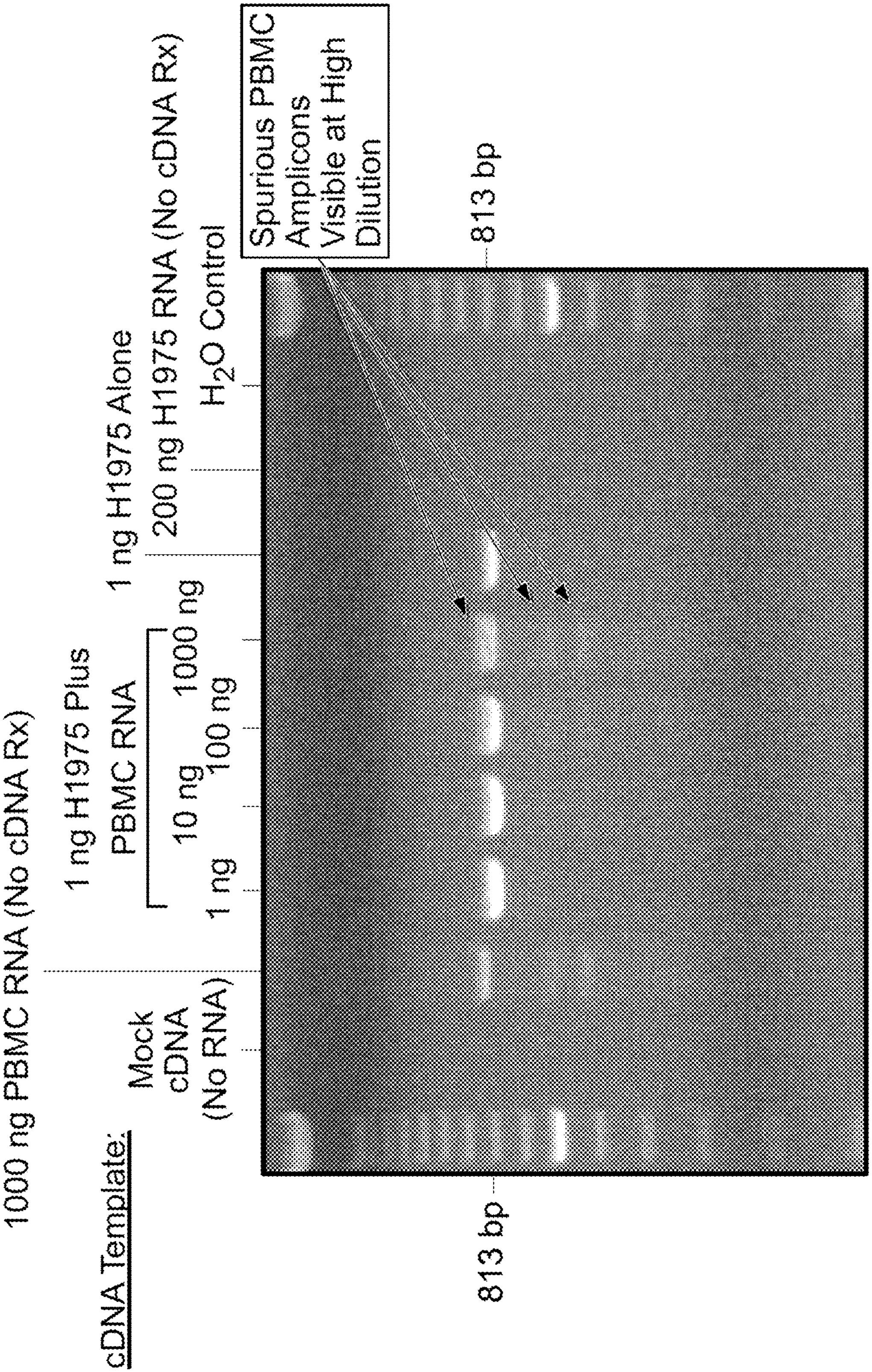
FIGS. 28A-B illustrate results of the first and second EGFR PCR reactions.
Figure 28B:
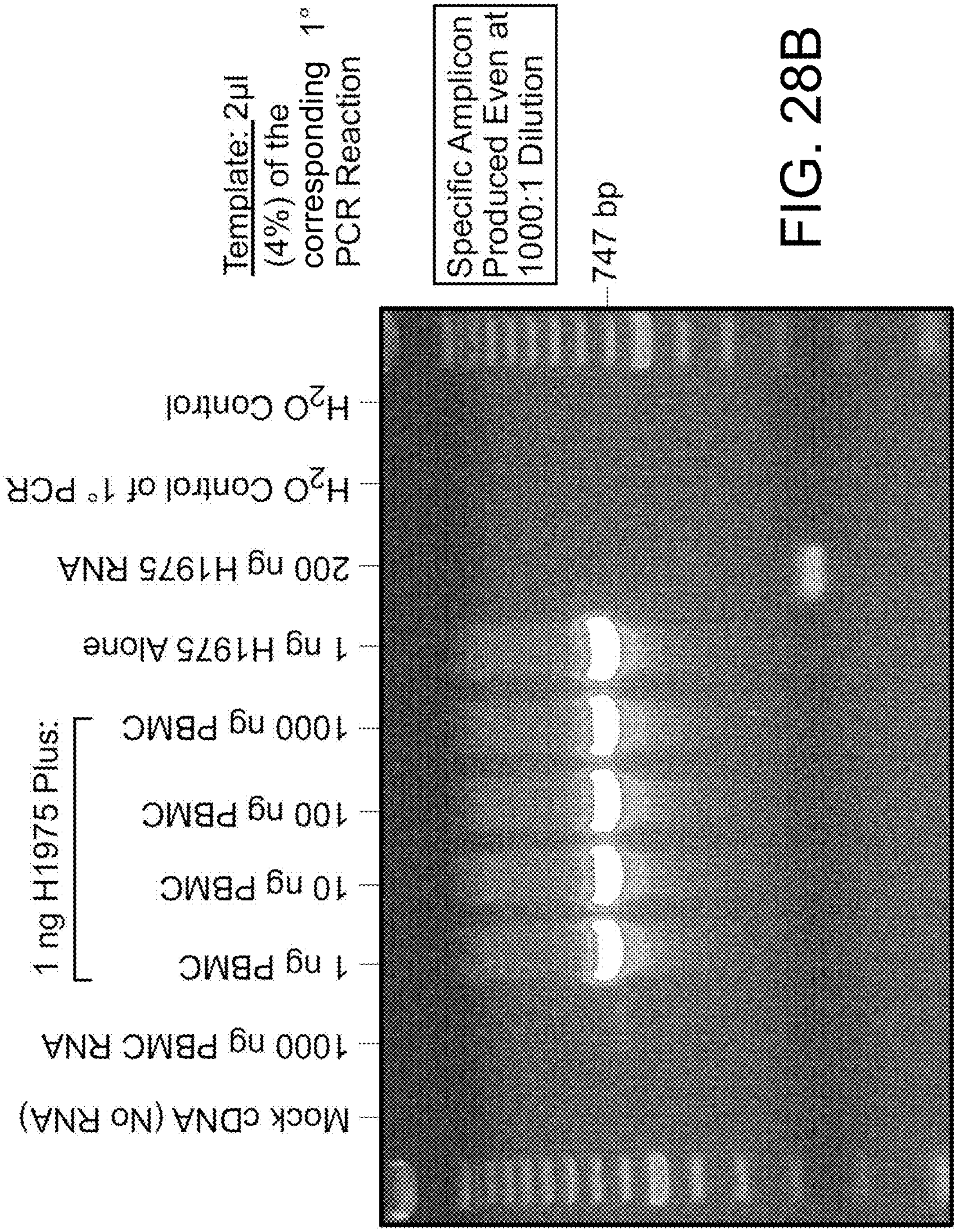

Next, samples containing 1 ng of NCI-H1975 RNA were mixed with varying quantities of peripheral blood mononuclear cell (PBMC) RNA ranging from 1 ng to 1 μg and used in PCR reactions as before. As shown in FIG. 28A, the first set of PCR reactions demonstrated that, while amplification occurred in all cases, spurious bands appeared at the highest contamination level. However, as shown in FIG. 28B, after the second, nested set of PCR reactions, the desired specific amplicon was produced without spurious bands even at the highest contamination level. Therefore, this example demonstrates that the EGFR PCR assays described herein are effective even when the target RNA occupies a tiny fraction of the total RNA in the sample being tested.

Table 8 lists the RNA yield in a variety of cells and shows that the yield per cell is widely variable, depending on the cell type. This information is useful in order to estimate the amount of target and background RNA in a sample based on cell counts. For example, 1 ng of NCL-H1975 RNA corresponds to approximately 100 cells, while 1 μg of PBMC RNA corresponds to approximately $10^6$ cells. Thus, the highest contamination level in the above-described experiment, 1,000:1 of PBMC RNA to NCL-H1975 RNA, actually corresponds to a 10,000:1 ratio of PBMCs to NCL-H1975 cells. Thus, these data indicate that EGFR may be sequenced from as few as 100 CTCs contaminated by as many as $10^6$ leukocytes.

TABLE 8

RNA Yield versus Cell Type

| Cells | Count | RNA Yield | [RNA]/Cell |
|---|---|---|---|
| NCI-H1975 | 2 × $10^6$ | 26.9 μg | 13.5 μg |
| NCI-H1650 | 2 × $10^6$ | 26.1 μg | 13.0 μg |
| H358 | 2 × $10^6$ | 26.0 μg | 13.0 μg |
| HT29 | 2 × $10^6$ | 21.4 μg | 10.7 μg |
| MCF7 | 2 × $10^6$ | 25.4 μg | 12.7 μg |
| PBMC #1 | 19 × $10^6$ | 10.2 μg | 0.5 μg |
| PBMC #2 | 16.5 × $10^6$ | 18.4 μg | 1.1 μg |

Figure 29:
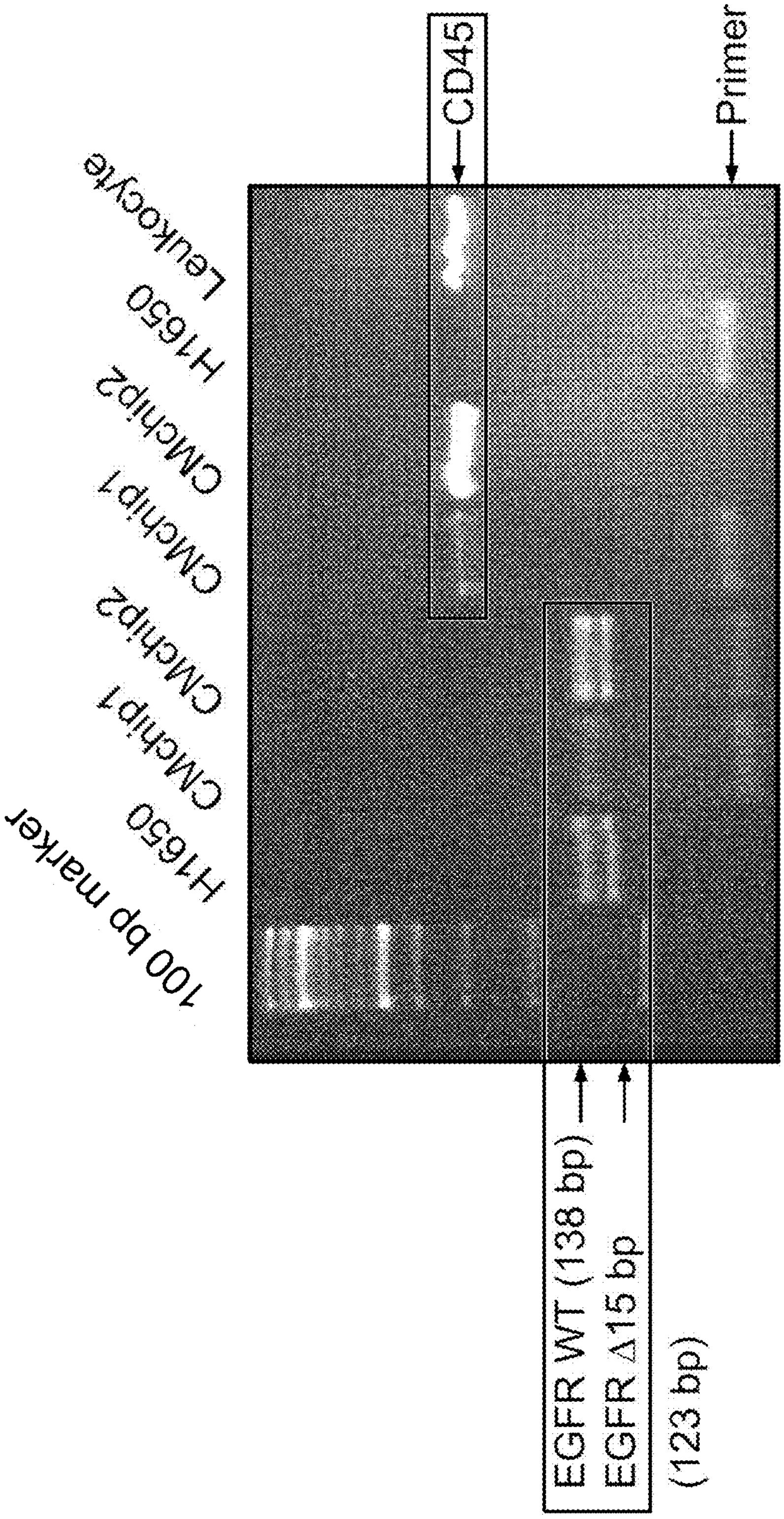
FIG. 29 illustrates that EGFR wild type and mutant amplified fragments are readily detected, despite the high leukocyte background.

Next, whole blood spiked with 1,000 cells/ml of Cell Tracker (Invitrogen)-labeled H1650 cells was run through the capture module chip of FIG. 19C. To avoid inefficiency in RNA extraction from fixed samples, the captured H1650 cells were immediately counted after running and subsequently lysed for RNA extraction without formaldehyde fixation. Approximately 800 captured H1650 cells and >10,000 contaminated leukocytes were lysed on the chip with 0.5 ml of 4M guanidine thiocyanate solution. The lysate was extracted with 0.5 ml of phenol/chloroform and precipitated with 1 ml of ethanol in the presence of 10 mg of yeast tRNA as carrier. The precipitated RNAs were DNase I-treated for 30 minutes and then extracted with phenol/chloroform and precipitated with ethanol prior to first strand cDNA synthesis and subsequent PCR amplification. These steps were repeated with a second blood sample and a second chip. The cDNA synthesized from chip1 and chip2 RNAs along with H1650 and leukocyte cDNAs were PCR amplified using two sets of primers, CD45_1 and CD45_2 (Table 7) as well as EGFR_5 (forward primer, 5'-GTTCGGCACGGTGTATAAGG-3') (SEQ ID NO: 65 and EGFR_6 (reverse primer, 5'-CTGGCCATCACGTAGGCTTC-3') (SEQ ID NO: 66. EGFR_5 and EGFR_6 produce a 138 bp wild type amplified fragment and a 123 bp mutant amplified fragment in H1650 cells. The PCR products were separated on a 2.5% agarose gel. As shown in FIG. 29, EGFR wild type and mutant amplified fragments were readily detected, despite the high leukocyte background, demonstrating that the EGFR assay is robust and does not require a highly purified sample.

What is claimed is:

1. A method for determining a presence or absence of a fetal aneuploidy of a fetus in a maternal blood sample from a woman who is pregnant or who is suspected of being pregnant, the method comprising:

(a) obtaining a mixture of fetal and maternal cells from the maternal blood sample and dividing the mixture into discrete locations such that no more than one cell is located per discrete location;

(b) obtaining genomic DNA from fetal cells or maternal cells located within the discrete locations;

(c) conducting multiplex polymerase chain reaction (PCR) to amplify target regions in the genomic DNA to obtain amplified nucleic acid molecules, wherein each amplified nucleic acid molecule comprises a tag that identifies the nucleic acid molecule as coming from a specific discrete location;

(d) pooling the amplified nucleic acid molecules with tagged amplicons from at least one other multiplex PCR;

(e) conducting quantitative genotyping to quantify DNA regions of at least one chromosome being tested for aneuploidy and of at least one control chromosome that is presumed to be diploid; and (f) determining the presence or absence of a fetal aneuploidy for the at least one chromosome being tested for aneuploidy from quantification of the chromosomal DNA regions of step (e).

2. The method of claim 1, wherein the fetal aneuploidy is segmental aneuploidy.

3. The method of claim 1, wherein the fetal aneuploidy comprises monosomy, trisomy, tetrasomy, or pentasomy of one or more chromosomes.

4. The method of claim 3, wherein the one or more chromosomes are sex chromosomes.

5. The method of claim 3, wherein the fetal aneuploidy comprises trisomy.

6. The method of claim 5, wherein the trisomy comprises trisomy 13, trisomy 18, or trisomy 21.

7. The method of claim 3, wherein the fetal aneuploidy comprises monosomy, and wherein the monosomy comprises monosomy X.

8. The method of claim 1, wherein the at least one chromosome being tested for aneuploidy is selected from the group consisting of chromosome 13, chromosome 18, chromosome 21, chromosome X, and chromosome Y.

9. The method of claim 1, wherein the tag comprises a sequencing element.

10. The method of claim 9, wherein the sequencing element is about 4, 6, 8, 10, 18, 20, 28, 36, 46, or 50 nucleotide bases in length.

11. The method of claim 9, wherein the quantitative genotyping comprises sequencing-by-synthesis initiated using sequencing primers complementary to the sequencing element.

12. The method of claim 11, wherein the sequencing-by-synthesis involves synthesizing nucleic acid strands complementary to the amplified nucleic acid molecules and inferring nucleic acid sequences of the amplified nucleic acid molecules from the complementary synthesized nucleic acid strands.

13. The method of claim 11, wherein the sequencing-by-synthesis comprises detecting an identity of each nucleotide immediately after or upon incorporation of a labeled nucleotide or nucleotide analog into a growing nucleic acid strand complementary to the amplified nucleic acid molecules.

14. The method of claim 1, wherein the DNA regions comprise polymorphisms and wherein computer executable logic fits data of a quantity of allele abundance for each polymorphism into one or more data models.

15. The method of claim 1, wherein the quantitative genotyping comprises ultra-deep sequencing, wherein the ultra-deep sequencing comprises further amplification of the amplified nucleic acid molecules to produce at least one million copies of individual amplified nucleic acid molecules in parallel.

16. The method of claim 15, wherein the further amplification comprises bridge amplification.

17. The method of claim 15, wherein the further amplification comprises whole genome amplification or rolling circle amplification.

18. The method of claim 1, wherein the DNA regions comprise short tandem repeats (STRs) or single nucleotide polymorphisms (SNPs), or both, and wherein ultra-deep sequencing is used to provide an accurate and quantitative measurement of the allele abundances for each STR or each SNP.

* * * * *

SEQUENCE LISTING

```
Sequence total quantity: 70
SEQ ID NO: 1          moltype = DNA  length = 17
FEATURE               Location/Qualifiers
source                1..17
                      mol_type = other DNA
                      organism = synthetic construct
SEQUENCE: 1
ttgctgctgg tggtggc                                                   17

SEQ ID NO: 2          moltype = DNA  length = 20
FEATURE               Location/Qualifiers
source                1..20
                      mol_type = other DNA
                      organism = synthetic construct
SEQUENCE: 2
cagggattcc gtcatatggc                                                20
```

```
SEQ ID NO: 3            moltype = DNA  length = 18
FEATURE                 Location/Qualifiers
source                  1..18
                        mol_type = other DNA
                        organism = synthetic construct
SEQUENCE: 3
gatcggcctc ttcatgcg                                         18

SEQ ID NO: 4            moltype = DNA  length = 22
FEATURE                 Location/Qualifiers
source                  1..22
                        mol_type = other DNA
                        organism = synthetic construct
SEQUENCE: 4
gatccaaagg tcatcaactc cc                                    22

SEQ ID NO: 5            moltype = DNA  length = 18
FEATURE                 Location/Qualifiers
source                  1..18
                        mol_type = other DNA
                        organism = synthetic construct
SEQUENCE: 5
gctgtccaac gaatgggc                                         18

SEQ ID NO: 6            moltype = DNA  length = 20
FEATURE                 Location/Qualifiers
source                  1..20
                        mol_type = other DNA
                        organism = synthetic construct
SEQUENCE: 6
ggcgttctcc tttctccagg                                       20

SEQ ID NO: 7            moltype = DNA  length = 19
FEATURE                 Location/Qualifiers
source                  1..19
                        mol_type = other DNA
                        organism = synthetic construct
SEQUENCE: 7
atgcactggg ccaggtctt                                        19

SEQ ID NO: 8            moltype = DNA  length = 21
FEATURE                 Location/Qualifiers
source                  1..21
                        mol_type = other DNA
                        organism = synthetic construct
SEQUENCE: 8
cgatggtaca tatgggtggc t                                     21

SEQ ID NO: 9            moltype = DNA  length = 19
FEATURE                 Location/Qualifiers
source                  1..19
                        mol_type = other DNA
                        organism = synthetic construct
SEQUENCE: 9
aggctgtcca acgaatggg                                        19

SEQ ID NO: 10           moltype = DNA  length = 19
FEATURE                 Location/Qualifiers
source                  1..19
                        mol_type = other DNA
                        organism = synthetic construct
SEQUENCE: 10
ctgagggagg cgttctcct                                        19

SEQ ID NO: 11           moltype = DNA  length = 22
FEATURE                 Location/Qualifiers
source                  1..22
                        mol_type = other DNA
                        organism = synthetic construct
SEQUENCE: 11
tcagagcctg tgtttctacc aa                                    22

SEQ ID NO: 12           moltype = DNA  length = 22
FEATURE                 Location/Qualifiers
source                  1..22
                        mol_type = other DNA
                        organism = synthetic construct
SEQUENCE: 12
tggtctcaca ggaccactga tt                                    22
```

```
SEQ ID NO: 13          moltype = DNA  length = 20
FEATURE                Location/Qualifiers
source                 1..20
                       mol_type = other DNA
                       organism = synthetic construct
SEQUENCE: 13
tccaaatgag ctggcaagtg                                                20

SEQ ID NO: 14          moltype = DNA  length = 23
FEATURE                Location/Qualifiers
source                 1..23
                       mol_type = other DNA
                       organism = synthetic construct
SEQUENCE: 14
tcccaaacac tcagtgaaac aaa                                            23

SEQ ID NO: 15          moltype = DNA  length = 24
FEATURE                Location/Qualifiers
source                 1..24
                       mol_type = other DNA
                       organism = synthetic construct
SEQUENCE: 15
aaataatcag tgtgattcgt ggag                                           24

SEQ ID NO: 16          moltype = DNA  length = 22
FEATURE                Location/Qualifiers
source                 1..22
                       mol_type = other DNA
                       organism = synthetic construct
SEQUENCE: 16
gaggccagtg ctgtctctaa gg                                             22

SEQ ID NO: 17          moltype = DNA  length = 20
FEATURE                Location/Qualifiers
source                 1..20
                       mol_type = other DNA
                       organism = synthetic construct
SEQUENCE: 17
gtgcatcgct ggtaacatcc                                                20

SEQ ID NO: 18          moltype = DNA  length = 20
FEATURE                Location/Qualifiers
source                 1..20
                       mol_type = other DNA
                       organism = synthetic construct
SEQUENCE: 18
tgtggagatg agcagggtct                                                20

SEQ ID NO: 19          moltype = DNA  length = 21
FEATURE                Location/Qualifiers
source                 1..21
                       mol_type = other DNA
                       organism = synthetic construct
SEQUENCE: 19
acttcacagc cctgcgtaaa c                                              21

SEQ ID NO: 20          moltype = DNA  length = 21
FEATURE                Location/Qualifiers
source                 1..21
                       mol_type = other DNA
                       organism = synthetic construct
SEQUENCE: 20
atgggacagg cactgatttg t                                              21

SEQ ID NO: 21          moltype = DNA  length = 20
FEATURE                Location/Qualifiers
source                 1..20
                       mol_type = other DNA
                       organism = synthetic construct
SEQUENCE: 21
atcgcattca tgcgtcttca                                                20

SEQ ID NO: 22          moltype = DNA  length = 20
FEATURE                Location/Qualifiers
source                 1..20
                       mol_type = other DNA
                       organism = synthetic construct
SEQUENCE: 22
```

```
atccccatgg caaactcttg                                             20

SEQ ID NO: 23          moltype = DNA  length = 22
FEATURE                Location/Qualifiers
source                 1..22
                       mol_type = other DNA
                       organism = synthetic construct
SEQUENCE: 23
gcagcgggtt acatcttctt tc                                          22

SEQ ID NO: 24          moltype = DNA  length = 22
FEATURE                Location/Qualifiers
source                 1..22
                       mol_type = other DNA
                       organism = synthetic construct
SEQUENCE: 24
cagctctggc tcacactacc ag                                          22

SEQ ID NO: 25          moltype = DNA  length = 22
FEATURE                Location/Qualifiers
source                 1..22
                       mol_type = other DNA
                       organism = synthetic construct
SEQUENCE: 25
gcagcgggtt acatcttctt tc                                          22

SEQ ID NO: 26          moltype = DNA  length = 19
FEATURE                Location/Qualifiers
source                 1..19
                       mol_type = other DNA
                       organism = synthetic construct
SEQUENCE: 26
catcctcccc tgcatgtgt                                              19

SEQ ID NO: 27          moltype = DNA  length = 20
FEATURE                Location/Qualifiers
source                 1..20
                       mol_type = other DNA
                       organism = synthetic construct
SEQUENCE: 27
ccgcagcatg tcaagatcac                                             20

SEQ ID NO: 28          moltype = DNA  length = 25
FEATURE                Location/Qualifiers
source                 1..25
                       mol_type = other DNA
                       organism = synthetic construct
SEQUENCE: 28
tccttctgca tggtattctt tctct                                       25

SEQ ID NO: 29          moltype = DNA  length = 14
FEATURE                Location/Qualifiers
source                 1..14
                       mol_type = other DNA
                       organism = synthetic construct
SEQUENCE: 29
tttgggctgg ccaa                                                   14

SEQ ID NO: 30          moltype = DNA  length = 14
FEATURE                Location/Qualifiers
source                 1..14
                       mol_type = other DNA
                       organism = synthetic construct
SEQUENCE: 30
ttttgggcgg gcca                                                   14

SEQ ID NO: 31          moltype = DNA  length = 17
FEATURE                Location/Qualifiers
source                 1..17
                       mol_type = other DNA
                       organism = synthetic construct
SEQUENCE: 31
atggccagcg tggacaa                                                17

SEQ ID NO: 32          moltype = DNA  length = 23
FEATURE                Location/Qualifiers
source                 1..23
                       mol_type = other DNA
                       organism = synthetic construct
```

```
SEQUENCE: 32
agcaggtact gggagccaat att                                          23

SEQ ID NO: 33           moltype = DNA  length = 16
FEATURE                 Location/Qualifiers
source                  1..16
                        mol_type = other DNA
                        organism = synthetic construct
SEQUENCE: 33
atgagctgcg tgatga                                                  16

SEQ ID NO: 34           moltype = DNA  length = 16
FEATURE                 Location/Qualifiers
source                  1..16
                        mol_type = other DNA
                        organism = synthetic construct
SEQUENCE: 34
atgagctgca tgatga                                                  16

SEQ ID NO: 35           moltype = DNA  length = 22
FEATURE                 Location/Qualifiers
source                  1..22
                        mol_type = other DNA
                        organism = synthetic construct
SEQUENCE: 35
gcctcttaca cccagtggag aa                                           22

SEQ ID NO: 36           moltype = DNA  length = 18
FEATURE                 Location/Qualifiers
source                  1..18
                        mol_type = other DNA
                        organism = synthetic construct
SEQUENCE: 36
gcctgtgcca gggacctt                                                18

SEQ ID NO: 37           moltype = DNA  length = 14
FEATURE                 Location/Qualifiers
source                  1..14
                        mol_type = other DNA
                        organism = synthetic construct
SEQUENCE: 37
accggagccc agca                                                    14

SEQ ID NO: 38           moltype = DNA  length = 14
FEATURE                 Location/Qualifiers
source                  1..14
                        mol_type = other DNA
                        organism = synthetic construct
SEQUENCE: 38
accggagctc agca                                                    14

SEQ ID NO: 39           moltype = DNA  length = 14
FEATURE                 Location/Qualifiers
source                  1..14
                        mol_type = other DNA
                        organism = synthetic construct
SEQUENCE: 39
accggagcac agca                                                    14

SEQ ID NO: 40           moltype = DNA  length = 24
FEATURE                 Location/Qualifiers
source                  1..24
                        mol_type = other DNA
                        organism = synthetic construct
SEQUENCE: 40
acagcagggt cttctctgtt tcag                                         24

SEQ ID NO: 41           moltype = DNA  length = 21
FEATURE                 Location/Qualifiers
source                  1..21
                        mol_type = other DNA
                        organism = synthetic construct
SEQUENCE: 41
atcttgacat gctgcggtgt t                                            21

SEQ ID NO: 42           moltype = DNA  length = 14
FEATURE                 Location/Qualifiers
source                  1..14
                        mol_type = other DNA
```

```
                        organism = synthetic construct
SEQUENCE: 42
ttggtgcacc gcga                                                 14

SEQ ID NO: 43           moltype = DNA  length = 14
FEATURE                 Location/Qualifiers
source                  1..14
                        mol_type = other DNA
                        organism = synthetic construct
SEQUENCE: 43
tggtgctccg cgac                                                 14

SEQ ID NO: 44           moltype = DNA  length = 19
FEATURE                 Location/Qualifiers
source                  1..19
                        mol_type = other DNA
                        organism = synthetic construct
SEQUENCE: 44
agtcaggacc catgcacgg                                            19

SEQ ID NO: 45           moltype = DNA  length = 20
FEATURE                 Location/Qualifiers
source                  1..20
                        mol_type = other DNA
                        organism = synthetic construct
SEQUENCE: 45
acccaagatg cagcagtgtg                                           20

SEQ ID NO: 46           moltype = DNA  length = 21
FEATURE                 Location/Qualifiers
source                  1..21
                        mol_type = other DNA
                        organism = synthetic construct
SEQUENCE: 46
gatgtcctcc ttgttctact c                                         21

SEQ ID NO: 47           moltype = DNA  length = 22
FEATURE                 Location/Qualifiers
source                  1..22
                        mol_type = other DNA
                        organism = synthetic construct
SEQUENCE: 47
tacagggaat aatcgagcat gc                                        22

SEQ ID NO: 48           moltype = DNA  length = 22
FEATURE                 Location/Qualifiers
source                  1..22
                        mol_type = other DNA
                        organism = synthetic construct
SEQUENCE: 48
gaagggaaat agcaaatgga ca                                        22

SEQ ID NO: 49           moltype = DNA  length = 20
FEATURE                 Location/Qualifiers
source                  1..20
                        mol_type = other DNA
                        organism = synthetic construct
SEQUENCE: 49
cgatggagtc caagttctgg                                           20

SEQ ID NO: 50           moltype = DNA  length = 20
FEATURE                 Location/Qualifiers
source                  1..20
                        mol_type = other DNA
                        organism = synthetic construct
SEQUENCE: 50
agcacttaca gctctggcca                                           20

SEQ ID NO: 51           moltype = DNA  length = 22
FEATURE                 Location/Qualifiers
source                  1..22
                        mol_type = other DNA
                        organism = synthetic construct
SEQUENCE: 51
gactgaacat aactgtaggc tg                                        22

SEQ ID NO: 52           moltype = DNA  length = 21
FEATURE                 Location/Qualifiers
source                  1..21
```

```
                        mol_type = other DNA
                        organism = synthetic construct
SEQUENCE: 52
tggatcccag aaggtgagaa a                                            21

SEQ ID NO: 53           moltype = DNA  length = 24
FEATURE                 Location/Qualifiers
source                  1..24
                        mol_type = other DNA
                        organism = synthetic construct
SEQUENCE: 53
agcagaaact cacatcgagg attt                                         24

SEQ ID NO: 54           moltype = DNA  length = 19
FEATURE                 Location/Qualifiers
source                  1..19
                        mol_type = other DNA
                        organism = synthetic construct
SEQUENCE: 54
aaggaattaa gagaagcaa                                               19

SEQ ID NO: 55           moltype = DNA  length = 16
FEATURE                 Location/Qualifiers
source                  1..16
                        mol_type = other DNA
                        organism = synthetic construct
SEQUENCE: 55
ctatcaaaac atctcc                                                  16

SEQ ID NO: 56           moltype = DNA  length = 16
FEATURE                 Location/Qualifiers
source                  1..16
                        mol_type = other DNA
                        organism = synthetic construct
SEQUENCE: 56
ctatcaagac atctcc                                                  16

SEQ ID NO: 57           moltype = DNA  length = 19
FEATURE                 Location/Qualifiers
source                  1..19
                        mol_type = other DNA
                        organism = synthetic construct
SEQUENCE: 57
tcgagtgcat tccattccg                                               19

SEQ ID NO: 58           moltype = DNA  length = 21
FEATURE                 Location/Qualifiers
source                  1..21
                        mol_type = other DNA
                        organism = synthetic construct
SEQUENCE: 58
atggaatggc atcaaacgga a                                            21

SEQ ID NO: 59           moltype = DNA  length = 15
FEATURE                 Location/Qualifiers
source                  1..15
                        mol_type = other DNA
                        organism = synthetic construct
SEQUENCE: 59
tggctgtcca ttcca                                                   15

SEQ ID NO: 60           moltype = DNA  length = 65
FEATURE                 Location/Qualifiers
source                  1..65
                        mol_type = other DNA
                        organism = synthetic construct
SEQUENCE: 60
atgcagcaag gcacagacta arcaaggaga sgcaaaattt tcrtagggga gagaaatggg  60
tcatt                                                              65

SEQ ID NO: 61           moltype = DNA  length = 22
FEATURE                 Location/Qualifiers
source                  1..22
                        mol_type = other DNA
                        organism = synthetic construct
SEQUENCE: 61
atgcagcaag gcacagacta cg                                           22

SEQ ID NO: 62           moltype = DNA  length = 23
```

```
FEATURE                Location/Qualifiers
source                 1..23
                       mol_type = other DNA
                       organism = synthetic construct
SEQUENCE: 62
agaggggaga gaaatgggtc att                                          23

SEQ ID NO: 63          moltype = DNA  length = 25
FEATURE                Location/Qualifiers
source                 1..25
                       mol_type = other DNA
                       organism = synthetic construct
SEQUENCE: 63
caaggcacag actaagcaag gagag                                        25

SEQ ID NO: 64          moltype = DNA  length = 35
FEATURE                Location/Qualifiers
source                 1..35
                       mol_type = other DNA
                       organism = synthetic construct
SEQUENCE: 64
ggcaaaattt tcatagggga gagaaatggg tcatt                             35

SEQ ID NO: 65          moltype = DNA  length = 20
FEATURE                Location/Qualifiers
source                 1..20
                       mol_type = other DNA
                       organism = synthetic construct
SEQUENCE: 65
gttcggcacg gtgtataagg                                              20

SEQ ID NO: 66          moltype = DNA  length = 20
FEATURE                Location/Qualifiers
source                 1..20
                       mol_type = other DNA
                       organism = synthetic construct
SEQUENCE: 66
ctggccatca cgtaggcttc                                              20

SEQ ID NO: 67          moltype = DNA  length = 13
FEATURE                Location/Qualifiers
source                 1..13
                       mol_type = other DNA
                       organism = synthetic construct
SEQUENCE: 67
cggagatggc cca                                                     13

SEQ ID NO: 68          moltype = DNA  length = 15
FEATURE                Location/Qualifiers
source                 1..15
                       mol_type = other DNA
                       organism = synthetic construct
SEQUENCE: 68
gcaactcatc atgca                                                   15

SEQ ID NO: 69          moltype = DNA  length = 15
FEATURE                Location/Qualifiers
source                 1..15
                       mol_type = other DNA
                       organism = synthetic construct
SEQUENCE: 69
ttttgggcgg gccaa                                                   15

SEQ ID NO: 70          moltype = DNA  length = 19
FEATURE                Location/Qualifiers
source                 1..19
                       mol_type = other DNA
                       organism = synthetic construct
SEQUENCE: 70
gaccgtttgg gagttgata                                               19
```